United States Patent
Marsters, Jr. et al.

[11] Patent Number: 5,532,359
[45] Date of Patent: Jul. 2, 1996

[54] RAS FARNESYL TRANSFERASE INHIBITORS

[75] Inventors: James C. Marsters, Jr., Oakland, Calif.; Michael S. Brown, Dallas, Tex.; Craig W. Crowley, Portola Valley, Calif.; Joseph L. Goldstein; Guy L. James, both of Dallas, Tex.; Robert S. McDowell, San Francisco, Calif.; David Oare, Belmont, Calif.; Thomas E. Rawson, Mountain View, Calif.; Mark Reynolds, So. San Francisco, Calif.; Todd C. Somers, Montara, Calif.

[73] Assignees: Genentech, Inc., South San Francisco, Calif.; Board of Regents, The University of Texas System, Austin, Tex.

[21] Appl. No.: 328,595

[22] Filed: Oct. 25, 1994

Related U.S. Application Data

[63] Continuation of Ser. No. 82,202, Jun. 24, 1993, abandoned, which is a continuation-in-part of Ser. No. 61,961, May 14, 1993, abandoned.

[51] Int. Cl.$^6$ .................... A61K 31/55; C07D 223/16; C07D 223/18
[52] U.S. Cl. .................... 540/522; 540/523; 540/493; 540/497; 540/498; 540/499; 540/504; 540/509; 540/558
[58] Field of Search .................... 540/522, 523; 514/213, 217

[56] References Cited

U.S. PATENT DOCUMENTS

| | | | |
|---|---|---|---|
| 4,692,522 | 9/1987 | Parsons et al. | 540/523 |
| 5,055,464 | 10/1991 | Murakami et al. | 514/211 |
| 5,141,851 | 8/1992 | Brown et al. | 435/15 |
| 5,206,234 | 4/1993 | Bock et al. | 514/213 |
| 5,238,922 | 8/1993 | Graham et al. | 514/18 |
| 5,245,061 | 9/1993 | Singh | 554/121 |

FOREIGN PATENT DOCUMENTS

| | | |
|---|---|---|
| 0166357 | 1/1986 | European Pat. Off. . |
| 0167919 | 1/1986 | European Pat. Off. . |
| 0322779 | 7/1989 | European Pat. Off. . |
| WO92/01683 | 2/1992 | WIPO . |
| WO94/04561 | 3/1994 | WIPO . |

OTHER PUBLICATIONS

James, G. et al., "Benzodiazepine peptidomimetics: potent inhibitors of ras farnesylation in animal cells" *Science* 260:1937–1941 (1993).

*Primary Examiner*—Philip I. Datlow
*Attorney, Agent, or Firm*—Daryl B. Winter

[57] ABSTRACT

Benzodiazepine derivatives are disclosed that act as potent inhibitors of ras farnesyl:protein transferase. Pharmaceutical compositions containing these benzodiazepines are provided for treatment of diseases for which inhibition of the ras farnesyl:protein transferase is indicated. Also disclosed are benzazepines of the following general formula (II) having similar utility as the aforementioned benzodiazepines:

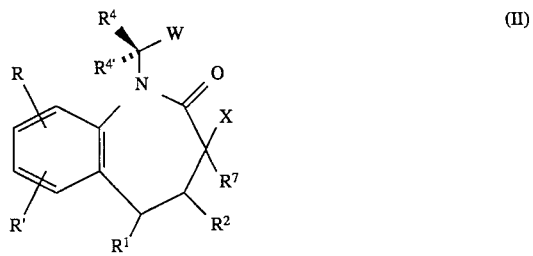

10 Claims, 7 Drawing Sheets

RAS FARNESYL TRANSFERASE INHIBITORS

This is a continuation of application Ser. No. 08/082,202 filed on 24 Jun. 1993, now abandoned which application is a continuation-in-part of Ser. No. 08/061,961 filed on 14 May 1993 now abandoned.

FIELD OF THE INVENTION

This invention relates generally to non-peptidyl inhibitors of farnesyl:protein transferase, an enzyme capable of catalizing farnesylation of p21$^{ras}$ and related low molecular weight G-proteins. More specifically, the instant inhibitors are analogs of benzodiazepine and structurally related 6–7 fused ring systems. The invention further relates to use of these inhibitors in situations where inhibition of posttranslational farnesylation of p21$^{ras}$ and related proteins is indicated.

BACKGROUND OF THE INVENTION

Proteins encoded by the ras proto-oncogene act as molecular switches responding to growth stimuli and signaling to the intracellular machinery the occurrence of an extracellular event such as binding of a growth hormone to a growth hormone receptor molecule. Binding of the hormone to its receptor (the external signal) switches the ras protein to the "on" position characterized by exchange of ras bound GDP for GTP. The tightly bound GTP in turn stimulates downstream target proteins, ultimately triggering a cascade of reactions leading to specific gene transcription and ultimately cell division [Barbacid, M., Ann. Rev. Biochem. 56:779 (1987), McCormick F., Nature 363:15–16 (1993)]. The normal (i.e. non-transformed) ras protein eventually switches to the off position by hydrolyzing bound GTP to GDP and the cell is poised to receive the next external signal.

Mutations to the ras proto-oncogene translate into amino acid substitutions in the GTP binding domain, activating the ras protein (p21$^{ras}$) and biasing this molecular switch in the "on" position. Thus, the ras transformed cell behaves like a cell with a faulty switch, signaling extracellular hormone binding when none is present. Cells transformed in this way grow and differentiate in an abnormal way.

Transforming ras genes are the oncogenes most frequently identified in human cancers. Clinical investigations have identified activated ras genes in a wide variety of human neoplasms, including carcinomas, sarcomas, leukemias, and lymphomas. It is estimated that 40% of all human colon cancers and 95% of human pancreatic cancers contain activated ras oncogenes [Kuzumaki, N. Anticancer Res., 11:313–320 (1991)].

Recently, it has been discovered that the ras protein must be properly posttranslationally modified before it can function as a molecular switch. Stable modification of the carboxy terminus of ras proteins appears to be essential for correct localization within the cell membrane so that extracellular signals for cell growth and differentiation can be correctly passed along to the intracellular messengers. The ras proteins are posttranslationally modified by farnesylation of a cysteine residue located four residues from the carboxy terminus, followed by proteolytic cleavage of the three following amino acid residues and methylation of the free cysteine carboxyl. The farnesylation reaction is catalyzed by a 94 kda heterodimeric Zn$^{2+}$ metalloenzyme, farnesyl:protein transferase, which transfers the farnesyl group, a 15 carbon isoprenoid lipid derived from mevalonate (a cholesterol precursor), from farnesyl pyrophosphate to the carboxy terminus cysteine sulfur of ras forming a stable thioether linkage. The farnesyl:protein transferase recognizes the ras carboxy terminus consensus sequence, CAAX, where the cysteine (C) is followed by two aliphatic (A) amino acids (usually valine, leucine, or isoleucine) and any amino acid X (including methionine). This consensus sequence or motif is frequently referred to as the "CAAX box" and is found in other ras related GTP-binding proteins such as fungal mating factors, nuclear lamins, the gamma subunit of transducin, rhodopsin kinase, and the alpha subunit of cGMP-phosphodiesterase.

Surprisingly, this enzyme does not require intact ras protein for transferase activity and can utilize tetrapeptides with the CAAX motif as substrates (Reiss et al., Cell, 62: 81–88 (1990)). This observation suggested that small tetrapeptides like CAAX or nonpeptide analogs thereof could compete with p21$^{ras}$ for the active site of the transferase and therefore might be of therapeutic utility.

Previously, it had been observed that mutation of the cysteine in the CAAX carboxy sequence of p21$^{ras}$ to serine prevented farnesylation, proteolysis, and methylation (Hancock, J. et al., Cell 57:1167–1177 (1989); Reiss et al., PNAS, 88:732–736 (1991)). Additionally, cells incubated with an inhibitor of mevalonate synthesis prevented ras farnesylation and the cells were no longer capable of cell division (Schafer et al., Science, 245: 379–385 (1989)).

These results, taken together, suggest that inhibition of farnesyl:protein transferase with peptides containing the CAAX motif would prevent farnesylation of p21$^{ras}$ and block the ability of ras to transform normal cells to cancer cells. (see e.g. EP 0 461 869 A2, EP 0 496 162 A2, EP 0 523 873, and EP 0 520 823). Thus it is believed that intracellular delivery of peptides having the CAAX motif to transformed cells would be an effective anti-neoplastic therapy.

Generally, however, small linear peptides do not make good therapeutics because of their susceptibility to proteolysis, oxidation, and lack of transportability across cell membranes. Accordingly, a need exists for a stable and potent non-peptidyl farnesyl:protein transferase inhibitor that is permeable to cell membranes.

Recently, several non-peptidyl ras farnesyl transferase inhibitors were identified through microbial screening. Several antibiotics (UCF1-A through UCF1-C) structurally related to manumycin inhibited growth of Ki-ras-transformed fibrosarcoma [Hara, M., et al. Proc. Natl. Sci. USA, 90:2281–2285 (1993)].

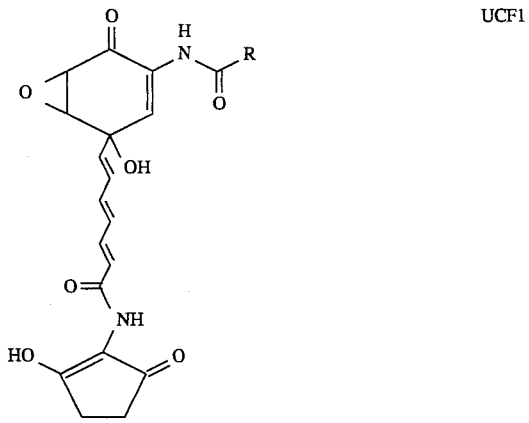

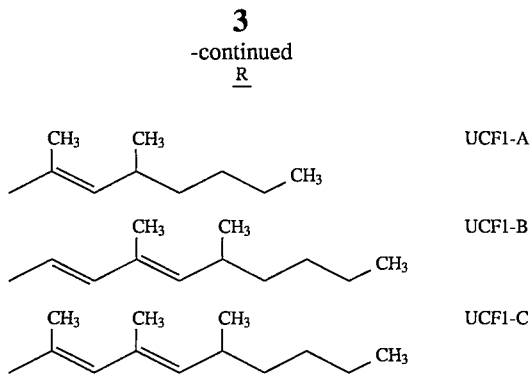

| | |
|---|---|
| | UCF1-A |
| | UCF1-B |
| | UCF1-C |

These inhibitors are reported to have potential application in cancer therapy.

Burk, R., et al. WO 92/20336(Merck) also describe nonpeptidyl farnesyltransferase inhibitors prepared by modification of natural products having structures similar to the following compound:

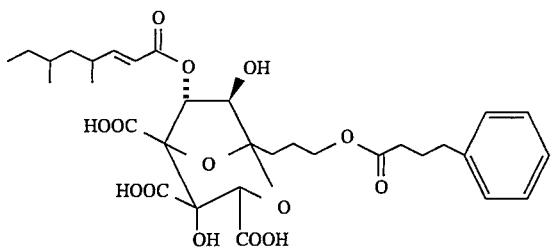

These compounds are reported to be useful in treating cancer, especially colorectal carcinoma, exocrine pancreatic carcinoma, and myloid leukemia.

Benzodiazepines and analogs thereof have been widely exploited as therapeutics, but have not been reported to be inhibitors of farnesylation of G-proteins such as p21$^{ras}$. Benzodiazepines are well known as central nervous system (CNS) drugs effecting the neuro-inhibitory postsynaptic GABA receptor and chloride ionophore channel (see eg. Watjen et al., *J. Med. Chem.* 32:2282–2291]1989]). Benzodiazepine analogs have been employed as intermediates in the synthesis of various anti-HIV-1 compounds [see e.g. Kukla, M. J. et al., *J. Med. Chem.* 34:3187–3197 (1991)] and as antagonists of gastrin and cholecystokinin (CCK) [see e.g. EP 0 284 256, assigned to Merck, and Friedinger, *Med. Res, Rev.,* 9 271 (1989)]. More recently, benzodiazepine analogs have been reported to be fibrinogen antagonists, inhibiting platelet aggregation [see e.g. WO 93/00095 assigned to SmithKline Beecham.]

It was therefore an object of this invention to identify nonpeptidyl compounds that more effectively antagonize farnesylation of low molecular weight G-proteins such as p21$^{ras}$ in disease states in animals, preferably mammals, and especially humans. It was a further object of this invention to identify compounds that inhibit isoprenylation of proteins in microorganisms, such as yeast and fungi, that produce disease states in plants or animals, preferably mammals, and especially humans. These and other objects of this invention will be apparent from consideration of the specification and claims as a whole.

SUMMARY OF THE INVENTION

The objects of this invention are accomplished by providing a nonpeptidyl compound represented by structural formula (A):

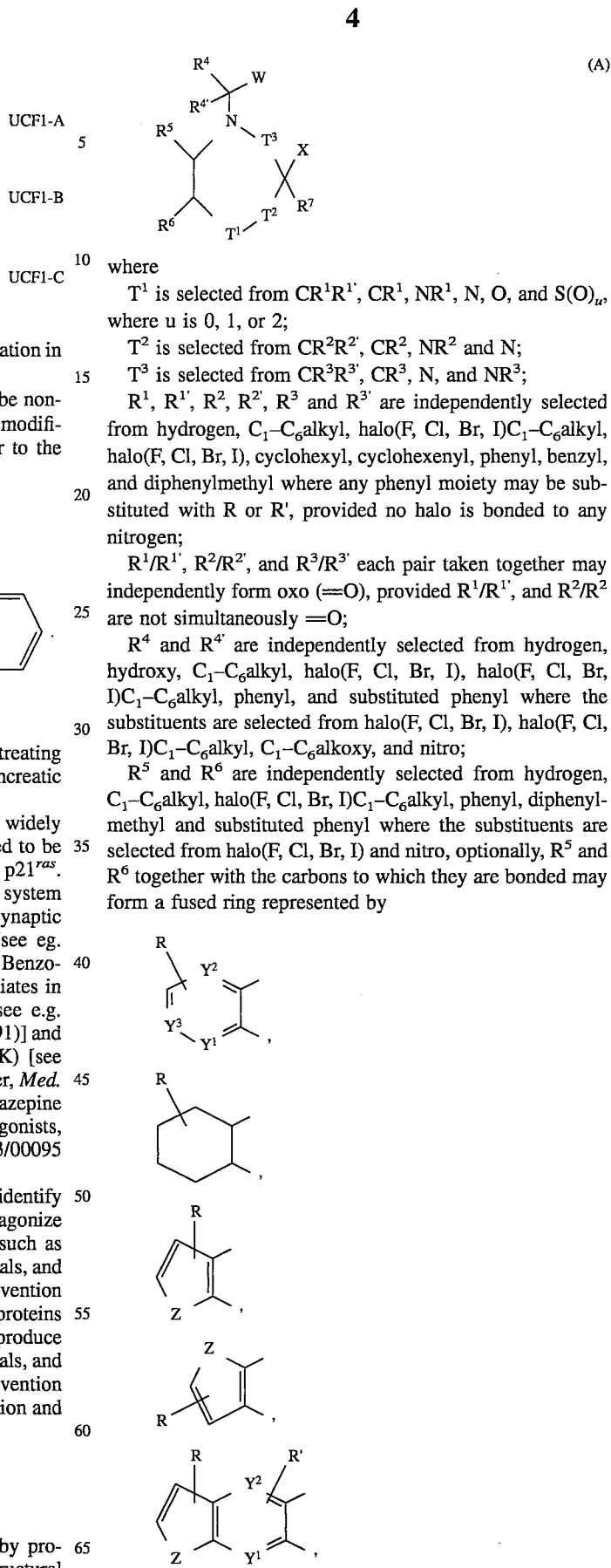

where $T^1$ is selected from $CR^1R^{1'}$, $CR^1$, $NR^1$, N, O, and $S(O)_u$, where u is 0, 1, or 2;

$T^2$ is selected from $CR^2R^{2'}$, $CR^2$, $NR^2$ and N;

$T^3$ is selected from $CR^3R^{3'}$, $CR^3$, N, and $NR^3$;

$R^1$, $R^{1'}$, $R^2$, $R^{2'}$, $R^3$ and $R^{3'}$ are independently selected from hydrogen, $C_1$–$C_6$alkyl, halo(F, Cl, Br, I)$C_1$–$C_6$alkyl, halo(F, Cl, Br, I), cyclohexyl, cyclohexenyl, phenyl, benzyl, and diphenylmethyl where any phenyl moiety may be substituted with R or R', provided no halo is bonded to any nitrogen;

$R^1/R^{1'}$, $R^2/R^{2'}$, and $R^3/R^{3'}$ each pair taken together may independently form oxo (=O), provided $R^1/R^{1'}$, and $R^2/R^2$ are not simultaneously =O;

$R^4$ and $R^{4'}$ are independently selected from hydrogen, hydroxy, $C_1$–$C_6$alkyl, halo(F, Cl, Br, I), halo(F, Cl, Br, I)$C_1$–$C_6$alkyl, phenyl, and substituted phenyl where the substituents are selected from halo(F, Cl, Br, I), halo(F, Cl, Br, I)$C_1$–$C_6$alkyl, $C_1$–$C_6$alkoxy, and nitro;

$R^5$ and $R^6$ are independently selected from hydrogen, $C_1$–$C_6$alkyl, halo(F, Cl, Br, I)$C_1$–$C_6$alkyl, phenyl, diphenylmethyl and substituted phenyl where the substituents are selected from halo(F, Cl, Br, I) and nitro, optionally, $R^5$ and $R^6$ together with the carbons to which they are bonded may form a fused ring represented by -continued

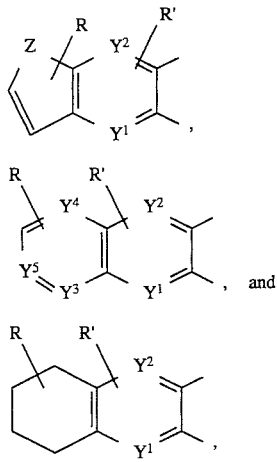

$R^5$, $R^6$, and $R^1$ together with the carbons to which they are bonded may form a fused ring system represented by

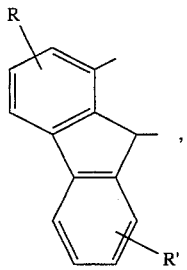

R and R' are one to three optional groups independently selected from hydrogen, halo(F, Cl, Br, I), cyano, carboxamido, carbamoyloxy, carboxy$C_1$-$C_{12}$alkyl, formyloxy, formyl, azido, nitro, ureido, thioureido, hydroxy, mercapto, sulfonamido, and an optionally substituted radical selected from $C_1$-$C_{12}$ alkyl, $C_2$-$C_{12}$ alkenyl, $C_3$-$C_{12}$ alkynyl, $C_3$-$C_{12}$ cycloalkyl, $C_6$-$C_{14}$aryl, $C_6$-$C_{10}$ aryl-$C_1$-$C_8$ alkyl, $C_1$-$C_{12}$ alkyloxy, $C_6$-$C_{14}$ aryloxy, and $C_1$-$C_{12}$alkanoylamino, where the substituents are selected from halo(F, Cl, Br, I), cyano, azido, nitro, hydroxy, mercapto, sulfonamido, ureido, thioureido, carboxamido, carbamoyloxy, formyloxy, formyl, $C_1$-$C_4$ alkyl, $C_1$-$C_4$ alkoxy, phenyl, and phenoxy;

X is the side chain of any α-amino acid preferably an L-α-amino acid and preferably selected from the group —$NR^{24}$—C(=O)—$R^{25}$, —$NR^{24}$—C(=O)—$R^8$, —$NR^{24}$—C(=O)$NR^{7'}R^8$, —$NR^{24}$—C(=O)O—$R^8$, —$NR^{24}$—C(=O)S—$R^8$, —$(CH_2)_{1-4}$—$NR^{24}$—C(=O)— $R^{25}$, —$(CH_2)_{1-4}$—C(=O)—$R^{25}$, —$(CH_2)_{1-4}$— C(=O)NH—$R^{25}$, —$(CH_2)_{0-4}$—$NR^{24}$—CH(OH—$R^{25}$, —$CHR^{24}$phenyl-$R^{25}$, —$CHR^{24}$phenoxy-$R^{25}$, —$CHR^{24}$— O—$R^{25}$, —$(CH_2)_{0-4}$—$NR^{24}$—$CH_2$—$R^{25}$, —$(CH_2)_{0-4}$— $NR^{24}$—S(O)$_u$—$R^{25}$ where u is 0, 1, or 2, —$CHR^{24}$— $CH_2R^{25}$, —$CHR^{24}$—$R^{25}$, —$CR^{24}$=$CHR^{25}$ (E or Z), —$(CH_2)_{0-4}$—$C_6$-$C_{10}$aryl-$R^{25}$, —$(CH_2)_{0-4}$-heterocycle-$R^{25}$, —$C_1$-$C_2$haloalkyl-$C_6$-$C_{10}$aryl-$R^{25}$, and —$C_1$-$C_2$haloalkyl-heterocycle-$R^{25}$, where any heterocycle is a 5- or 6-member saturated or unsaturated ring containing 1 to 3 heteroatoms selected from O, N, and S;

X together with the carbon to which it is bound and $T^2$ may form a heterocycle, where the heterocycle is a 5 or 6-member saturated or unsaturated fused ring having from 1–3 hetero atoms selected from O, N, and S, where any carbon atom of the heterocycle is optionally substituted with oxo (=O) or R, $Y^1$, $Y^2$, $Y^3$, $Y^4$ and $Y^5$ are independently selected from CH, CR, CR', and N;

Z is S or O;

W is selected from the group —C(=O)—$NR^{7'}R^8$, —C(=O)—O—$R^8$, —$CR^{8'}$(OH)—$CHR^{7'}R^8$, —$CHR^{8'}$— $CHR^{7'}R^8$, —$CR^{8'}$=$CR^{7'}R^8$ (E or Z), —C(=O)—$CHR^{7'}R^8$, —$CHR^{8'}$—$NR^{7'}R^8$, —$CHR^{8'}$—O—$R^8$, —$CHR^{8'}$—S(O)$_u$— $R^8$ where u is 0, 1, or 2; —$CR^{8'}$=N—$R^8$, —$CHR^{8'}$—$R^8$, —$C_6$-$C_{12}$aryl-W', —$C_6$-$C_{12}$aryl-$C_1$-$C_3$alkyl-W', -heterocycle-W', -heterocycle-$C_1$-$C_3$alkyl-W', -$C_1$-$C_2$alkyl-$C_6$-$C_{10}$aryl-W', and -$C_1$-$C_2$alkyl-heterocycle-W', where any heterocycle is a 5- or 6-member saturated or unsaturated ring containing 1 to 3 heteroatoms selected from O, N, and S;

W/$R^{4'}$ together with W/$R^{3'}$ and the carbon atoms to which they are bound may form heterocycle-W' or heterocycle-$C_1$-$C_6$alkyl -W', where the heterocycle is a 5- or 6-member saturated or unsaturated ring containing 1 to 3 heteroatoms selected from O, N, and S and where the heterocycle is unsubstituted or substituted with one or two substituents selected from the group (i) —OH, (ii) —SH, (iii) —($C_1$-$C_4$alkyl), (iv) —$C_1$-$C_4$alkoxyl, (v) $CF_3$, (vi) halo(F, Cl, Br, I), (vii) $NO_2$, (viii) —COOH, (ix) —COO— ($C_1$-$C_4$alkyl), (x) —$NH_2$, (xi) —NH($C_1$-$C_4$alkyl), and (xii) —N($C_1$-$C_4$alkyl)$_2$;

W' is selected from one to three substituents selected from the group hydrogen, —$SR^9$, —$SSR^9$, SC(=O)—$R^9$, —$OR^9$, —C(=NH)—$NH_2$, —N=CH—$NH_2$, —NH— CH=NH, $R^8$, and V;

$R^7$ is independently selected from the group hydrogen, $C_1$-$C_4$alkyl, halo(F, Cl, Br, I), and halo(F, Cl, Br, I)$C_1$-$C_4$alkyl;

$R^7$ and X together may form

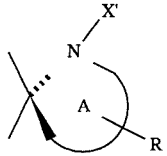

where

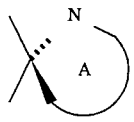

represents a heterocycle bonded to the benzodiazepine moiety through a spiro linkage, where the heterocycle is a 5- or 6-member saturated or unsaturated nitrogen containing ring having from 0 to 2 additional heteroatoms selected from O, N, and S, the ring optionally containing a keto [—C(=O)—] group; and where X' is selected from the group C(=O)—$R^{25}$, CH(OH)—$R^{25}$, $CHR^{24}$—$R^{25}$, S(O)$_u$— $R^{25}$ where u is 0, 1, or 2, $CHR^{24}$—$R^{25}$, $R^{25}$, $C_6$-$C_{10}$aryl-$R^{25}$, heterocycle-$R^{25}$, $C_1$-$C_2$alkyl-$C_6$-$C_{10}$aryl-$R^{25}$, and $C_1$-$C_2$alkyl-heterocycle-$R^{25}$, where any heterocycle is a 5- or 6-member saturated or unsaturated ring containing 1 to 3 heteroatoms selected from O, N, and S;

$R^{7'}$ and $R^{8'}$ are selected from the group hydrogen, $C_1$-$C_4$alkyl, and halo(F, Cl, Br, I)$C_1$-$C_4$alkyl;

$R^{7'}$ and $R^8$ together with the nitrogen to which they are bonded may form a heterocyclic 5-, 6-, or 7-member ring containing 0, 1, or 2 additional heteroatoms selected from N, S, and O, optionally substituted with one or two groups selected from oxo(=O), —$SR^9$, —$SSR^9$, SC(=O)—$R^9$, —$OR^9$, —C(=O)NHOH, —$NHR^9$, —C(=O)$NR^{27}R^{28}$, and —V;

R$^{8'}$ together with R$^3$ and R$^{8'}$ together with R$^{3'}$ may independently form a divalent radical selected from =CH—, —CH=, —CH$_2$—, —CH$_2$—CH$_2$—, =CH$_2$—CH$_2$—, —CH=CH—, and —CH$_2$—CH=;

R$^8$ is selected from the group hydrogen, C$_1$–C$_8$alkyl, C$_1$–C$_4$alkyl-Z—C$_1$–C$_4$alkyl, where Z is S or O, C$_2$–C$_4$alkyl-NR—C$_2$–C$_4$alkyl, C$_2$–C$_8$alkenyl, C$_6$–C$_{12}$arylC$_1$–C$_3$alkyl, indol-3-yl-C$_1$–C$_3$alkyl, and imidazol-4-yl-C$_1$–C$_3$alkyl, where any aryl moiety is optionally substituted with —OR$^9$ and V, and where any alkyl or alkenyl group is optionally substituted with one to three groups selected from —SR$^9$, —SSR$^9$, SC(=O)—R$^9$, —OR$^9$, —C(=NH)—NH$_2$, —N=CH—NH$_2$, —NH—CH=NH, —NH—C(=NH)—NH$_2$, —C(=O)NHOH, —NHR$^9$, —C(=O)NR$^{27}$R$^{28}$, and V;

V is selected from (a) —COR$^{10}$, (b) —SO$_3$R$^{13}$, (c) —NHSO$_2$CF$_3$, (d) —PO(OR$^{13}$)$_2$, (e) —SO$_2$NHR$^{10}$, (f) —CONHOR$^{13}$, (g) —C(OH)R$^{10}$PO(OR$^{13}$)$_2$, (h) —CN, (i) —SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group (i) —OH, (ii) —SH, (iii) —(C$_1$–C$_4$alkyl), (iv) —C$_1$–C$_4$alkoxyl, (v) CF$_3$, (vi) halo(F, Cl, Br, I), (vii) NO$_2$, (viii) —COOH, (ix) —COO—(C$_1$–C$_4$alkyl), (x) —NH$_2$, (xi) —NH(C$_1$–C$_4$alkyl), and (xii) —N(C$_1$–C$_4$alkyl)$_2$, (j) —CH$_2$SO$_2$-heterocycle, (k) —SO$_2$NHCOR$^{10}$, (l) —CH$_2$SO$_2$NHCOR$^{10}$, (m) —CONHSO$_2$R$^{15}$, (n) —CH$_2$CONHSO$_2$R$^{15}$, (o) —NHCONHSO$_2$R$^{15}$, (p) —NHSO$_2$NHCOR$^{15}$, (q) —CONHNHSO$_2$CF$_3$, (r) CON(OH)R$^{13}$, (s) —CONHCOCF$_3$, (t) —CONHSO$_2$R$^{10}$, (u) —CONHSO$_2$R$^{11}$, (v) —CONHSO$_2$R$^{13}$,

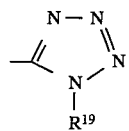 (w)

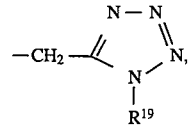 (x)

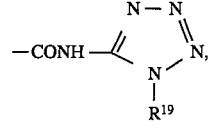 (y)

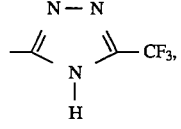 (z)

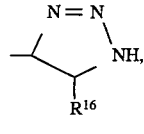 (aa)

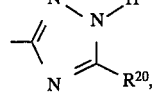 (ab)

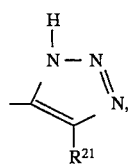 (ac)

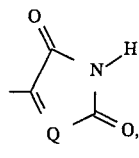 (ad)

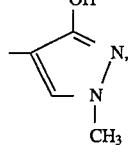 (ae)

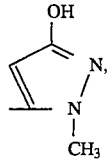 (af)

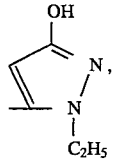 (ag)

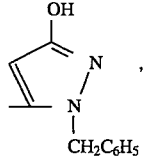 (ah)

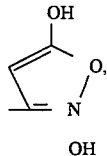 (ai)

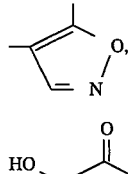 (aj)

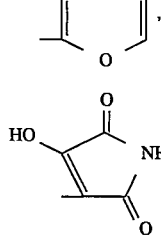 (ak)

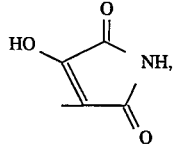 (al)

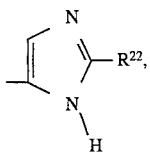 (am)

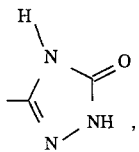 (an)

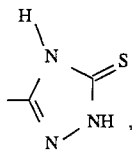 (ao)

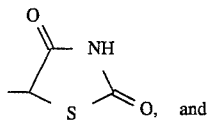 (ap)

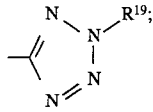 (aq)

$R^9$ is selected from hydrogen, methyl, ethyl, isopropyl, phenyl, and benzyl;

$R^{10}$ is selected from the group consisting of (a) hydroxy, (b) $C_1$–$C_8$-alkoxy, (c) $C_3$–$C_{12}$-alkenoxy, (d) $C_6$–$C_{12}$-aryloxy, (e) $C_1$–$C_6$-alkyl-$C_6$–$C_{12}$-aryloxy, (f) di-$C_1$–$C_8$-alkylamino-$C_1$–$C_8$-alkoxy, (g) alkanoylamino-$C_1$–$C_8$-alkoxy selected from the group (i) acetylaminoethoxy, (ii) nicotinoylaminoethoxy, and (iii) succinamidoethoxy, (h) $C_1$–$C_8$-alkanoyloxy-$C_1$–$C_8$-alkoxy, (i) $C_6$–$C_{12}$-aryl-$C_1$–$C_8$-alkoxy where the aryl group is unsubstituted or substituted with one to three of the groups (i) nitro, (ii) halo (F, Cl, Br, I), (iii) $C_1$–$C_4$-alkoxy, and (iv) amino, (j) hydroxy-$C_2$–$C_8$-alkoxy, (k) dihydroxy-$C_3$–$C_8$-alkoxy, and (l) $NR^{11}R^{12}$;

$R^{11}$ and $R^{12}$ are independently selected from the group consisting of (a) hydrogen, (b) $C_1$–$C_6$ alkyl, (c) $C_2$–$C_6$ alkanoyl, (d) $C_1$–$C_6$ alkanoyl unsubstituted or substituted with one to three of the groups (i) nitro, (ii) halo (F, Cl, Br, I), (iii) $C_1$–$C_4$-alkoxy, and (iv) amino, and (e) $C_6$–$C_{12}$-aryl-$C_1$–$C_8$-alkyl where the aryl group is unsubstituted or substituted with one to three of the groups (i) nitro, (ii) halo (F, Cl, Br, I), and (iii) $C_1$–$C_4$-alkoxy;

$R^{13}$ is selected from the group consisting of (a) H, (b) $C_1$–$C_6$ alkyl, (c) halo(F, Cl, Br, I)-$C_1$–$C_6$ alkyl, (d) phenyl, (e) benzyl, and (f) —$CH_2$—O—$COCH_3$;

$R^{14}$ is selected from the group consisting of (a) H, (b) benzyl and (c) —$CH(R^{17})$—O—$C(O)R^{17}$;

$R^{15}$ is selected from the group consisting of (a) $C_6$–$C_{14}$-aryl, (b) heteroaryl, (c) ($C_3$–$C_7$)-cycloalkyl, (d) ($C_1$–$C_4$)-alkyl, unsubstituted or substituted with a substituent selected from the group consisting of (i) aryl, (ii) heteroaryl, (iii) —OH, (iv) —SH, (v) ($C_1$–$C_4$)-alkyl, (vi) ($C_1$–$C_4$)-alkoxy, (vii) ($C_1$–$C_4$)-alkylthio, (viii) —$CF_3$, (ix) halo (F, Cl, Br, I), (x) —$NO_2$, (xi) —$CO_2H$, (xii) $CO_2$—($C_1$–$C_4$)-alkyl, (xiii) —$NH_2$, (xiv) —N[($C_1$–$C_4$)-alkyl]$_2$, (xv) —NH[($C_1$–$C_4$)-alkyl], (xvi) $PO_3H$ and (xvii) PO(OH)($C_1$–$C_4$)-alkoxy, and (e) ($C_1$–$C_4$)-perfluoroalkyl;

$R^{16}$ is selected from the group consisting of (a) —CN, (b) —$NO_2$, (c) —$COOR^{13}$, (d) $C_1$–$C_6$-perfluoroalkyl, and (e) $CF_3$;

$R^{17}$ is independently selected from the group consisting of (a) H, (b) ($C_1$–$C_6$)-alkyl, ($C_2$–$C_6$)-alkenyl, ($C_2$–$C_6$)-alkynyl or ($C_3$–$C_8$)-cycloalkyl, each of which is unsubstituted or substituted with (i) OH, (ii) ($C_1$–$C_4$)-alkoxy, (iii) $CO_2R^{15}$, (iv) $OCOR^{15}$, (v) $CONHR^{15}$, (vi) $CON(R^{15})_2$, (vii) $N(R^{15})C(O)R^{15}$, (viii) $NH_2$, (ix) ($C_1$–$C_4$)-alkylamino, (x) di[($C_1$–$C_4$)-alkyl]amino, (xi) aryl, and (xii) heteroaryl, (c) —C(O)-aryl, (d)-$NO_2$, (e) halo(Cl, Br, I, F), (f) —OH, (g) —$OR^{18}$, (h) ($C_1$–$C_4$)-perfluoroalkyl, (i) —SH, (j) —$S(O)_{1-2}$($C_1$–$C_4$)-alkyl, (k) $CO_2R^{15}$, (l) —$SO_3H$, (m) —$NR^{15}R^{18}$, (n) —$NR^{15}C(O)R^{18}$, (o) —$NR^{15}COOR^{14}$, (p) —$SO_2NHR^{14}$, (q) —$SO_2NR^{15}R^{15}$, (r) —$NHSO_2R^{14}$, (s) —$C(O)NHSO_2R^{14}$, (t) aryl, (u) heteroaryl, (v) morpholin-4-yl, (w) $CONH_2$, and (y) 1H-tetrazol-5-yl;

$R^{18}$ is selected from the group consisting of (a) H and (b) ($C_1$–$C_4$)-alkyl unsubstituted or substituted with (i) $NH_2$, (ii) NH[($C_1$–$C_4$)-alkyl], (iii) N[($C_1$–$C_4$)-alkyl]$_2$, (iv) $CO_2H$, (v) $CO_2$($C_1$–$C_4$)-alkyl, (vi) OH, (vii) $SO_3H$, and (viii) $SO_2NH_2$;

$R^{19}$ is selected from the group consisting of (a) H, (b) ($C_1$–$C_6$)-alkyl, (c) ($C_2$–$C_6$)-alkenyl, (d) ($C_1$–$C_6$)-alkoxy, (e) ($C_2$–$C_6$)-alkoxyalkyl, (f) —$CH_2$—O—$COCH_3$, or (g) benzyl, where the phenyl moiety is unsubstituted or substituted with a group selected from —$NO_2$, —$NH_2$, —OH, or —$OCH_3$;

$R^{20}$, $R^{21}$, and $R^{22}$ are each independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CH_3$, $SO_2CF_3$ and $SO_2C_6F_5$, where Q is selected from O, S, $NR^{23}$ and $CH_2$;

$R^{23}$ is selected from hydrogen, $CH_3$, and $CH_2C_6H_5$;

$R^{24}$ is selected from hydrogen, $C_1$–$C_6$alkyl, benzyl, halo(F, Cl, Br, I)benzyl, and halo(F, Cl, Br, I)$C_1$–$C_6$alkyl;

$R^{24}$ and $R^7$ together may form an ethylene, ethenylene, propylene, propenylene, butylene, or butenylene bridge;

$R^{25}$ is selected from $R^{25'}$,

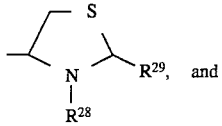

and

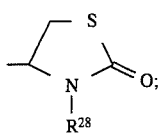

$R^{25'}$ is selected from —$SR^{26}$, —$SSR^{26}$, —$OR^{26}$, —$NOR^{26}$, $C_1$–$C_6$alkyl, $C_2$–$C_6$alkenyl, and halo(F, Cl, Br, I)$C_1$–$C_6$alkyl where any alkyl or alkenyl moiety is optionally substituted with one to three groups selected from —$SR^{26}$, —$SSR^{26}$, —$OR^{26}$, —$NOR^{26}$ and —$NR^{27}R^{28}$;

$R^{26}$ is selected from hydrogen, $C_1$–$C_6$alkyl, halo(F, Cl, Br, I)$C_1$–$C_6$alkyl, and $C_1$–$C_6$alkanoyl;

$R^{27}$ and $R^{28}$ are independently selected from hydrogen, $C_1$–$C_6$alkyl, phenyl, napthyl, benzyl, —$CH_2$-napthyl, $C_1$–$C_6$alkanoyl, $C_2$–$C_6$alkanoyl optionally substituted with —COOH and —$NH_2$, $C_1$–$C_6$cycloalkanoyl, $C_6$–$C_{10}$aroyl, $C_6$–$C_{10}$aryl$C_1$–$C_6$alkanoyl, $C_1$–$C_6$alkylsulfonyl, $C_6$–$C_{10}$arylsulfonyl, $C_6$–$C_{10}$aryl$C_1$–$C_6$alkylcarbamoyl, cinnamoyl, heterocyclecarbonyl, $C_1$–$C_6$alkoxycarbonyl, $C_6$–$C_{10}$aryloxycarbonyl, $C_6$–$C_{10}$aryl$C_1$–$C_6$alkoxycarbonyl, and pyroglutamyl;

$R^{27}$ and $R^{24}$ together may form a diradical selected from —$CH_2$—, —C(=O)—, —$CH_2$—$CH_2$—, and —$CH_2$—C(=O)—;

R²⁷ and R²⁸ together with the nitrogen atom to which they are bonded may form

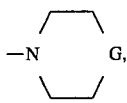

or a cyclic imide represented by

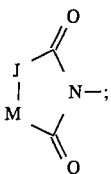

G is selected from —CH₂—, O, S(O)$_u$ where u is 0, 1, or 2, and NR²⁸;

J-M is selected from C₂-C₄alkylene and C₂-C₄alkenylene;

R²⁹ is selected from hydrogen, C₁-C₆alkyl, halo(F, Cl, Br, I)C₁-C₆alkyl, phenyl, benzyl, and pyridyl where any phenyl moiety may be substituted with halo(F and Cl), —CF₃, —NO₂, —NH₂, —OH, and —OCH₃; and pharmaceutically acceptable salts thereof.

Preferably the compounds of this invention are selected from those represented by structural formulae I–IX:

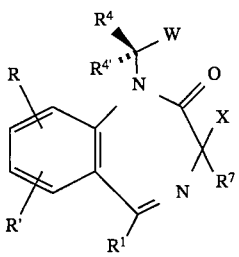
(I)

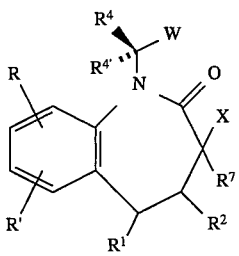
(II)

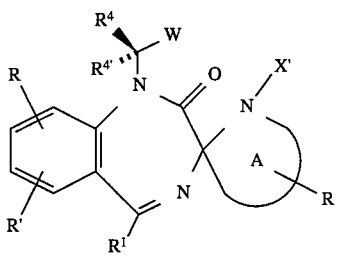
(III)

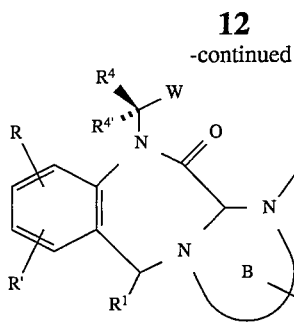
(IV)

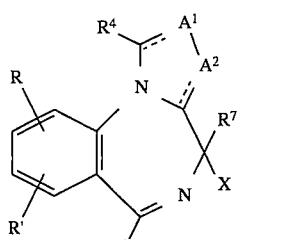
(V)

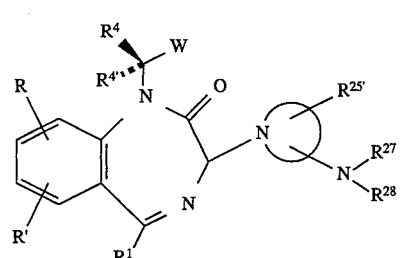
(VI)

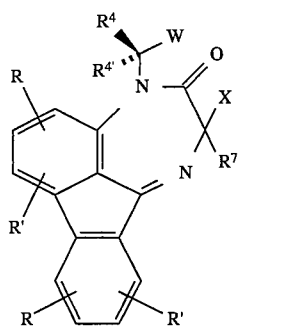
(VII)

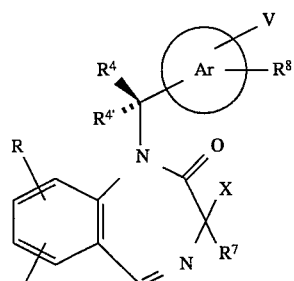
(VIII)

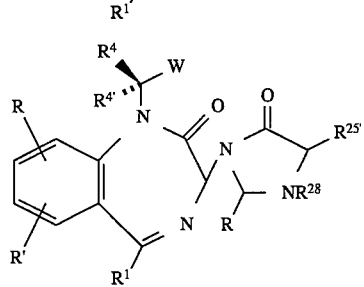
(IXa)

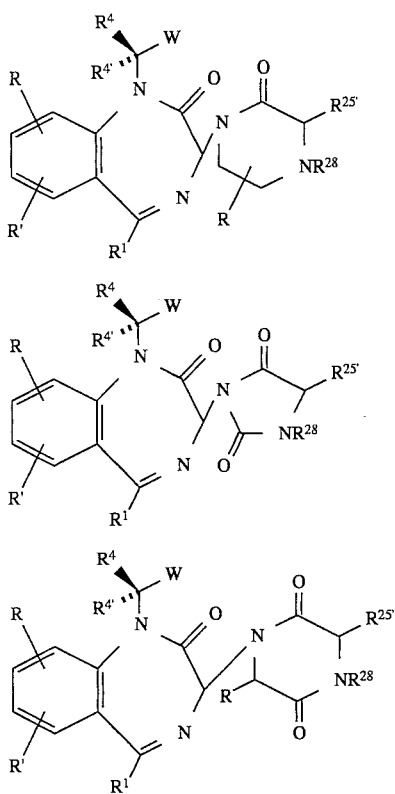

 (IXb)

 (IXc)

(IXd)

where R, R', $R^1$, $R^4$, $R^{4'}$, $R^7$, $R^{7'}$, $R^8$, $R^{8'}$, $R^9$, $R^{10}$, $R^{11}$, $R^{12}$, $R^{13}$, $R^{15}$, $R^{16}$, $R^{19}$, $R^{24}$, $R^{25}$, $R^{25'}$, $R^{26}$, $R^{27}$, $R^{28}$, $R^{29}$, W, W', V, X, X', G, and J-M are defined above;

Optionally, $R^1$ and $R^2$ taken together may form a covalent bond or fused benzene substituted with R and R';

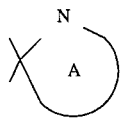

represents a heterocycle bonded to the benzodiazepine moiety through a spiro linkage, where the heterocycle is a 5- or 6-member saturated or unsaturated nitrogen containing ring having from 0 to 2 additional heteroatoms selected from O, N, and S, the ring optionally containing a keto [—C(=O)—] group;

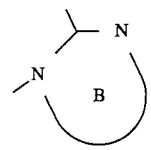

represents a heterocycle fused to the benzodiazepine moiety, where the heterocycle is a 5- or 6-member saturated or unsaturated di-nitrogen containing ring having from 0 to 1 additional heteroatom selected from O, N, and S, the ring optionally containing a keto [—C(=O)—] group;

represents a heterocycle bonded to the benzodiazepine moiety through a ring nitrogen, where the heterocycle is a 5- or 6-member saturated or unsaturated nitrogen containing ring having from 0 to 2 additional heteroatoms selected from O, N, and S, the ring optionally containing a keto [—C(=O)—] group;

represents $C_6$–$C_{10}$aryl or a heteroaryl where the heteroaryl is a 5- or 6-member aromatic ring containing 1 to 3 heteroatoms selected from O, N, and S, the $C_6$–$C_{10}$aryl or heteroaryl is optionally substituted with V and $R^8$;

$A^1$ and $A^2$ are independently selected from CRR', CR', $CRR^8$, $CR^8$, N, O, and S provided one of $A^1$ and $A^2$ is $CRR^8$ or $CR^8$; and

==== represents a single or double bond.

Most preferred compounds of the instant invention are represented by formulae (Ia)–(Ie):

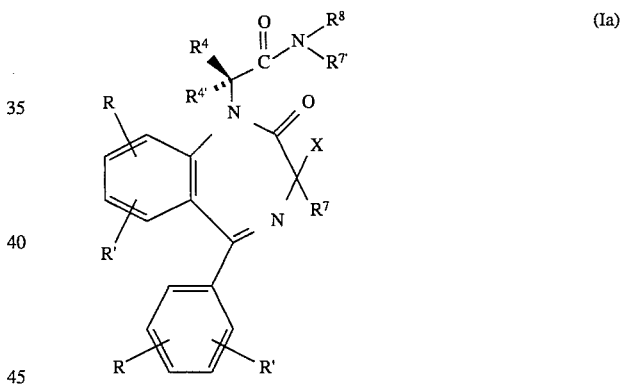 (Ia)

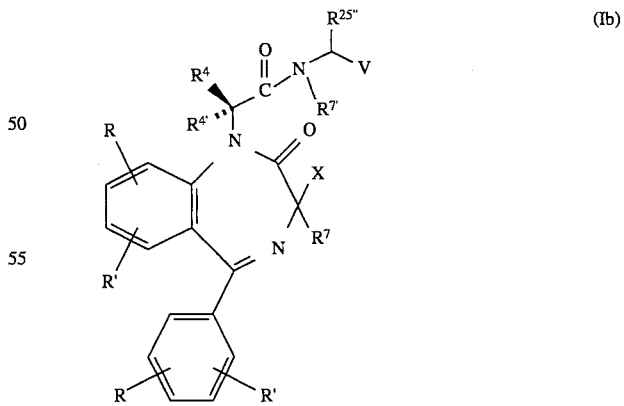 (Ib)

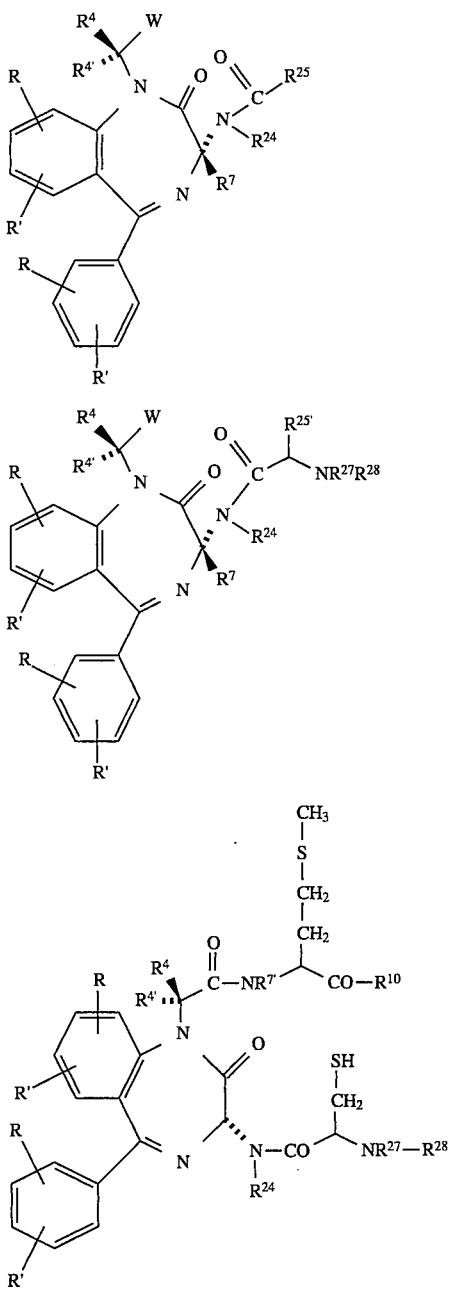

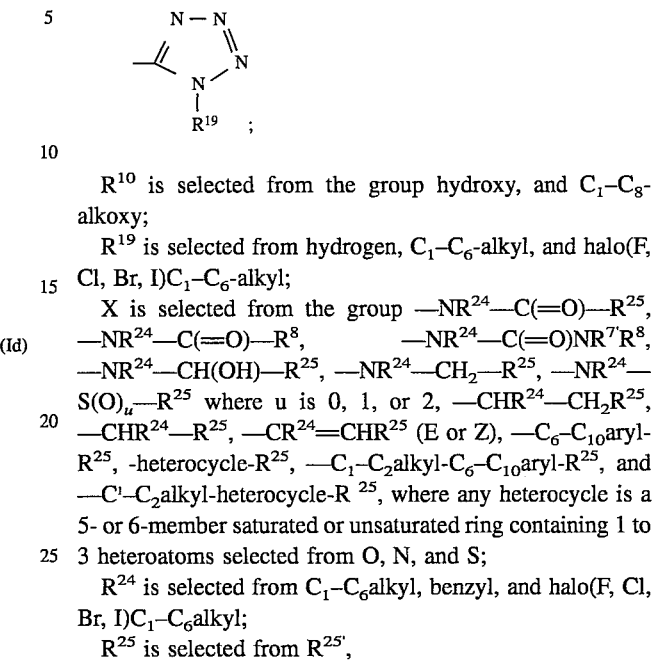

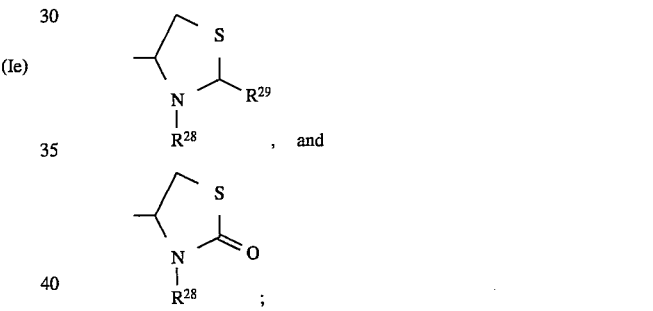

R and R' are independently selected from the group hydrogen, halo(F, Cl, Br, I), halo(F, Cl, Br, I)$C_1$–$C_6$ alkyl, and $C_1$–$C_6$ alkoxy;

$R^4$ and $R^{4'}$ are independently selected from hydrogen, halo(F, Cl, Br, I), $C_1$–$C_6$ alkyl, and halo(F, Cl, Br, I)$C_1$–$C_6$ alkyl, $R^7$ is hydrogen;

$R^{7'}$ is selected from the group hydrogen, $C_1$–$C_4$alkyl, and halo(F, Cl, Br, I)$C_1$–$C_4$alkyl;

$R^8$ is selected from the group unsubstituted and substituted $C_1$–$C_8$alkyl, phenyl-$C_1$–$C_3$alkyl, indol-3-yl-$C_1$–$C_3$alkyl, and imidazol-4-yl-$C_1$–$C_3$alkyl, where any phenyl moiety is optionally substituted with —$OR^9$ and where any alkyl group is optionally substituted with one or two groups selected from —$SR^9$, —$SSR^9$, —SC(=O)—$R^9$, —$OR^9$, —C(=O)NHOH, —$NHR^9$, —C(=O)$NR^{27}R^{28}$, and —V;

$R^9$ is selected from hydrogen, methyl, ethyl, isopropyl, phenyl, and benzyl;

V is selected from the group —$COR^{10}$, and $R^{10}$ is selected from the group hydroxy, and $C_1$–$C_8$-alkoxy;

$R^{19}$ is selected from hydrogen, $C_1$–$C_6$-alkyl, and halo(F, Cl, Br, I)$C_1$–$C_6$-alkyl;

X is selected from the group —$NR^{24}$—C(=O)—$R^{25}$, —$NR^{24}$—C(=O)—$R^8$, —$NR^{24}$—C(=O)$NR^{7'}R^8$, —$NR^{24}$—CH(OH)—$R^{25}$, —$NR^{24}$—$CH_2$—$R^{25}$, —$NR^{24}$—S(O)$_u$—$R^{25}$ where u is 0, 1, or 2, —$CHR^{24}$—$CH_2R^{25}$, —$CHR^{24}$—$R^{25}$, —$CR^{24}$=$CHR^{25}$ (E or Z), —$C_6$–$C_{10}$aryl-$R^{25}$, -heterocycle-$R^{25}$, —$C_1$–$C_2$alkyl-$C_6$–$C_{10}$aryl-$R^{25}$, and —$C^1$–$C_2$alkyl-heterocycle-$R^{25}$, where any heterocycle is a 5- or 6-member saturated or unsaturated ring containing 1 to 3 heteroatoms selected from O, N, and S;

$R^{24}$ is selected from $C_1$–$C_6$alkyl, benzyl, and halo(F, Cl, Br, I)$C_1$–$C_6$alkyl;

$R^{25}$ is selected from $R^{25'}$, $R^{25'}$ is selected from —$SR^{26}$, —$SSR^{26}$, —$OR^{26}$, —(C=O)$NOR^{26}$, $C_1$–$C_6$alkyl, $C_6$–$C_{12}$aryl$C_1$–$C_6$alkyl, $C_2$–$C_6$alkenyl, $C_1$–$C_6$alkylamine, $C_2$–$C_6$alkenylamine, and halo(F, Cl, Br, I)$C_1$–$C_6$alkyl where any alkyl or alkenyl moiety is optionally substituted with —$SR^{26}$, —$SSR^{26}$, —$OR^{26}$, —(C=O)$NOR^{26}$ and —$NR^{27}R^{28}$, and where any amine moiety is optionally substituted with $R^{27}$ or $R^{28}$;

$R^{25''}$ is selected from hydrogen, $C_1$–$C_6$alkyl, halo(F, Cl, Br, I)$C_1$–$C_6$alkyl, $C_6$–$C_{12}$aryl, $C_6$–$C_{12}$aryl$C_1$–$C_6$alkyl, where any alkyl or aryl moiety may optionally be substituted with a group selected from —$SR^{26}$, —$SSR^{26}$, —$OR^{26}$, $COR^{10}$, and $NOR^{26}$;

$R^{26}$ is selected from hydrogen, $C_1$–$C_6$alkyl, halo(F, Cl, Br, I)$C_1$–$C_6$alkyl, and $C_1$–$C_6$alkanoyl;

$R^{27}$ and $R^{28}$ are independently selected from hydrogen, $C_1$–$C_6$alkyl, phenyl, napthyl, benzyl, —$CH_2$-napthyl, $C_1$–$C_6$alkanoyl, $C_1$–$C_6$cycloalkanoyl. $C_6$–$C_{10}$aroyl, $C_6$–$C_{10}$aryl$C_1$–$C_6$alkanoyl, $C_1$–$C_6$alkylsulfonyl, $C_6$–$C_{10}$arylsulfonyl, $C_6$–$C_{10}$aryl$C_1$–$C_6$alkylcarbamoyl, cinnamoyl, heterocyclecarbonyl, $C_1$–$C_6$alkoxycarbonyl, $C_6$–$C_{10}$aryloxycarbonyl, $C_6$–$C_{10}$aryl$C_1$–$C_6$alkoxycarbonyl, and pyroglutamyl;

$R^{27}$ and $R^{28}$ together with the nitrogen atom to which they are bonded may form a cyclic amine represented by $$-N\underset{\underset{}{\diagdown}}{\diagup}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!G ;$$

G is selected from —$CH_2$—, O, $S(O)_u$ where u is 0, 1, or 2, and $NR^{28}$, and pharmaceutically acceptable salts thereof.

The very most preferred compounds of this invention include;

N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-methionine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-methionine isopentyl ester, N-[[3-(2- Amino-3-mercapto-1-oxopropyl)methylamino]-2,3-dihydro-2-oxo- 5-phenyl-1H-1,4-benzodiazepin-1-yl]acetyl]-(D or L)-methionine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-methionine ethyl ester, N-[[3-(2-Amino-3-mercapto- 1-oxopropyl)methylamino]-2,3-dihydro-2-oxo- 5-phenyl-1H-1,4-benzodiazepin-1-yl]acetyl]-(D or L)-methionine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-methionine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-methionine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine cyclohexyl ester, N-[[3-(2-Amino-3-mercapto-1-oxopropyl)methylamino]-2,3-dihydro-2-oxo- 5oxo-5-phenyl-1H-1,4-benzodiazepin-1-yl]acetyl]-(D or L)-leucine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-leucine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-phenylalanine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-isoleucine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-norleucine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-valine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tyrosine isobutyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan cyclohexyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan isopentyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan morpholino-N-ethyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan ethyl ester, N-[[3-(2-Amino-3-mercapto-1-oxopropyl)methylamino]-2,3-dihydro-2-oxo-5-phenyl-1H-1,4-benzodiazepin-1-yl]acetyl]-(D or L)-tryptophan methyl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan cholesteryl ester, N-[[3-(2-Amino-3-mercapto-1-oxopropyl)methylamino]-2,3-dihydro-2-oxo- 5-phenyl-1H-1,4-benzodiazepin-1-yl]acetyl]-(D or L)-tryptophan isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methionine cyclohexyl ester, N-[[3-(2-Amino-3-ethylthiomercapto-1-oxopropyl)methylamino]-2,3-dihydro-2-oxo-5-phenyl-1H-1,4-benzodiazepin-1-yl]acetyl]-(D or L)-methionine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methionine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methionine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methionine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methioine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-methionine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-leucine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-phenylalanine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl] acetyl]-(D or L)-isoleucine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-isoleucine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-norleucine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-valine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tyrosine isobutyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan cyclohexyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan isopentyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan morpholino-N-ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan ethyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan methyl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan cholesteryl ester, N-[[3-(2-Amino-3-ethylthiomercapto-1-oxopropyl)methylamino]-2,3-dihydro- 2-oxo-5-phenyl-1H-1,4-benzodiazepin-1-yl]acetyl]-(D or L)-tryptophan isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-methionine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine cyclohexyl ester, N-[[3-(2-Amino-3-tert-butylthiomercapto-1-oxopropyl)methylamino]-2,3-dihydro- 2-oxo-5-phenyl-1H-14-benzodiazepin-1-yl]acetyl]-(D or L)-leucine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-leucine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-phenylalanine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-isoleucine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-norleucine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-valine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-valine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-valine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl] acetyl]-(D or L)-valine ethyl ester, N-[[3-(2-Amino-3-tert-butylthiomercapto-1-oxopropyl) methylamino]-2,3-dihydro- 2-oxo-5-phenyl-1H-1,4-benzodiazepin-1-yl]acetyl]-(D or L)-valine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-valine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-valine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine ethyl ester, 2N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tyrosine isobutyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan cyclohexyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan isopentyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan morpholino-N-ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan ethyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan methyl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan cholesteryl ester, N-[[3-(2-Amino-3-tert-butylthiomercapto-1-oxopropyl)methylamino]-2,3-dihydro- 2-oxo-5-phenyl-1H-1,4-benzodiazepin-1-yl]acetyl]-(D or L)-tryptophan isobutyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine cyclohexyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine isopenyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine morpholinoethyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine ethyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine methyl ester, N-[[3(S)-3-(2-Amino-3-mercapto-1-oxopropyl)methylamino]-2,3,4,5-tetrahydro- 2-oxo-1H-1-benzazepin-1-yl]acetyl]-L-methionine cholesteryl ester, and N-[[3(S)-3-(2-Amino-3-mercapto-1-oxopropyl)methylamino]-2,3,4,5-tetrahydro- 2-oxo-1H-1-benzazepin-1-yl]acetyl]-L-methionine isobutyl ester.

The invention provides a pharmaceutical composition comprising a pharmaceutically acceptable excipient and the compound of formulae A, I–IX, or IXa–IXd and a method of inhibiting farnesyl:protein transferse comprising administering to a subject in need of such treatment a therapeutically effective amount of the composition. The invention also provides a method of inhibiting farnesylation of the oncogene protein ras in a subject and a method of amelioration of a neoplastic or proliferative condition in a subject having such a condition comprising administering to the subject in need of such treatment a therapeutically effective amount of the pharmaceutical composition.

The invention further provides a method of inhibiting fungal growth or reproduction in a living organism (or an area where growth or reproduction is to be controlled) in need of such treatment comprising administering an antifungally effective amount of the compound of formulae A, I–IX, or IXa–IXd.

DETAILED DESCRIPTION OF THE INVENTION

A. Definitions

Figure 1A:
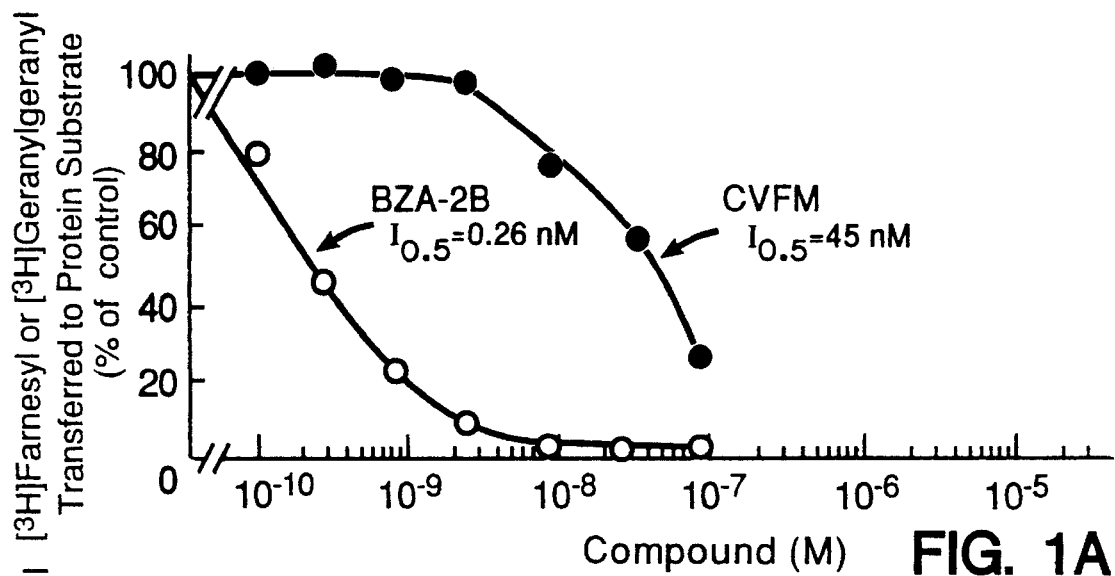
FIGS. 1A–1C Differential inhibition of CAAX farnesyltransferase (A), CAAX GG transferase (B) and Rab GG transferase (C) by compound 27 B (denoted as BZA-2B in the figure, open circles) and the tetrapeptide Cys-Val-Phe-Met (CVFM) (solid circles).

Terms used in the claims and specification are defined as set forth below unless otherwise specified.

The term "alkyl" means a branched or unbranched, saturated aliphatic hydrocarbon radical, having the number of carbon atoms specified, or if no number is specified, having up to 12 carbon atoms. Examples of alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like. The terms "lower alkyl" and "$C_1$–$C_6$ alkyl" are synonymous and used interchangeably. A preferred "$C_1$–$C_6$ alkyl" group is methyl.

The term "substituted $C_n$-$C_m$ alkyl" where m and n are integers identifying the range of carbon atoms contained in the alkyl group, denotes the above alkyl groups that are substituted by one, two or three; halogen(F, Cl. Br, I), hydroxy, protected hydroxy, amino, protected amino, $C_1$–$C_6$ acyloxy, nitro, carboxy, protected carboxy, carbamoyl, carbamoyloxy, cyano, methylsulfonylamino or $C_1$–$C_6$ alkoxy groups. The substituted alkyl groups may be substituted once, twice or three times with the same or with different substituents.

Examples of the above substituted alkyl groups include but are not limited to; cyanomethyl, nitromethyl, hydroxymethyl, trityloxymethyl, propionyloxymethyl, aminomethyl, carboxymethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluromethyl, 6-hydroxyhexyl, 2,4-dichloro(n-butyl), 2-amino(isopropyl), 2-carbamoyloxyethyl and the like. A preferred group of examples within the above "$C_1$–$C_{12}$ substituted alkyl" group includes the substituted methyl group, e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluromethyl, chloromethyl, bromomethyl and iodomethyl.

The terms "$C_1$–$C_6$ alkyloxy" or "$C_1$–$C_6$ alkoxy" are used interchangeably herein and denote groups such as methoxy, ethoxy, n-propoxy, isopropoxy, n-butoxy, t-butoxy and like groups.

The terms "$C_1$–$C_{12}$ acyloxy" or "$C_1$–$C_{12}$ alkanoyloxy" are used interchangeably and denote herein groups such as formyloxy, acetoxy, propionyloxy, butyryloxy, pentanoyloxy, hexanoyloxy, heptanoyloxy, and the like.

The terms "$C_1$–$C_{12}$ alkylcarbonyl", "$C_1$–$C_{12}$ alkanoyl" and "$C_1$–$C_{12}$ acyl" are used interchangeably herein encompass groups such as formyl, acetyl, propionyl, butyryl, pentanoyl, hexanoyl, heptanoyl, benzoyl and the like.

The term "cycloalkyl" as used herein refers to a mono-, bi-, or tricyclic aliphatic ring having 3 to 14 carbon atoms and preferably 3 to 7 carbon atoms.

The term "alkenyl" means a branched or unbranched hydrocarbon radical having the number of carbon atoms designated containing one or more carbon-carbon double bonds, each double bond being independently cis, trans, or a nongeometric isomer.

The terms "$C_1$–$C_{12}$ alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone means a homocyclic hydrocarbon aromatic radical, whether or not fused, having the number of carbon atoms designated. Preferred aryl groups include phenyl, napthyl, biphenyl, phenanthrenyl, naphthacenyl, and the like (see e.g. *Lang's Handbook of Chemistry* (Dean, J. A., ed) 13$^{th}$ ed. Table 7-2 [1985]).

The term "substituted phenyl" or "substituted aryl" denotes a phenyl group or aryl group substituted with one, two or three substituents chosen from halogen(F, Cl, Br, I), hydroxy, protected hydroxy, cyano, nitro, $C_1$–$C_6$ alkyl, $C_1$–$C_6$ alkoxy, carboxy, protected carboxy, carboxymethyl, protected carboxymethyl, hydroxymethyl, protected hydroxymethyl, aminomethyl, protected aminomethyl, trifluoromethyl N-(methylsulfonylamino) or other groups specified.

Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4- trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups wherein the substituents are different, for example, 3-methyl-4-hydroxyphenyl, 3-chloro- 4-hydroxyphenyl, 2-methoxy-4-bromophenyl, 4-ethyl-2-hydroxyphenyl, 3-hydroxy- 4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The term "arylalkyl" means one, two, or three aryl groups having the number of carbon atoms designated, appended to an alkyl radical having the number of carbon atoms designated including but not limited to; benzyl, napthylmethyl, phenethyl, benzyhydryl (diphenylmethyl), trityl, and the like. A preferred arylalkyl group is the benzyl group.

The term "substituted $C_6$–$C_{12}$aryl-$C_1$–$C_6$alkyl" denotes a $C_1$–$C_6$alkyl group substituted at any carbon with a $C_6$–$C_{12}$aryl group bonded to the alkyl group through any aryl ring position and substituted on the $C_1$–$C_6$alkyl portion with one, two or three groups chosen from halogen (F, Cl, Br, I), hydroxy, protected hydroxy, amino, protected amino, $C_1$–$C_6$acyloxy, nitro, carboxy, protected carboxy, carbamoyl, carbamoyloxy, cyano, $C_1$–$C_6$alkylthio, N-(methylsulfonylamino) or $C_1$–$C_6$alkoxy. Optionally the aryl group may be substituted with one, two, or three groups chosen from halogen, hydroxy, protected hydroxy, nitro, $C_1$–$C_6$alkyl, $C_1$–$C_4$alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_6$alkyl portion or the aryl portion or both are disubstituted, the substituents can be the same or different.

Examples of the term "substituted $C_6$–$C_{10}$aryl-$C_1$–$C_6$alkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl,4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other postions of the benzodiazepinedione molecule and can be removed at the appropriate point without disrupting the remainder of the molecule. In particular, it is important not to subject the carboxy-protected benzodiazepinedione molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substituents of the benzodiazepinedione. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, NY, 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

Unless otherwise specified, the terms "heterocycle", "heterocyclic group", "heterocyclic" or "heterocyclyl" are used interchangeably herein and refer to any mono-, bi-, or tricyclic saturated, unsaturated, or aromatic ring having the number of ring atoms designated where at least one ring is a 5-, 6- or 7-membered hydrocarbon ring containing from one to four heteroatoms selected from nitrogen, oxygen, and sulfur, preferably at least one heteroatom is nitrogen (*Lang's Handbook of Chemistry*, supra). Preferably, the heterocycle is a 5- or 6-member saturated, unsaturated, or aromatic hydrocarbon ring containing 1, 2, or 3 heteroatoms selected from O, N, and S. Typically, the 5-membered ring has 0 to 2 double bonds and the 6- or 7-membered ring has 0 to 3 double bonds and the nitrogen or sulfur heteroatoms may optionally be oxidized, and any nitrogen heteroatom may optionally be quaternized. Included in the definition are any bicyclic groups where any of the above heterocyclic rings are fused to a benzene ring. Heterocyclics in which nitrogen is the heteroatom are preferred.

The following ring systems are examples of the heterocyclic (whether substituted or unsubstituted) radicals denoted by the term "heterocylic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol- 5-yl, 1,2,4-triazol-5-yl, and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocylic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin- 2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl radicals, are a preferred group. Optionally preferred 6-membered ring heterocycles are; piperazinyl, piperazin-2-yl, piperidyl, piperid-2-yl, piperid-3-yl, piperid-4-yl, morpholino, morpholin-2-yl, and morpholin-3-yl.

The substituents for the optionally substituted heterocyclic ring systems, and further examples of the 5- and 6-membered ring systems discussed above can be found in W. Durckheimer et al., U.S. Pat. No. 4,278,793.

An optionally preferred group of "heterocyclics" include; 1,3-thiazol-2-yl, 4-(carboxymethyl)-5-methyl-1,3-thiazol-2-yl, 4-(carboxymethyl)-5-methyl-1,3-thiazol- 2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1, 3,4-triazol-5-yl, 2-carboxy-4-methyl-1,3,4-triazol-5-yl sodium salt, 2-carboxy-4-methyl-1,3,4-triazol- 5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4 -thiadiazol-5-yl, 1H-tetrazol-5-yl, 1-methyl-1H-tetrazol-5-yl, 1-(1-(dimethylamino)eth- 2-yl)-1H-tetrazol-5-yl, 1-(carboxymethyl)-1H-tetrazol-5-yl, 1-(carboxymethyl)- 1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol- 5-yl, 1,2,3-triazol-5-yl, 1-methyl-1,2, 3-triazol-5-yl, 2-methyl-1,2,3-triazol 5-yl, 4-methyl-1,2,3-triazol-5-yl, pyrid-2-yl N-oxide, 6-methoxy-2-(n-oxide)-pyridaz- 3-yl, 6-hydroxypyridaz-3-yl, 1-methylpyrid-2-yl, 1-methylpyrid-4-yl, 2-hydroxypyrimid- 4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo- 6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy- 2-methyl-as-triazin-3-yl, 2,5-dihydro-5-oxo-as-triazin-3-yl, 2,5-dihydro-5-oxo-2 -methyl-as-triazin-3-yl, 2,5-dihydro-5-oxo-2,6-dimethyl-as-triazin-3-yl, tetrazolo[1,5-b ]pyridazin-6-yl and 8-aminotetrazolo[1,5-b] -pyridazin-6-yl.

An alternative group of "heterocyclics" includes; 4-(carboxymethyl)-5-methyl- 1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1 H-tetrazol-5-yl, 1-(1-(dimethylamino)eth-2-yl)-1H-tetrazol-5-yl, 1-(carboxymethyl)- 1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo- 6-hydroxy-2-methyl-as-triazin-3-yl sodium salt, 2,5-dihydro-5-oxo-6-hydroxy- 2-methyl-as-triazin-3-yl, tetrazolo[1,5-b]pyridazin-6-yl, and 8-aminotetrazolo[1,5-b] pyridazin-6-yl.

The terms "heteroaryl group" or "heteroaryl" are used interchangeably herein and refer to any mono-, bi-, or tricyclic aromatic rings having the number of ring atoms designated where at least one ring is a 5-, 6- or 7-membered hydrocarbon ring containing from one to four heteroatoms selected from nitrogen, oxygen, and sulfur, preferably at least one heteroatom is nitrogen. The aryl portion of the term "heteroaryl" refers to aromaticity, a term known to those skilled in the art and defined in greater detail in *Advanced Organic Chemistry* J. March, 3$^{rd}$ ed., pages 37–69, John Wiley & Sons, New York (1985).

Each substituent or term used in any formula or expression herein, e.g., $T^1$, $T^2$, W, $R^n$, $R^{n'}$, Z, $Y^n$, Ar, $A^n$, X, V, $C_1$–$C_6$alkyl, etc. when it appears more than once, is independent of its definition elsewhere in that or any other formula or structure.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, maloneic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used here means a pharmacologically inactive derivative of a parent drug molecule that requires biotransformation, either spontaneous or enzymatic, within the organism to release the active drug.

B. Utility

The present invention is the result of the unexpected discovery that substituted benzodiazepines and analogs thereof defined by formulae A, and I–VIII inhibit farnesyl-:protein transferase and the farnesylation of $p21^{ras}$. Accordingly, pharmaceutical compositions containing the compounds of structural formula A inhibit farnesylation of the oncogene protein ras and are useful as pharmaceutical agents for mammals, especially humans, for the treatment of diseases where inhibition of farnesylation is indicated. In one embodiment of the invention inhibition of farnesylation is indicated for neoplastic and proliferative diseases including but not limited to, colorectal carcinoma, exocrine pancreatic carcinoma, and myeloid leukemias. In an alternative embodiment, inhibition of farnesylation is contemplated to be useful for proliferating skin diseases where ras positive cells are found in the differentiated layer, including but not limited to, psoriasis vulgaris, lichen planus, verruca vulgaris, verruca plana juvenills, and seborrheic keratosis. Other ras positive diseases contemplated to be usefully treated with the inhibitors of this invention include; neurofibromatosis, rheumatoid arthritis, human papilloma viral infection, Kapoli's sarcoma, scleroderma and Aleution disease viral infection.

The present invention is also useful in a method directed to treating fungal infections in an organism in need of such treatment, which method comprises administering a non toxic (to the organism) therapeutically effective amount of compounds represented by structural formulae A and I–IX. In one embodiment, the fungaily infected orgamisms are animal, preferably mammal, most preferably human, especially immunologically compromised individuals. In an alternative embodiment the organisms are plants infected with or succeptable to blight, rust, and mildew (especially fusarium wilt). Optionally, nonliving material such as soil may be usefully treated with the instant compounds to prevent fungal infection of an organism.

Finally, the instant compounds may be usefully employed as metal ion and metalloprotein chelators.

C. Preferred Embodiments

One preferred embodiment of the invention comprises a compound capable of inhibiting farnesyl:protein transferase at a concentration equal to or lower than that of the tetrapeptide CVFM represented by Formula I'

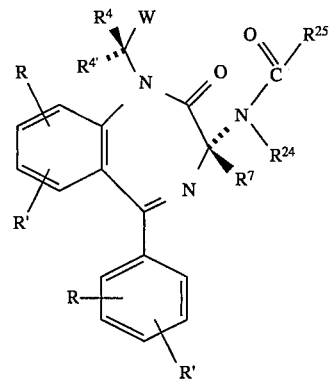

where the substituents R, and R' are hydrogen or perflurolower alkyl, $R^4$ and $R^{4'}$ are hydrogen or lower alkyl, and $R^7$, W, $R^{24}$, and $R^{25}$ are selected according to Table I'.

TABLE I'

| $R^7$ | W | $R^{24}$ | $R^{25}$ |
|---|---|---|---|
| H | OCH3) | $CH_3$ | -CH(SH)(NH2) |
| H | OCH2CH3) | $CH_3$ | -CH(SH)(NH2) |

TABLE I'-continued

| R[7] | W | R[24] | R[25] |
|---|---|---|---|
| H | 4-(COOCH₃)-phenyl | CH₃ | CH₂(SH)CH(NH₂)– |
| H | 3-(COOH)-phenyl | CH₃ | CH₂(SH)CH(NH₂)– |
| H | 2'-(H₃COOC)-biphenyl-4-yl | CH₃ | CH₂(SH)CH(NH₂)– |
| H | 2-(COOCH₃)-biphenyl-4-yl | CH₃ | CH₂(SH)CH(NH₂)– |
| H | 4-methylcyclohexyl-1-COOH | CH₃ | CH₂(SH)CH(NH₂)– |
| H | 4-(tetrazol-5-yl)phenyl | CH₃ | CH₂(SH)CH(NH₂)– |
| H | 3-(tetrazol-5-yl)phenyl | CH₃ | CH₂(SH)CH(NH₂)– |
| H | 2'-(tetrazol-5-yl)biphenyl-4-yl | CH₃ | CH₂(SH)CH(NH₂)– |
| H | 2-(tetrazol-5-yl)biphenyl-4-yl | CH₃ | CH₂(SH)CH(NH₂)– |

TABLE I'-continued

| R⁷ | W | R²⁴ | R²⁵ |
|---|---|---|---|
| H | *p-tolyl-pyrrole-tetrazole* | CH₃ | CH₂(SH)CH(NH₂)- |
| H | *6-methyl-2-(methylthioethyl)pyridin-3-yl with tetrazole* | CH₃ | CH₂(SH)CH(NH₂)- |
| H | *6-methyl-2-(methyldithiomethyl)pyridin-3-yl with tetrazole* | CH₃ | CH₂(SH)CH(NH₂)- |
| H | *5-methylpyrrole with CH(CH₂SCH₃)-tetrazole* | CH₃ | CH₂(SH)CH(NH₂)- |
| H | *5-methyl-2-(methylthioethyl)pyrrol-3-yl with tetrazole* | CH₃ | CH₂(SH)CH(NH₂)- |
| H | *5-methylthiophene with CH(CH₂SCH₃)-tetrazole* | CH₃ | CH₂(SH)CH(NH₂)- |
| H | *5-methyl-2-(methylthioethyl)thien-3-yl with tetrazole* | CH₃ | CH₂(SH)CH(NH₂)- |
| H | *5-methyl-2-(methylthiomethyl)furan* | CH₃ | CH₂(SH)CH(NH₂)- |

TABLE I'-continued
| R⁷ | W | R²⁴ | R²⁵ |
|---|---|---|---|
| H | 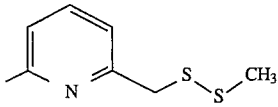 | CH₃ | 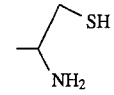 |
| H | 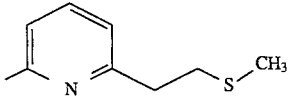 | CH₃ | 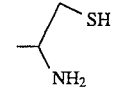 |
| H | 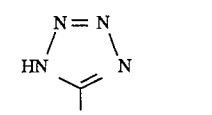 | CH₃ | 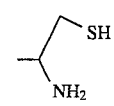 |
| H | 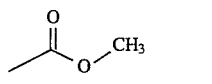 | CH₃ | 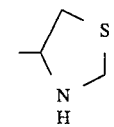 |
| H | 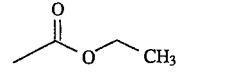 | CH₃ | 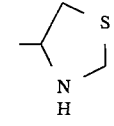 |
| H | 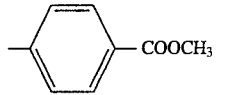 | CH₃ | 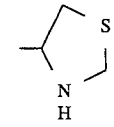 |
| H | 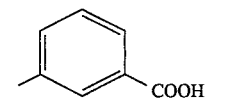 | CH₃ | 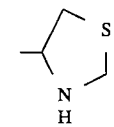 |
| H | 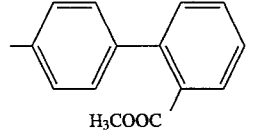 | CH₃ | 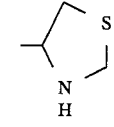 |
| H | 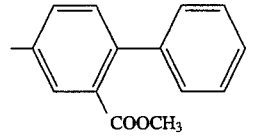 | CH₃ | 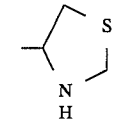 |
| H | 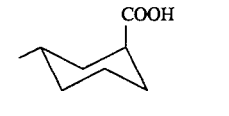 | CH₃ | 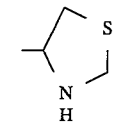 |
| H | 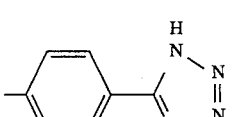 | CH₃ | 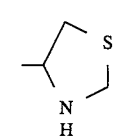 |

TABLE I'-continued
| R⁷ | W | R²⁴ | R²⁵ |
|---|---|---|---|
| H | 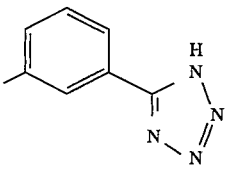 | CH₃ | 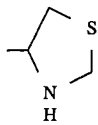 |
| H | 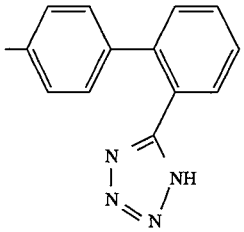 | CH₃ | 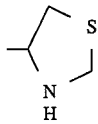 |
| H | 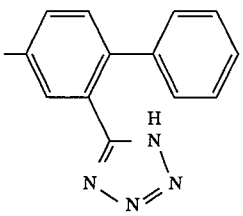 | CH₃ | 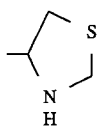 |
| H | 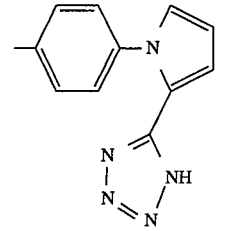 | CH₃ | 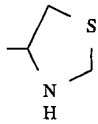 |
| H | 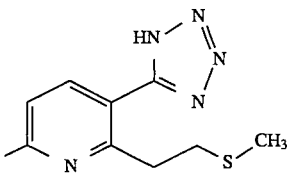 | CH₃ | 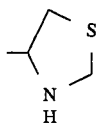 |
| H | 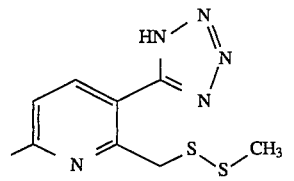 | CH₃ | 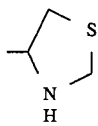 |
| H | 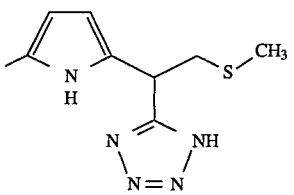 | CH₃ | 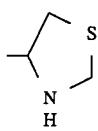 |

TABLE I'-continued
| R⁷ | W | R²⁴ | R²⁵ |
|---|---|---|---|
| H | 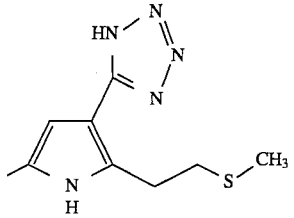 | CH₃ | 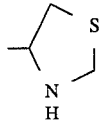 |
| H | 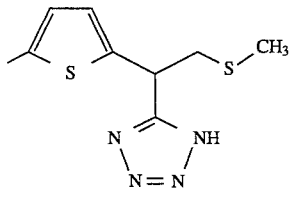 | CH₃ | 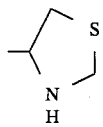 |
| H | 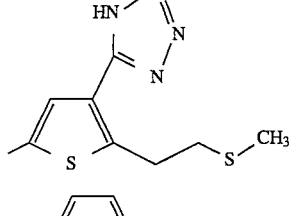 | CH₃ | 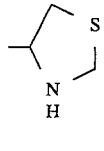 |
| H | 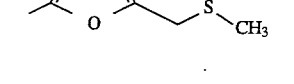 | CH₃ | 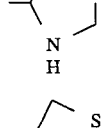 |
| H | 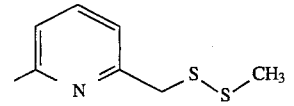 | CH₃ | 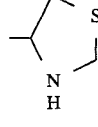 |
| H | 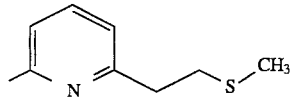 | CH₃ | 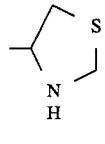 |
| H | 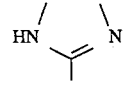 | CH₃ | 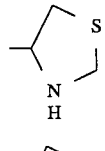 |
| H | 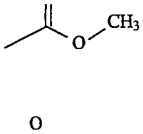 | CH₃ | 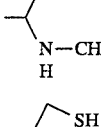 |
| H | 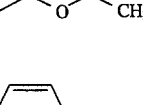 | CH₃ | 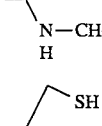 |
| H | 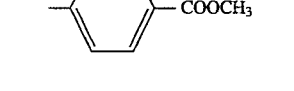 | CH₃ | 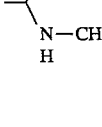 |

TABLE I'-continued

| R⁷ | W | R²⁴ | R²⁵ |
|---|---|---|---|
| H | 3-carboxyphenyl | CH₃ | CH₂SH-CH(NHCH₃)- |
| H | 4'-(2-H₃COOC)biphenyl | CH₃ | CH₂SH-CH(NHCH₃)- |
| H | 4'-(2-COOCH₃)biphenyl | CH₃ | CH₂SH-CH(NHCH₃)- |
| H | cyclohexyl-COOH | CH₃ | CH₂SH-CH(NHCH₃)- |
| H | 4-(tetrazol-5-yl)phenyl | CH₃ | CH₂SH-CH(NHCH₃)- |
| H | 3-(tetrazol-5-yl)phenyl | CH₃ | CH₂SH-CH(NHCH₃)- |
| H | 4'-[2-(tetrazol-5-yl)]biphenyl | CH₃ | CH₂SH-CH(NHCH₃)- |
| H | 4'-[2-(tetrazol-5-yl)]biphenyl (isomer) | CH₃ | CH₂SH-CH(NHCH₃)- |
| H | 1-(4-methylphenyl)-5-(tetrazol-5-yl)pyrrol-2-yl | CH₃ | CH₂SH-CH(NHCH₃)- |

TABLE I'-continued
| R[7] | W | R[24] | R[25] |
|---|---|---|---|
| H | 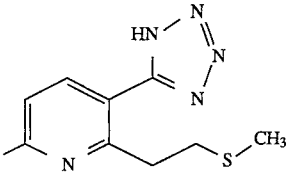 | CH$_3$ | 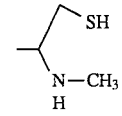 |
| H | 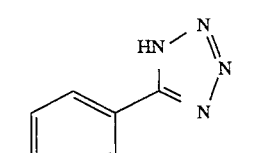 | CH$_3$ | 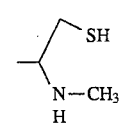 |
| H | 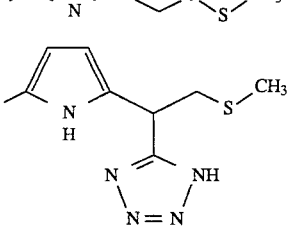 | CH$_3$ | 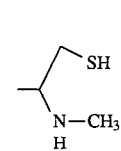 |
| H | 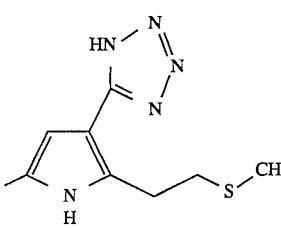 | CH$_3$ | 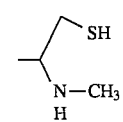 |
| H | 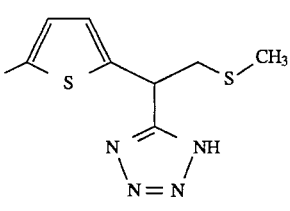 | CH$_3$ | 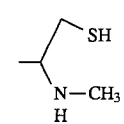 |
| H | 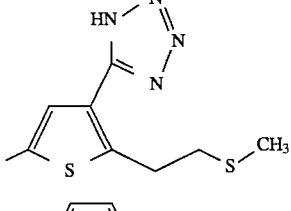 | CH$_3$ | 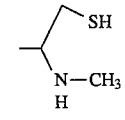 |
| H | 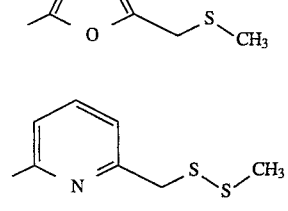 | CH$_3$ | 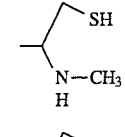 |
| H | 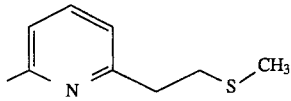 | CH$_3$ | |
| H | 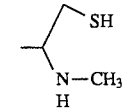 | CH$_3$ | |

TABLE I'-continued

| R⁷ | W | R²⁴ | R²⁵ |
|---|---|---|---|
| H | 5-methyl-1H-tetrazol-yl (HN-N=N-N= with CH₃) | CH₃ | -CH(NHCH₃)-CH₂-SH |
| H | -C(O)-O-CH₃ | CH₃ | -CH(NHCH₃)-CH₂-S-S-CH₂CH₃ |
| H | -C(O)-O-CH₂CH₃ | CH₃ | -CH(NHCH₃)-CH₂-S-S-CH₂CH₃ |
| H | 4-(COOCH₃)-phenyl | CH₃ | -CH(NHCH₃)-CH₂-S-S-CH₂CH₃ |
| H | 3-(COOH)-phenyl | CH₃ | -CH(NHCH₃)-CH₂-S-S-CH₂CH₃ |
| H | 4'-yl-2-(H₃COOC)-biphenyl | CH₃ | -CH(NHCH₃)-CH₂-S-S-CH₂CH₃ |
| H | 4'-yl-2-(COOCH₃)-biphenyl | CH₃ | -CH(NHCH₃)-CH₂-S-S-CH₂CH₃ |
| H | 4-(COOH)-cyclohexyl | CH₃ | -CH(NHCH₃)-CH₂-S-S-CH₂CH₃ |
| H | 4-(1H-tetrazol-5-yl)-phenyl | CH₃ | -CH(NHCH₃)-CH₂-S-S-CH₂CH₃ |
| H | 3-(1H-tetrazol-5-yl)-phenyl | CH₃ | -CH(NHCH₃)-CH₂-S-S-CH₂CH₃ |
| H | 4'-yl-2-(1H-tetrazol-5-yl)-biphenyl | CH₃ | -CH(NHCH₃)-CH₂-S-S-CH₂CH₃ |

TABLE I'-continued

| R[7] | W | R[24] | R[25] |
|---|---|---|---|
| H | [biphenyl-tetrazole structure] | CH₃ | [CH₂-S-S-CH₂CH₃ with CH(NH-CH₃)] |
| H | [tolyl-pyrrole-tetrazole structure] | CH₃ | [CH₂-S-S-CH₂CH₃ with CH(NH-CH₃)] |
| H | [methylpyridine with tetrazole-NH and CH₂CH₂SCH₃ structure] | CH₃ | [CH₂-S-S-CH₂CH₃ with CH(NH-CH₃)] |
| H | [methylpyridine with tetrazole-NH and CH₂-S-S-CH₃ structure] | CH₃ | [CH₂-S-S-CH₂CH₃ with CH(NH-CH₃)] |
| H | [methylpyrrole with CH(CH₂SCH₃)-tetrazole structure] | CH₃ | [CH₂-S-S-CH₂CH₃ with CH(NH-CH₃)] |
| H | [methylpyrrole with tetrazole-NH and CH₂CH₂SCH₃ structure] | CH₃ | [CH₂-S-S-CH₂CH₃ with CH(NH-CH₃)] |
| H | [methylthiophene with CH(CH₂SCH₃)-tetrazole structure] | CH₃ | [CH₂-S-S-CH₂CH₃ with CH(NH-CH₃)] |

TABLE I'-continued

| R⁷ | W | R²⁴ | R²⁵ |
|---|---|---|---|
| H | 5-methyl-thiophene with tetrazole and -CH₂CH₂SCH₃ substituents | CH₃ | -CH(NHCH₃)-CH₂-S-S-CH₂CH₃ |
| H | 5-methyl-furan with -CH₂SCH₃ | CH₃ | -CH(NHCH₃)-CH₂-S-S-CH₂CH₃ |
| H | 6-methyl-pyridine with -CH₂-S-S-CH₃ | CH₃ | -CH(NHCH₃)-CH₂-S-S-CH₂CH₃ |
| H | 6-methyl-pyridine with -CH₂CH₂SCH₃ | CH₃ | -CH(NHCH₃)-CH₂-S-S-CH₂CH₃ |
| H | 5-methyl-tetrazole | CH₃ | -CH(NHCH₃)-CH₂-S-S-CH₂CH₃ |
| H | -CH₂C(O)OCH₃ | CH₃ | thiazolidinone-CH₂- |
| H | -CH₂C(O)OCH₂CH₃ | CH₃ | thiazolidinone-CH₂- |
| H | 4-(COOCH₃)-phenyl | CH₃ | thiazolidinone-CH₂- |
| H | 3-(COOH)-phenyl | CH₃ | thiazolidinone-CH₂- |
| H | 4'-methyl-2-(COOCH₃)-biphenyl | CH₃ | thiazolidinone-CH₂- |
| H | 4'-methyl-2-(COOCH₃)-biphenyl | CH₃ | thiazolidinone-CH₂- |

TABLE I'-continued

| R⁷ | W | R²⁴ | R²⁵ |
|---|---|---|---|
| H | cyclohexyl-COOH | CH₃ | thiazolidinone-CH₂- |
| H | 4-(tetrazol-5-yl)phenyl- | CH₃ | thiazolidinone-CH₂- |
| H | 3-(tetrazol-5-yl)phenyl- | CH₃ | thiazolidinone-CH₂- |
| H | 4'-(2-(tetrazol-5-yl)phenyl)phenyl- | CH₃ | thiazolidinone-CH₂- |
| H | 3'-(2-(tetrazol-5-yl)phenyl)phenyl- | CH₃ | thiazolidinone-CH₂- |
| H | 4-(2-(tetrazol-5-yl)pyrrol-1-yl)phenyl- | CH₃ | thiazolidinone-CH₂- |
| H | 6-methyl-2-(2-(methylthio)ethyl)-3-(tetrazol-5-yl)pyridin-yl- | CH₃ | thiazolidinone-CH₂- |
| H | 6-methyl-2-((methyldithio)methyl)-3-(tetrazol-5-yl)pyridin-yl- | CH₃ | thiazolidinone-CH₂- |

TABLE I'-continued
| R⁷ | W | R²⁴ | R²⁵ |
|---|---|---|---|
| H | 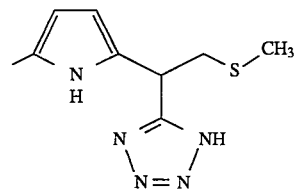 | CH₃ | 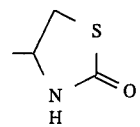 |
| H | 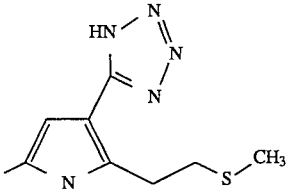 | CH₃ | 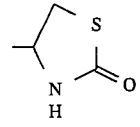 |
| H | 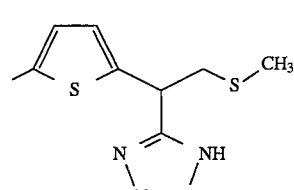 | CH₃ | 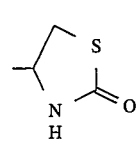 |
| H | 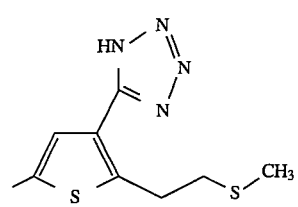 | CH₃ | 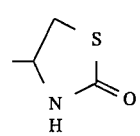 |
| H | 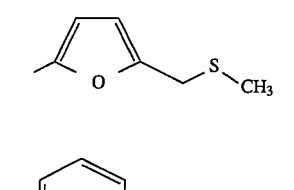 | CH₃ | 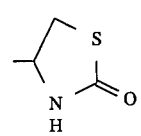 |
| H | 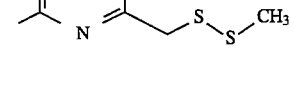 | CH₃ | 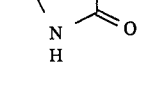 |
| H | 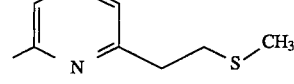 | CH₃ | 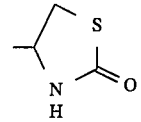 |
| H | 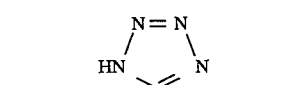 | CH₃ | 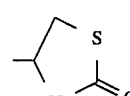 |
| H | 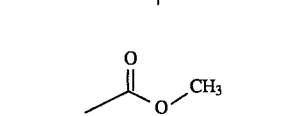 | CH₃ | 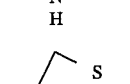 |

TABLE I'-continued

| R⁷ | W | R²⁴ | R²⁵ |
|---|---|---|---|
| H | ethyl acetate group | CH₃ | N-methyl thiazolidinethione |
| H | 4-COOCH₃-phenyl | CH₃ | N-methyl thiazolidinethione |
| H | 3-COOH-phenyl | CH₃ | N-methyl thiazolidinethione |
| H | 4'-(2-COOCH₃)biphenyl | CH₃ | N-methyl thiazolidinethione |
| H | 4'-(2-COOCH₃)biphenyl | CH₃ | N-methyl thiazolidinethione |
| H | cyclohexyl-COOH | CH₃ | N-methyl thiazolidinethione |
| H | 4-(tetrazol-5-yl)phenyl | CH₃ | N-methyl thiazolidinethione |
| H | 3-(tetrazol-5-yl)phenyl | CH₃ | N-methyl thiazolidinethione |
| H | 4'-[2-(tetrazol-5-yl)]biphenyl | CH₃ | N-methyl thiazolidinethione |

TABLE I'-continued
| R⁷ | W | R²⁴ | R²⁵ |
|---|---|---|---|
| H | 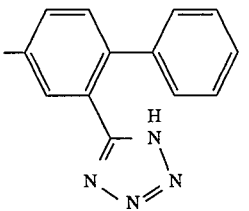 | CH₃ | 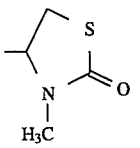 |
| H | 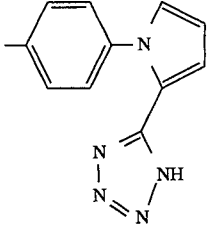 | CH₃ | 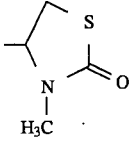 |
| H | 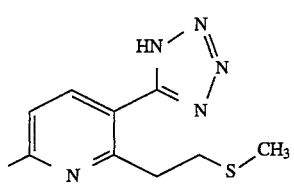 | CH₃ | 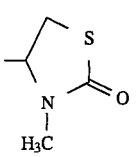 |
| H | 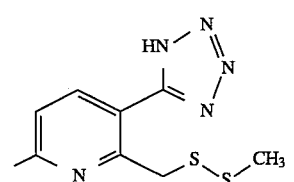 | CH₃ | 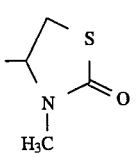 |
| H | 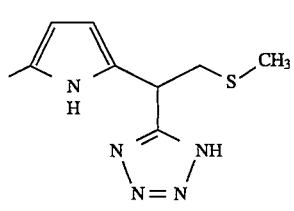 | CH₃ | 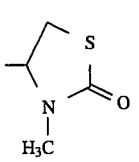 |
| H | 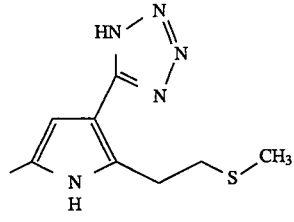 | CH₃ | 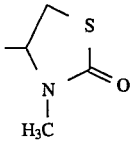 |
| H | 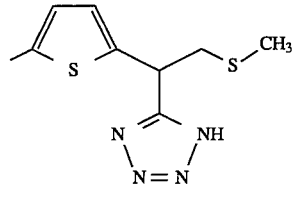 | CH₃ | 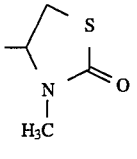 |

TABLE I-continued
| R⁷ | W | R²⁴ | R²⁵ |
|---|---|---|---|
| H | 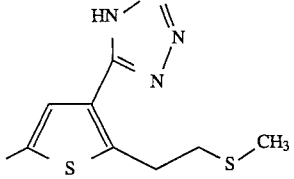 | CH₃ | 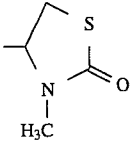 |
| H | 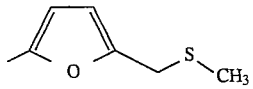 | CH₃ | 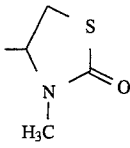 |
| H | 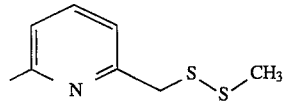 | CH₃ | 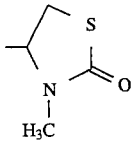 |
| H | 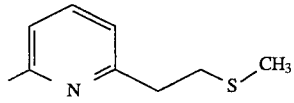 | CH₃ | 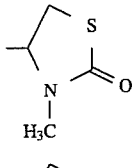 |
| H | 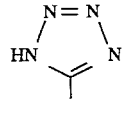 | CH₃ | 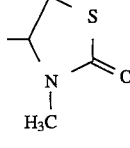 |
| H | 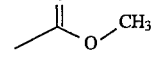 | CH₃ | 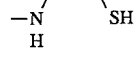 |
| H | 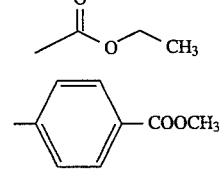 | CH₃ | 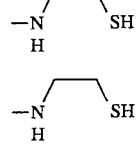 |
| H | 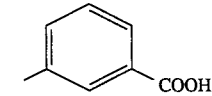 | CH₃ | 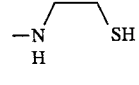 |
| H | 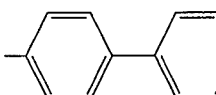 | CH₃ | 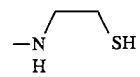 |
| H | 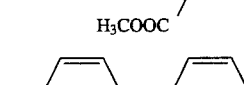 | CH₃ | 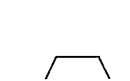 |
| H | 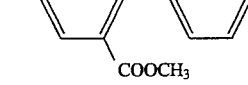 | CH₃ | 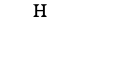 |
| H |  | CH₃ | 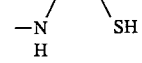 |

TABLE I'-continued

| R[7] | W | R[24] | R[25] |
|---|---|---|---|
| H | 4-(tetrazol-5-yl)phenyl | CH$_3$ | —NH—CH$_2$CH$_2$—SH |
| H | 3-(tetrazol-5-yl)phenyl | CH$_3$ | —NH—CH$_2$CH$_2$—SH |
| H | 4'-[2-(tetrazol-5-yl)]biphenyl | CH$_3$ | —NH—CH$_2$CH$_2$—SH |
| H | 4'-methyl-2-[(tetrazol-5-yl)methyl]biphenyl | CH$_3$ | —NH—CH$_2$CH$_2$—SH |
| H | 4-[2-(tetrazol-5-yl)pyrrol-1-yl]phenyl | CH$_3$ | —NH—CH$_2$CH$_2$—SH |
| H | 6-methyl-2-[2-(methylthio)ethyl]-3-(tetrazol-5-yl)pyridine | CH$_3$ | —NH—CH$_2$CH$_2$—SH |
| H | 6-methyl-2-[(methyldithio)methyl]-3-(tetrazol-5-yl)pyridine | CH$_3$ | —NH—CH$_2$CH$_2$—SH |
| H | 5-methyl-2-[1-(methylthiomethyl)-1-(tetrazol-5-yl)methyl]pyrrole | CH$_3$ | —NH—CH$_2$CH$_2$—SH |

TABLE I'-continued
| R[7] | W | R[24] | R[25] |
|---|---|---|---|
| H | 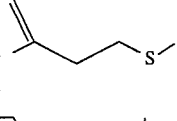 | CH$_3$ |  |
| H | 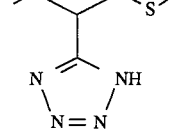 | CH$_3$ |  |
| H | 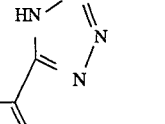 | CH$_3$ | 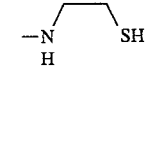 |
| H | 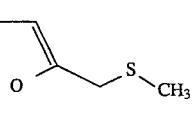 | CH$_3$ | 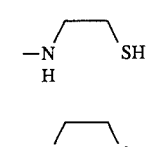 |
| H | 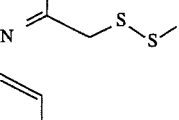 | CH$_3$ | 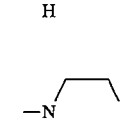 |
| H | 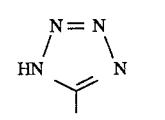 | CH$_3$ | 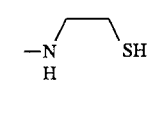 |
| H | 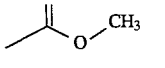 | CH$_3$ |  |
| H | 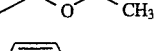 | CH$_3$ | 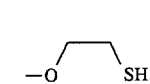 |
| H |  | CH$_3$ |  |
| H | 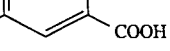 | CH$_3$ |  |
| H | 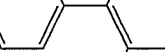 | CH$_3$ |  |

TABLE I'-continued
| R⁷ | W | R²⁴ | R²⁵ |
|---|---|---|---|
| H | 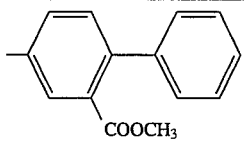 | CH₃ | 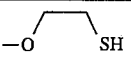 |
| H | 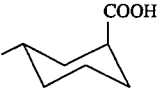 | CH₃ |  |
| H | 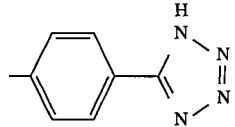 | CH₃ | 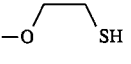 |
| H | 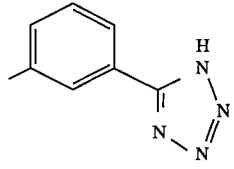 | CH₃ | 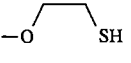 |
| H | 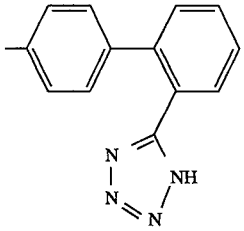 | CH₃ | 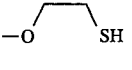 |
| H | 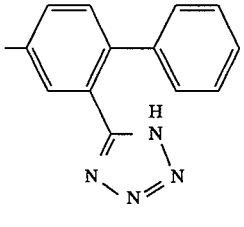 | CH₃ |  |
| H | 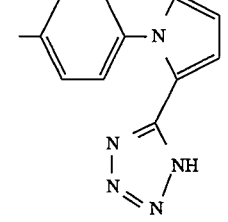 | CH₃ |  |
| H | 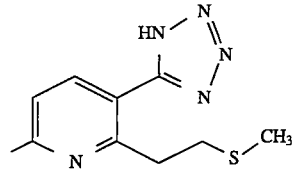 | CH₃ |  |

TABLE I'-continued
| R[7] | W | R[24] | R[25] |
|---|---|---|---|
| H | 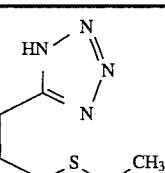 | CH₃ |  |
| H | 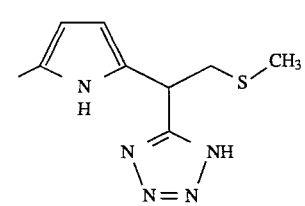 | CH₃ | 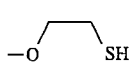 |
| H | 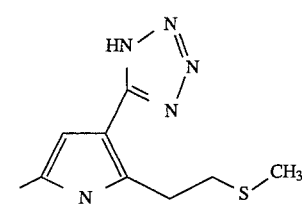 | CH₃ | 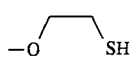 |
| H | 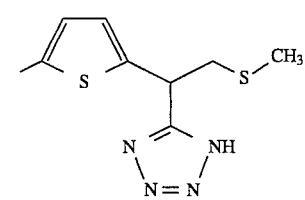 | CH₃ | 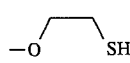 |
| H | 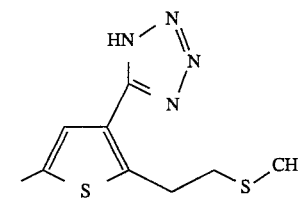 | CH₃ | 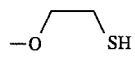 |
| H | 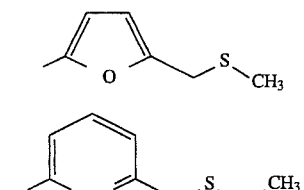 | CH₃ | 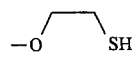 |
| H | 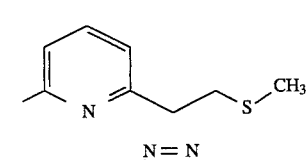 | CH₃ | 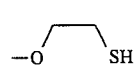 |
| H | 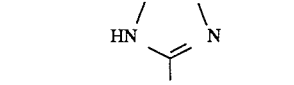 | CH₃ | 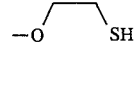 |
| H | 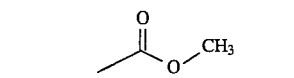 | CH₃ |  |

TABLE I'-continued

| R⁷ | W | R²⁴ | R²⁵ |
|---|---|---|---|
| H | ethyl acetate group (CH₃-C(=O)-O-CH₂-) | CH₃ | -N(CH₂CH₂)₂S (thiomorpholine) |
| H | 4-(COOCH₃)-phenyl- | CH₃ | -N(CH₂CH₂)₂S |
| H | 3-(COOH)-phenyl- | CH₃ | -N(CH₂CH₂)₂S |
| H | 4'-methyl-2,2'-(H₃COOC)-biphenyl- | CH₃ | -N(CH₂CH₂)₂S |
| H | 4-methyl-2-(COOCH₃)-biphenyl- | CH₃ | -N(CH₂CH₂)₂S |
| H | 4-(COOH)-cyclohexyl- | CH₃ | -N(CH₂CH₂)₂S |
| H | 4-(1H-tetrazol-5-yl)phenyl- | CH₃ | -N(CH₂CH₂)₂S |
| H | 3-(1H-tetrazol-5-yl)phenyl- | CH₃ | -N(CH₂CH₂)₂S |
| H | 4'-methyl-2-(1H-tetrazol-5-yl)biphenyl- | CH₃ | -N(CH₂CH₂)₂S |
| H | 4-methyl-2-(1H-tetrazol-5-yl)biphenyl- | CH₃ | -N(CH₂CH₂)₂S |

TABLE I'-continued
| R⁷ | W | R²⁴ | R²⁵ |
|---|---|---|---|
| H | 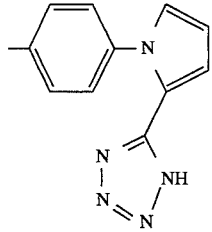 | CH₃ | 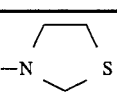 |
| H | 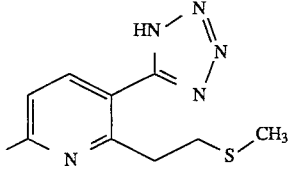 | CH₃ | 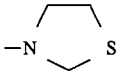 |
| H | 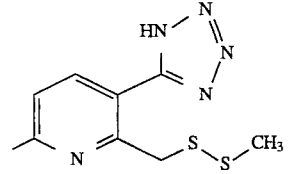 | CH₃ | 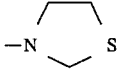 |
| H | 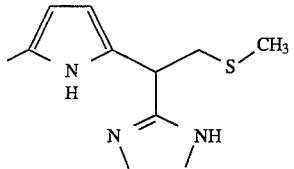 | CH₃ | 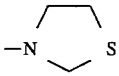 |
| H | 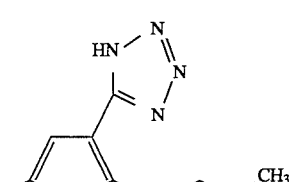 | CH₃ | 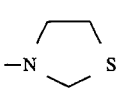 |
| H | 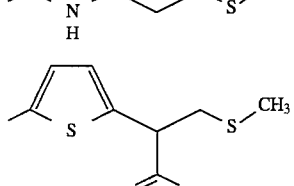 | CH₃ |  |
| H | 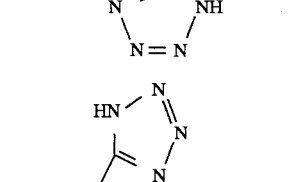 | CH₃ |  |
| H | 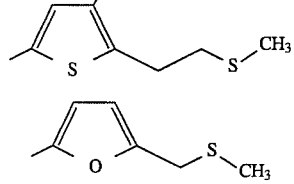 | CH₃ |  |

TABLE I'-continued
| R⁷ | W | R²⁴ | R²⁵ |
|---|---|---|---|
| H | 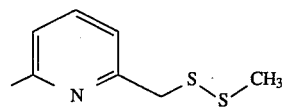 | CH₃ | 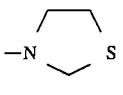 |
| H | 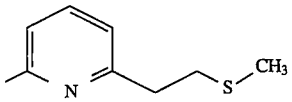 | CH₃ | 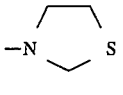 |
| H | 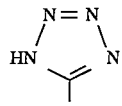 | CH₃ | 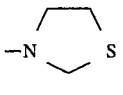 |
| H | 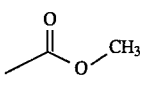 | CH₃ | 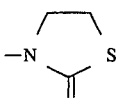 |
| H | 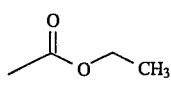 | CH₃ | 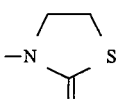 |
| H | 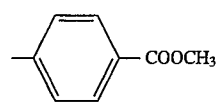 | CH₃ | 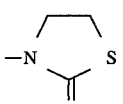 |
| H | 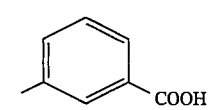 | CH₃ | 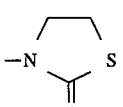 |
| H | 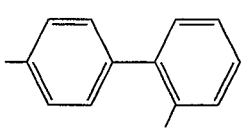 | CH₃ | 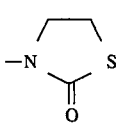 |
| H | 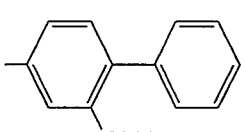 | CH₃ | 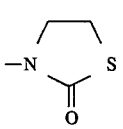 |
| H | 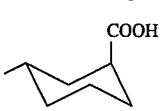 | CH₃ | 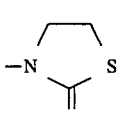 |
| H | 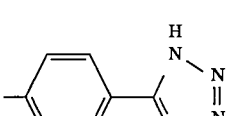 | CH₃ | 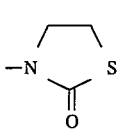 |
| H | 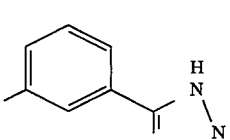 | CH₃ | 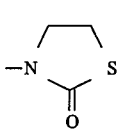 |

TABLE I'-continued

| R⁷ | W | R²⁴ | R²⁵ |
|---|---|---|---|
| H | (biphenyl-tetrazole structure) | CH₃ | (thiazolidinone) |
| H | (biphenyl-tetrazole structure) | CH₃ | (thiazolidinone) |
| H | (tolyl-pyrrole-tetrazole structure) | CH₃ | (thiazolidinone) |
| H | (methylpyridine with tetrazole and SCH₃ side chain) | CH₃ | (thiazolidinone) |
| H | (methylpyridine with tetrazole and SSCH₃ side chain) | CH₃ | (thiazolidinone) |
| H | (pyrrole with SCH₃ and tetrazole) | CH₃ | (thiazolidinone) |
| H | (methylpyrrole with tetrazole and SCH₃ side chain) | CH₃ | (thiazolidinone) |

TABLE I'-continued
| R[7] | W | R[24] | R[25] |
|---|---|---|---|
| H | 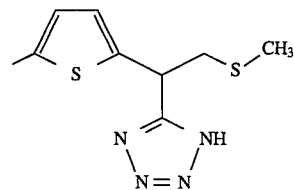 | CH$_3$ | 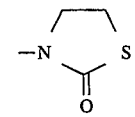 |
| H | 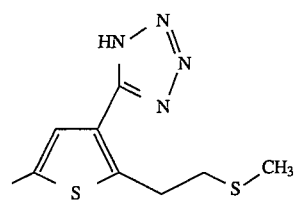 | CH$_3$ | 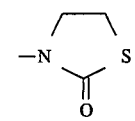 |
| H | 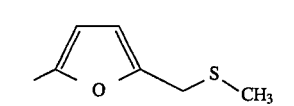 | CH$_3$ | 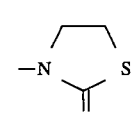 |
| H | 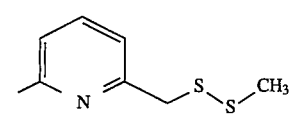 | CH$_3$ | 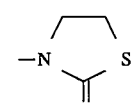 |
| H | 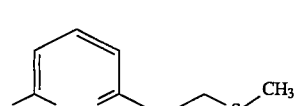 | CH$_3$ | 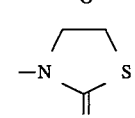 |
| H | 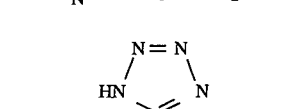 | CH$_3$ | 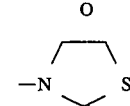 |
| H | 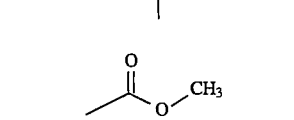 | CH$_3$ | 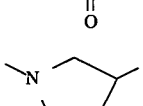 |
| H | 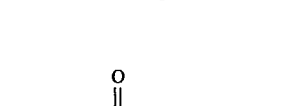 | CH$_3$ | 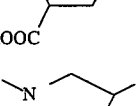 |
| H | 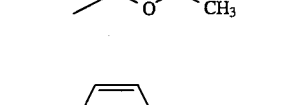 | CH$_3$ | 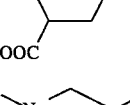 |
| H | 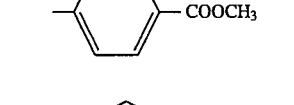 | CH$_3$ | 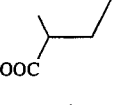 |
| H | 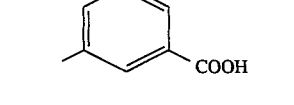 | CH$_3$ | 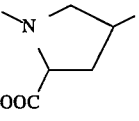 |

TABLE I'-continued
| R[7] | W | R[24] | R[25] |
|---|---|---|---|
| H | 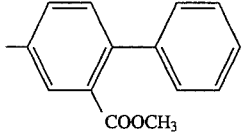 | CH₃ |  |
| H | 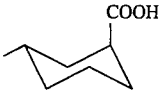 | CH₃ | 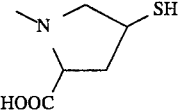 |
| H | 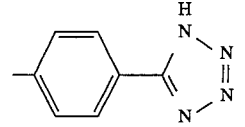 | CH₃ | 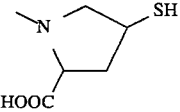 |
| H | 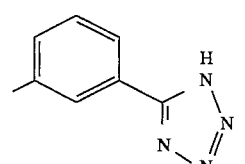 | CH₃ | 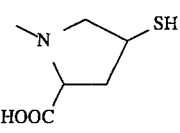 |
| H | 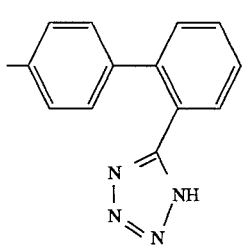 | CH₃ | 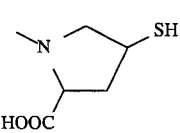 |
| H | 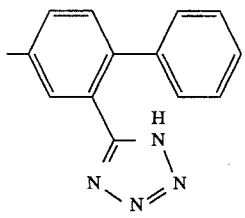 | CH₃ | 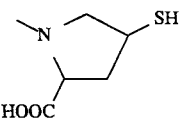 |
| H | 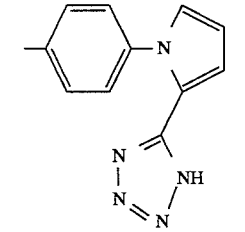 | CH₃ | 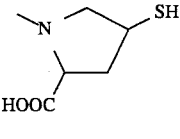 |
| H | 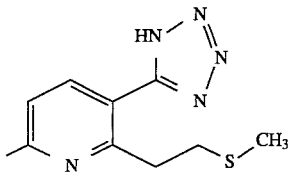 | CH₃ | 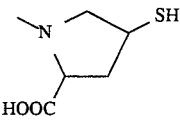 |

TABLE I'-continued
| R[7] | W | R[24] | R[25] |
|---|---|---|---|
| H | 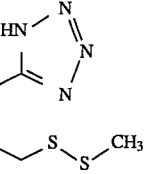 | CH3 | 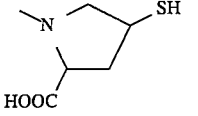 |
| H | 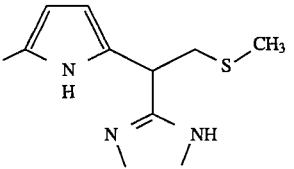 | CH3 | 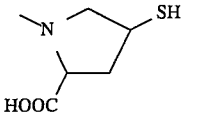 |
| H | 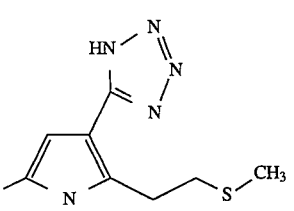 | CH3 | 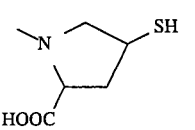 |
| H | 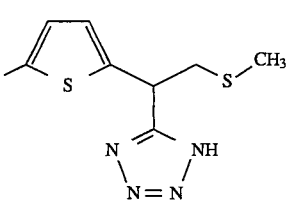 | CH3 | 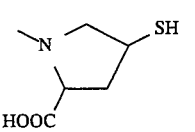 |
| H | 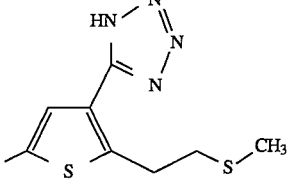 | CH3 | 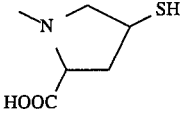 |
| H | 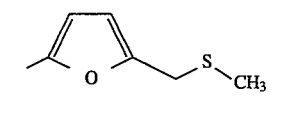 | CH3 | 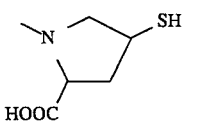 |
| H | 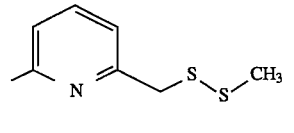 | CH3 | 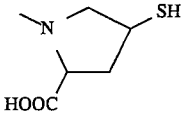 |
| H | 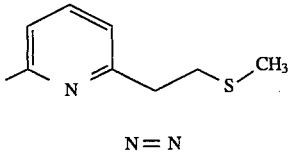 | CH3 | 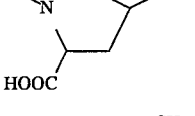 |
| H | 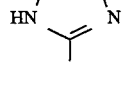 | CH3 | 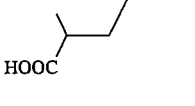 |

TABLE I'-continued
| R⁷ | W | R²⁴ | R²⁵ |
|---|---|---|---|
| H | 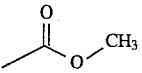 | CH₃ | 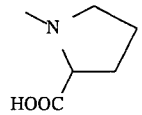 |
| H | 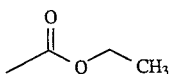 | CH₃ | 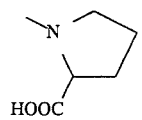 |
| H | 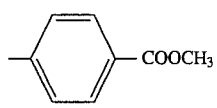 | CH₃ | 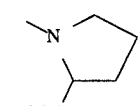 |
| H | 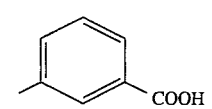 | CH₃ | 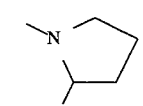 |
| H | 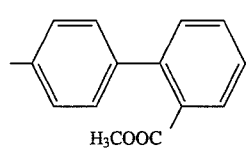 | CH₃ | 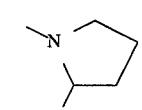 |
| H | 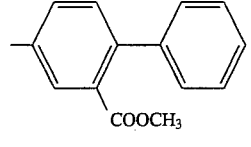 | CH₃ | 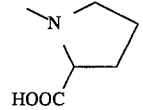 |
| H | 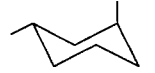 | CH₃ | 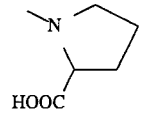 |
| H | 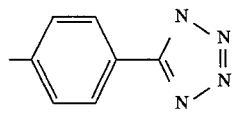 | CH₃ | 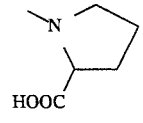 |
| H | 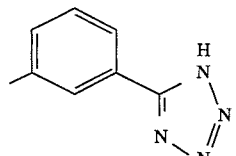 | CH₃ | 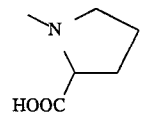 |
| H | 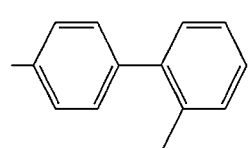 | CH₃ | 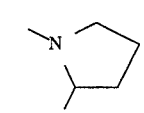 |

TABLE I'-continued

| R⁷ | W | R²⁴ | R²⁵ |
|---|---|---|---|
| H | biphenyl with tetrazole | CH₃ | N-methylpyrrolidine-2-COOH |
| H | phenyl-pyrrole with tetrazole | CH₃ | N-methylpyrrolidine-2-COOH |
| H | methylpyridine with SCH₃ side chain and tetrazole | CH₃ | N-methylpyrrolidine-2-COOH |
| H | methylpyridine with SSCH₃ side chain and tetrazole | CH₃ | N-methylpyrrolidine-2-COOH |
| H | methylpyrrole with CH(SCH₃)- and tetrazole | CH₃ | N-methylpyrrolidine-2-COOH |
| H | methylpyrrole with ethyl-SCH₃ and tetrazole | CH₃ | N-methylpyrrolidine-2-COOH |
| H | methylthiophene with CH(SCH₃)- and tetrazole | CH₃ | N-methylpyrrolidine-2-COOH |

TABLE I'-continued

| $R^7$ | W | $R^{24}$ | $R^{25}$ |
|---|---|---|---|
| H | 3-(1H-tetrazol-5-yl)-4-methyl-5-(2-(methylthio)ethyl)thiophene | $CH_3$ | proline (N-linked, 2-COOH) |
| H | 5-methyl-2-((methylthio)methyl)furan | $CH_3$ | proline (N-linked, 2-COOH) |
| H | 6-methyl-2-(((methyldithio)methyl))pyridine | $CH_3$ | proline (N-linked, 2-COOH) |
| H | 6-methyl-2-(2-(methylthio)ethyl)pyridine | $CH_3$ | proline (N-linked, 2-COOH) |
| H | 5-methyl-1H-tetrazole | $CH_3$ | proline (N-linked, 2-COOH) |
| H | methyl acetate derivative (–CH(CH$_3$)C(O)OCH$_3$) | $CH_3$ | –NH–CH$_2$–COOH |
| H | ethyl acetate derivative (–CH(CH$_3$)C(O)OC$_2$H$_5$) | $CH_3$ | –NH–CH$_2$–COOH |
| H | 4-(methoxycarbonyl)phenyl | $CH_3$ | –NH–CH$_2$–COOH |
| H | 3-carboxyphenyl | $CH_3$ | –NH–CH$_2$–COOH |
| H | 2'-(methoxycarbonyl)biphenyl-4-yl | $CH_3$ | –NH–CH$_2$–COOH |
| H | 2-(methoxycarbonyl)biphenyl-4-yl | $CH_3$ | –NH–CH$_2$–COOH |
| H | 4-carboxycyclohexyl | $CH_3$ | –NH–CH$_2$–COOH |

TABLE I'-continued

| R⁷ | W | R²⁴ | R²⁵ |
|---|---|---|---|
| H | 4-(tetrazol-5-yl)phenyl | CH₃ | —NH—CH₂—COOH |
| H | 3-(tetrazol-5-yl)phenyl | CH₃ | —NH—CH₂—COOH |
| H | 4'-methyl-2-(tetrazol-5-yl)biphenyl | CH₃ | —NH—CH₂—COOH |
| H | 2'-phenyl-2-(tetrazol-5-yl)methyl-biphenyl | CH₃ | —NH—CH₂—COOH |
| H | 1-(4-methylphenyl)-2-(tetrazol-5-yl)pyrrole | CH₃ | —NH—CH₂—COOH |
| H | 6-methyl-2-(2-(methylthio)ethyl)-3-(tetrazol-5-yl)pyridine | CH₃ | —NH—CH₂—COOH |
| H | 6-methyl-2-((methyldithio)methyl)-3-(tetrazol-5-yl)pyridine | CH₃ | —NH—CH₂—COOH |
| H | 5-methyl-2-(1-(methylthiomethyl)-1-(tetrazol-5-yl)methyl)pyrrole | CH₃ | —NH—CH₂—COOH |

TABLE I'-continued
| R[7] | W | R[24] | R[25] |
|---|---|---|---|
| H | 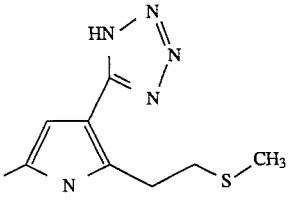 | CH$_3$ | 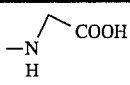 |
| H | 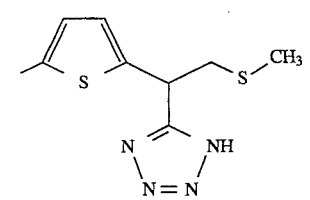 | CH$_3$ | 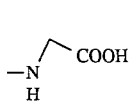 |
| H | 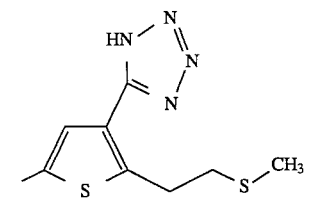 | CH$_3$ | 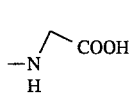 |
| H | 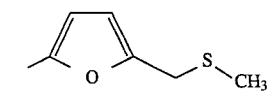 | CH$_3$ | 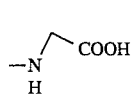 |
| H | 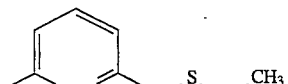 | CH$_3$ | 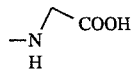 |
| H |  | CH$_3$ | 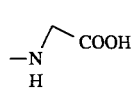 |
| H | 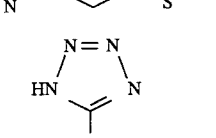 | CH$_3$ | 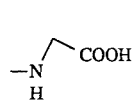 |
| H | 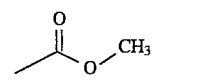 | CH$_3$ | 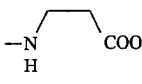 |
| H | 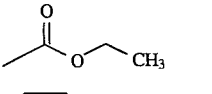 | CH$_3$ | 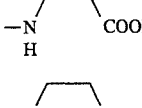 |
| H | 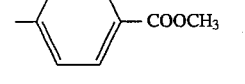 | CH$_3$ | 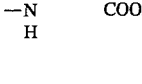 |
| H | 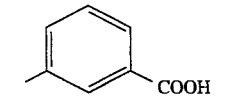 | CH$_3$ | 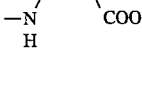 |
| H |  | CH$_3$ | 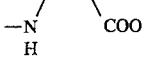 |

TABLE I'-continued
| R[7] | W | R[24] | R[25] |
|---|---|---|---|
| H | 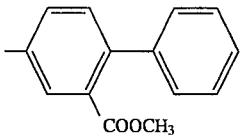 | CH₃ | 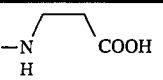 |
| H |  | CH₃ | 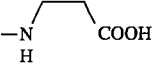 |
| H | 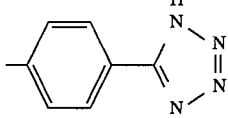 | CH₃ | 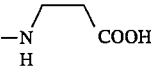 |
| H | 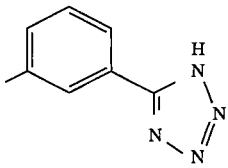 | CH₃ | 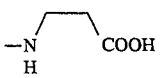 |
| H | 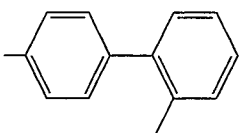 | CH₃ | 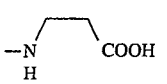 |
| H | 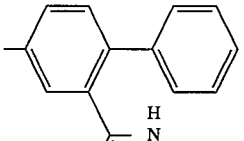 | CH₃ | 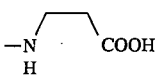 |
| H | 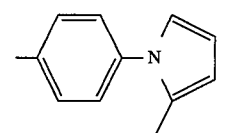 | CH₃ | 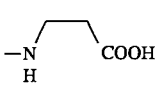 |
| H | 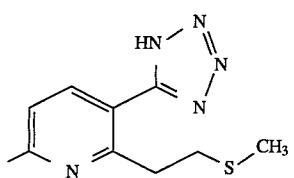 | CH₃ | 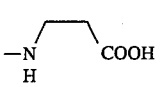 |

TABLE I'-continued
| R[7] | W | R[24] | R[25] |
|---|---|---|---|
| H | 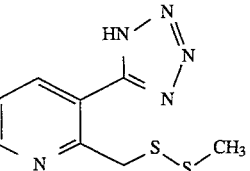 | CH$_3$ | 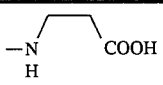 |
| H | 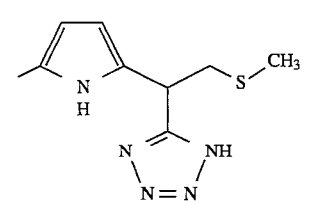 | CH$_3$ | 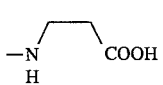 |
| H | 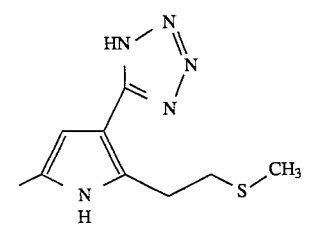 | CH$_3$ | 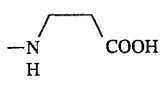 |
| H | 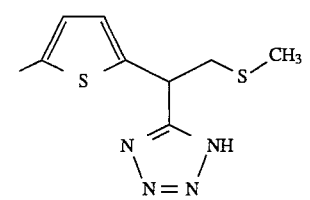 | CH$_3$ | 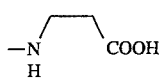 |
| H | 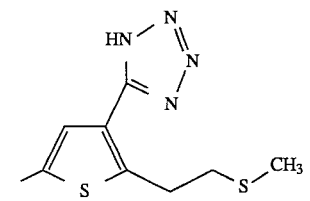 | CH$_3$ | 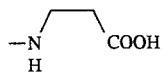 |
| H | 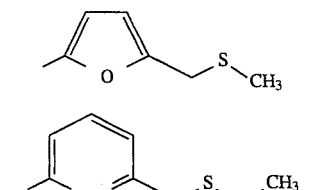 | CH$_3$ | 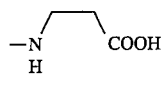 |
| H | 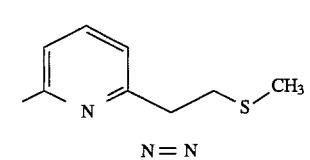 | CH$_3$ | 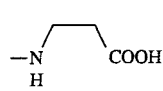 |
| H | 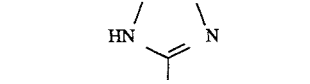 | CH$_3$ | 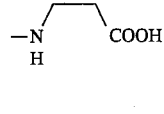 |
| H | 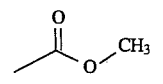 | CH$_3$ | 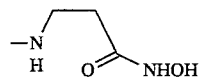 |

TABLE I'-continued

| R⁷ | W | R²⁴ | R²⁵ |
|---|---|---|---|
| H | ethyl acetate group (–CH₂–C(=O)–O–CH₂CH₃) | CH₃ | –NH–CH₂CH₂–C(=O)–NHOH |
| H | 4-(methoxycarbonyl)phenyl (–C₆H₄–COOCH₃) | CH₃ | –NH–CH₂CH₂–C(=O)–NHOH |
| H | 3-carboxyphenyl (–C₆H₄–COOH) | CH₃ | –NH–CH₂CH₂–C(=O)–NHOH |
| H | 4'-substituted-2-(methoxycarbonyl)biphenyl (H₃COOC-) | CH₃ | –NH–CH₂CH₂–C(=O)–NHOH |
| H | 2-(methoxycarbonyl)biphenyl (COOCH₃) | CH₃ | –NH–CH₂CH₂–C(=O)–NHOH |
| H | 4-carboxycyclohexyl (COOH) | CH₃ | –NH–CH₂CH₂–C(=O)–NHOH |
| H | 4-(1H-tetrazol-5-yl)phenyl | CH₃ | –NH–CH₂CH₂–C(=O)–NHOH |
| H | 3-(1H-tetrazol-5-yl)phenyl | CH₃ | –NH–CH₂CH₂–C(=O)–NHOH |
| H | 2'-(1H-tetrazol-5-yl)biphenyl-4-yl | CH₃ | –NH–CH₂CH₂–C(=O)–NHOH |
| H | 2-(1H-tetrazol-5-yl)biphenyl | CH₃ | –NH–CH₂CH₂–C(=O)–NHOH |

TABLE I'-continued
| R⁷ | W | R²⁴ | R²⁵ |
|---|---|---|---|
| H | 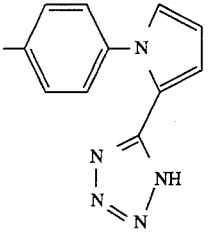 | CH₃ | 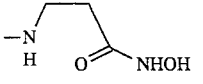 |
| H | 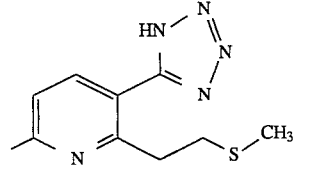 | CH₃ | 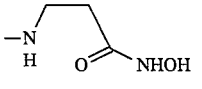 |
| H | 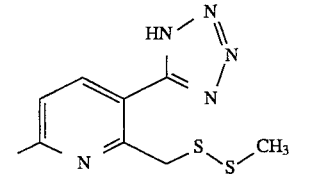 | CH₃ | 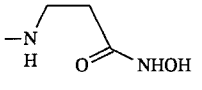 |
| H | 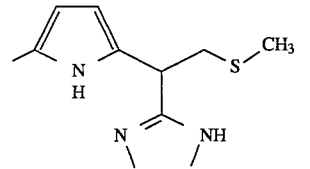 | CH₃ | 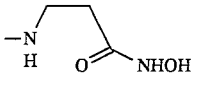 |
| H | 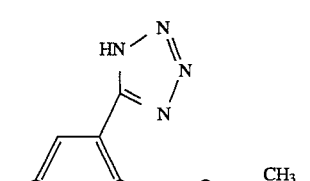 | CH₃ | 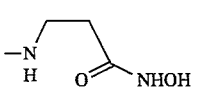 |
| H | 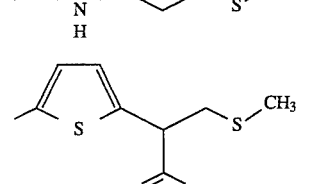 | CH₃ | 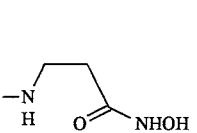 |
| H | 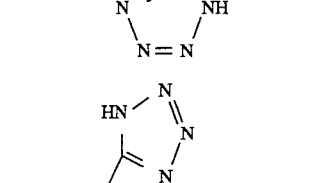 | CH₃ |  |
| H | 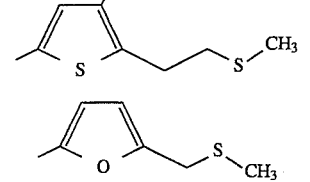 | CH₃ |  |

TABLE I'-continued

| R[7] | W | R[24] | R[25] |
|---|---|---|---|
| H | 6-methylpyridin-2-yl-CH$_2$-S-S-CH$_3$ | CH$_3$ | -NH-CH$_2$CH$_2$-C(O)-NHOH |
| H | 6-methylpyridin-2-yl-CH$_2$CH$_2$-S-CH$_3$ | CH$_3$ | -NH-CH$_2$CH$_2$-C(O)-NHOH |
| H | 5-methyl-1H-tetrazol-... | CH$_3$ | -NH-CH$_2$CH$_2$-C(O)-NHOH |

An alternate preferred embodiment of the invention comprises a compound capable of inhibiting farnesyl:protein transferase at a concentration equal to or lower than that of the tetrapeptide CVFM represented by Formula Ia'.

where the substituents R, and R' are as defined above, $R^4$ and $R^{4'}$ are hydrogen or lower alkyl, and $R^{7'}$, $R^8$, $R^{24}$, and $R^{25}$ are selected according to Table Ia'.

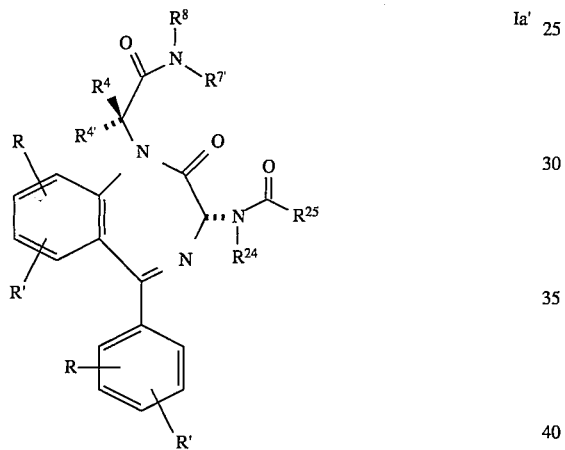

Ia'

TABLE Ia'

| R[7'] | R[8] | R[24] | R[25] |
|---|---|---|---|
| H | CH$_3$-CH(COOH)-CH$_2$CH$_2$-S-CH$_3$ | CH$_3$ | -CH(NH$_2$)-CH$_2$-SH |
| H | CH$_3$-CH(COOCH$_3$)-CH$_2$CH$_2$-S-CH$_3$ | CH$_3$ | -CH(NH$_2$)-CH$_2$-SH |
| H | CH$_3$-CH(COOH)-CH$_2$CH$_2$-S-S-CH$_2$CH$_3$ | CH$_3$ | -CH(NH$_2$)-CH$_2$-SH |
| H | CH$_3$-CH(COOH)-CH$_2$-C(CH$_3$)$_2$-H | CH$_3$ | -CH(NH$_2$)-CH$_2$-SH |
| H | CH$_3$-CH(COOH)-CH(CH$_3$)-CH$_2$-CH$_3$ | CH$_3$ | -CH(NH$_2$)-CH$_2$-SH |

TABLE Ia'-continued
| R[7'] | R[8] | R[24] | R[25] |
|---|---|---|---|
| H | 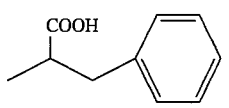 | CH$_3$ | 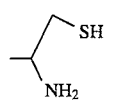 |
| H | 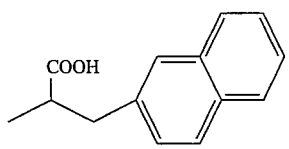 | CH$_3$ | 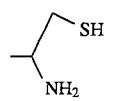 |
| H | 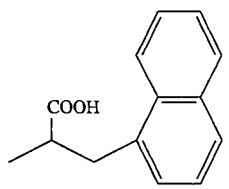 | CH$_3$ | 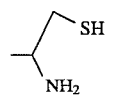 |
| H | 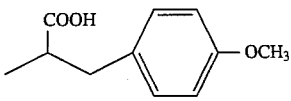 | CH$_3$ | 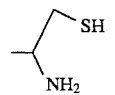 |
| H | 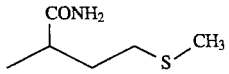 | CH$_3$ | 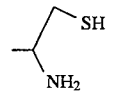 |
| H | 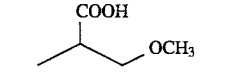 | CH$_3$ | 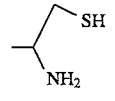 |
| H |  | CH$_3$ | 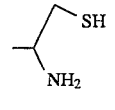 |
| H | 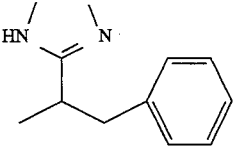 | CH$_3$ | 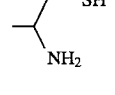 |
| H | 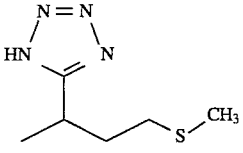 | CH$_3$ | 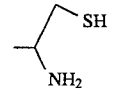 |
| H | 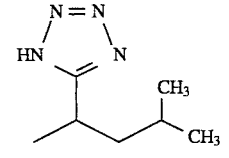 | CH$_3$ | 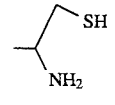 |
| H | 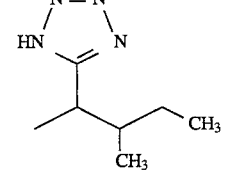 | CH$_3$ | 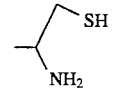 |

TABLE Ia'-continued

| R⁷' | R⁸ | R²⁴ | R²⁵ |
|---|---|---|---|
| H | 2-methyl-4-(methylthio)butanoic acid | CH₃ | 2-amino-3-(ethyldisulfanyl)propyl |
| H | methyl 2-methyl-4-(methylthio)butanoate | CH₃ | 2-amino-3-(ethyldisulfanyl)propyl |
| H | 2-methyl-4-(ethyldisulfanyl)butanoic acid | CH₃ | 2-amino-3-(ethyldisulfanyl)propyl |
| H | 2,4-dimethylpentanoic acid | CH₃ | 2-amino-3-(ethyldisulfanyl)propyl |
| H | 2,3-dimethylpentanoic acid | CH₃ | 2-amino-3-(ethyldisulfanyl)propyl |
| H | 2-methyl-3-phenylpropanoic acid | CH₃ | 2-amino-3-(ethyldisulfanyl)propyl |
| H | 2-methyl-3-(naphthalen-2-yl)propanoic acid | CH₃ | 2-amino-3-(ethyldisulfanyl)propyl |
| H | 2-methyl-3-(naphthalen-1-yl)propanoic acid | CH₃ | 2-amino-3-(ethyldisulfanyl)propyl |
| H | 2-methyl-3-(4-methoxyphenyl)propanoic acid | CH₃ | 2-amino-3-(ethyldisulfanyl)propyl |
| H | 2-methyl-4-(methylthio)butanamide | CH₃ | 2-amino-3-(ethyldisulfanyl)propyl |
| H | 2-methyl-3-methoxypropanoic acid | CH₃ | 2-amino-3-(ethyldisulfanyl)propyl |
| H | 2-methyl-3-cyclohexylpropanoic acid | CH₃ | 2-amino-3-(ethyldisulfanyl)propyl |
| H | 5-(1-phenylpropan-2-yl)-1H-tetrazole | CH₃ | 2-amino-3-(ethyldisulfanyl)propyl |

TABLE Ia'-continued

| R⁷' | R⁸ | R²⁴ | R²⁵ |
|---|---|---|---|
| H | 5-(1-methyl-3-(methylthio)propyl)-1H-tetrazole | $CH_3$ | 2-amino-1-(ethyldithio)propyl |
| H | 5-(1,3-dimethylbutyl)-1H-tetrazole | $CH_3$ | 2-amino-1-(ethyldithio)propyl |
| H | 5-(1-methyl-2-methylbutyl)-1H-tetrazole | $CH_3$ | 2-amino-1-(ethyldithio)propyl |
| H | 2-methyl-4-(methylthio)butanoic acid | $CH_3$ | 2-(methylamino)-1-mercaptopropyl |
| H | methyl 2-methyl-4-(methylthio)butanoate | $CH_3$ | 2-(methylamino)-1-mercaptopropyl |
| H | 2-methyl-4-(ethyldithio)butanoic acid | $CH_3$ | 2-(methylamino)-1-mercaptopropyl |
| H | 2,4-dimethylpentanoic acid | $CH_3$ | 2-(methylamino)-1-mercaptopropyl |
| H | 2,3-dimethylpentanoic acid | $CH_3$ | 2-(methylamino)-1-mercaptopropyl |
| H | 2-methyl-3-phenylpropanoic acid | $CH_3$ | 2-(methylamino)-1-mercaptopropyl |
| H | 2-methyl-3-(2-naphthyl)propanoic acid | $CH_3$ | 2-(methylamino)-1-mercaptopropyl |
| H | 2-methyl-3-(1-naphthyl)propanoic acid | $CH_3$ | 2-(methylamino)-1-mercaptopropyl |

TABLE Ia'-continued
| R7' | R8 | R24 | R25 |
|---|---|---|---|
| H | 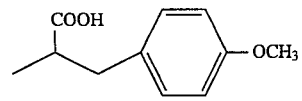 | CH3 | 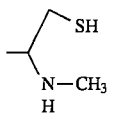 |
| H | 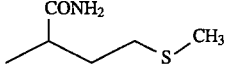 | CH3 | 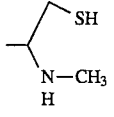 |
| H | 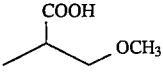 | CH3 | 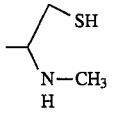 |
| H | 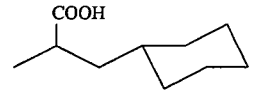 | CH3 | 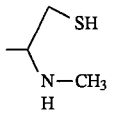 |
| H | 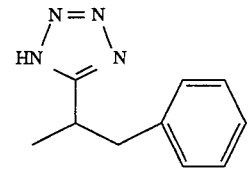 | CH3 | 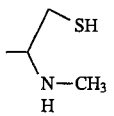 |
| H | 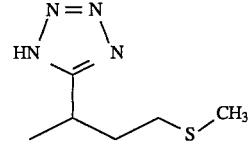 | CH3 | 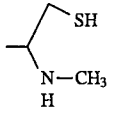 |
| H | 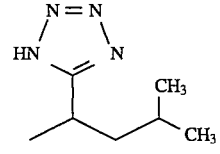 | CH3 | 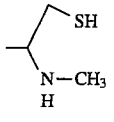 |
| H | 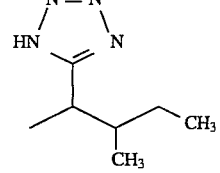 | CH3 | 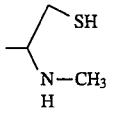 |
| H | 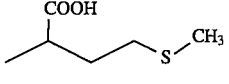 | C2H5 | 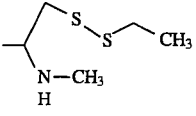 |
| H | 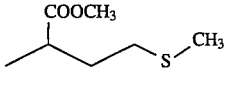 | C2H5 | 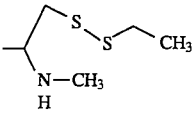 |
| H | 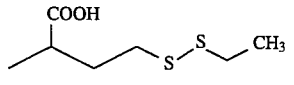 | C2H5 | 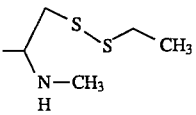 |

TABLE Ia'-continued

| R[7'] | R[8] | R[24] | R[25] |
|---|---|---|---|
| H | CH₃-CH(COOH)-CH₂-CH(CH₃)-CH₃ | C₂H₅ | CH₃-CH(NH-CH₃)-CH₂-S-S-C₂H₅ |
| H | CH₃-CH(COOH)-CH(CH₃)-CH₂-CH₃ | C₂H₅ | CH₃-CH(NH-CH₃)-CH₂-S-S-C₂H₅ |
| H | CH₃-CH(COOH)-CH₂-C₆H₅ | C₂H₅ | CH₃-CH(NH-CH₃)-CH₂-S-S-C₂H₅ |
| H | CH₃-CH(COOH)-CH₂-(2-naphthyl) | C₂H₅ | CH₃-CH(NH-CH₃)-CH₂-S-S-C₂H₅ |
| H | CH₃-CH(COOH)-CH₂-(1-naphthyl) | C₂H₅ | CH₃-CH(NH-CH₃)-CH₂-S-S-C₂H₅ |
| H | CH₃-CH(COOH)-CH₂-C₆H₄-OCH₃ (p) | C₂H₅ | CH₃-CH(NH-CH₃)-CH₂-S-S-C₂H₅ |
| H | CH₃-CH(CONH₂)-CH₂-CH₂-S-CH₃ | C₂H₅ | CH₃-CH(NH-CH₃)-CH₂-S-S-C₂H₅ |
| H | CH₃-CH(COOH)-CH₂-OCH₃ | C₂H₅ | CH₃-CH(NH-CH₃)-CH₂-S-S-C₂H₅ |
| H | CH₃-CH(COOH)-CH₂-cyclohexyl | C₂H₅ | CH₃-CH(NH-CH₃)-CH₂-S-S-C₂H₅ |
| H | CH₃-CH(tetrazol-5-yl)-CH₂-C₆H₅ | C₂H₅ | CH₃-CH(NH-CH₃)-CH₂-S-S-C₂H₅ |
| H | CH₃-CH(tetrazol-5-yl)-CH₂-CH₂-S-CH₃ | C₂H₅ | CH₃-CH(NH-CH₃)-CH₂-S-S-C₂H₅ |

TABLE Ia'-continued
| R⁷' | R⁸ | R²⁴ | R²⁵ |
|---|---|---|---|
| H | 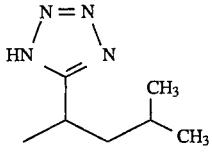 | C₂H₅ | 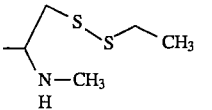 |
| H | 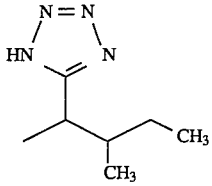 | C₂H₅ | 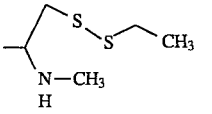 |
| H | 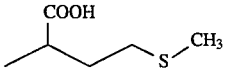 | CH₃ | 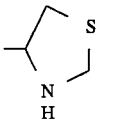 |
| H | 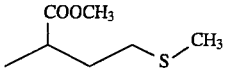 | CH₃ | 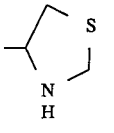 |
| H | 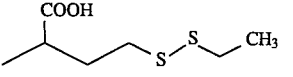 | CH₃ | 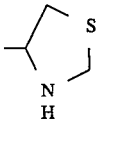 |
| H | 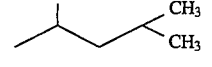 | CH₃ | 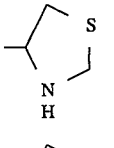 |
| H | 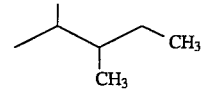 | CH₃ | 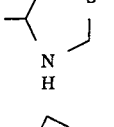 |
| H | 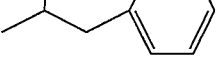 | CH₃ | 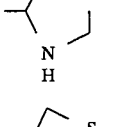 |
| H | 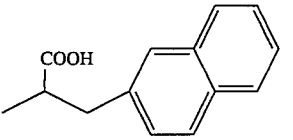 | CH₃ | 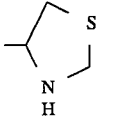 |
| H | 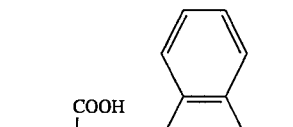 | CH₃ | 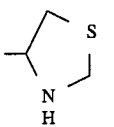 |

TABLE Ia'-continued

| R$^{7'}$ | R$^8$ | R$^{24}$ | R$^{25}$ |
|---|---|---|---|
| H | 2-(4-methoxybenzyl)propanoic acid group (COOH, CH with CH3, CH2-C6H4-OCH3) | CH$_3$ | thiazolidine (S, N-H ring attached via CH) |
| H | 2-methyl-4-(methylthio)butanamide (CONH2, CH-CH3, CH2CH2-S-CH3) | CH$_3$ | thiazolidine |
| H | 2-methyl-3-methoxypropanoic acid (COOH, CH-CH3, CH2-OCH3) | CH$_3$ | thiazolidine |
| H | 2-methyl-3-cyclohexylpropanoic acid (COOH, CH-CH3, CH2-cyclohexyl) | CH$_3$ | thiazolidine |
| H | 1-(tetrazol-5-yl)-2-phenyl substituent (HN-N=N-N=N tetrazole, CH-CH3, CH2-C6H5) | CH$_3$ | thiazolidine |
| H | 1-(tetrazol-5-yl) with CH-CH3, CH2CH2-S-CH3 | CH$_3$ | thiazolidine |
| H | 1-(tetrazol-5-yl) with CH-CH3, CH2-CH(CH3)2 | CH$_3$ | thiazolidine |
| H | 1-(tetrazol-5-yl) with CH-CH3, CH(CH3)-CH2CH3 | CH$_3$ | thiazolidine |
| H | 2-methyl-4-(methylthio)butanoic acid (COOH, CH-CH3, CH2CH2-S-CH3) | H$_3$C-CH-CH$_3$ (isobutyl) | N-methyl thiazolidine |
| H | methyl 2-methyl-4-(methylthio)butanoate (COOCH3, CH-CH3, CH2CH2-S-CH3) | H$_3$C-CH-CH$_3$ (isobutyl) | N-methyl thiazolidine |

TABLE Ia'-continued

| $R^{7'}$ | $R^8$ | $R^{24}$ | $R^{25}$ |
|---|---|---|---|
| H | 2-methyl-4-(ethyldithio)butanoic acid (COOH, CH-CH3, CH2CH2-S-S-CH2CH3) | isobutyl (H3C-CH(CH3)-) | 2-(methylamino)-1-(thiiranyl)... (pyrrolidine-type with S, N-CH3) |
| H | 2,4-dimethylpentanoic acid (COOH, CH-CH3, CH2-CH(CH3)2) | isobutyl | same as above |
| H | 2,3-dimethylpentanoic acid (COOH, CH-CH3, CH(CH3)-CH2CH3) | isobutyl | same as above |
| H | 2-methyl-3-phenylpropanoic acid (COOH, CH-CH3, CH2-C6H5) | isobutyl | same as above |
| H | 2-methyl-3-(2-naphthyl)propanoic acid | isobutyl | same as above |
| H | 2-methyl-3-(1-naphthyl)propanoic acid | isobutyl | same as above |
| H | 2-methyl-3-(4-methoxyphenyl)propanoic acid (COOH, CH-CH3, CH2-C6H4-OCH3) | isobutyl | same as above |
| H | 2-methyl-4-(methylthio)butanamide (CONH2, CH-CH3, CH2CH2-S-CH3) | isobutyl | same as above |
| H | 2-methyl-3-methoxypropanoic acid (COOH, CH-CH3, CH2-OCH3) | isobutyl | same as above |
| H | 2-methyl-3-cyclohexylpropanoic acid (COOH, CH-CH3, CH2-cyclohexyl) | isobutyl | same as above |

TABLE Ia'-continued

| R⁷' | R⁸ | R²⁴ | R²⁵ |
|---|---|---|---|
| H | 5-(1-phenylmethyl-ethyl)-2H-tetrazole [CH(CH₃)CH₂C₆H₅] | CH(CH₃)₂ | N-methylthiazolidine |
| H | 5-[1-(2-methylthioethyl)-ethyl]-2H-tetrazole [CH(CH₃)CH₂CH₂SCH₃] | CH(CH₃)₂ | N-methylthiazolidine |
| H | 5-[1-(2-methylpropyl)-ethyl]-2H-tetrazole [CH(CH₃)CH₂CH(CH₃)₂] | CH(CH₃)₂ | N-methylthiazolidine |
| H | 5-[1-(1-methylpropyl)-ethyl]-2H-tetrazole [CH(CH₃)CH(CH₃)CH₂CH₃] | CH(CH₃)₂ | N-methylthiazolidine |
| CH₃ | CH(CH₃)CH₂CH₂SCH₃, COOH | CH₃ | 2-methylthiazolidine (NH, CH₃) |
| CH₃ | CH(CH₃)CH₂CH₂SCH₃, COOCH₃ | CH₃ | 2-methylthiazolidine (NH, CH₃) |
| CH₃ | CH(CH₃)CH₂CH₂SSCH₂CH₃, COOH | CH₃ | 2-methylthiazolidine (NH, CH₃) |
| CH₃ | CH(CH₃)CH₂CH(CH₃)₂, COOH | CH₃ | 2-methylthiazolidine (NH, CH₃) |
| CH₃ | CH(CH₃)CH(CH₃)CH₂CH₃, COOH | CH₃ | 2-methylthiazolidine (NH, CH₃) |
| CH₃ | CH(CH₃)CH₂C₆H₅, COOH | CH₃ | 2-methylthiazolidine (NH, CH₃) |

TABLE Ia'-continued

| R[7'] | R[8] | R[24] | R[25] |
|---|---|---|---|
| CH₃ | 2-(6-methoxynaphthalen... | CH₃ | (thiazolidine-like) |

Due to the complexity of the chemical structures in this table, a faithful textual transcription is not feasible. The table contains rows with:

| R[7'] | R[8] | R[24] | R[25] |
|---|---|---|---|
| CH₃ | α-methyl-2-naphthylacetic acid derivative (2-(naphthalen-2-yl)propanoic acid, COOH) | CH₃ | NH-CH(CH₃)-S-CH₂- ring |
| CH₃ | α-methyl-1-naphthylacetic acid derivative | CH₃ | NH-CH(CH₃)-S-CH₂- ring |
| CH₃ | 2-(4-methoxyphenyl)propanoic acid with COOH | CH₃ | NH-CH(CH₃)-S-CH₂- ring |
| CH₃ | CH(CH₃)(CONH₂)-CH₂-CH₂-S-CH₃ | CH₃ | NH-CH(CH₃)-S-CH₂- ring |
| CH₃ | CH(CH₃)(COOH)-CH₂-OCH₃ | CH₃ | NH-CH(CH₃)-S-CH₂- ring |
| CH₃ | CH(CH₃)(COOH)-CH₂-cyclohexyl | CH₃ | NH-CH(CH₃)-S-CH₂- ring |
| CH₃ | 5-(1-phenylpropan-2-yl)-1H-tetrazole | CH₃ | NH-CH(CH₃)-S-CH₂- ring |
| CH₃ | 5-[1-methyl-3-(methylthio)propyl]-1H-tetrazole | CH₃ | NH-CH(CH₃)-S-CH₂- ring |
| CH₃ | 5-(1,3-dimethylbutyl)-1H-tetrazole | CH₃ | NH-CH(CH₃)-S-CH₂- ring |
| CH₃ | 5-(1,2-dimethylbutyl)-1H-tetrazole | CH₃ | NH-CH(CH₃)-S-CH₂- ring |

TABLE Ia'-continued

| R[7'] | R[8] | R[24] | R[25] |
|---|---|---|---|
| H | COOH, CH(CH₃)CH₂CH₂SCH₃ | CH₃ | thiazolidinone-CH₂- |
| H | COOCH₃, CH(CH₃)CH₂CH₂SCH₃ | CH₃ | thiazolidinone-CH₂- |
| H | COOH, CH(CH₃)CH₂CH₂SSCH₂CH₃ | CH₃ | thiazolidinone-CH₂- |
| H | COOH, CH(CH₃)CH₂CH(CH₃)₂ | CH₃ | thiazolidinone-CH₂- |
| H | COOH, CH(CH₃)CH(CH₃)CH₂CH₃ | CH₃ | thiazolidinone-CH₂- |
| H | COOH, CH(CH₃)CH₂-C₆H₅ | CH₃ | thiazolidinone-CH₂- |
| H | COOH, CH(CH₃)CH₂-(2-naphthyl) | CH₃ | thiazolidinone-CH₂- |
| H | COOH, CH(CH₃)CH₂-(1-naphthyl) | CH₃ | thiazolidinone-CH₂- |
| H | COOH, CH(CH₃)CH₂-(4-OCH₃-C₆H₄) | CH₃ | thiazolidinone-CH₂- |
| H | CONH₂, CH(CH₃)CH₂CH₂SCH₃ | CH₃ | thiazolidinone-CH₂- |
| H | COOH, CH(CH₃)CH₂OCH₃ | CH₃ | thiazolidinone-CH₂- |

TABLE Ia'-continued

| R[7'] | R[8] | R[24] | R[25] |
|---|---|---|---|
| H | COOH, CH(CH₃)CH₂-cyclohexyl | CH₃ | thiazolidinone-CH₂- (NH) |
| H | tetrazole-CH(CH₃)CH₂-phenyl | CH₃ | thiazolidinone-CH₂- (NH) |
| H | tetrazole-CH(CH₃)CH₂CH₂SCH₃ | CH₃ | thiazolidinone-CH₂- (NH) |
| H | tetrazole-CH(CH₃)CH₂CH(CH₃)₂ | CH₃ | thiazolidinone-CH₂- (NH) |
| H | tetrazole-CH(CH₃)CH(CH₃)CH₂CH₃ | CH₃ | thiazolidinone-CH₂- (NH) |
| H | COOH, CH(CH₃)CH₂CH₂SCH₃ | C₄H₉ | thiazolidinone-CH₂- (NCH₃) |
| H | COOCH₃, CH(CH₃)CH₂CH₂SCH₃ | C₄H₉ | thiazolidinone-CH₂- (NCH₃) |
| H | COOH, CH(CH₃)CH₂CH₂SCH₃ | C₄H₉ | thiazolidinone-CH₂- (NCH₃) |
| H | COOH, CH(CH₃)CH₂CH(CH₃)₂ | C₄H₉ | thiazolidinone-CH₂- (NCH₃) |
| H | COOH, CH(CH₃)CH(CH₃)CH₂CH₃ | C₄H₉ | thiazolidinone-CH₂- (NCH₃) |

TABLE Ia'-continued

| R⁷' | R⁸ | R²⁴ | R²⁵ |
|---|---|---|---|
| H | 2-phenyl-1-methylethyl with COOH (α-methyl-phenylpropanoic acid) | C₄H₉ | N-methyl-2-thioxothiazolidinyl (methyl substituent) |
| H | α-methyl-(naphthalen-2-yl)propanoic acid | C₄H₉ | N-methyl-2-thioxothiazolidinyl |
| H | α-methyl-(naphthalen-1-yl)propanoic acid | C₄H₉ | N-methyl-2-thioxothiazolidinyl |
| H | α-methyl-(4-methoxyphenyl)propanoic acid | C₄H₉ | N-methyl-2-thioxothiazolidinyl |
| H | 2-methyl-4-(methylthio)butanamide (CONH₂, S-CH₃) | C₄H₉ | N-methyl-2-thioxothiazolidinyl |
| H | 2-methyl-3-methylpentanoic acid (COOH, CH₃, CH₃) | C₄H₉ | N-methyl-2-thioxothiazolidinyl |
| H | 2-methyl-3-cyclohexylpropanoic acid (COOH) | C₄H₉ | N-methyl-2-thioxothiazolidinyl |
| H | 5-(1-methyl-2-phenylethyl)-1H-tetrazole | C₄H₉ | N-methyl-2-thioxothiazolidinyl |
| H | 5-[1-methyl-3-(methylthio)propyl]-1H-tetrazole | C₄H₉ | N-methyl-2-thioxothiazolidinyl |
| H | 5-(1,4-dimethylpentyl)-1H-tetrazole | C₄H₉ | N-methyl-2-thioxothiazolidinyl |

TABLE Ia'-continued

| R⁷' | R⁸ | R²⁴ | R²⁵ |
|---|---|---|---|
| H | 5-(3-methylpentan-2-yl)-1H-tetrazole | C₄H₉ | 3-methyl-thiazolidin-2-thione (N-methyl, C=S, ring S) |
| H | HOOC-CH(CH₃)-CH₂-CH₂-S-CH₃ | CH₃ | -NH-CH₂-CH₂-SH |
| H | CH₃OOC-CH(CH₃)-CH₂-CH₂-S-CH₃ | CH₃ | -NH-CH₂-CH₂-SH |
| H | HOOC-CH(CH₃)-CH₂-CH₂-S-S-CH₂CH₃ | CH₃ | -NH-CH₂-CH₂-SH |
| H | HOOC-CH(CH₃)-CH₂-CH(CH₃)₂ | CH₃ | -NH-CH₂-CH₂-SH |
| H | HOOC-CH(CH₃)-CH(CH₃)-CH₂-CH₃ | CH₃ | -NH-CH₂-CH₂-SH |
| H | HOOC-CH(CH₃)-CH₂-C₆H₅ | CH₃ | -NH-CH₂-CH₂-SH |
| H | HOOC-CH(CH₃)-CH₂-(2-naphthyl) | CH₃ | -NH-CH₂-CH₂-SH |
| H | HOOC-CH(CH₃)-CH₂-(1-naphthyl) | CH₃ | -NH-CH₂-CH₂-SH |
| H | HOOC-CH(CH₃)-CH₂-C₆H₄-OCH₃ (para) | CH₃ | -NH-CH₂-CH₂-SH |
| H | H₂NOC-CH(CH₃)-CH₂-CH₂-S-CH₃ | CH₃ | -NH-CH₂-CH₂-SH |
| H | HOOC-CH(CH₃)-CH₂-OCH₃ | CH₃ | -NH-CH₂-CH₂-SH |
| H | HOOC-CH(CH₃)-CH₂-cyclohexyl | CH₃ | -NH-CH₂-CH₂-SH |

TABLE Ia'-continued
| R⁷' | R⁸ | R²⁴ | R²⁵ |
|---|---|---|---|
| H | 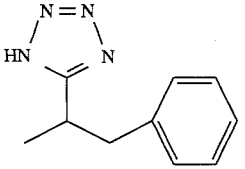 | CH₃ |  |
| H | 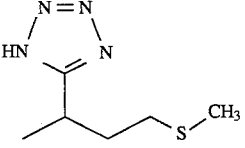 | CH₃ | 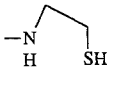 |
| H | 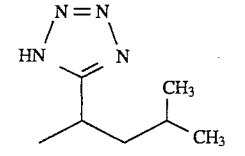 | CH₃ | 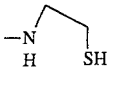 |
| H | 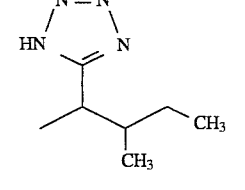 | CH₃ | 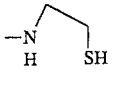 |
| H | 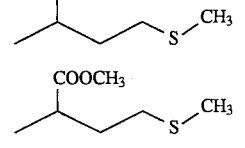 | CH₃ | 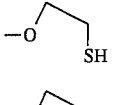 |
| H | 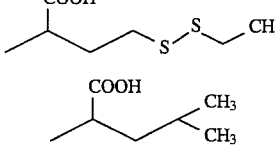 | CH₃ | 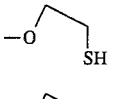 |
| H | 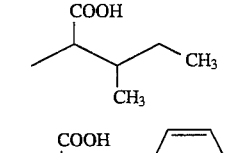 | CH₃ | 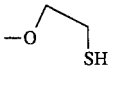 |
| H | 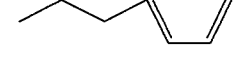 | CH₃ |  |
| H | 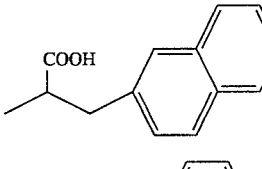 | CH₃ | 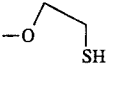 |
| H | 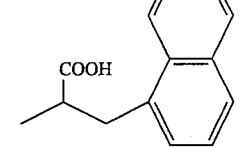 | CH₃ | 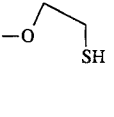 |

TABLE Ia'-continued

| R⁷' | R⁸ | R²⁴ | R²⁵ |
|---|---|---|---|
| H | 2-(4-methoxybenzyl)propanoic acid [CH(COOH)(CH₃)-CH₂-C₆H₄-OCH₃] | CH₃ | -O-CH₂CH₂-SH |
| H | 2-methyl-4-(methylthio)butanamide [CH(CONH₂)(CH₃)-CH₂CH₂-S-CH₃] | CH₃ | -O-CH₂CH₂-SH |
| H | 2-methyl-3-methoxypropanoic acid [CH(COOH)(CH₃)-CH₂-OCH₃] | CH₃ | -O-CH₂CH₂-SH |
| H | 2-methyl-3-cyclobutylpropanoic acid [CH(COOH)(CH₃)-CH₂-cyclobutyl] | CH₃ | -O-CH₂CH₂-SH |
| H | 5-(1-methyl-2-phenylethyl)-1H-tetrazole | CH₃ | -O-CH₂CH₂-SH |
| H | 5-(1-methyl-3-(methylthio)propyl)-1H-tetrazole | CH₃ | -O-CH₂CH₂-SH |
| H | 5-(1,3-dimethylbutyl)-1H-tetrazole | CH₃ | -O-CH₂CH₂-SH |
| H | 5-(1,2-dimethylbutyl)-1H-tetrazole | CH₃ | -O-CH₂CH₂-SH |
| H | 2-methyl-4-(methylthio)butanoic acid [CH(COOH)(CH₃)-CH₂CH₂-S-CH₃] | CH₃ | -N(thiazolidine) |
| H | methyl 2-methyl-4-(methylthio)butanoate [CH(COOCH₃)(CH₃)-CH₂CH₂-S-CH₃] | CH₃ | -N(thiazolidine) |
| H | 2-methyl-4-(ethyldithio)butanoic acid [CH(COOH)(CH₃)-CH₂CH₂-S-S-CH₂CH₃] | CH₃ | -N(thiazolidine) |
| H | 2,4-dimethylpentanoic acid [CH(COOH)(CH₃)-CH₂-CH(CH₃)₂] | CH₃ | -N(thiazolidine) |

TABLE Ia'-continued

| $R^{7'}$ | $R^8$ | $R^{24}$ | $R^{25}$ |
|---|---|---|---|
| H | 2-methyl-3-methylbutanoic acid (COOH, CH(CH3)CH(CH3)CH3) | $CH_3$ | thiazolidin-3-yl |
| H | 2-benzyl propanoic acid | $CH_3$ | thiazolidin-3-yl |
| H | 2-(naphthalen-2-ylmethyl)propanoic acid | $CH_3$ | thiazolidin-3-yl |
| H | 2-(naphthalen-1-ylmethyl)propanoic acid | $CH_3$ | thiazolidin-3-yl |
| H | 2-(4-methoxybenzyl)propanoic acid | $CH_3$ | thiazolidin-3-yl |
| H | 2-methyl-4-(methylthio)butanamide (CONH2) | $CH_3$ | thiazolidin-3-yl |
| H | 2-methyl-3-methoxypropanoic acid (COOH, OCH3) | $CH_3$ | thiazolidin-3-yl |
| H | 2-(cyclohexylmethyl)propanoic acid | $CH_3$ | thiazolidin-3-yl |
| H | 5-(1-methyl-2-phenylethyl)-1H-tetrazole | $CH_3$ | thiazolidin-3-yl |
| H | 5-(1-methyl-3-methylthiopropyl)-1H-tetrazole | $CH_3$ | thiazolidin-3-yl |
| H | 5-(1,4-dimethylpentyl)-1H-tetrazole | $CH_3$ | thiazolidin-3-yl |

TABLE Ia'-continued

| R⁷' | R⁸ | R²⁴ | R²⁵ |
|---|---|---|---|
| H | HN-N=N tetrazole-CH(CH₃)-CH(CH₃)-CH₂CH₃ | CH₃ | -N(CH₂CH₂S) (thiazolidine) |
| H | -CH(CH₃)-CH₂-CH₂-S-CH₃ with COOH | CH₃ | -N(CO)(CH₂CH₂S) |
| H | -CH(COOCH₃)-CH₂-CH₂-S-CH₃ | CH₃ | -N(CO)(CH₂CH₂S) |
| H | -CH(COOH)-CH₂-CH₂-S-S-CH₂CH₃ | CH₃ | -N(CO)(CH₂CH₂S) |
| H | -CH(COOH)-CH₂-CH(CH₃)₂ | CH₃ | -N(CO)(CH₂CH₂S) |
| H | -CH(COOH)-CH(CH₃)-CH₂CH₃ (actually -CH(COOH)-CH₂-CH(CH₃)CH₂CH₃) | CH₃ | -N(CO)(CH₂CH₂S) |
| H | -CH(COOH)-CH₂-C₆H₅ | CH₃ | -N(CO)(CH₂CH₂S) |
| H | -CH(COOH)-CH₂-(2-naphthyl) | CH₃ | -N(CO)(CH₂CH₂S) |
| H | -CH(COOH)-CH₂-(1-naphthyl) | CH₃ | -N(CO)(CH₂CH₂S) |
| H | -CH(COOH)-CH₂-C₆H₄-OCH₃ (para) | CH₃ | -N(CO)(CH₂CH₂S) |

TABLE Ia'-continued

| R⁷' | R⁸ | R²⁴ | R²⁵ |
|---|---|---|---|
| H | CONH₂, CH(CH₃)CH₂CH₂SCH₃ | CH₃ | N-(thiazolidin-2-one) |
| H | COOH, CH(CH₃)CH₂OCH₃ | CH₃ | N-(thiazolidin-2-one) |
| H | COOH, CH(CH₃)CH₂-cyclohexyl | CH₃ | N-(thiazolidin-2-one) |
| H | tetrazolyl-CH(CH₃)CH₂-phenyl | CH₃ | N-(thiazolidin-2-one) |
| H | tetrazolyl-CH(CH₃)CH₂CH₂SCH₃ | CH₃ | N-(thiazolidin-2-one) |
| H | tetrazolyl-CH(CH₃)CH₂CH(CH₃)₂ | CH₃ | N-(thiazolidin-2-one) |
| H | tetrazolyl-CH(CH₃)CH(CH₃)CH₂CH₃ | CH₃ | N-(thiazolidin-2-one) |
| H | COOH, CH(CH₃)CH₂CH₂SCH₃ | CH₃ | N-methyl-4-mercapto-2-carboxypyrrolidine |
| H | COOCH₃, CH(CH₃)CH₂CH₂SCH₃ | CH₃ | N-methyl-4-mercapto-2-carboxypyrrolidine |
| H | COOH, CH(CH₃)CH₂CH₂S-S-CH₂CH₃ | CH₃ | N-methyl-4-mercapto-2-carboxypyrrolidine |

TABLE Ia'-continued

| R⁷' | R⁸ | R²⁴ | R²⁵ |
|---|---|---|---|
| H | CH(COOH)CH₂CH(CH₃)₂ (2-methyl-3-methylbutyl with COOH) | CH₃ | 4-mercapto-pyrrolidine-2-carboxylic acid (N-methyl) |
| H | CH(COOH)CH(CH₃)CH₂CH₃ | CH₃ | 4-mercapto-pyrrolidine-2-carboxylic acid (N-methyl) |
| H | CH(COOH)CH₂-phenyl | CH₃ | 4-mercapto-pyrrolidine-2-carboxylic acid (N-methyl) |
| H | CH(COOH)CH₂-(2-naphthyl) | CH₃ | 4-mercapto-pyrrolidine-2-carboxylic acid (N-methyl) |
| H | CH(COOH)CH₂-(1-naphthyl) | CH₃ | 4-mercapto-pyrrolidine-2-carboxylic acid (N-methyl) |
| H | CH(COOH)CH₂-(4-methoxyphenyl) | CH₃ | 4-mercapto-pyrrolidine-2-carboxylic acid (N-methyl) |
| H | CH(CONH₂)CH₂CH₂SCH₃ | CH₃ | 4-mercapto-pyrrolidine-2-carboxylic acid (N-methyl) |
| H | CH(COOH)CH₂OCH₃ | CH₃ | 4-mercapto-pyrrolidine-2-carboxylic acid (N-methyl) |
| H | CH(COOH)CH₂-cyclohexyl | CH₃ | 4-mercapto-pyrrolidine-2-carboxylic acid (N-methyl) |
| H | CH(tetrazol-5-yl)CH₂-phenyl | CH₃ | 4-mercapto-pyrrolidine-2-carboxylic acid (N-methyl) |
| H | CH(tetrazol-5-yl)CH₂CH₂SCH₃ | CH₃ | 4-mercapto-pyrrolidine-2-carboxylic acid (N-methyl) |

TABLE Ia'-continued

| R[7'] | R[8] | R[24] | R[25] |
|---|---|---|---|
| H | 5-(1,3-dimethylbutyl)-tetrazole derivative with CH(CH₃)CH₂CH(CH₃)₂ | CH₃ | 1-methyl-4-mercapto-pyrrolidine-2-carboxylic acid |
| H | 5-(1,2-dimethylbutyl)-tetrazole derivative with CH(CH₃)CH(CH₃)CH₂CH₃ | CH₃ | 1-methyl-4-mercapto-pyrrolidine-2-carboxylic acid |
| H | CH(COOH)CH(CH₃)CH₂CH₂SCH₃ | CH₃ | 1-methyl-pyrrolidine-2-carboxylic acid |
| H | CH(COOCH₃)CH(CH₃)CH₂CH₂SCH₃ | CH₃ | 1-methyl-pyrrolidine-2-carboxylic acid |
| H | CH(COOH)CH(CH₃)CH₂CH₂SSCH₂CH₃ | CH₃ | 1-methyl-pyrrolidine-2-carboxylic acid |
| H | CH(COOH)CH(CH₃)CH(CH₃)₂ | CH₃ | 1-methyl-pyrrolidine-2-carboxylic acid |
| H | CH(COOH)CH(CH₃)CH(CH₃)CH₂CH₃ | CH₃ | 1-methyl-pyrrolidine-2-carboxylic acid |
| H | CH(COOH)CH(CH₃)CH₂-phenyl | CH₃ | 1-methyl-pyrrolidine-2-carboxylic acid |
| H | CH(COOH)CH₃-CH₂-(2-naphthyl) | CH₃ | 1-methyl-pyrrolidine-2-carboxylic acid |
| H | CH(COOH)CH₃-CH₂-(1-naphthyl) | CH₃ | 1-methyl-pyrrolidine-2-carboxylic acid |
| H | CH(COOH)CH₃-CH₂-(4-methoxyphenyl) | CH₃ | 1-methyl-pyrrolidine-2-carboxylic acid |

TABLE Ia'-continued

| R[7'] | R[8] | R[24] | R[25] |
|---|---|---|---|
| H | CH(CONH$_2$)-CH(CH$_3$)-CH$_2$-CH$_2$-S-CH$_3$ | CH$_3$ | proline (N-linked, 2-COOH) |
| H | CH(COOH)-CH(CH$_3$)-CH$_2$-OCH$_3$ | CH$_3$ | proline (N-linked, 2-COOH) |
| H | CH(COOH)-CH(CH$_3$)-CH$_2$-cyclobutyl | CH$_3$ | proline (N-linked, 2-COOH) |
| H | C(=tetrazolyl-NH)-CH(CH$_3$)-CH$_2$-C$_6$H$_5$ | CH$_3$ | proline (N-linked, 2-COOH) |
| H | C(=tetrazolyl-NH)-CH(CH$_3$)-CH$_2$-CH$_2$-S-CH$_3$ | CH$_3$ | proline (N-linked, 2-COOH) |
| H | C(=tetrazolyl-NH)-CH(CH$_3$)-CH$_2$-CH(CH$_3$)$_2$ | CH$_3$ | proline (N-linked, 2-COOH) |
| H | C(=tetrazolyl-NH)-CH(CH$_3$)-CH(CH$_3$)-CH$_2$-CH$_3$ | CH$_3$ | proline (N-linked, 2-COOH) |
| H | CH(COOH)-CH(CH$_3$)-CH$_2$-CH$_2$-S-CH$_3$ | CH$_3$ | -NH-CH$_2$-COOH |
| H | CH(COOCH$_3$)-CH(CH$_3$)-CH$_2$-CH$_2$-S-CH$_3$ | CH$_3$ | -NH-CH$_2$-COOH |
| H | CH(COOH)-CH(CH$_3$)-CH$_2$-CH$_2$-S-S-CH$_2$-CH$_3$ | CH$_3$ | -NH-CH$_2$-COOH |
| H | CH(COOH)-CH(CH$_3$)-CH$_2$-CH(CH$_3$)$_2$ | CH$_3$ | -NH-CH$_2$-COOH |
| H | CH(COOH)-CH(CH$_3$)-CH(CH$_3$)-CH$_2$-CH$_3$ | CH$_3$ | -NH-CH$_2$-COOH |

TABLE Ia'-continued

| R⁷' | R⁸ | R²⁴ | R²⁵ |
|---|---|---|---|
| H | 2-methyl-3-phenylpropanoic acid (CH(CH₃)CH₂-Ph with COOH) | CH₃ | -NH-CH₂-COOH |
| H | 2-methyl-3-(naphthalen-2-yl)propanoic acid | CH₃ | -NH-CH₂-COOH |
| H | 2-methyl-3-(naphthalen-1-yl)propanoic acid | CH₃ | -NH-CH₂-COOH |
| H | 2-methyl-3-(4-methoxyphenyl)propanoic acid | CH₃ | -NH-CH₂-COOH |
| H | 2-methyl-4-(methylthio)butanamide (CONH₂) | CH₃ | -NH-CH₂-COOH |
| H | 2-methyl-3-methoxypropanoic acid | CH₃ | -NH-CH₂-COOH |
| H | 2-methyl-3-cyclohexylpropanoic acid | CH₃ | -NH-CH₂-COOH |
| H | 1-methyl-2-phenylethyl tetrazole (HN-N=N-N=C-CH(CH₃)CH₂Ph) | CH₃ | -NH-CH₂-COOH |
| H | tetrazolyl with CH(CH₃)CH₂CH₂SCH₃ | CH₃ | -NH-CH₂-COOH |
| H | tetrazolyl with CH(CH₃)CH₂CH(CH₃)₂ | CH₃ | -NH-CH₂-COOH |
| H | tetrazolyl with CH(CH₃)CH(CH₃)CH₂CH₃ | CH₃ | -NH-CH₂-COOH |
| H | 2-methyl-4-(methylthio)butanoic acid (COOH) | CH₃ | -NH-CH₂CH₂-COOH |

TABLE Ia'-continued

| R[7'] | R[8] | R[24] | R[25] |
|---|---|---|---|
| H | methyl 2-methyl-4-(methylthio)butanoate | CH$_3$ | —NH—CH$_2$CH$_2$—COOH |
| H | 2-methyl-4-(ethyldithio)butanoic acid | CH$_3$ | —NH—CH$_2$CH$_2$—COOH |
| H | 2,4-dimethylpentanoic acid | CH$_3$ | —NH—CH$_2$CH$_2$—COOH |
| H | 2,3-dimethylpentanoic acid | CH$_3$ | —NH—CH$_2$CH$_2$—COOH |
| H | 2-methyl-3-phenylpropanoic acid | CH$_3$ | —NH—CH$_2$CH$_2$—COOH |
| H | 2-methyl-3-(2-naphthyl)propanoic acid | CH$_3$ | —NH—CH$_2$CH$_2$—COOH |
| H | 2-methyl-3-(1-naphthyl)propanoic acid | CH$_3$ | —NH—CH$_2$CH$_2$—COOH |
| H | 2-methyl-3-(4-methoxyphenyl)propanoic acid | CH$_3$ | —NH—CH$_2$CH$_2$—COOH |
| H | 2-methyl-4-(methylthio)butanamide | CH$_3$ | —NH—CH$_2$CH$_2$—COOH |
| H | 2-methyl-3-methoxypropanoic acid | CH$_3$ | —NH—CH$_2$CH$_2$—COOH |
| H | 2-methyl-3-cyclohexylpropanoic acid | CH$_3$ | —NH—CH$_2$CH$_2$—COOH |
| H | 5-(1-methyl-2-phenylethyl)-1H-tetrazole | CH$_3$ | —NH—CH$_2$CH$_2$—COOH |
| H | 5-[1-methyl-3-(methylthio)propyl]-1H-tetrazole | CH$_3$ | —NH—CH$_2$CH$_2$—COOH |

TABLE Ia'-continued
| R[7'] | R[8] | R[24] | R[25] |
|---|---|---|---|
| H | 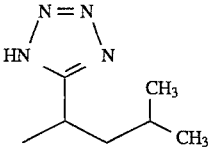 | CH$_3$ | 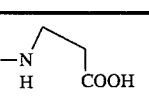 |
| H | 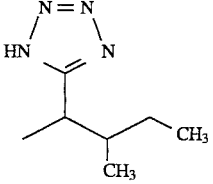 | CH$_3$ | 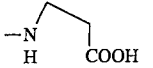 |
| H | 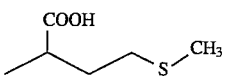 | CH$_3$ | 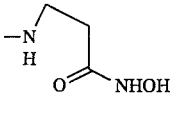 |
| H | 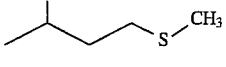 | CH$_3$ | 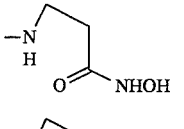 |
| H | 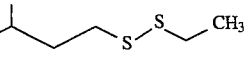 | CH$_3$ | 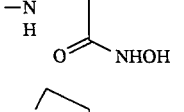 |
| H | 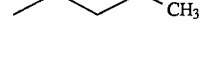 | CH$_3$ | 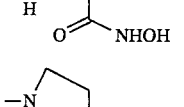 |
| H | 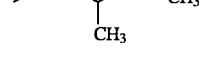 | CH$_3$ | 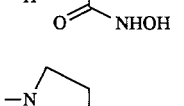 |
| H |  | CH$_3$ | 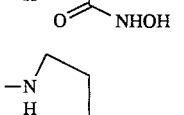 |
| H | 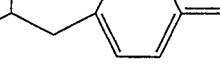 | CH$_3$ | 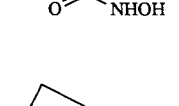 |
| H | 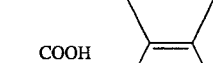 | CH$_3$ | 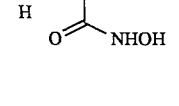 |
| H |  | CH$_3$ | 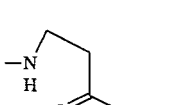 |
| H | 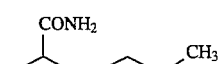 | CH$_3$ | 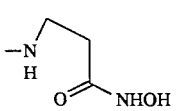 |

TABLE Ia'-continued

| R⁷' | R⁸ | R²⁴ | R²⁵ |
|---|---|---|---|
| H | CH(COOH)CH₂OCH₃ (2-methoxymethyl propanoic acid substituent) | CH₃ | -NH-CH₂CH₂-C(O)-NHOH |
| H | 2-methyl-3-cyclohexyl propanoic acid | CH₃ | -NH-CH₂CH₂-C(O)-NHOH |
| H | 1H-tetrazol-5-yl with CH(CH₃)CH₂-phenyl | CH₃ | -NH-CH₂CH₂-C(O)-NHOH |
| H | 1H-tetrazol-5-yl with CH(CH₃)CH₂CH₂SCH₃ | CH₃ | -NH-CH₂CH₂-C(O)-NHOH |
| H | 1H-tetrazol-5-yl with CH(CH₃)CH(CH₃)₂ | CH₃ | -NH-CH₂CH₂-C(O)-NHOH |
| H | 1H-tetrazol-5-yl with CH(CH₃)CH(CH₃)CH₂CH₃ | CH₃ | -NH-CH₂CH₂-C(O)-NHOH |
| H | CH(COOH)CH₂CH₂SCH₃ | CH₃ | -NH-CH(CH₂Ph)-COOH |
| H | CH(COOCH₃)CH₂CH₂SCH₃ | CH₃ | -NH-CH(CH₂Ph)-COOH |
| H | CH(COOH)CH₂CH₂S-S-CH₂CH₃ | CH₃ | -NH-CH(CH₂Ph)-COOH |
| H | CH(COOH)CH₂CH(CH₃)₂ | CH₃ | -NH-CH(CH₂Ph)-COOH |

TABLE Ia'-continued
| $R^{7'}$ | $R^8$ | $R^{24}$ | $R^{25}$ |
|---|---|---|---|
| H | 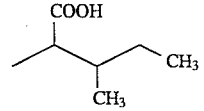 | $CH_3$ | 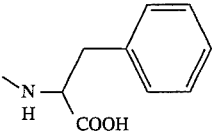 |
| H | 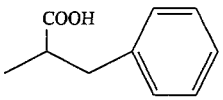 | $CH_3$ | 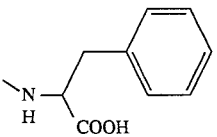 |
| H | 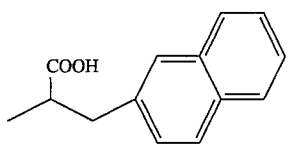 | $CH_3$ | 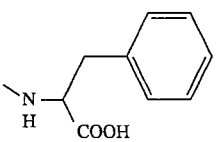 |
| H | 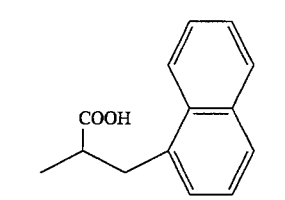 | $CH_3$ | 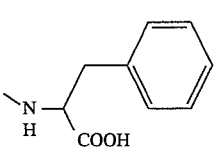 |
| H | 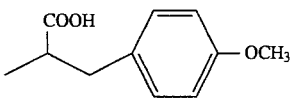 | $CH_3$ | 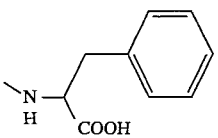 |
| H | 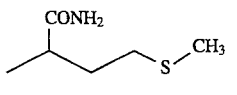 | $CH_3$ | 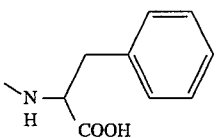 |
| H | 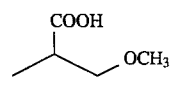 | $CH_3$ | 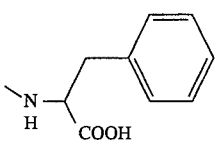 |
| H | 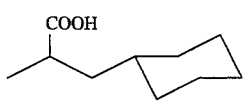 | $CH_3$ | 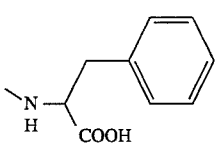 |
| H | 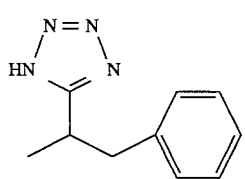 | $CH_3$ | 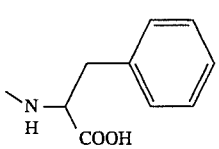 |
| H | 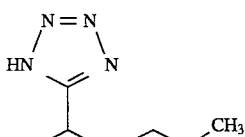 | $CH_3$ | 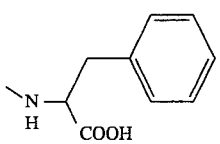 |

TABLE Ia'-continued

| $R^{7'}$ | $R^8$ | $R^{24}$ | $R^{25}$ |
|---|---|---|---|
| H | 1-(tetrazol-5-yl)-3-methylbutyl with methyl branch (CH(CH₃)CH₂CH(CH₃)CH₃ bearing tetrazole) | $CH_3$ | N-methyl-phenylalanine residue (–NH–CH(CH₂Ph)–COOH with N–CH₃) |
| H | 1-(tetrazol-5-yl)-2-methylbutyl (CH(CH₃)CH(CH₃)CH₂CH₃ bearing tetrazole) | $CH_3$ | N-methyl-phenylalanine residue |
| H | 2-methyl-4-(methylthio)butanoic acid (CH(CH₃)(COOH)CH₂CH₂SCH₃) | $CH_3$ | 1,4-dithia-7-azepane (–N in 7-membered ring with S–S) |
| H | methyl 2-methyl-4-(methylthio)butanoate (CH(CH₃)(COOCH₃)CH₂CH₂SCH₃) | $CH_3$ | 1,4-dithia-7-azepane |
| H | 2-methyl-4-(ethyldithio)butanoic acid (CH(CH₃)(COOH)CH₂CH₂S–S–CH₂CH₃) | $CH_3$ | 1,4-dithia-7-azepane |
| H | 2,4-dimethyl-pentanoic acid (CH(CH₃)(COOH)CH₂CH(CH₃)₂) | $CH_3$ | 1,4-dithia-7-azepane |
| H | 2-methyl-3-methylpentanoic acid (CH(CH₃)(COOH)CH(CH₃)CH₂CH₃) | $CH_3$ | 1,4-dithia-7-azepane |
| H | 2-methyl-3-phenylpropanoic acid (CH(CH₃)(COOH)CH₂Ph) | $CH_3$ | 1,4-dithia-7-azepane |
| H | 2-methyl-3-(2-naphthyl)propanoic acid | $CH_3$ | 1,4-dithia-7-azepane |
| H | 2-methyl-3-(1-naphthyl)propanoic acid | $CH_3$ | 1,4-dithia-7-azepane |

TABLE Ia'-continued

| R[7'] | R[8] | R[24] | R[25] |
|---|---|---|---|
| H | 2-(4-methoxyphenyl)propanoic acid (ibuprofen-like, COOH, CH₃, C₆H₄-OCH₃) | CH₃ | -N(cyclic)-S-S (1,2-dithiepane via N) |
| H | CH₃-CH(CONH₂)-CH₂-CH₂-S-CH₃ | CH₃ | -N(cyclic)-S-S |
| H | CH₃-CH(COOH)-CH₂-OCH₃ | CH₃ | -N(cyclic)-S-S |
| H | CH₃-CH(COOH)-CH₂-cyclohexyl | CH₃ | -N(cyclic)-S-S |
| H | 5-(1-benzyl-ethyl)-1H-tetrazole | CH₃ | -N(cyclic)-S-S |
| H | 5-[1-methyl-3-(methylthio)propyl]-1H-tetrazole | CH₃ | -N(cyclic)-S-S |
| H | 5-(1,3-dimethylbutyl)-1H-tetrazole | CH₃ | -N(cyclic)-S-S |
| H | 5-(1,2-dimethylbutyl)-1H-tetrazole | CH₃ | -N(cyclic)-S-S |
| H | CH₃-CH(COOH)-CH₂-CH₂-S-CH₃ | CH₃ | HOOC-CH(NH-)-CH₂-SH |
| H | CH₃-CH(COOCH₃)-CH₂-CH₂-S-CH₃ | CH₃ | HOOC-CH(NH-)-CH₂-SH |

TABLE Ia'-continued

| R⁷' | R⁸ | R²⁴ | R²⁵ |
|---|---|---|---|
| H | 2-methyl-4-(ethyldithio)butanoic acid | CH₃ | HOOC-CH(NH-)-CH₂-SH |
| H | 2,4-dimethyl-pentanoic acid (with COOH) | CH₃ | HOOC-CH(NH-)-CH₂-SH |
| H | 2-methyl-3-methyl-pentanoic acid | CH₃ | HOOC-CH(NH-)-CH₂-SH |
| H | 2-methyl-3-phenyl-propanoic acid | CH₃ | HOOC-CH(NH-)-CH₂-SH |
| H | 2-methyl-3-(2-naphthyl)propanoic acid | CH₃ | HOOC-CH(NH-)-CH₂-SH |
| H | 2-methyl-3-(1-naphthyl)propanoic acid | CH₃ | HOOC-CH(NH-)-CH₂-SH |
| H | 2-methyl-3-(4-methoxyphenyl)propanoic acid | CH₃ | HOOC-CH(NH-)-CH₂-SH |
| H | 2-methyl-4-(methylthio)butanamide | CH₃ | HOOC-CH(NH-)-CH₂-SH |
| H | 2-methyl-3-methoxy-propanoic acid | CH₃ | HOOC-CH(NH-)-CH₂-SH |
| H | 2-methyl-3-cyclohexyl-propanoic acid | CH₃ | HOOC-CH(NH-)-CH₂-SH |
| H | 5-(1-methyl-2-phenylethyl)-1H-tetrazole | CH₃ | HOOC-CH(NH-)-CH₂-SH |

TABLE Ia'-continued

| R[7'] | R[8] | R[24] | R[25] |
|---|---|---|---|
| H | (tetrazolyl-CH(CH₃)CH₂CH₂SCH₃) | CH₃ | HOOC-CH(NH-)-CH₂-SH |
| H | (tetrazolyl-CH(CH₃)CH(CH₃)₂ variant with isobutyl) | CH₃ | HOOC-CH(NH-)-CH₂-SH |
| H | (tetrazolyl-CH(CH₃)CH(CH₃)CH₂CH₃) | CH₃ | HOOC-CH(NH-)-CH₂-SH |
| H | CH(COOH)(CH₃)CH₂CH₂SCH₃ | CH₃ | HOOC-CH(NH-)-CH₂CH₂-COOH |
| H | CH(COOCH₃)(CH₃)CH₂CH₂SCH₃ | CH₃ | HOOC-CH(NH-)-CH₂CH₂-COOH |
| H | CH(COOH)(CH₃)CH₂CH₂S-S-CH₂CH₃ | CH₃ | HOOC-CH(NH-)-CH₂CH₂-COOH |
| H | CH(COOH)(CH₃)CH₂CH(CH₃)₂ | CH₃ | HOOC-CH(NH-)-CH₂CH₂-COOH |
| H | CH(COOH)(CH₃)CH(CH₃)CH₂CH₃ | CH₃ | HOOC-CH(NH-)-CH₂CH₂-COOH |
| H | CH(COOH)(CH₃)CH₂-phenyl | CH₃ | HOOC-CH(NH-)-CH₂CH₂-COOH |
| H | CH(COOH)(CH₃)CH₂-naphthyl | CH₃ | HOOC-CH(NH-)-CH₂CH₂-COOH |

TABLE Ia'-continued

| R⁷' | R⁸ | R²⁴ | R²⁵ |
|---|---|---|---|
| H | 1-(1-naphthyl)-2-methylpropanoic acid substituent | CH₃ | HOOC-CH(-NH-)-CH₂CH₂-COOH |
| H | 2-methyl-3-(4-methoxyphenyl)propanoic acid substituent | CH₃ | HOOC-CH(-NH-)-CH₂CH₂-COOH |
| H | CH(CONH₂)-CH₂-CH₂-S-CH₃ substituent | CH₃ | HOOC-CH(-NH-)-CH₂CH₂-COOH |
| H | CH(COOH)-CH₂-OCH₃ substituent | CH₃ | HOOC-CH(-NH-)-CH₂CH₂-COOH |
| H | CH(COOH)-cyclobutyl substituent | CH₃ | HOOC-CH(-NH-)-CH₂CH₂-COOH |
| H | tetrazole-CH(CH₃)-CH₂-phenyl substituent | CH₃ | HOOC-CH(-NH-)-CH₂CH₂-COOH |
| H | tetrazole-CH(CH₃)-CH₂-CH₂-S-CH₃ substituent | CH₃ | HOOC-CH(-NH-)-CH₂CH₂-COOH |
| H | tetrazole-CH(CH₃)-CH(CH₃)₂ substituent | CH₃ | HOOC-CH(-NH-)-CH₂CH₂-COOH |
| H | tetrazole-CH(CH₃)-CH(CH₃)-CH₃ substituent | CH₃ | HOOC-CH(-NH-)-CH₂CH₂-COOH |

An alternative preferred embodiment of the invention comprises a compound capable of inhibiting farnesyl:protein transferase at a concentration equal to or lower than that of the tetrapeptide CVFM represented by Formula II'

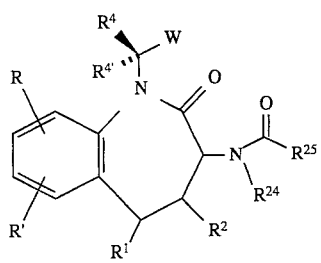

II' where the substituents R and R' are as defined above, $R^4$ and $R^{4'}$ are hydrogen or lower alkyl, and where W, $R^1$ and $R^2$, $R^{24}$ and $R^{25}$, are selected according to Table II'.

TABLE II'

| $R^1$ and $R^2$ | W | $R^{24}$ | $R^{25}$ |
|---|---|---|---|
| $CF_3$, H | —C(O)—O—$CH_3$ | $CH_3$ | —CH$_2$—CH(NH$_2$)—SH |
| $CF_3$, H | —C(O)—O—$CH_2CH_3$ | $CH_3$ | —CH$_2$—CH(NH$_2$)—SH |
| $CF_3$, H | —C$_6$H$_4$—COOCH$_3$ | $CH_3$ | —CH$_2$—CH(NH$_2$)—SH |
| $CF_3$, H | —C$_6$H$_4$—COOH | $CH_3$ | —CH$_2$—CH(NH$_2$)—SH |
| $CF_3$, H | biphenyl-COOCH$_3$ | $CH_3$ | —CH$_2$—CH(NH$_2$)—SH |
| $CF_3$, H | biphenyl-COOCH$_3$ | $CH_3$ | —CH$_2$—CH(NH$_2$)—SH |
| $CF_3$, H | cyclohexyl-COOH | $CH_3$ | —CH$_2$—CH(NH$_2$)—SH |
| $CF_3$, H | phenyl-tetrazole | $CH_3$ | —CH$_2$—CH(NH$_2$)—SH |
| $CF_3$, H | phenyl-tetrazole | $CH_3$ | —CH$_2$—CH(NH$_2$)—SH |

TABLE II'-continued

| R¹ and R² | W | R²⁴ | R²⁵ |
|---|---|---|---|
| CF₃, H | biphenyl-tetrazole | CH₃ | CH₂SH, CHNH₂ |
| CF₃, H | biphenyl-methyl-tetrazole | CH₃ | CH₂SH, CHNH₂ |
| CF₃, H | phenyl-pyrrole-tetrazole | CH₃ | CH₂SH, CHNH₂ |
| CF₃, H | pyridine with tetrazole and SCH₃ ethyl | CH₃ | CH₂SH, CHNH₂ |
| CF₃, H | pyridine with tetrazole and SSCH₃ methyl | CH₃ | CH₂SH, CHNH₂ |
| CF₃, H | pyrrole with SCH₃ and tetrazole | CH₃ | CH₂SH, CHNH₂ |
| CF₃, H | pyrrole with tetrazole and SCH₃ ethyl | CH₃ | CH₂SH, CHNH₂ |

TABLE II'-continued
| R¹ and R² | W | R²⁴ | R²⁵ |
|---|---|---|---|
| CF₃, H | 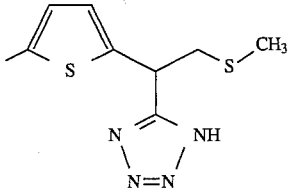 | CH₃ |  |
| CF₃, H | 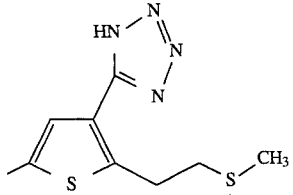 | CH₃ |  |
| CF₃, H | 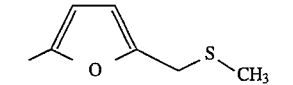 | CH₃ |  |
| CF₃, H | 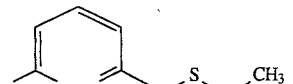 | CH₃ |  |
| CF₃, H | 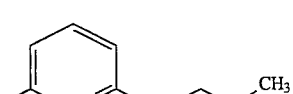 | CH₃ |  |
| CF₃, H | 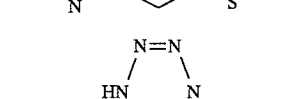 | CH₃ |  |
| covalent bond | 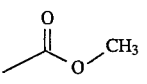 | CH₃ | 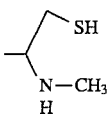 |
| covalent bond | 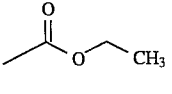 | CH₃ | 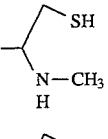 |
| covalent bond | 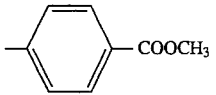 | CH₃ | 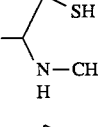 |
| covalent bond | 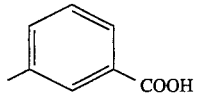 | CH₃ | 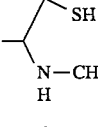 |
| covalent bond | 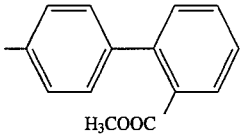 | CH₃ | 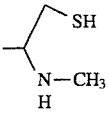 |

TABLE II'-continued

| R¹ and R² | W | R²⁴ | R²⁵ |
|---|---|---|---|
| covalent bond | 4-(2-COOCH₃-phenyl)phenyl | CH₃ | CH₂SH, CH(NHCH₃)CH₃ |
| covalent bond | 4-COOH-cyclohexyl | CH₃ | CH₂SH, CH(NHCH₃)CH₃ |
| covalent bond | 4-(1H-tetrazol-5-yl)phenyl | CH₃ | CH₂SH, CH(NHCH₃)CH₃ |
| covalent bond | 3-(1H-tetrazol-5-yl)phenyl | CH₃ | CH₂SH, CH(NHCH₃)CH₃ |
| covalent bond | 6-methyl-2-(2-(methylthio)ethyl)pyridin-? | CH₃ | CH₂SH, CH(NHCH₃)CH₃ |
| covalent bond | 1H-tetrazol-5-yl | CH₃ | CH₂SH, CH(NHCH₃)CH₃ |
| phenyl | CH₂COOCH₃ | CH₃ | CH₂SSC₂H₅, CH(NHCH₃)CH₃ |
| phenyl | CH₂COOC₂H₅ | CH₃ | CH₂SSC₂H₅, CH(NHCH₃)CH₃ |
| phenyl | 4-COOCH₃-phenyl | CH₃ | CH₂SSC₂H₅, CH(NHCH₃)CH₃ |
| phenyl | 3-COOH-phenyl | CH₃ | CH₂SSC₂H₅, CH(NHCH₃)CH₃ |
| phenyl | 4-(2-COOCH₃-phenyl)phenyl | CH₃ | CH₂SSC₂H₅, CH(NHCH₃)CH₃ |
| phenyl | 4-(2-COOCH₃-phenyl)phenyl | CH₃ | CH₂SSC₂H₅, CH(NHCH₃)CH₃ |

TABLE II'-continued
| $R^1$ and $R^2$ | W | $R^{24}$ | $R^{25}$ |
|---|---|---|---|
| covalent bond | 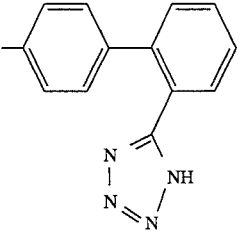 | $CH_3$ | 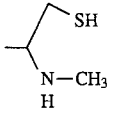 |
| covalent bond | 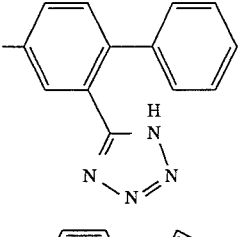 | $CH_3$ | 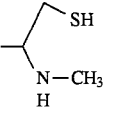 |
| covalent bond | 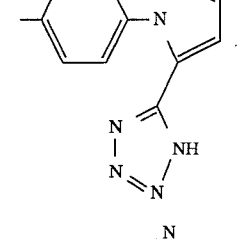 | $CH_3$ | 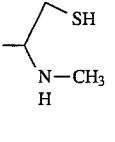 |
| covalent bond | 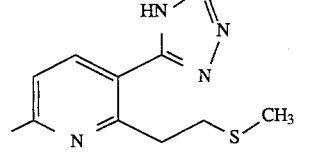 | $CH_3$ | 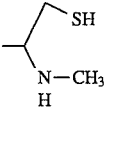 |
| covalent bond | 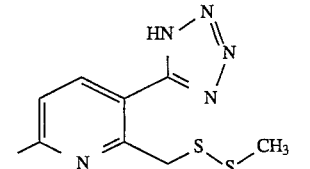 | $CH_3$ | 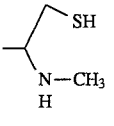 |
| covalent bond | 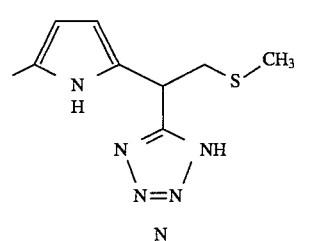 | $CH_3$ | 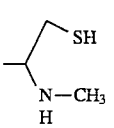 |
| covalent bond | 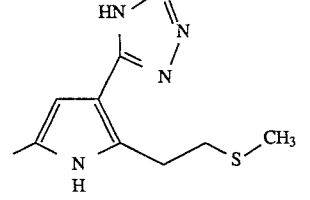 | $CH_3$ | 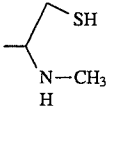 |

TABLE II'-continued

| R¹ and R² | W | R²⁴ | R²⁵ |
|---|---|---|---|
| covalent bond | (5-methyl-thiophene with CH(CH₂SCH₃) substituted with tetrazole) | CH₃ | CH₂SH, CH(NH-CH₃) |
| covalent bond | (thiophene with tetrazole and CH₂CH₂SCH₃ substituents, 5-methyl) | CH₃ | CH₂SH, CH(NH-CH₃) |
| covalent bond | (5-methyl-furan-2-yl-CH₂-S-CH₃) | CH₃ | CH₂SH, CH(NH-CH₃) |
| covalent bond | (6-methyl-pyridin-2-yl-CH₂-S-S-CH₃) | CH₃ | CH₂SH, CH(NH-CH₃) |
| phenyl | (cyclohexyl-COOH) | CH₃ | CH₂-S-S-CH₂CH₃, CH(NH-CH₃) |
| phenyl | (4-tetrazol-5-yl-phenyl) | CH₃ | CH₂-S-S-CH₂CH₃, CH(NH-CH₃) |
| phenyl | (3-tetrazol-5-yl-phenyl) | CH₃ | CH₂-S-S-CH₂CH₃, CH(NH-CH₃) |
| phenyl | (biphenyl-2-tetrazol-5-yl) | CH₃ | CH₂-S-S-CH₂CH₃, CH(NH-CH₃) |
| phenyl | (biphenyl with tetrazole) | CH₃ | CH₂-S-S-CH₂CH₃, CH(NH-CH₃) |

TABLE II'-continued
| R¹ and R² | W | R²⁴ | R²⁵ |
|---|---|---|---|
|  | 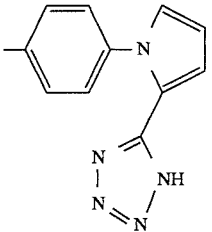 | CH₃ | 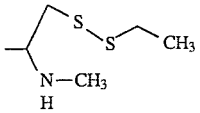 |
|  | 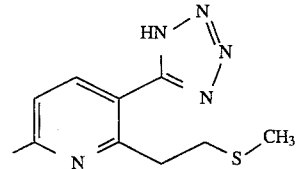 | CH₃ | 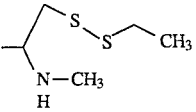 |
| 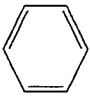 | 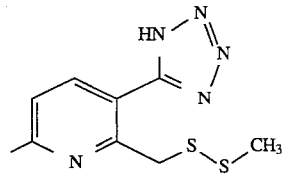 | CH₃ | 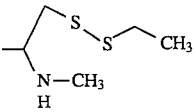 |
|  | 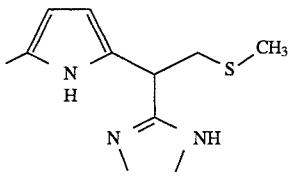 | CH₃ | 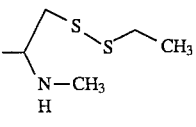 |
|  | 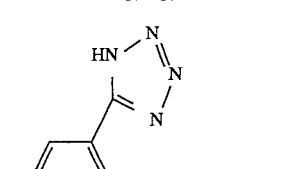 | CH₃ | 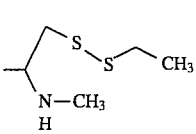 |
|  | 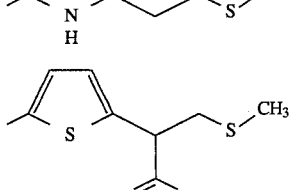 | CH₃ | 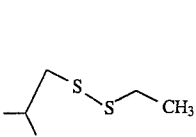 |
|  | 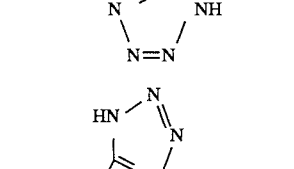 | CH₃ | 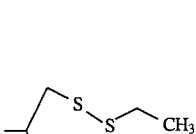 |
|  | 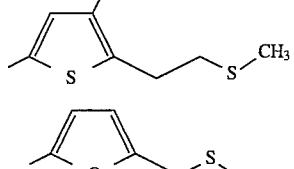 | CH₃ | 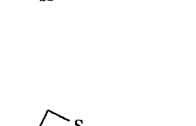 |

TABLE II'-continued
| R¹ and R² | W | R²⁴ | R²⁵ |
|---|---|---|---|
|  | 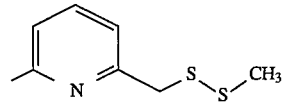 | CH₃ | 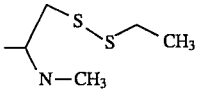 |
|  | 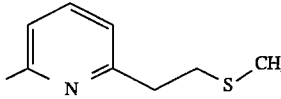 | CH₃ | 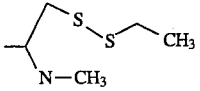 |
|  | 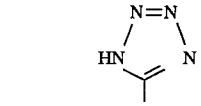 | CH₃ | 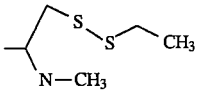 |
| 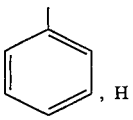, H | 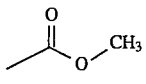 | CH₃ | 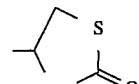 |
| 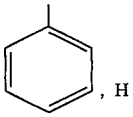, H | 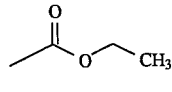 | CH₃ | 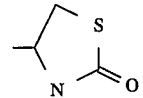 |
| 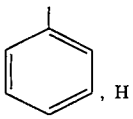, H | 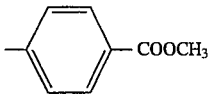 | CH₃ | 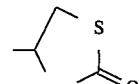 |
| 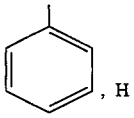, H | 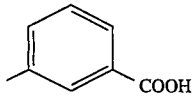 | CH₃ | 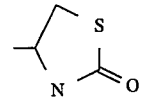 |
| 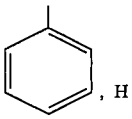, H | 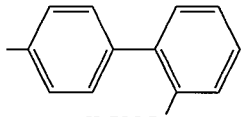 | CH₃ | 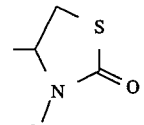 |
| 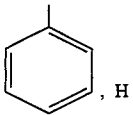, H | 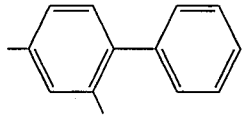 | CH₃ | 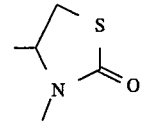 |
| 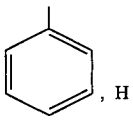, H |  | CH₃ | 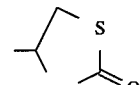 |
| 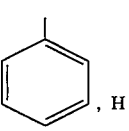, H |  | CH₃ | 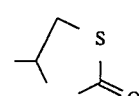 |

TABLE II'-continued
| R¹ and R² | W | R²⁴ | R²⁵ |
|---|---|---|---|
| 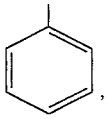, H | 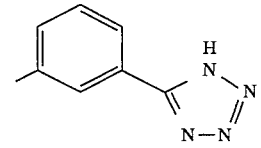 | CH₃ | 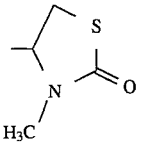 |
| 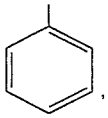, H | 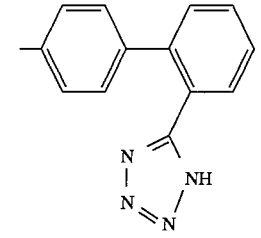 | CH₃ | 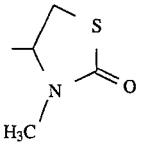 |
| 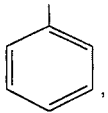, H | 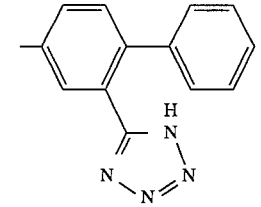 | CH₃ | 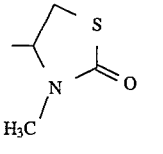 |
| 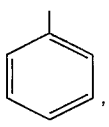, H | 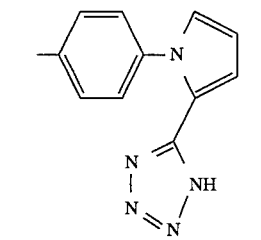 | CH₃ | 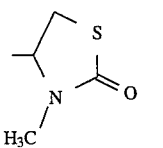 |
| 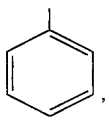, H | 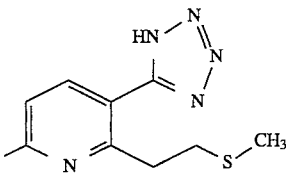 | CH₃ | 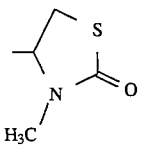 |
| 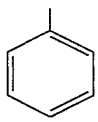, H | 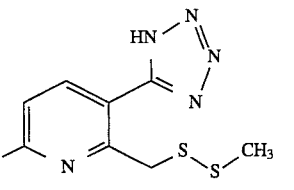 | CH₃ | 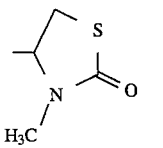 |
| 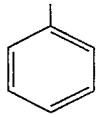, H | 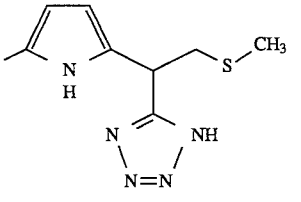 | CH₃ | 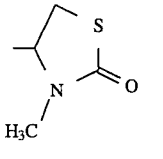 |

TABLE II'-continued
| R¹ and R² | W | R²⁴ | R²⁵ |
|---|---|---|---|
| 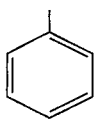, H | 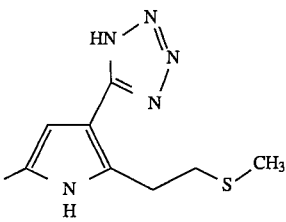 | CH₃ | 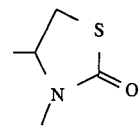 |
| 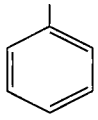, H | 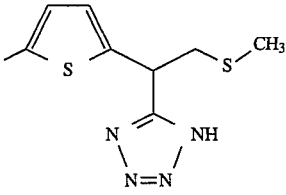 | CH₃ | 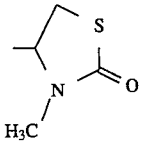 |
| 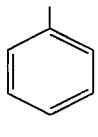, H | 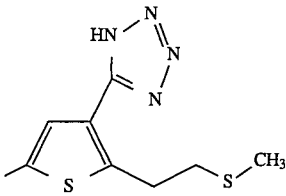 | CH₃ | 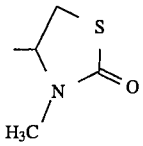 |
| 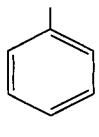, H | 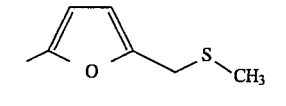 | CH₃ | 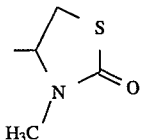 |
| 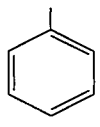, H | 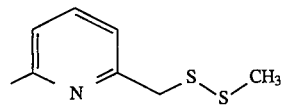 | CH₃ | 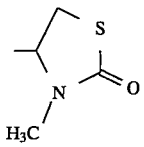 |
| 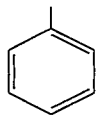, H | 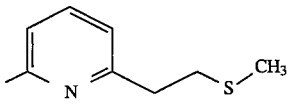 | CH₃ | 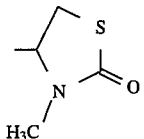 |
| 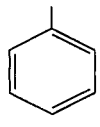, H | 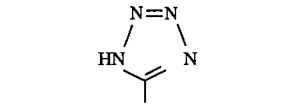 | CH₃ | 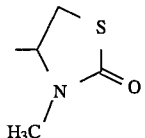 |
An alternative preferred embodiment of the invention comprises a compound capable of inhibiting farnesyl:protein transferase at a concentration equal to or lower than that of the tetrapeptide CVFM represented by Formula III'

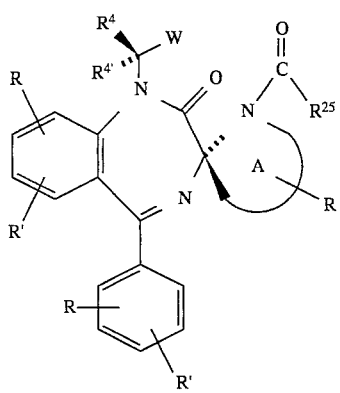

III'

where the substituents R and R' are as defined above, $R^4$ and $R^{4'}$ are hydrogen or lower alkyl, and W, $R^{25}$ and are selected according to Table III'.

TABLE III'

| W | (N-A-R ring) | $R^{25}$ |
|---|---|---|
| -C(O)-O-CH₃ | pyrrolidinyl | -CH(SH)-NH₂ (CH₂SH, CHNH₂) |
| -C(O)-O-CH₂CH₃ | pyrrolidinyl | -CH(SH)-NH₂ |
| -C₆H₄-COOCH₃ | pyrrolidinyl | -CH(SH)-NH₂ |
| -C₆H₄-COOH | pyrrolidinyl | -CH(SH)-NH₂ |
| biphenyl-COOCH₃ (H₃COOC) | pyrrolidinyl | -CH(SH)-NH₂ |
| biphenyl-COOCH₃ | pyrrolidinyl | -CH(SH)-NH₂ |
| cyclohexyl-COOH | pyrrolidinyl | -CH(SH)-NH₂ |
| -C₆H₄-(tetrazole) | pyrrolidinyl | -CH(SH)-NH₂ |

TABLE III'-continued
| W | 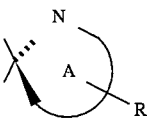 | R25 |
|---|---|---|
| 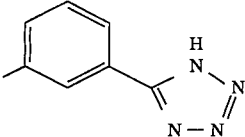 | 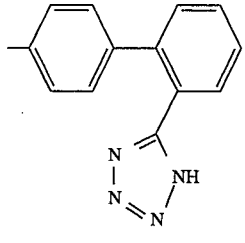 | 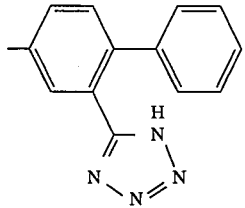 |
|  |  | 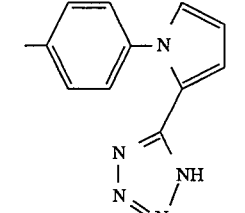 |
|  |  | 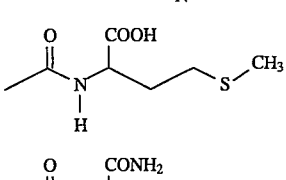 |
|  |  | 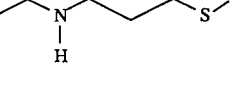 |
|  |  | 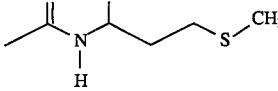 |
|  |  | 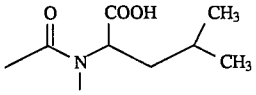 |
|  | | |
|  | | |
| 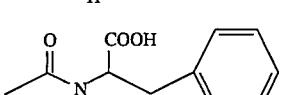 | | |
|  | | |
|  | | |

TABLE III'-continued

TABLE III'-continued
| W | 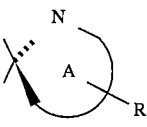 | $R^{25}$ |
|---|---|---|
| 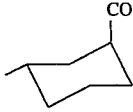 |  | 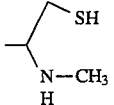 |
| 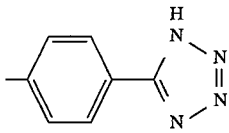 |  | 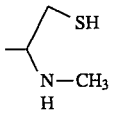 |
| 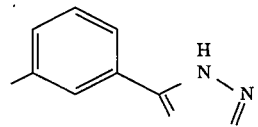 |  | 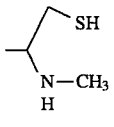 |
| 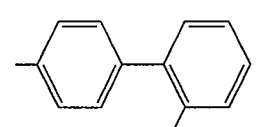 | 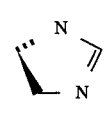 | 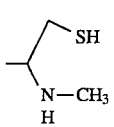 |
| 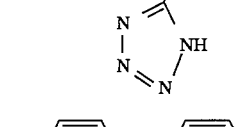 |  |  |
| 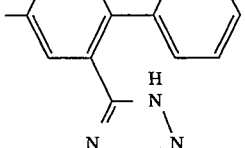 |  | 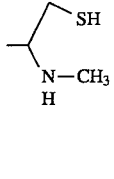 |
| 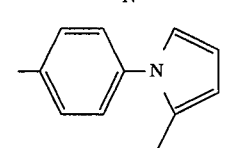 |  | 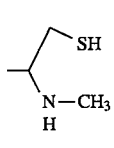 |
| 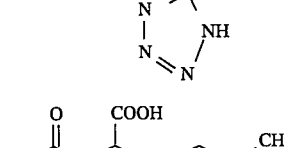 | 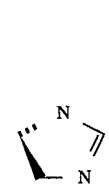 | 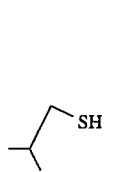 |
| 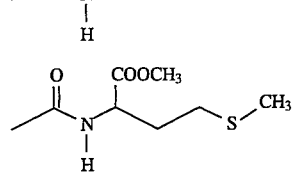 |  | 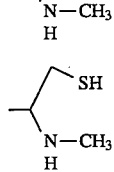 |

TABLE III'-continued

TABLE III'-continued
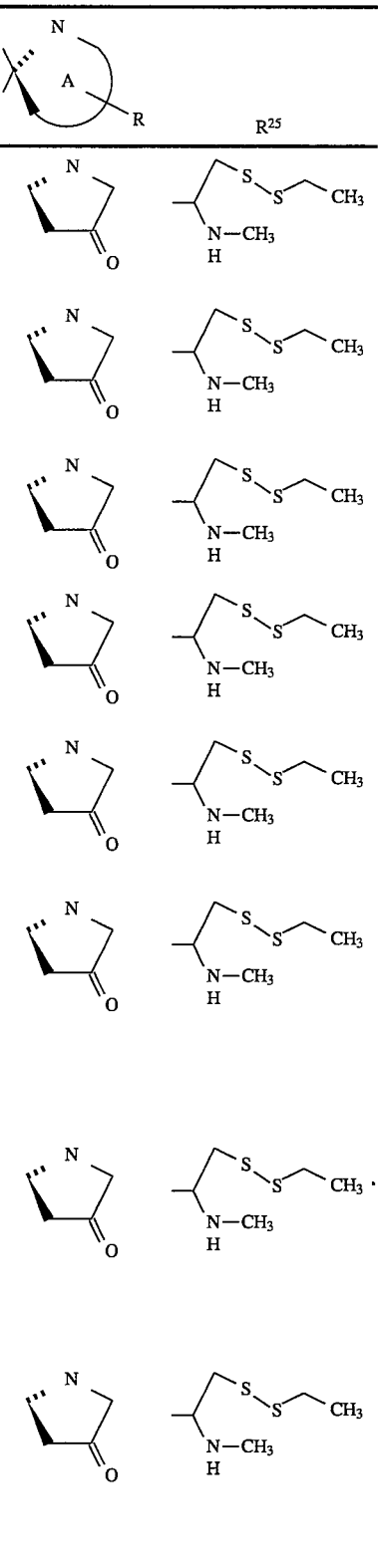

TABLE III'-continued

TABLE III'-continued
| W | 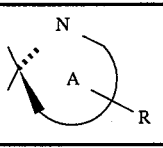 | R25 |
|---|---|---|
| 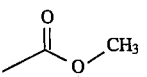 |  | 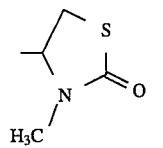 |
| 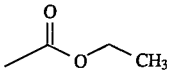 |  | 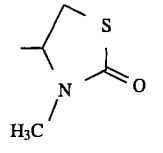 |
| 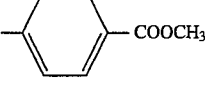 |  | 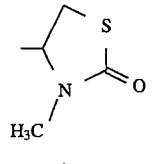 |
| 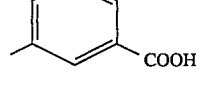 |  | 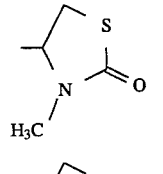 |
| 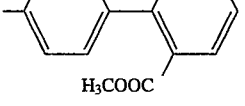 |  | 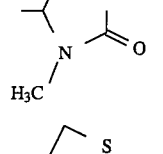 |
| 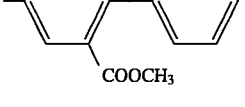 |  | 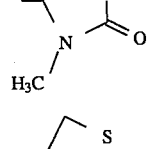 |
| 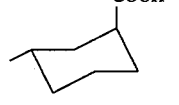 |  | 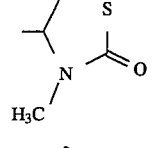 |
| 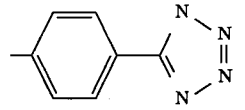 |  | 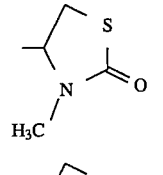 |
| 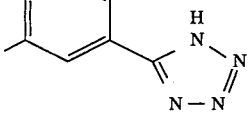 |  | 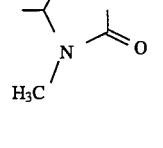 |

TABLE III'-continued

| W | (ring with N, A, R) | R²⁵ |
|---|---|---|

TABLE III'-continued

| W | (N, A, R) | R²⁵ |
|---|---|---|

[Table rows contain chemical structures]

An alternative preferred embodiment of the invention comprises a compound capable of inhibiting farnesyl:protein transferase at a concentration equal to or lower than that of the tetrapeptide CVFM represented by Formula IV'

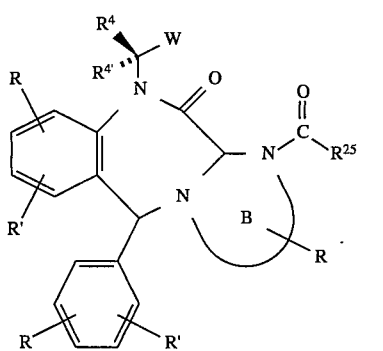

IV' where the substituents R and R' are as defined above, R⁴ and R⁴' are hydrogen or lower alkyl, and W, R²⁵ and

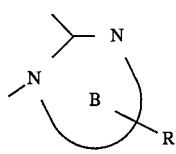

are selected according to Table IV'.

TABLE IV'

| W | (B with R) | R²⁵ |
|---|---|---|
| methyl acetate | N-CH-N-CH₂-C(O)- ring | CH(SH)(NH₂)-CH₂ |
| ethyl acetate | N-CH-N-CH₂-C(O)- ring | CH(SH)(NH₂)-CH₂ |
| 4-(COOCH₃)-phenyl | N-CH-N-CH₂-C(O)- ring | CH(SH)(NH₂)-CH₂ |
| 3-(COOH)-phenyl | N-CH-N-CH₂-C(O)- ring | CH(SH)(NH₂)-CH₂ |
| 2'-(COOCH₃)-biphenyl-4-yl | N-CH-N-CH₂-C(O)- ring | CH(SH)(NH₂)-CH₂ |
| 2'-(COOCH₃)-biphenyl-3-yl | N-CH-N-CH₂-C(O)- ring | CH(SH)(NH₂)-CH₂ |
| 4-(COOH)-cyclohexyl | N-CH-N-CH₂-C(O)- ring | CH(SH)(NH₂)-CH₂ |
| 4-(tetrazol-5-yl)phenyl | N-CH-N-CH₂-C(O)- ring | CH(SH)(NH₂)-CH₂ |
| 3-(tetrazol-5-yl)phenyl | N-CH-N-CH₂-C(O)- ring | CH(SH)(NH₂)-CH₂ |

TABLE IV'-continued
| W | B R | R²⁵ |
|---|---|---|
| 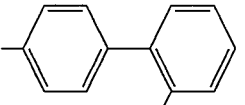 | 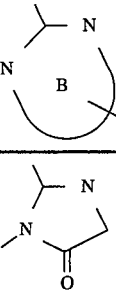 | 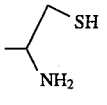 |
| 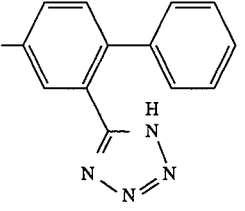 | 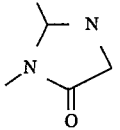 | 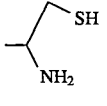 |
| 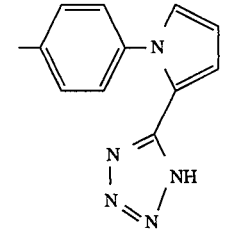 | 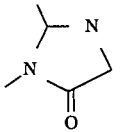 | 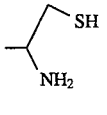 |
| 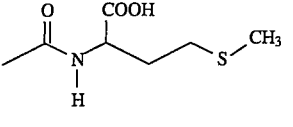 | 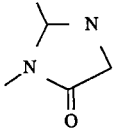 | 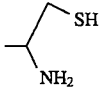 |
| 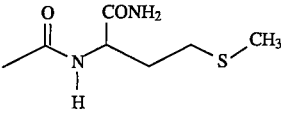 | 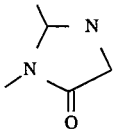 | 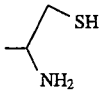 |
| 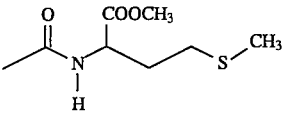 | 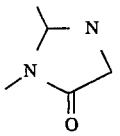 | 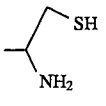 |
| 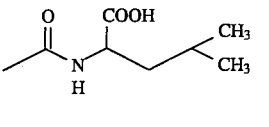 | 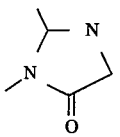 | 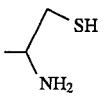 |
| 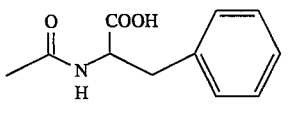 | 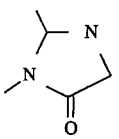 | 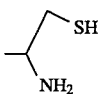 |

TABLE IV'-continued

TABLE IV'-continued
| W | 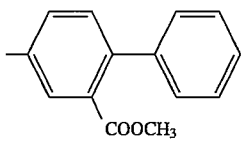 R | R²⁵ |
|---|---|---|
| 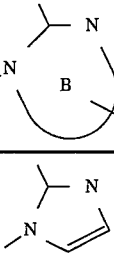 | 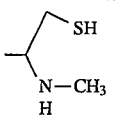 | 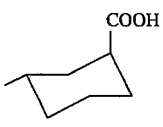 |
| 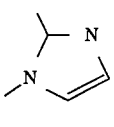 | 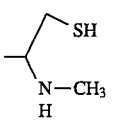 | 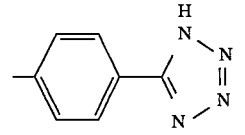 |
| 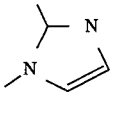 | 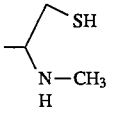 | 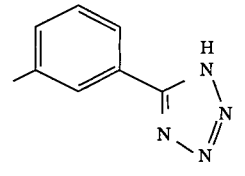 |
| 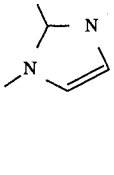 | 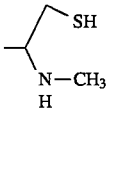 | 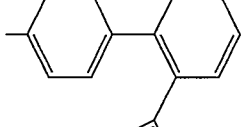 |
| 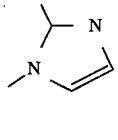 | 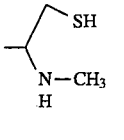 | 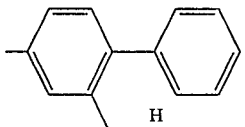 |
| 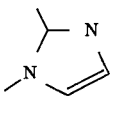 | 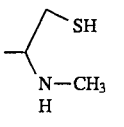 | 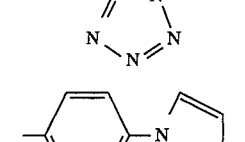 |
| 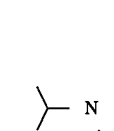 | 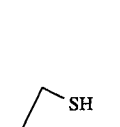 | 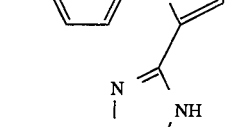 |
| 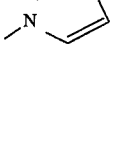 | 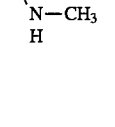 | 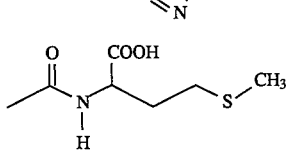 |

TABLE IV'-continued

| W | (B with R) | R²⁵ |
|---|---|---|

TABLE IV'-continued

TABLE IV'-continued

TABLE IV'-continued

TABLE IV'-continued
| W | 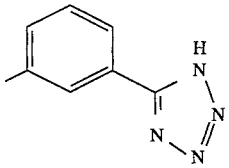 | R25 |
|---|---|---|

TABLE IV'-continued

| W | [ring with B, R] | R25 |
|---|---|---|

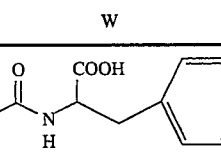

An alternative preferred embodiment of the invention comprises a compound capable of inhibiting farnesyl:protein transferase at a concentration equal to or lower than that of the tetrapeptide CVFM represented by Formula V'

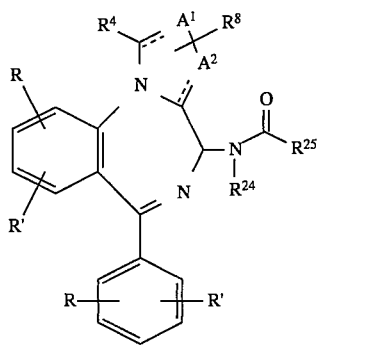

where the substituents R and R' are halo or perfluro-loweralkyl, $R^4$ is hydrogen or lower alkyl, and $R^{24}$, $R^{25}$ and

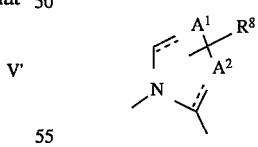

are selected according to Table V'.

TABLE V'

| | $R^8$ | $R^{24}$ | $R^{25}$ |
|---|---|---|---|
| N-methylimidazole with R⁸ | CH₂-C(CH₂-)(COOH)-phenyl | CH₃ | CH(CH₂SH)(NH₂) |
| N-methylimidazole with R⁸ | CH₂-C(CH₂-)(tetrazol-5-yl)-phenyl | CH₃ | CH(CH₂SH)(NH₂) |
| N-methylimidazole with R⁸ | CH(CH₂-)(COOH)-(CH₂)₂-SCH₃ | CH₃ | CH(CH₂SH)(NH₂) |
| N-methylimidazole with R⁸ | CH(CH₂-)(tetrazol-5-yl)-(CH₂)₂-SCH₃ | CH₃ | CH(CH₂SH)(NH₂) |
| N-methylimidazole with R⁸ | CH₂-C(CH₂-)(COOCH₃)-phenyl | CH₃ | CH(CH₂SH)(NH₂) |
| N-methylimidazole with R⁸ | CH(CH₂-)(COOCH₃)-(CH₂)₂-SCH₃ | CH₃ | CH(CH₂SH)(NH₂) |
| N-methylimidazole with R⁸ | CH₂-C(CH₂-)(COOC₂H₅)-phenyl | CH₃ | CH(CH₂SH)(NH₂) |

TABLE V'-continued
| | R⁸ | R²⁴ | R²⁵ |
|---|---|---|---|
| 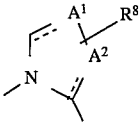 | 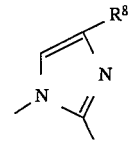 | CH₃ | 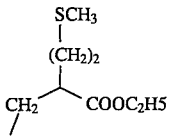 |
| 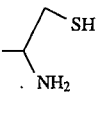 | 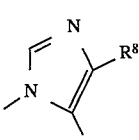 | CH₃ | 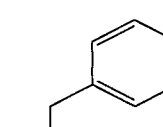 |
| 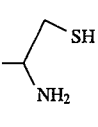 | 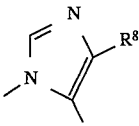 | CH₃ | 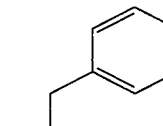 |
| 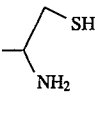 | 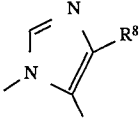 | CH₃ | 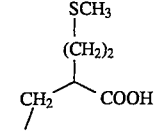 |
| 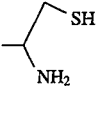 | 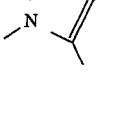 | CH₃ | 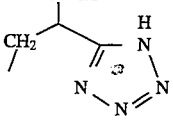 |
|  | 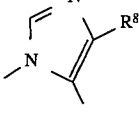 | CH₃ | 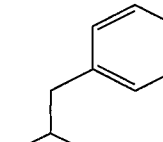 |
| 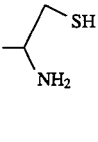 | 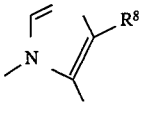 | CH₃ | 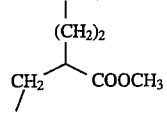 |

TABLE V'-continued
| | R⁸ | R²⁴ | R²⁵ |
|---|---|---|---|
| 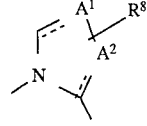 | 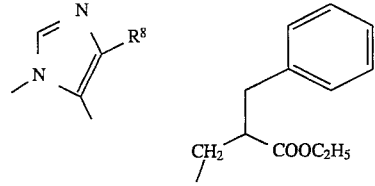 | CH₃ | 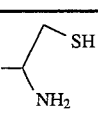 |
| 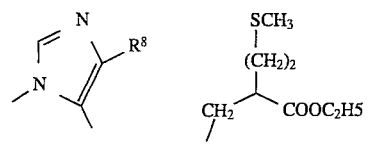 | 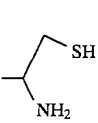 | CH₃ | 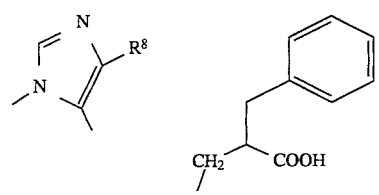 |
| 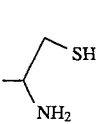 | 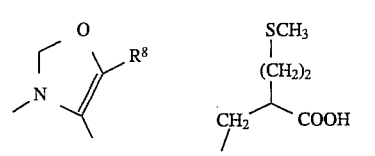 | CH₃ | 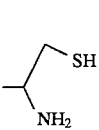 |
| 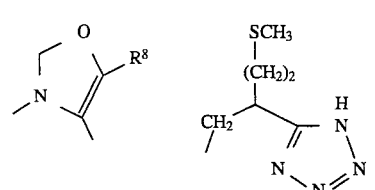 | 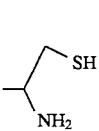 | CH₃ | 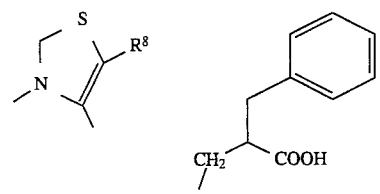 |
| 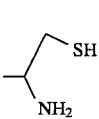 | 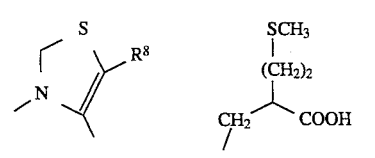 | CH₃ | 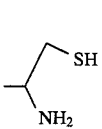 |
| 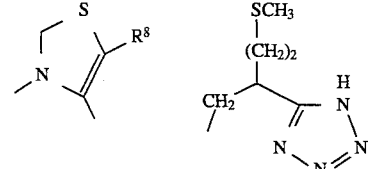 | 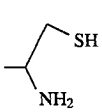 | CH₃ | |

TABLE V'-continued

| | R[8] | R[24] | R[25] |
|---|---|---|---|

TABLE V'-continued
| | R[8] | R[24] | R[25] |
|---|---|---|---|
| 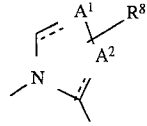 | 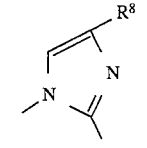 SCH₃, (CH₂)₂, CH₂, COOC₂H₅ | CH₃ | 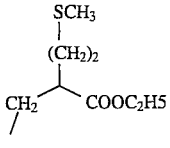 SH, N—CH₃, H |
| 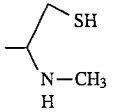 | 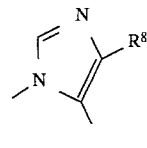 CH₂, COOH | CH₃ | 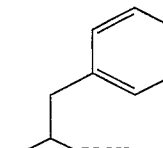 SH, N—CH₃, H |
| 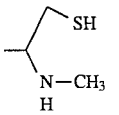 | 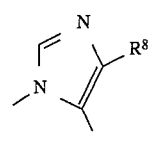 CH₂, tetrazole | CH₃ | 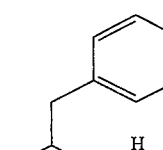 SH, N—CH₃, H |
| 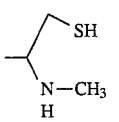 | 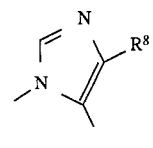 SCH₃, (CH₂)₂, CH₂, COOH | CH₃ | 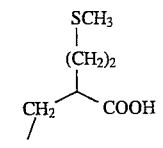 SH, N—CH₃, H |
| 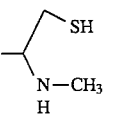 | 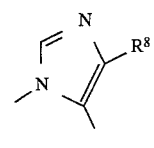 SCH₃, (CH₂)₂, CH₂, tetrazole | CH₃ | 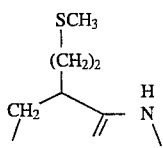 SH, N—CH₃, H |
| 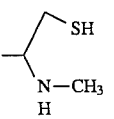 | 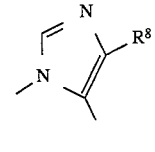 CH₂, COOCH₃ | CH₃ | 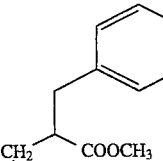 SH, N—CH₃, H |
| 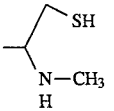 | 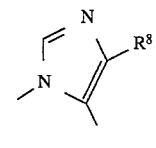 SCH₃, (CH₂)₂, CH₂, COOCH₃ | CH₃ | 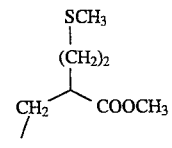 SH, N—CH₃, H |

TABLE V'-continued

| | R⁸ | R²⁴ | R²⁵ |
|---|---|---|---|
| imidazole-N-CH₃ | CH₂-CH(CH₂-C₆H₅)-COOC₂H₅ | CH₃ | CH₂-CH(NH-CH₃)-SH |
| imidazole-N-CH₃ | CH₂-CH(CH₂-CH₂-SCH₃)-COOC₂H₅ | CH₃ | CH₂-CH(NH-CH₃)-SH |
| oxazole-N-CH₃ | CH₂-CH(CH₂-C₆H₅)-COOH | CH₃ | CH₂-CH(NH-CH₃)-SH |
| oxazole-N-CH₃ | CH₂-CH(CH₂-CH₂-SCH₃)-COOH | CH₃ | CH₂-CH(NH-CH₃)-SH |
| oxazole-N-CH₃ | CH₂-CH(CH₂-CH₂-SCH₃)-CH₂-tetrazole | CH₃ | CH₂-CH(NH-CH₃)-SH |
| thiazole-N-CH₃ | CH₂-CH(CH₂-C₆H₅)-COOH | CH₃ | CH₂-CH(NH-CH₃)-SH |
| thiazole-N-CH₃ | CH₂-CH(CH₂-CH₂-SCH₃)-COOH | CH₃ | CH₂-CH(NH-CH₃)-SH |
| thiazole-N-CH₃ | CH₂-CH(CH₂-CH₂-SCH₃)-CH₂-tetrazole | CH₃ | CH₂-CH(NH-CH₃)-SH |

TABLE V'-continued
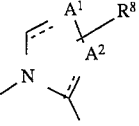
| | $R^8$ | $R^{24}$ | $R^{25}$ |
|---|---|---|---|
| 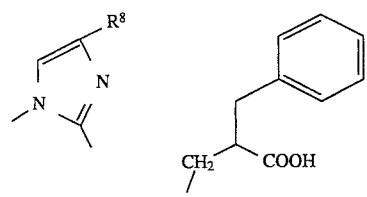 | 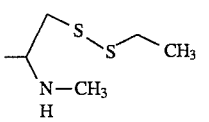 | CH$_3$ | 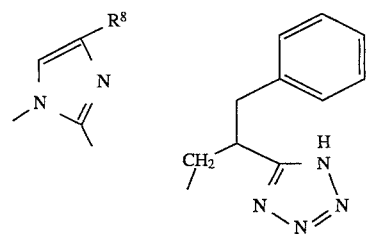 |
| 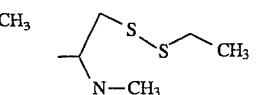 | 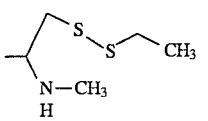 | CH$_3$ | 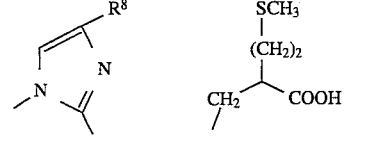 |
| 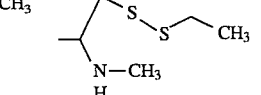 | 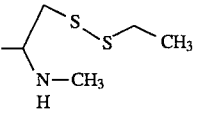 | CH$_3$ | 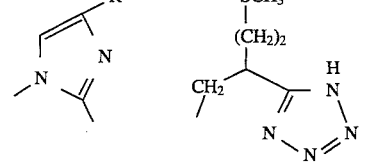 |
| 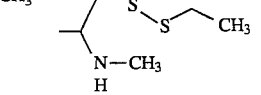 | 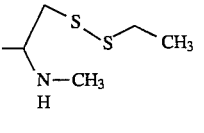 | CH$_3$ | 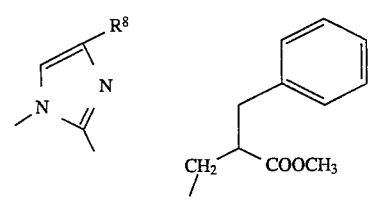 |
| 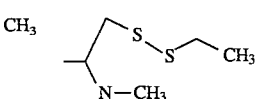 | 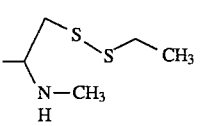 | CH$_3$ | 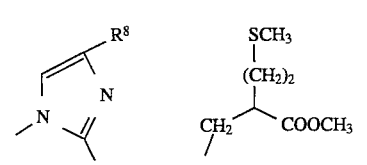 |
| 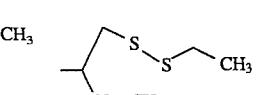 | 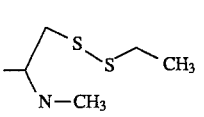 | CH$_3$ | 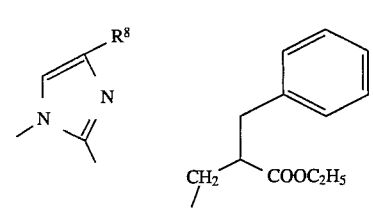 |
| 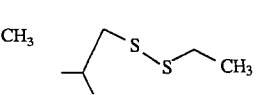 | 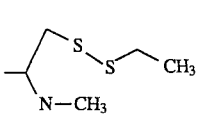 | CH$_3$ | |

TABLE V'-continued

| | R⁸ | R²⁴ | R²⁵ |
|---|---|---|---|
| imidazole-R⁸ | SCH₃-(CH₂)₂-CH(CH₂-)-COOC₂H₅ | CH₃ | CH(CH₃)-CH₂-S-S-CH₂-CH₃ with NH-CH₃ |
| imidazole-R⁸ | phenyl-CH₂-CH(CH₂-)-COOH | CH₃ | CH(CH₃)-CH₂-S-S-CH₂-CH₃ with NH-CH₃ |
| imidazole-R⁸ | phenyl-CH₂-CH(CH₂-)-tetrazole | CH₃ | CH(CH₃)-CH₂-S-S-CH₂-CH₃ with NH-CH₃ |
| imidazole-R⁸ | SCH₃-(CH₂)₂-CH(CH₂-)-COOH | CH₃ | CH(CH₃)-CH₂-S-S-CH₂-CH₃ with NH-CH₃ |
| imidazole-R⁸ | SCH₃-(CH₂)₂-CH(CH₂-)-tetrazole | CH₃ | CH(CH₃)-CH₂-S-S-CH₂-CH₃ with NH-CH₃ |
| imidazole-R⁸ | phenyl-CH₂-CH(CH₂-)-COOCH₃ | CH₃ | CH(CH₃)-CH₂-S-S-CH₂-CH₃ with NH-CH₃ |
| imidazole-R⁸ | SCH₃-(CH₂)₂-CH(CH₂-)-COOCH₃ | CH₃ | CH(CH₃)-CH₂-S-S-CH₂-CH₃ with NH-CH₃ |

TABLE V'-continued

| | R⁸ | R²⁴ | R²⁵ |
|---|---|---|---|
| (imidazole-N-CH₂) | CH₂-phenyl, CH(CH₂-)COOC₂H₅ | CH₃ | CH(CH₃)-CH₂-S-S-CH₂-CH₃, NH-CH₃ |
| (imidazole-N-CH₂) | CH₂-CH(CH₂CH₂SCH₃)-COOC₂H₅ | CH₃ | CH(CH₃)-CH₂-S-S-CH₂-CH₃, NH-CH₃ |
| (oxazole-N-CH₂) | CH₂-phenyl, CH(CH₂-)COOH | CH₃ | CH(CH₃)-CH₂-S-S-CH₂-CH₃, NH-CH₃ |
| (oxazole-N-CH₂) | CH₂-CH(CH₂CH₂SCH₃)-COOH | CH₃ | CH(CH₃)-CH₂-S-S-CH₂-CH₃, NH-CH₃ |
| (oxazole-N-CH₂) | CH₂-CH(CH₂CH₂SCH₃)-tetrazole | CH₃ | CH(CH₃)-CH₂-S-S-CH₂-CH₃, NH-CH₃ |
| (thiazole-N-CH₂) | CH₂-phenyl, CH(CH₂-)COOH | CH₃ | CH(CH₃)-CH₂-S-S-CH₂-CH₃, NH-CH₃ |
| (thiazole-N-CH₂) | CH₂-CH(CH₂CH₂SCH₃)-COOH | CH₃ | CH(CH₃)-CH₂-S-S-CH₂-CH₃, NH-CH₃ |
| (thiazole-N-CH₂) | CH₂-CH(CH₂CH₂SCH₃)-tetrazole | CH₃ | CH(CH₃)-CH₂-S-S-CH₂-CH₃, NH-CH₃ |

TABLE V'-continued
| | R8 | R24 | R25 |
|---|---|---|---|
| 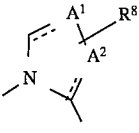 | 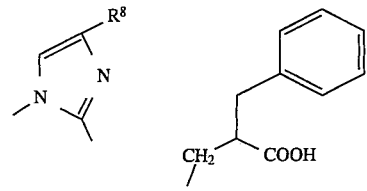 | CH3 | 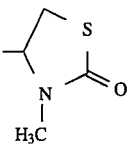 |
| 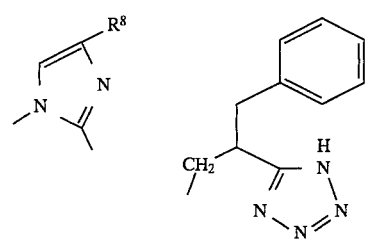 | 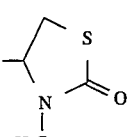 | CH3 | 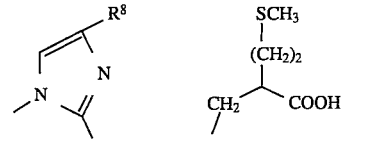 |
| 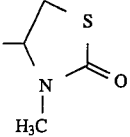 | 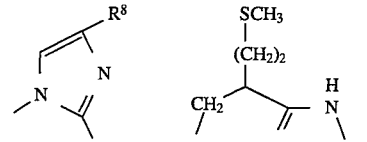 | CH3 | 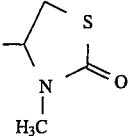 |
| 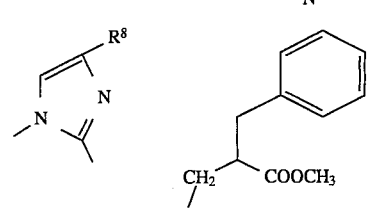 | 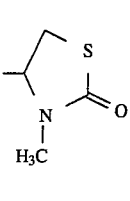 | CH3 | 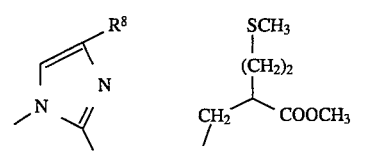 |
| 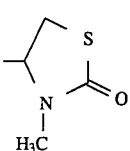 | 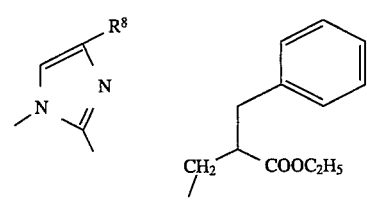 | CH3 | 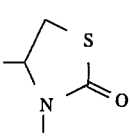 |

TABLE V'-continued
| | R⁸ | R²⁴ | R²⁵ |
|---|---|---|---|
| 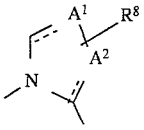 | 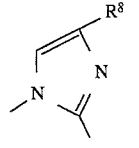 | CH₃ | 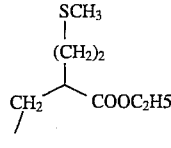 |
| 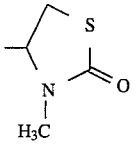 | 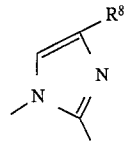 | CH₃ | 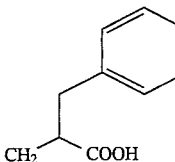 |
| 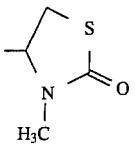 | 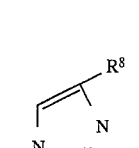 | CH₃ | 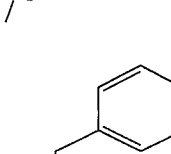 |
| 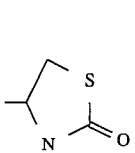 | 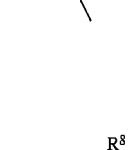 | CH₃ | 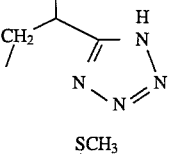 |
| 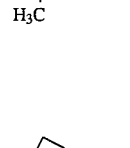 | 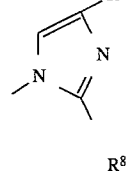 | CH₃ | 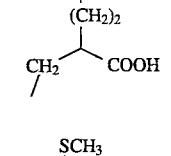 |
| 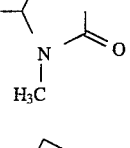 | 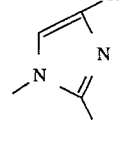 | CH₃ | 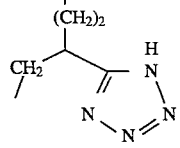 |
| 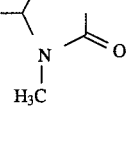 | 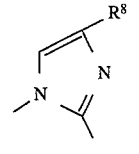 | CH₃ | 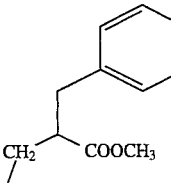 |

TABLE V'-continued
| | $R^8$ | $R^{24}$ | $R^{25}$ |
|---|---|---|---|
| 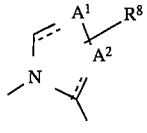 | 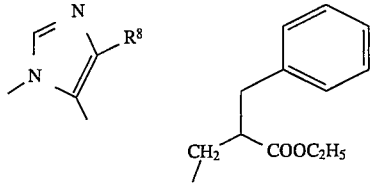 | $CH_3$ | 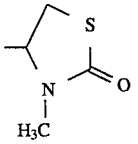 |
|  | 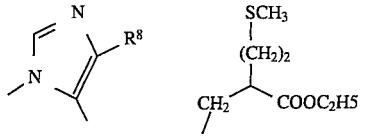 | $CH_3$ | 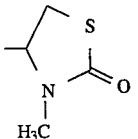 |
|  | 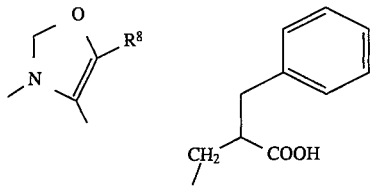 | $CH_3$ | 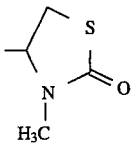 |
|  | 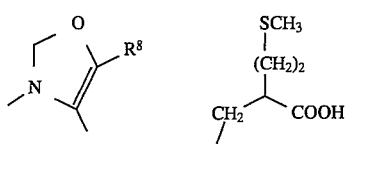 | $CH_3$ | 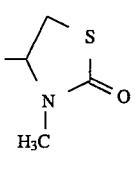 |
|  | 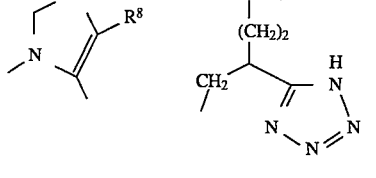 | $CH_3$ | 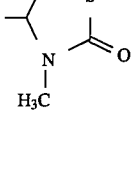 |
|  | 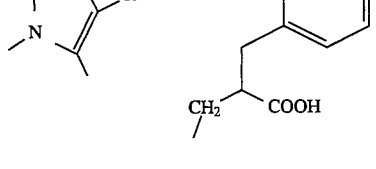 | $CH_3$ | 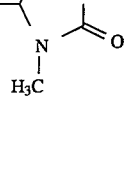 |
|  | 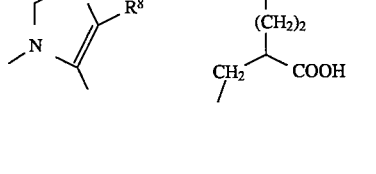 | $CH_3$ | 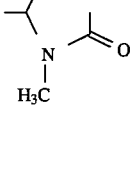 |

TABLE V'-continued

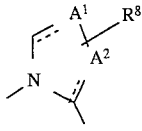

| | $R^8$ | $R^{24}$ | $R^{25}$ |
|---|---|---|---|
| 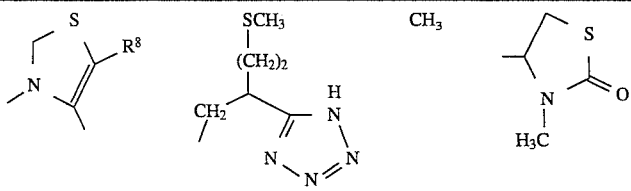 | 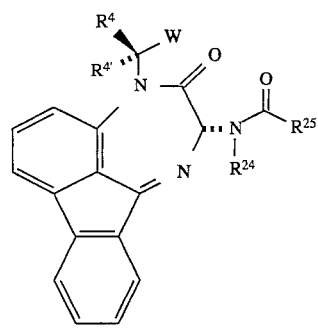 | CH$_3$ |  |

An alternative preferred embodiment of the invention comprises a compound capable of inhibiting farnesyl:protein transferase at a concentration equal to or lower than that of the tetrapeptide CVFM represented by Formula VII'

 VII' where the substituent $R^4$ and $R^{4'}$ are hydrogen or lower alkyl, and $R^{24}$, $R^{25}$ and W are selected according to Table VII.

TABLE VII'

| W | $R^{24}$ | $R^{25}$ |
|---|---|---|
|  | CH$_3$ |  |
|  | CH$_3$ | 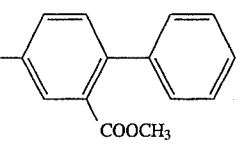 |
| 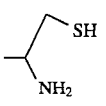 | CH$_3$ | 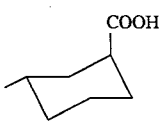 |
| 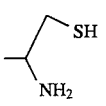 | CH$_3$ | 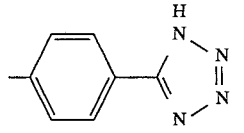 |
| 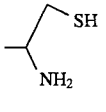 | CH$_3$ | 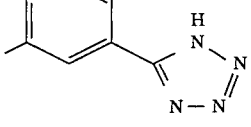 |

TABLE VII'-continued

| W | $R^{24}$ | $R^{25}$ |
|---|---|---|
| 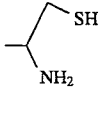 | CH$_3$ | 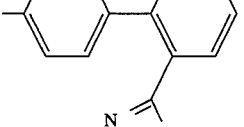 |
| 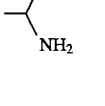 | CH$_3$ | 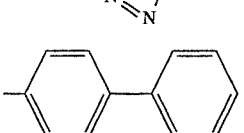 |
| 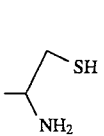 | CH$_3$ | 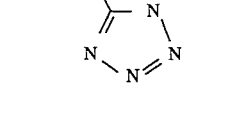 |
|  | CH$_3$ | |

TABLE VII'-continued

| W | R²⁴ | R²⁵ |
|---|---|---|
| (structures as shown) | CH₃ | various SH/NH₂ and SH/NHCH₃ groups |

TABLE VII'-continued
| W | R²⁴ | R²⁵ |
|---|---|---|
| 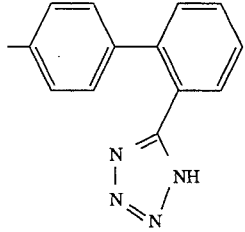 | CH₃ | 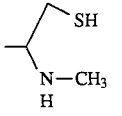 |
| 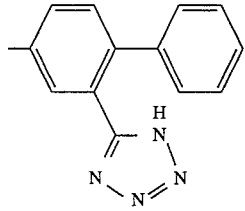 | CH₃ | 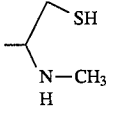 |
| 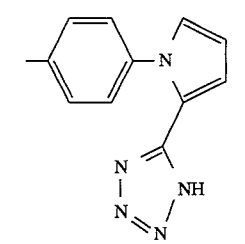 | CH₃ | 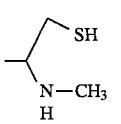 |
| 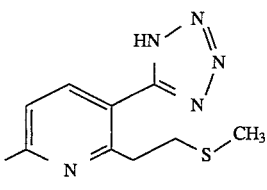 | CH₃ | 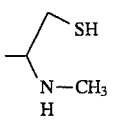 |
| 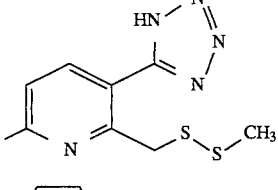 | CH₃ | 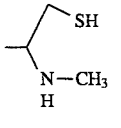 |
| 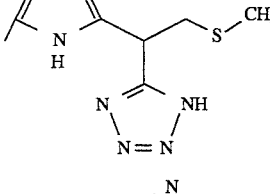 | CH₃ | 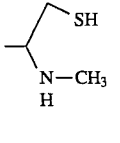 |
| 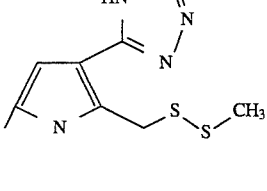 | CH₃ | 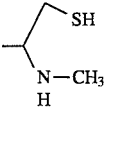 |
TABLE VII'-continued
| W | R²⁴ | R²⁵ |
|---|---|---|
| 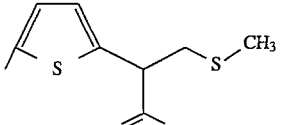 | CH₃ | 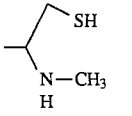 |
| 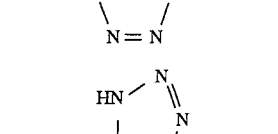 | CH₃ | 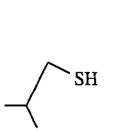 |
| 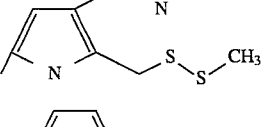 | CH₃ | 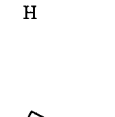 |
| 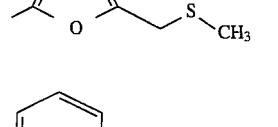 | CH₃ | 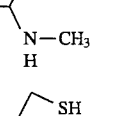 |
| 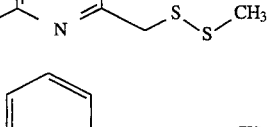 | CH₃ | 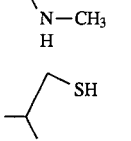 |
| 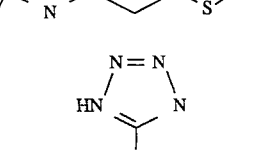 | CH₃ | 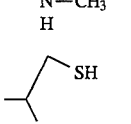 |
| 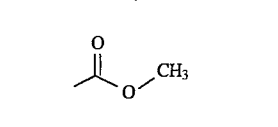 | CH₃ | 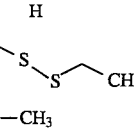 |
| 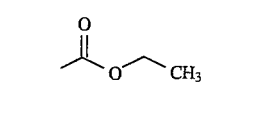 | CH₃ | 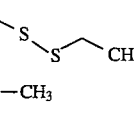 |
| 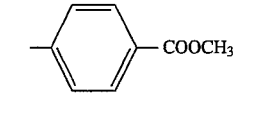 | CH₃ | 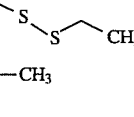 |
| 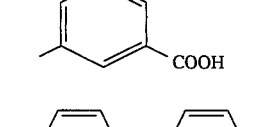 | CH₃ | 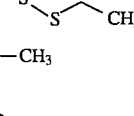 |
| 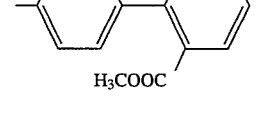 | CH₃ | 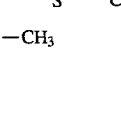 |

TABLE VII'-continued
| W | R²⁴ | R²⁵ |
|---|---|---|
|  | CH₃ |  |
|  | CH₃ |  |
| 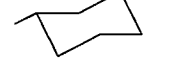 | CH₃ | 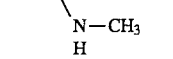 |
|  | CH₃ | 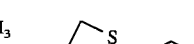 |
| 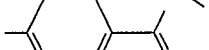 | CH₃ | 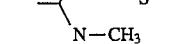 |
|  | CH₃ |  |
|  | CH₃ | 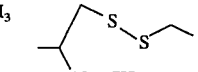 |
| 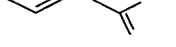 | CH₃ | 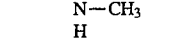 |
|  | CH₃ | 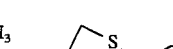 |
| 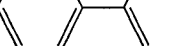 | CH₃ | 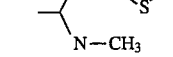 |
| 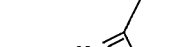 | CH₃ | 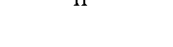 |
| 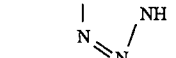 | CH₃ |  |
|  | CH₃ | 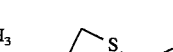 |
| 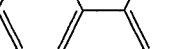 | CH₃ | 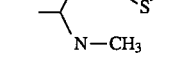 |
| 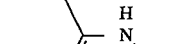 | CH₃ |  |
| 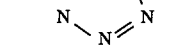 | CH₃ |  |
| 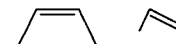 | CH₃ |  |
| 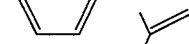 | CH₃ | 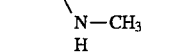 |
| 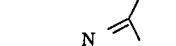 | CH₃ |  |
| 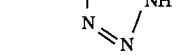 | CH₃ |  |

TABLE VII'-continued

TABLE VII'-continued

| W | R²⁴ | R²⁵ |
|---|---|---|
| (5-methylfuran-2-yl)methyl-S-CH₃ | CH₃ | N-methyl-thiazolidinone-methyl |
| (6-methylpyridin-2-yl)methyl-S-S-CH₃ | CH₃ | N-methyl-thiazolidinone-methyl |
| (6-methylpyridin-2-yl)ethyl-S-CH₃ | CH₃ | N-methyl-thiazolidinone-methyl |
| 5-methyl-tetrazole (N=N, HN-N) | CH₃ | N-methyl-thiazolidinone-methyl |

An alternative preferred embodiment of the invention comprises a compound capable of inhibiting farnesyl:protein transferase at a concentration equal to or lower than that of the tetrapeptide CVFM represented by Formula VIII'

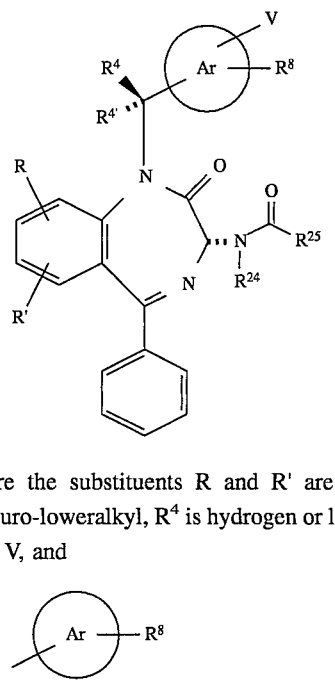

VIII' where the substituents R and R' are hydrogen, halo or perfluro-loweralkyl, R⁴ is hydrogen or lower alkyl, and $R^{24}$, $R^{25}$, V, and

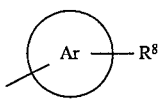

are selected according to Table VIII'.

TABLE VIII'

| V | Ar—R⁸ | R²⁴ | R²⁵ |
|---|---|---|---|
| COOH | meta-V phenyl | CH₃ | CH(SH)(CH₂)NH₂ |
| COOH | para-V phenyl | CH₃ | CH(SH)(CH₂)NH₂ |
| COOCH₃ | meta-V phenyl | CH₃ | CH(SH)(CH₂)NH₂ |
| COOCH₃ | para-V phenyl | CH₃ | CH(SH)(CH₂)NH₂ |
| COOC₂H₅ | meta-V phenyl | CH₃ | CH(SH)(CH₂)NH₂ |
| tetrazole (N=N, HN-N) | meta-V phenyl | CH₃ | CH(SH)(CH₂)NH₂ |

TABLE VIII'-continued

| V | Ar–R⁸ | R²⁴ | R²⁵ |
|---|---|---|---|
| 5-tetrazolyl (HN-N=N-N) | 3-methylphenyl-V | CH₃ | CH₂SH, CH-NH₂ |
| COOH | 4-methyl-2-(SCH₃-CH₂)phenyl-V | CH₃ | CH₂SH, CH-NH₂ |
| 5-tetrazolyl | 4-methyl-2-(SCH₃-CH₂)phenyl-V | CH₃ | CH₂SH, CH-NH₂ |
| COOCH₃ | 4-methyl-2-(SCH₃-CH₂)phenyl-V | CH₃ | CH₂SH, CH-NH₂ |
| COOH | 2-SH-4-methyl-imidazolyl | CH₃ | CH₂SH, CH-NH₂ |
| COOH | 5-methyl-furan-2-yl-V | CH₃ | CH₂SH, CH-NH₂ |
| COOH | 5-methyl-thiophen-2-yl-V | CH₃ | CH₂SH, CH-NH₂ |
| 5-tetrazolyl | 6-methyl-pyridin-2-yl-V | CH₃ | CH₂SH, CH-NH₂ |
| COOCH₃ | 2-methyl-4-(SCH₃-CH₂)-pyridin-6-yl-V | CH₃ | CH₂SH, CH-NH₂ |
| 5-tetrazolyl | 2-methyl-4-(SCH₃-CH₂)-pyridin-6-yl-V | CH₃ | CH₂SH, CH-NH₂ |
| COOH | 3-methylphenyl-V | CH₃ | CH₂-S-S-CH₂CH₃, CH-NH₂ |

TABLE VIII'-continued

| V | Ar—R⁸ | $R^{24}$ | $R^{25}$ |
|---|---|---|---|
| COOH | 1,4-phenylene (R⁸ at para, V at para) | $CH_3$ | $CH(NH_2)CH_2$-S-S-$CH_2CH_3$ |
| $COOCH_3$ | 1,3-phenylene | $CH_3$ | $CH(NH_2)CH_2$-S-S-$CH_2CH_3$ |
| $COOCH_3$ | 1,4-phenylene | $CH_3$ | $CH(NH_2)CH_2$-S-S-$CH_2CH_3$ |
| $COOCH_2H_5$ | 1,3-phenylene | $CH_3$ | $CH(NH_2)CH_2$-S-S-$CH_2CH_3$ |
| tetrazol-5-yl (HN-N=N-N=) | 1,3-phenylene | $CH_3$ | $CH(NH_2)CH_2$-S-S-$CH_2CH_3$ |
| tetrazol-5-yl | 1,3-phenylene | $CH_3$ | $CH(NH_2)CH_2$-S-S-$CH_2CH_3$ |
| COOH | phenyl with $SCH_3$ and V substituents | $CH_3$ | $CH(NH_2)CH_2$-S-S-$CH_2CH_3$ |
| tetrazol-5-yl | phenyl with $SCH_3$ and V substituents | $CH_3$ | $CH(NH_2)CH_2$-S-S-$CH_2CH_3$ |
| $COOCH_3$ | phenyl with $SCH_3$ and V substituents | $CH_3$ | $CH(NH_2)CH_2$-S-S-$CH_2CH_3$ |
| COOH | imidazole with $CH_2SH$ | $CH_3$ | $CH(NH_2)CH_2$-S-S-$CH_2CH_3$ |
| COOH | furan-2,5-diyl | $CH_3$ | $CH(NH_2)CH_2$-S-S-$CH_2CH_3$ |
| COOH | thiophene-2,5-diyl | $CH_3$ | $CH(NH_2)CH_2$-S-S-$CH_2CH_3$ |

TABLE VIII'-continued

| V | Ar–R⁸ | R²⁴ | R²⁵ |
|---|---|---|---|
| tetrazole (HN-N=N-N=) | 2,6-pyridinyl | CH₃ | CH₃-CH(NH₂)-CH₂-S-S-CH₂-CH₃ |
| COOCH₃ | 4-(SCH₃-CH₂)-2,6-pyridinyl | CH₃ | CH₃-CH(NH₂)-CH₂-S-S-CH₂-CH₃ |
| tetrazole | 4-(SCH₃-CH₂)-2,6-pyridinyl | CH₃ | CH₃-CH(NH₂)-CH₂-S-S-CH₂-CH₃ |
| COOH | 1,3-phenyl | CH₃ | CH₃-CH(NHCH₃)-CH₂-SH |
| COOH | 1,4-phenyl | CH₃ | CH₃-CH(NHCH₃)-CH₂-SH |
| COOCH₃ | 1,3-phenyl | CH₃ | CH₃-CH(NHCH₃)-CH₂-SH |
| COOCH₃ | 1,4-phenyl | CH₃ | CH₃-CH(NHCH₃)-CH₂-SH |
| COOC₂H₅ | 1,3-phenyl | CH₃ | CH₃-CH(NHCH₃)-CH₂-SH |
| tetrazole | 1,3-phenyl | CH₃ | CH₃-CH(NHCH₃)-CH₂-SH |
| tetrazole | 1,3-phenyl | CH₃ | CH₃-CH(NHCH₃)-CH₂-SH |
| COOH | 2-(SCH₃-CH₂)-1,4-phenyl | CH₃ | CH₃-CH(NHCH₃)-CH₂-SH |

TABLE VIII'-continued

| V | Ar—R⁸ | R²⁴ | R²⁵ |
|---|---|---|---|
| 5-tetrazolyl (HN-N=N-N=C-) | 4-methylphenyl with CH₂SCH₃ and V substituents | CH₃ | -CH₂-CH(SH)-N(H)-CH₃ (with CH₃ branch) |
| COOCH₃ | 4-methylphenyl with CH₂SCH₃ and V substituents | CH₃ | -CH₂-CH(SH)-N(H)-CH₃ |
| COOH | pyrimidine with CH₃ and CH₂SH | CH₃ | -CH₂-CH(SH)-N(H)-CH₃ |
| COOH | 5-methyl-2-furyl (with V) | CH₃ | -CH₂-CH(SH)-N(H)-CH₃ |
| COOH | 5-methyl-2-thienyl (with V) | CH₃ | -CH₂-CH(SH)-N(H)-CH₃ |
| 5-tetrazolyl | 6-methyl-2-pyridyl (with V) | CH₃ | -CH₂-CH(SH)-N(H)-CH₃ |
| COOCH₃ | 2-methyl-4-(CH₂SCH₃)-6-pyridyl | CH₃ | -CH₂-CH(SH)-N(H)-CH₃ |
| 5-tetrazolyl | 2-methyl-4-(CH₂SCH₃)-6-pyridyl | CH₃ | -CH₂-CH(SH)-N(H)-CH₃ |
| COOH | 3-methylphenyl (with V) | C₂H₅ | -CH₂-CH(S-S-C₂H₅)-N(H)-CH₃ |
| COOH | 4-methylphenyl (with V) | C₂H₅ | -CH₂-CH(S-S-C₂H₅)-N(H)-CH₃ |
| COOCH₃ | 3-methylphenyl (with V) | C₂H₅ | -CH₂-CH(S-S-C₂H₅)-N(H)-CH₃ |

TABLE VIII'-continued

| V | Ar—R⁸ | R²⁴ | R²⁵ |
|---|---|---|---|
| COOCH₃ | para-phenylene, R⁸=V | C₂H₅ | CH(NHCH₃)CH₂-S-S-CH₂CH₃ |
| COOC₂H₅ | meta-phenylene, R⁸=V | C₂H₅ | CH(NHCH₃)CH₂-S-S-CH₂CH₃ |
| tetrazol-5-yl (HN-N=N-N=C) | meta-phenylene, R⁸=V | C₂H₅ | CH(NHCH₃)CH₂-S-S-CH₂CH₃ |
| tetrazol-5-yl (HN-N=N-N=C) | meta-phenylene, R⁸=V | C₂H₅ | CH(NHCH₃)CH₂-S-S-CH₂CH₃ |
| COOH | phenylene with SCH₃ and R⁸=V substituents | C₂H₅ | CH(NHCH₃)CH₂-S-S-CH₂CH₃ |
| tetrazol-5-yl | phenylene with SCH₃ and R⁸=V substituents | C₂H₅ | CH(NHCH₃)CH₂-S-S-CH₂CH₃ |
| COOCH₃ | phenylene with SCH₃ and R⁸=V substituents | C₂H₅ | CH(NHCH₃)CH₂-S-S-CH₂CH₃ |
| COOH | imidazole with CH₂SH, R⁸=V | C₂H₅ | CH(NHCH₃)CH₂-S-S-CH₂CH₃ |
| COOH | furan-2,5-diyl | C₂H₅ | CH(NHCH₃)CH₂-S-S-CH₂CH₃ |
| COOH | thiophene-2,5-diyl | C₂H₅ | CH(NHCH₃)CH₂-S-S-CH₂CH₃ |
| tetrazol-5-yl | pyridine-2,6-diyl | C₂H₅ | CH(NHCH₃)CH₂-S-S-CH₂CH₃ |

TABLE VIII'-continued
| V | Ar—R⁸ | R²⁴ | R²⁵ |
|---|---|---|---|
| COOCH₃ | 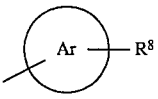 (pyridine with SCH₃ and V) | C₂H₅ |  |
| 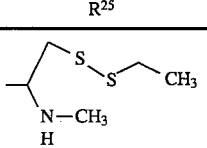 (tetrazole) | 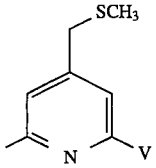 (pyridine with SCH₃ and V) | C₂H₅ | 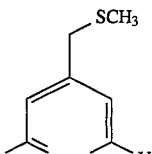 |
| COOH |  | CH₃ | 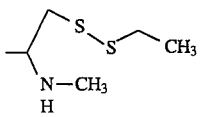 |
| COOH | 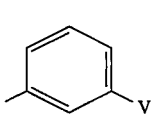 | CH₃ |  |
| COOCH₃ | 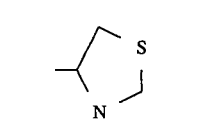 | CH₃ | 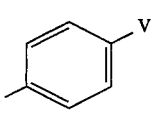 |
| COOCH₃ |  | CH₃ | 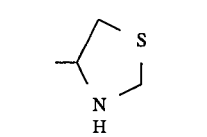 |
| COOC₂H₅ | 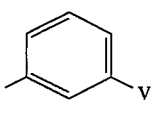 | CH₃ |  |
| 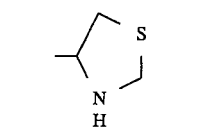 | 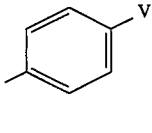 | CH₃ |  |
| 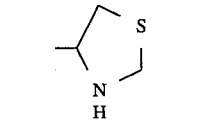 | 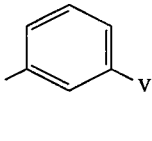 | CH₃ |  |
| COOH | 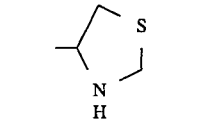 (benzene with SCH₃ and V) | CH₃ | 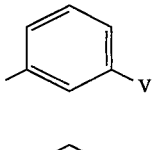 |

TABLE VIII'-continued

| V | Ar—R⁸ | R²⁴ | R²⁵ |
|---|---|---|---|
| 5-methyl-tetrazole (HN-N=N-N, with CH₃) | 4-methyl-2-(SCH₃-methyl)phenyl (V at 2-position) | CH₃ | thiazolidin-4-yl (NH) |
| COOCH₃ | 4-methyl-2-(SCH₃-methyl)phenyl (V at 2-position) | CH₃ | thiazolidin-4-yl (NH) |
| COOH | imidazole with CH₂SH substituent | CH₃ | thiazolidin-4-yl (NH) |
| COOH | 5-methyl-2-furyl (V) | CH₃ | thiazolidin-4-yl (NH) |
| COOH | 5-methyl-2-thienyl (V) | CH₃ | thiazolidin-4-yl (NH) |
| 5-methyl-tetrazole | 6-methyl-2-pyridyl (V) | CH₃ | thiazolidin-4-yl (NH) |
| COOCH₃ | 2-methyl-4-(SCH₃-methyl)-6-pyridyl (V) | CH₃ | thiazolidin-4-yl (NH) |
| 5-methyl-tetrazole | 2-methyl-4-(SCH₃-methyl)-6-pyridyl (V) | CH₃ | thiazolidin-4-yl (NH) |
| COOH | 3-methylphenyl (V) | CH(CH₃)₂ | N-methyl-thiazolidin-4-yl |
| COOH | 4-methylphenyl (V) | CH(CH₃)₂ | N-methyl-thiazolidin-4-yl |

TABLE VIII'-continued
| V | 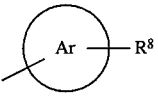 | $R^{24}$ | $R^{25}$ |
|---|---|---|---|
| COOCH$_3$ | 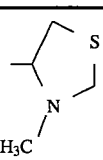 | 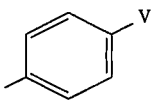 | 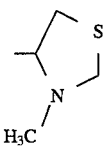 |
| COOCH$_3$ | 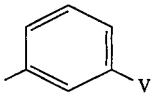 | 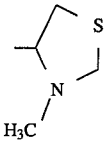 | 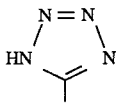 |
| COOC$_2$H$_5$ | 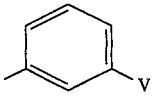 | 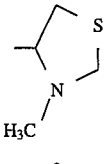 | 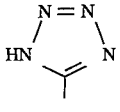 |
| 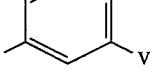 | 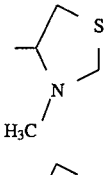 | 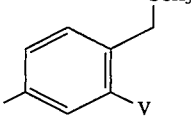 | 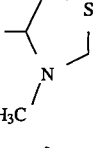 |
| 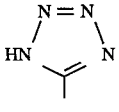 | 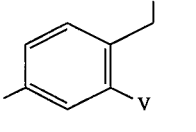 | | |
| COOH | 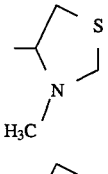 | | |
| 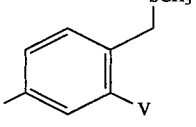 | 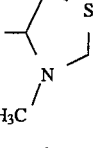 | | |
| COOCH$_3$ | 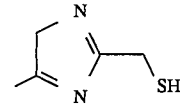 | | |
| COOH | 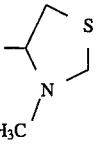 | | |
| COOH | 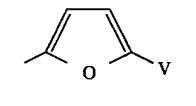 | | |

TABLE VIII'-continued
| V | Ar—R[8] | R[24] | R[25] |
|---|---|---|---|
| COOH | 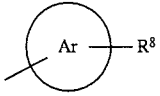 |  | 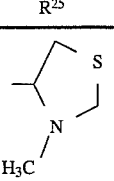 |
| 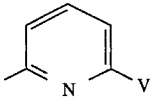 | 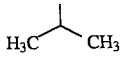 | 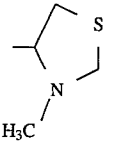 | 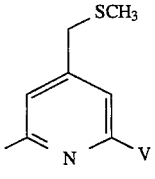 |
| COOCH₃ | 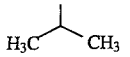 | 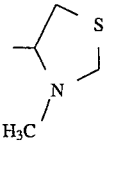 | 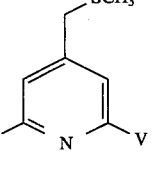 |
| 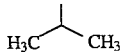 | 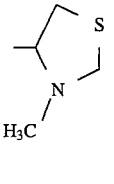 | 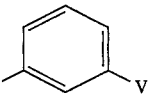 | 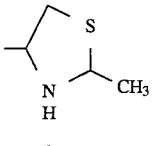 |
| COOH | 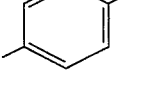 | CH₃ | 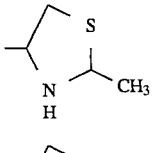 |
| COOH | 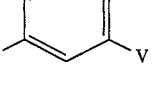 | CH₃ | 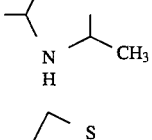 |
| COOCH₃ | 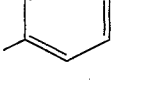 | CH₃ | 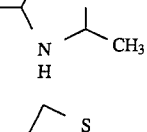 |
| COOCH₃ | 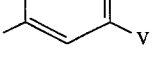 | CH₃ | 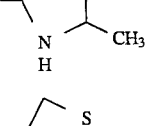 |
| COOC₂H₅ | 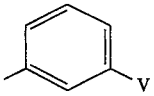 | CH₃ | 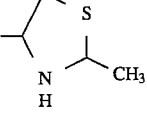 |
|  |  | CH₃ |  |

TABLE VIII'-continued

| V | Ar—R⁸ | R²⁴ | R²⁵ |
|---|---|---|---|
| tetrazole (N=N, HN-N) | phenyl-V (meta) | CH₃ | -CH₂-CH(S-CH(CH₃))-NH- |
| COOH | phenyl with SCH₃ and V | CH₃ | -CH₂-CH(S-CH(CH₃))-NH- |
| tetrazole | phenyl with SCH₃ and V | CH₃ | -CH₂-CH(S-CH(CH₃))-NH- |
| COOCH₃ | phenyl with SCH₃ and V | CH₃ | -CH₂-CH(S-CH(CH₃))-NH- |
| COOH | imidazole with SH | CH₃ | -CH₂-CH(S-CH(CH₃))-NH- |
| COOH | furan-V | CH₃ | -CH₂-CH(S-CH(CH₃))-NH- |
| COOH | thiophene-V | CH₃ | -CH₂-CH(S-CH(CH₃))-NH- |
| tetrazole | pyridine-V | CH₃ | -CH₂-CH(S-CH(CH₃))-NH- |
| COOCH₃ | pyridine with CH₂SCH₃ and V | CH₃ | -CH₂-CH(S-CH(CH₃))-NH- |
| tetrazole | pyridine with CH₂SCH₃ and V | CH₃ | -CH₂-CH(S-CH(CH₃))-NH- |

TABLE VIII'-continued
| V | 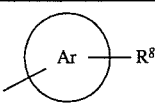 | $R^{24}$ | $R^{25}$ |
|---|---|---|---|
| COOH | 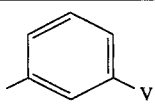 | $CH_3$ | 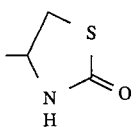 |
| COOH | 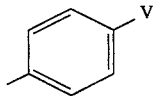 | $CH_3$ | 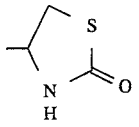 |
| $COOCH_3$ | 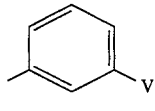 | $CH_3$ | 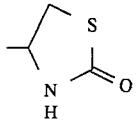 |
| $COOCH_3$ | 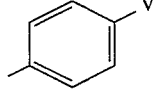 | $CH_3$ | 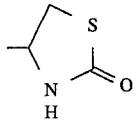 |
| $COOC_2H_5$ | 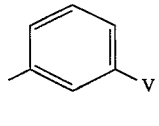 | $CH_3$ | 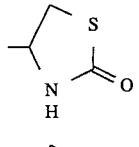 |
| 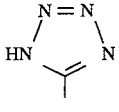 | 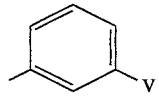 | $CH_3$ | 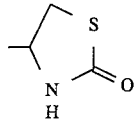 |
| 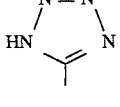 | 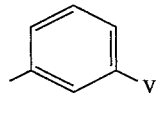 | $CH_3$ | 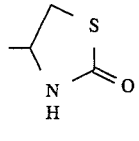 |
| COOH | 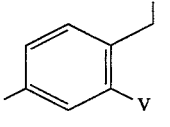 | $CH_3$ | 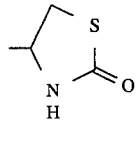 |
| 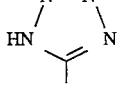 | 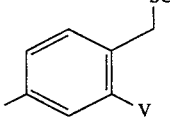 | $CH_3$ | 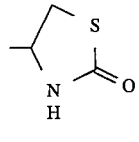 |
| $COOCH_3$ | 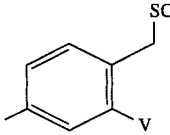 | $CH_3$ | 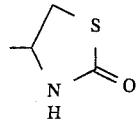 |
| COOH | 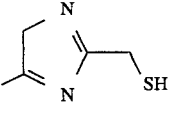 | $CH_3$ | 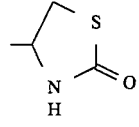 |

TABLE VIII'-continued

| V | Ar–R[8] | R[24] | R[25] |
|---|---|---|---|
| COOH | furan (2,5-disub, V at 5) | CH$_3$ | thiazolidinone-CH$_2$- (NH) |
| COOH | thiophene (2,5-disub, V at 5) | CH$_3$ | thiazolidinone-CH$_2$- (NH) |
| tetrazole (HN-N=N-N=) | pyridine (2,6-disub, V at 6) | CH$_3$ | thiazolidinone-CH$_2$- (NH) |
| COOCH$_3$ | pyridine with SCH$_3$ at 4, V at 2 | CH$_3$ | thiazolidinone-CH$_2$- (NH) |
| tetrazole (HN-N=N-N=) | pyridine with SCH$_3$ at 4, V at 2 | CH$_3$ | thiazolidinone-CH$_2$- (NH) |
| COOH | phenyl (1,3-disub) | C$_4$H$_9$ | thiazolidinone-CH$_2$- (N-CH$_3$) |
| COOH | phenyl (1,4-disub) | C$_4$H$_9$ | thiazolidinone-CH$_2$- (N-CH$_3$) |
| COOCH$_3$ | phenyl (1,3-disub) | C$_4$H$_9$ | thiazolidinone-CH$_2$- (N-CH$_3$) |
| COOCH$_3$ | phenyl (1,4-disub) | C$_4$H$_9$ | thiazolidinone-CH$_2$- (N-CH$_3$) |
| COOC$_2$H$_5$ | phenyl (1,3-disub) | C$_4$H$_9$ | thiazolidinone-CH$_2$- (N-CH$_3$) |

TABLE VIII'-continued

| V | Ar—R⁸ | R²⁴ | R²⁵ |
|---|---|---|---|
| 5-tetrazolyl (HN-N=N-N=) | phenyl (meta-V) | C₄H₉ | -CH₂-S-C(=O)-N(CH₃)-CH- |
| 5-tetrazolyl | phenyl (meta-V) | C₄H₉ | -CH₂-S-C(=O)-N(CH₃)-CH- |
| COOH | phenyl with SCH₃ and V substituents | C₄H₉ | -CH₂-S-C(=O)-N(CH₃)-CH- |
| 5-tetrazolyl | phenyl with SCH₃ and V substituents | C₄H₉ | -CH₂-S-C(=O)-N(CH₃)-CH- |
| COOCH₃ | phenyl with SCH₃ and V substituents | C₄H₉ | -CH₂-S-C(=O)-N(CH₃)-CH- |
| COOH | imidazolyl with SH substituent | C₄H₉ | -CH₂-S-C(=O)-N(CH₃)-CH- |
| COOH | furanyl (2,5-disubstituted) | C₄H₉ | -CH₂-S-C(=O)-N(CH₃)-CH- |
| COOH | thienyl (2,5-disubstituted) | C₄H₉ | -CH₂-S-C(=O)-N(CH₃)-CH- |
| 5-tetrazolyl | pyridinyl (2,6-disubstituted) | C₄H₉ | -CH₂-S-C(=O)-N(CH₃)-CH- |
| COOCH₃ | pyridinyl with SCH₃ substituent | C₄H₉ | -CH₂-S-C(=O)-N(CH₃)-CH- |

TABLE VIII'-continued

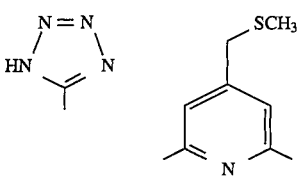

| V | Ar—R⁸ | R²⁴ | R²⁵ |
|---|---|---|---|
| 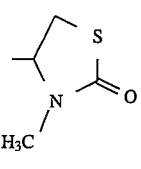 | 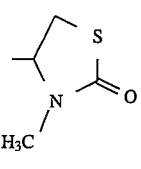 | C₄H₉ | 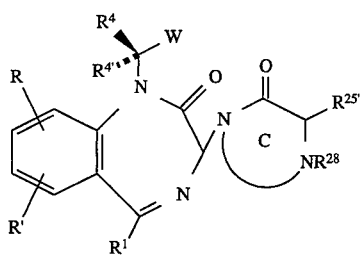 |

An alternative preferred embodiment of the invention comprises a compound capable of inhibiting farnesyl:protein transferase at a concentration equal to or lower than that of the tetrapeptide CVFM represented by Formula IX

 IX where the substituents R and R' are halo or perflurololoweralkyl, $R^1$ is $CF_3$ or phenyl optionally substituted with halo or haloloweralkyl, $R^4$, $R^{4'}$, and $R^{28}$ are hydrogen or lower alkyl, W is —(C=O)—$NR^{7'}R^8$ where $R^{7'}$ and $R^8$ are selected according to Table Ia', $R^{25'}$ is $C_1$–$C_4$alkyl-SH or $C_1$–$C_4$alkyl-S-$C_1$–$C_4$alkyl, and

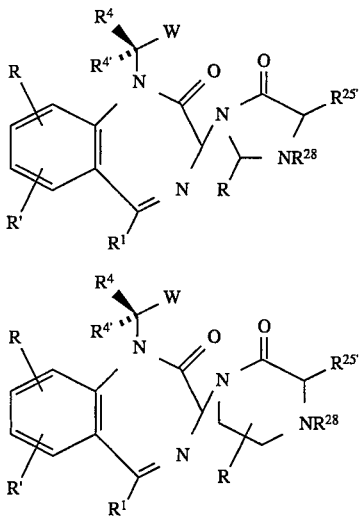

represents methylene, ethylene, or ethenylene, optionally substituted with oxo (=O), loweralkyl, or haloloweralkyl. Subgeneric preferred examples of IX include;

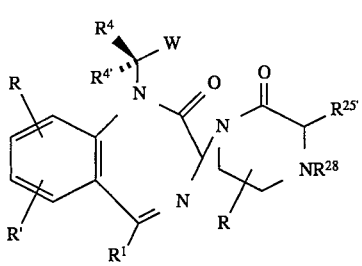 IXa

IXb

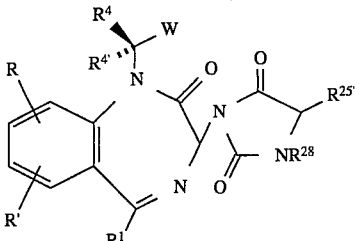 IXc

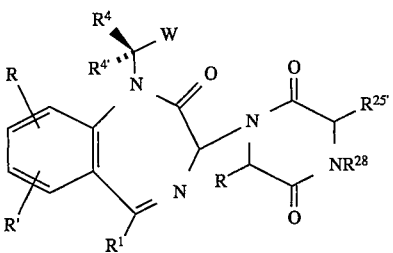 IXd where the substituents are as described above.

D. Methods of Making

In the schemes and examples below, the following standard abbreviations are employed.

| ABBREVIATIONS | |
|---|---|
| Boc or BOC | tert-butyloxycarbonyl |
| Fmoc or FMOC | fluorenylmethyloxycarbonyl |
| DCC | dicyclohexylcarbodiimide |
| PyBrOP | bromo-tri-pyrrolidinophosphoniumhexafluorophosphate |
| TFA | trifluoroacetic acid |
| DIPC | diisopropylcarbodiimide |
| BOP | benzotriazolyloxy-trisdimethylamino-phosphonium hexafluorophosphate |
| EDC | 1-(3-dimethylaminopropyl)-3-ethylcarbodiimide hydrochloride |
| DEAD | diethylazodicarboxylate |
| Ph₃P | triphenylphosphine |
| LDA | lithium diisopropylamine |
| NMM | N-methylmorpholine |
| EtN(iPr)₂ | diisopropylethylamine |
| SPPS | solid phase peptide synthesis |
| t-BuO₂C | tert-butoxycarbonyl |
| DMF | dimethylformamide |
| DTT | dithiothreitol |
| DMA | dimethylacetamide |
| DMAP | dimethylaminopyridine |
| DCM | dichloromethane |
| DMSO | dimethylsulfoxide |
| DIPEA | diisopropylethylamine |
| DMEM | Dulbecco's modified essential media |
| MBHA | methylbenzhydryamine |

ABBREVIATIONS

| | |
|---|---|
| ACN | acetonitrile |
| HPLC | high pressure liquid chromatography |

General methods of synthesis of the compounds of this invention are shown in Schemes I–XIV. Compounds bearing a 3-amino substituent in the benzodiazepine ring are synthesized as shown in Schemes I–III. Typically, a triply convergent route is employed, which joins the key intermediates 9 or 10 (Scheme I) with suitably functionalized amine and carboxyl components (Schemes II and III) using standard amide bond-forming procedures.

As shown in Scheme I, the protected amino acids 9 and 10 may be prepared from a suitably substituted 2-aminobenzophenone (1). Many 2-aminobenzophenones are known in the art or are available from commercial sources such as Aldrich Chemical Co. General methods for the synthesis of new 2-aminobenzophenones may be found in the literature (c.f. Walsh, D. A. *Synthesis*, 1980, 677–688).

SCHEME I

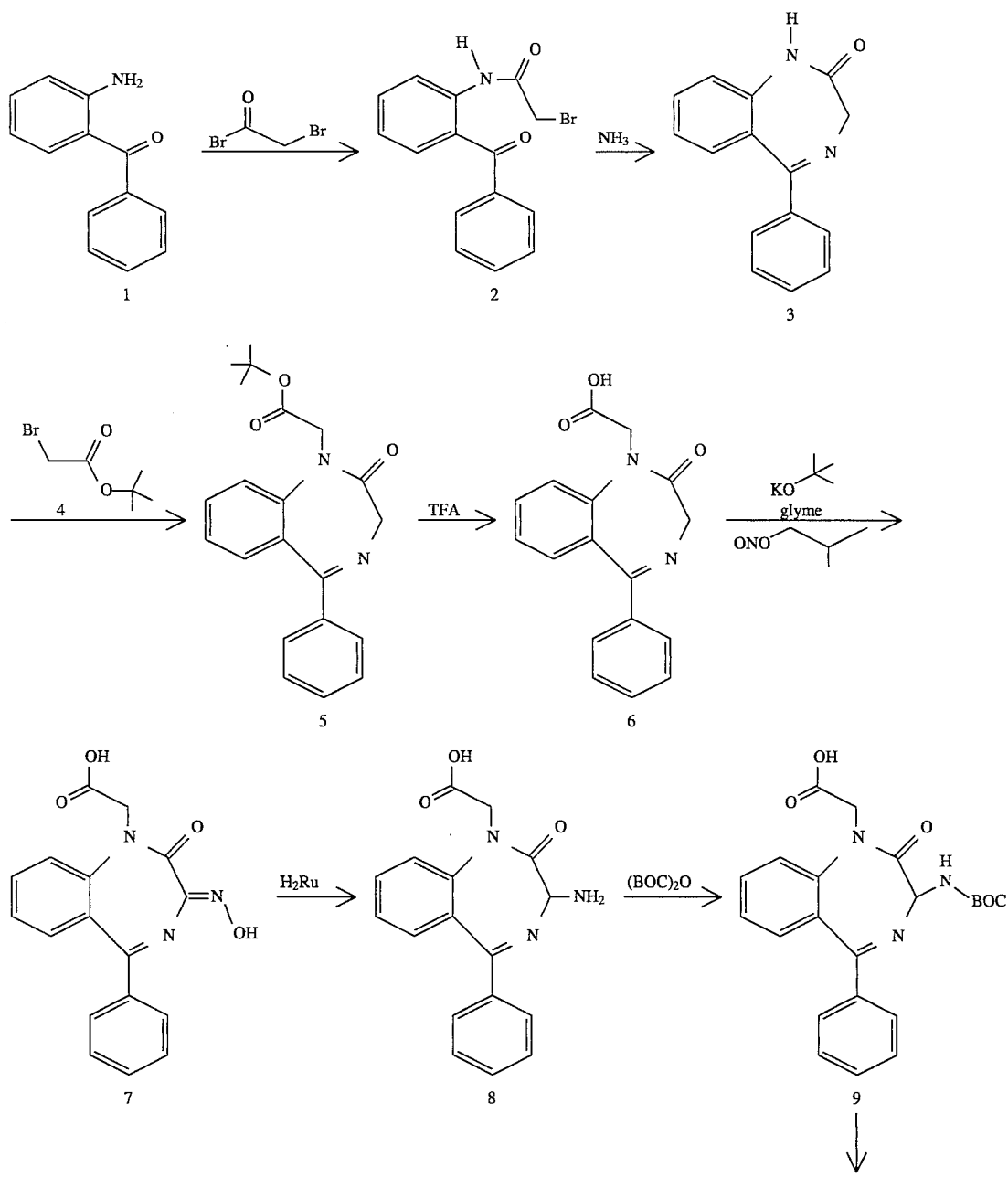

-continued
SCHEME I

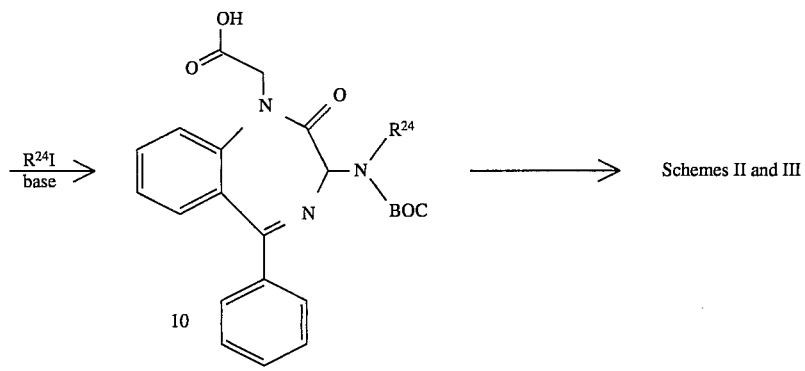

Acylation of 1 with a haloacetyl halide, such as bromoacetyl bromide in a suitable solvent mixture, such as water/$CH_2Cl_2$, typically at temperatures ranging from 0° C. to 25° C., produces amide 2. Reaction of 2 with ammonia in a polar solvent such as methanol at 25° to 75° C. then gives the 1,4-benzodiazepin-2-one 3, after evaporation of the solvent. Alkylation of 3 with a substituted organic ester (4), preferably tert-butyl bromoacetate, in the presence of a base, preferably $Cs_2CO_3$ in 1-methyl-2-pyrrolidinone at ambient temperature, gives 5. Alternatively, 3 may be alkylated at N-1 with a variety of other alkylating agents, for instance, esters of substituted or unsubstituted acrylates, 4-bromobutanoates, etc. Branched compounds (i.e. $R^4$ and/or $R^{4'} \neq H$), may be prepared by generation of the polyanion of 5 with base and alkylation with an appropriate alkyl halide.

Subsequent to alkylation, the ester of 5 may be cleaved with an acid such as TFA (for the tert-butyl esters) or under mild aqueous base hydrolysis (for other alkyl esters) at temperatures between 0° and 25° C.

The acid 6 is converted to amino acid 8 via reaction of the dianion, generated with at least two equivalents of a strong base with an electrophilic aminating agent. Alternatively, 6 may be halogenated and reacted with an amine source such as azide (followed by reduction) or ammonia. Preferably, 6 is reacted with 4 equivalents of potassium tert-butoxide in glyme at –5° C. for 30 min and treated with 1.1 equivalents of isobutyl nitrite. The resulting oxime 7 can then be reduced to the racemic amino acid 8 using a variety of reductants, preferably hydrogenation at 40 psig in the presence of Ruthenium on carbon or Raney nickel in methanol at 50° to 70° C. for 1–4 days.

Amino acid 8 is then suitably protected for selective coupling at the carboxyl terminus. For example, 8 can be converted to the N-BOC derivitive 9 using standard amino acid protection conditions, preferably, reaction with equimolar amounts of di-tert-butyl dicarbonate and triethyl amine in DMF/water at ambient temperature.

For compounds where $R^{24} \neq H$, 9 can be alkylated at nitrogen with a wide variety of alkylating agents including n-alkyl, branched alkyl, and benzyl, according to the standard procedure of Benoiton, et al., Can. J. Chem. 1977, 55, 906. For example, reaction of 9 with at least 2 equivalents of base and an alkylating agent in a polar, aprotic solvent at 0° to 50° C. for 0.5 to 48 h gives 10. Preferably, reaction with 3 equivalents of sodium hydride and 4 equivalents of methyl iodide in THF at –5° to 5° C. gives 10 ($R^{24}$=Me).

Compounds 9 and 10 can be further elaborated according to Schemes II and III. In general, the carboxylic acid function of 9 and 10 is reacted with a suitably protected amine component using standard solid phase (Scheme II) or solution phase (Scheme III) peptide synthesis procedures. The BOC or other protecting group on N-3 of the benzodiazapinone is removed and the amine function then coupled with a third component, for example, a suitably protected amino acid, and then deprotected, again employing standard procedures. The resulting product is subsequently purified by chromatography or crystallization.

SCHEME II

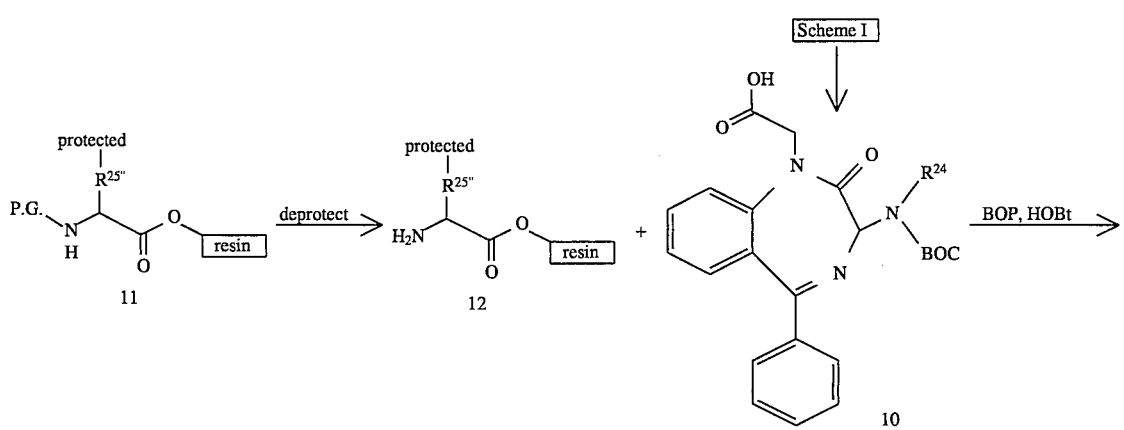

-continued
SCHEME II
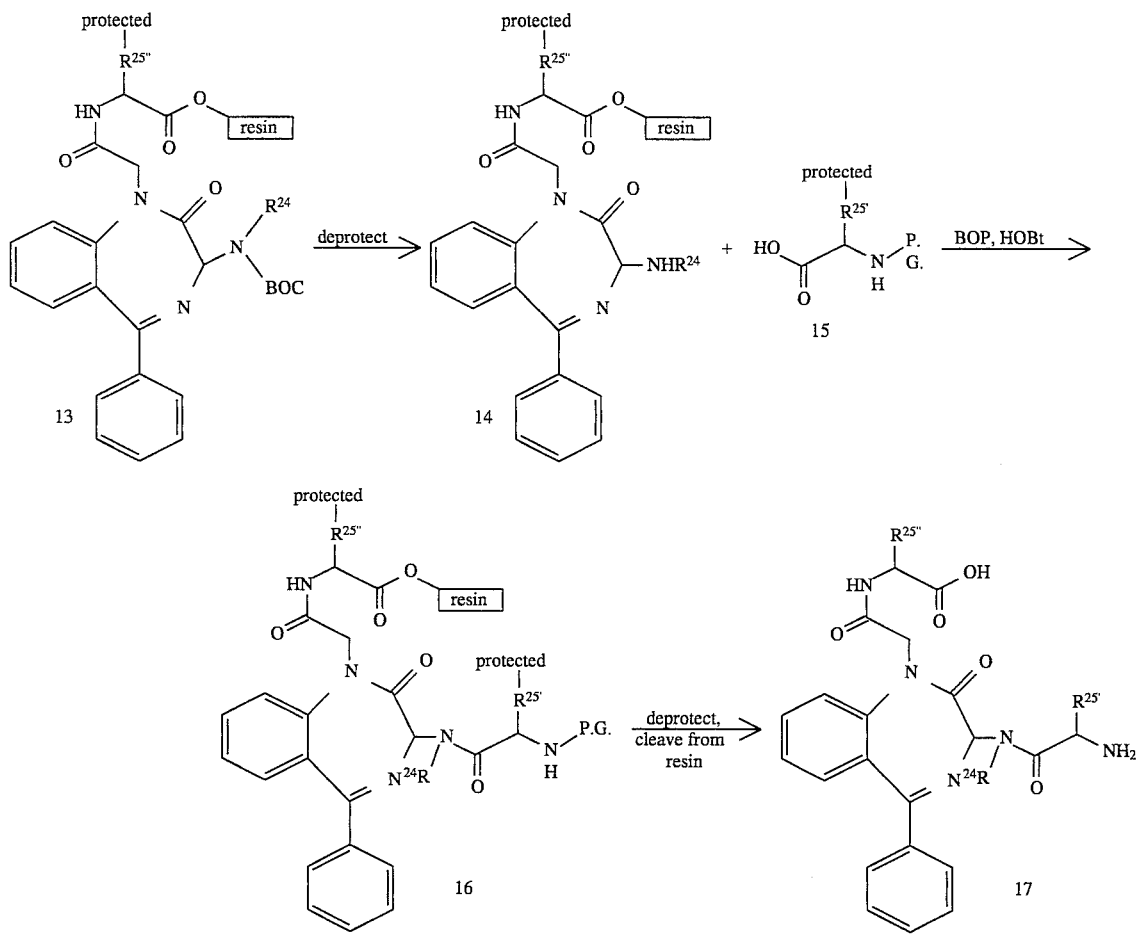
Once fully deprotected, compounds of the type 17 and 23, and salts thereof, may be further modified at the carboxy and/or amino terminus by esterification or acylation, respectively, employing standard procedures.
SCHEME III
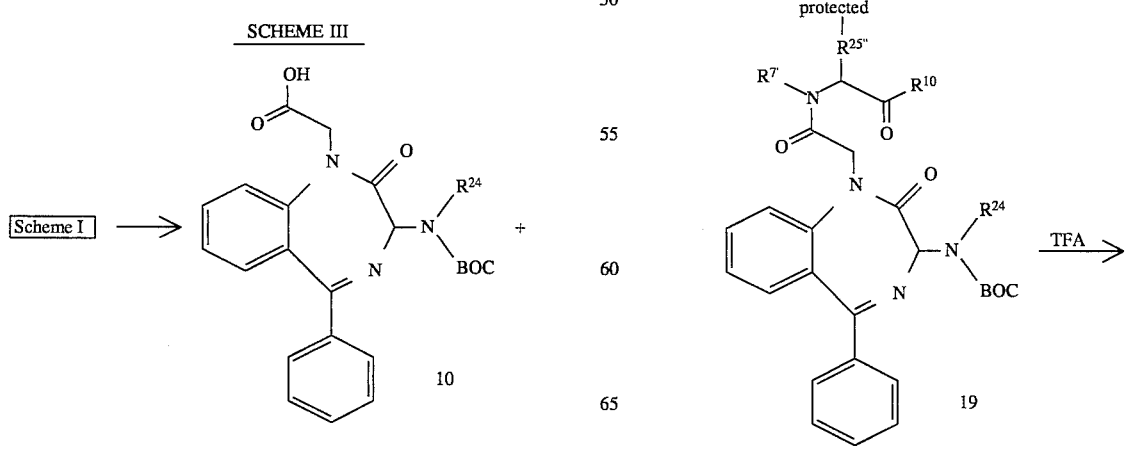

-continued
SCHEME III

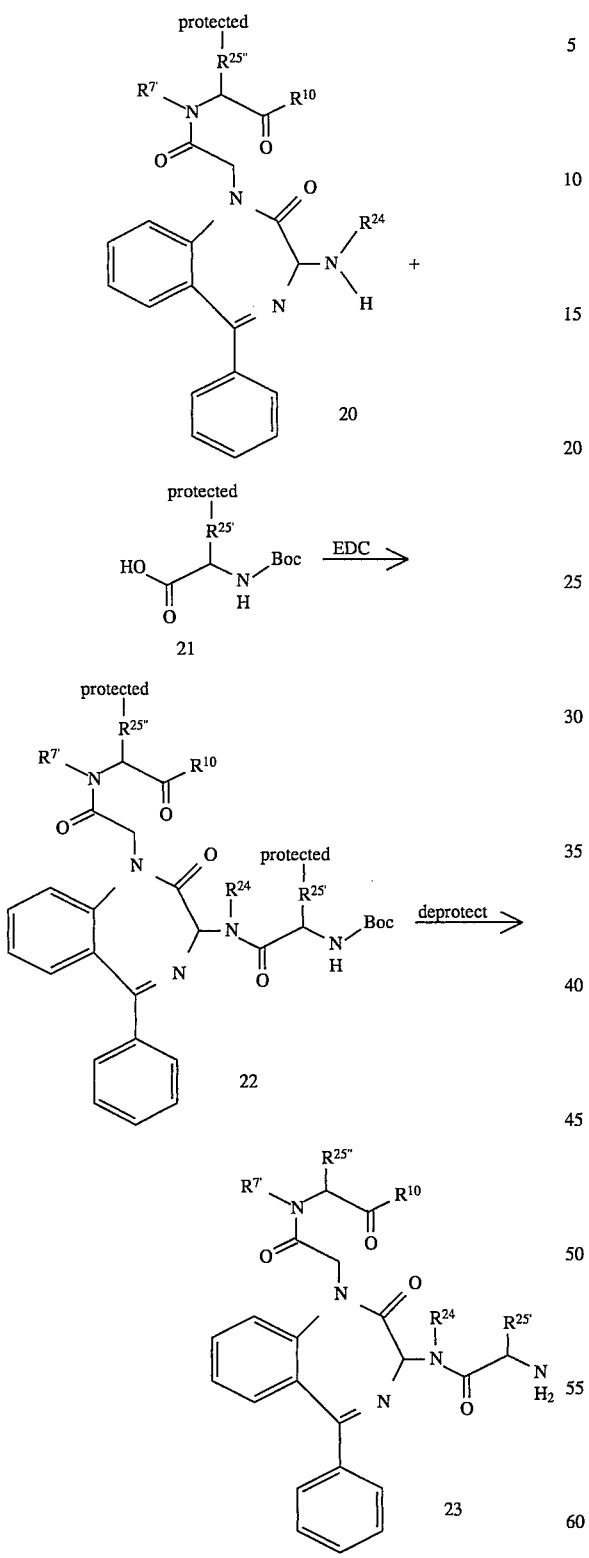

amino acid using DCC or the mixed anhydride method gives 25. A wide variety of protected amino acids 24 may be used in this reaction, including side chain protected natural amino acids (both D and L), substituted phenyl glycines, thiolysine, and the variety of synthetic, non-natural amino acids known to one skilled in the art (see e.g. U.S. Pat. No. 5,120,859, WO 93/04081 and 37 CFR 1.822(b)(2) and 1.822(p)(2)). Preferably, the side chain functions of the amino acid are protected orthogonally to the alpha-amine to facilitate selective deprotection. Treatment of the deblocked compound with base, preferably in methanol, gives the 3-substituted benzodiazepin-2-one 26. Alkylation at N-1 with a substituted ester as described for 3 (Scheme I) gives 7 which is deprotected and coupled to a protected amino acid using standard procedures to afford 29. Final deblocking of the side chain protecting groups and purification gives 30.

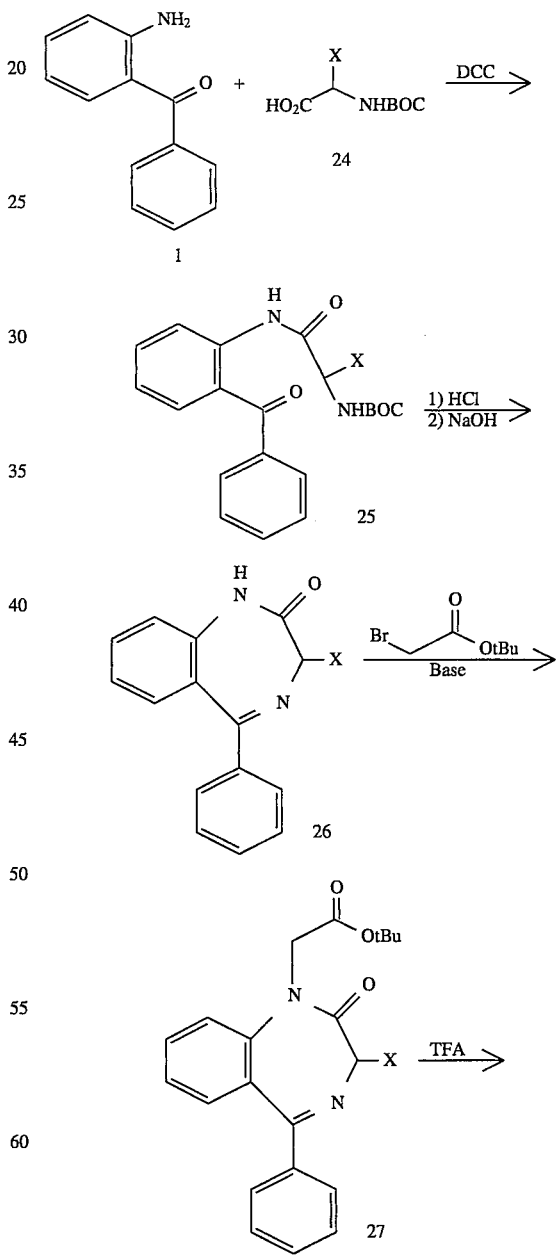

The synthesis of a second class of compounds of this invention is shown in Scheme IV. Acylation of the 2-aminobenzophenones 1 with an N-protected (preferably BOC)

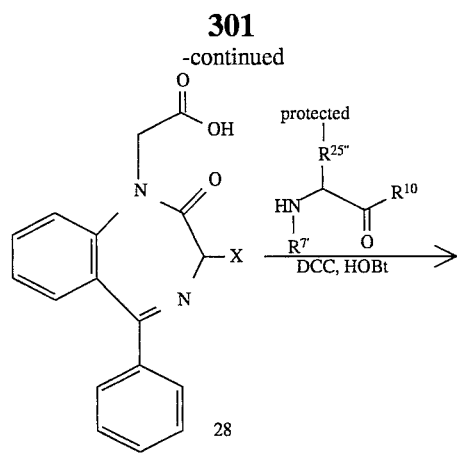

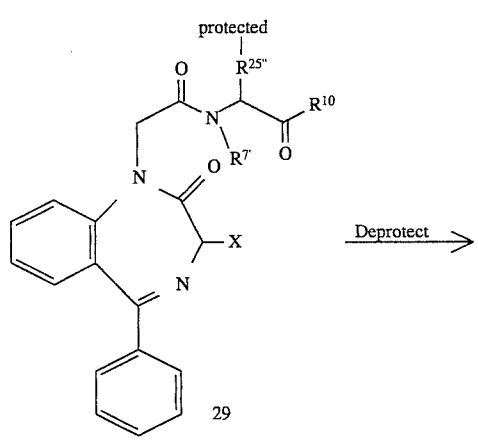

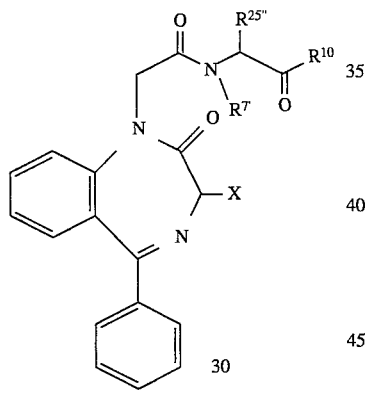

Alternatively, 26 may be directly alkylated with the "top" sidechain in one intact piece, as shown in Scheme V. Reaction of 26 with an alkyl halide such as a suitably substituted benzyl bromide, alkyl bromide, in the presence of a base, preferably NaH or $Cs_2CO_3$, gives 31. Deprotection under standard conditions and purification affords 32.

SCHEME V

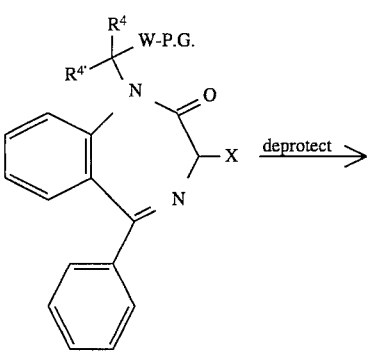

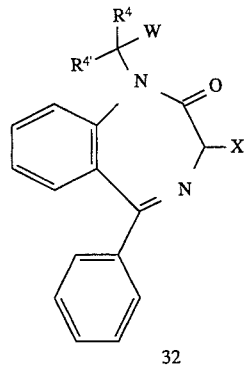

When the amino acid side chain of 32 is that of serine, futher manipulation is possible as described in Scheme VI. Deprotection of the hydroxyl function gives free alcohol 34 which can be alkylated or acylated at oxygen to give 35 using standard ether synthesis or acylation procedures. Compounds of the type 32, with the side chain of cysteine are treated in an analogous fashion to 33.

Alternatively, 34 may be converted to amine 36 under Mitsunobu conditions, preferably using $Ph_3P$, diethyl azodicarboxylate (DEAD), and $HN_3$. Reduction of the resulting azide, preferably by hydrogenation over Pd/C, gives amine 36. 36 is then alkylated or acylated to give 37 and 38, respectively, after deprotection and purification.

SCHEME VI

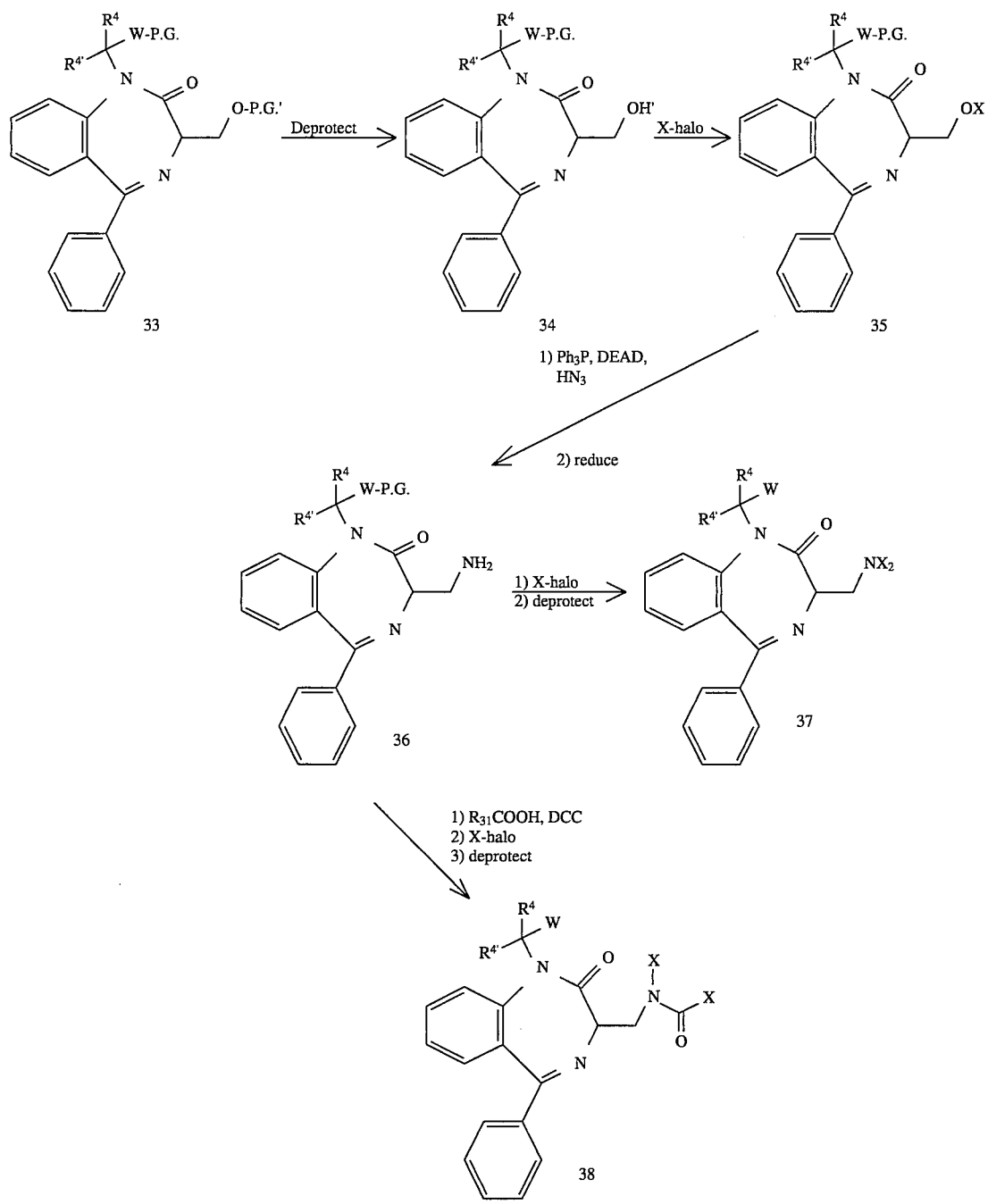

For compounds 32, with the side chains derived from aspartic or glutamic acids, further modification is carried out as per Scheme VII. Thus, selective removal of the side chain ester function, preferably benzyl or lower alkyl, using appropriate conditions, preferably aqueous NaOH, gives the free acid. Coupling to a second amine component, such as 2-mercaptoethyl amine, using standard conditions, preferably DCC, gives the protected amide which is fully deprotected and purified to afford 40.

SCHEME VII

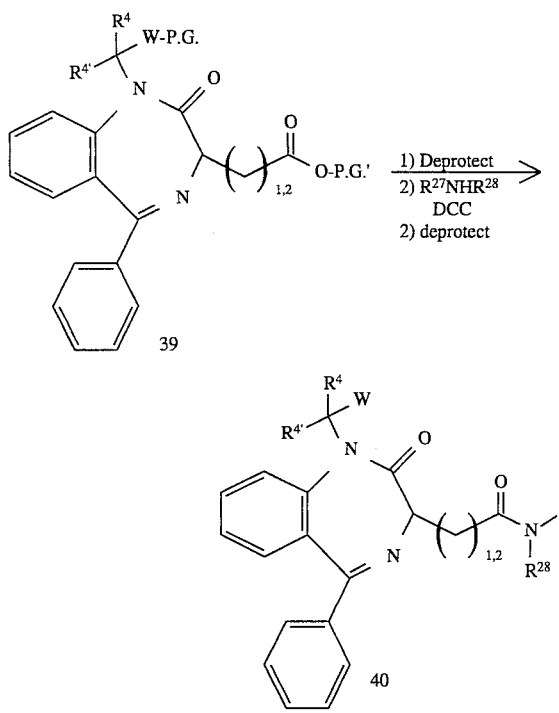

Another variety of compounds which are the subject of this invention are synthesized as shown in Scheme VIII. Alkylation at N-1 of benzodiazepinone 3 (as described for 31, Scheme V) gives 41. This alkylation may, for example, be conducted with any halo substituted loweralkyl, loweralkylaryl, or loweralkylheterocycle (—$CR^4R^{4'}$—W— in Scheme VIII). The alkyl, aryl, or heterocycle moieties may be substituted with protected (-P.G.) carboxyls, tetrazoles, thiols, etc, or precursors of these groups (e.g. nitriles for tetrazoles, etc.). Deprotonation at C-3 of the heterocycle, preferably with LDA in THF at less than 50° C., gives anion 42 which can be reacted with a variety of electrophiles. For example, reaction with substituted aldehydes, active esters, and alkyl halides gives, after deprotection and purification, products 43, 44, and 45, respectively.

SCHEME VIII

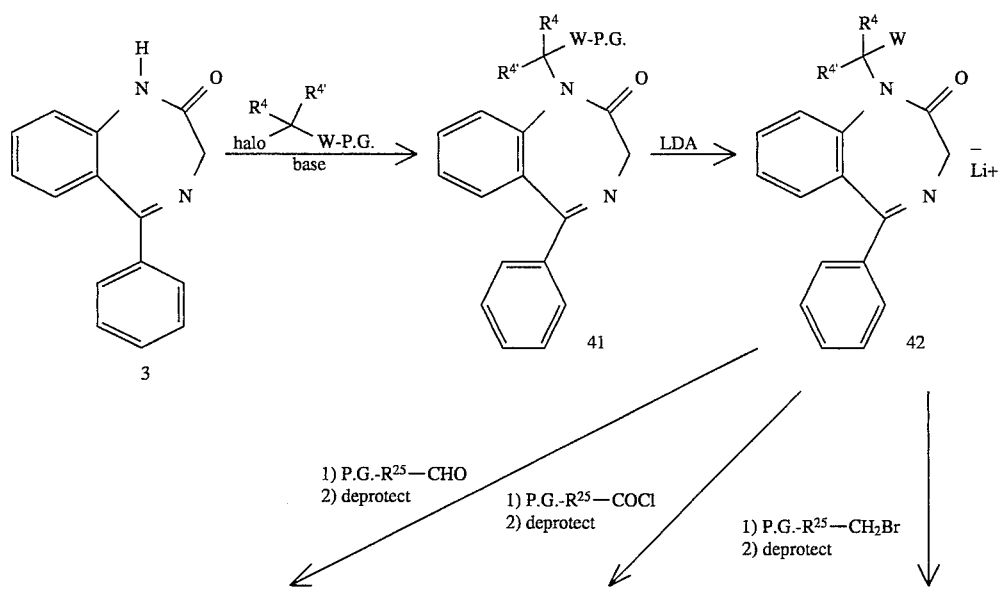

-continued
SCHEME VIII

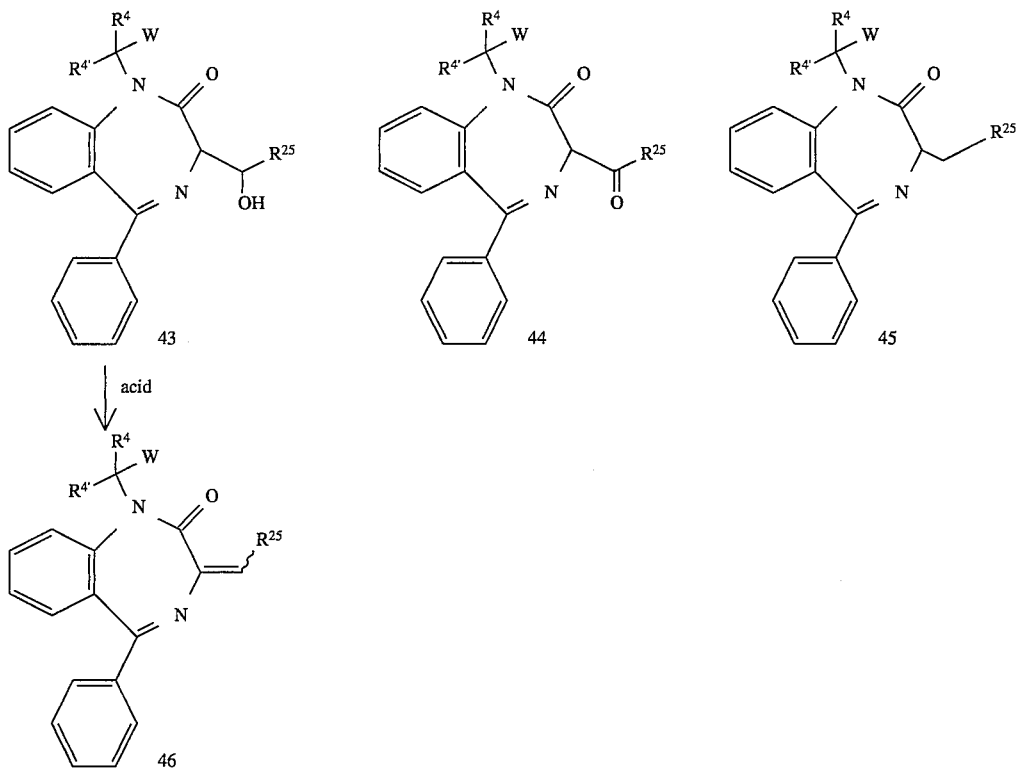

In cases where the starting materials are optically active, the chirality at C-3 of the benzodiazepinone is controlled by the starting materials. When racemic starting materials are employed, diastereomeric products are obtained. The diastereomers may be separated by chromatography.

Benzodiazepines of the instant invention with a spiro linkage at C-3 may be made according to Scheme IX. The C-3 amine is first coupled to a 9-phenylfluorenyl protected amino acid to give 48, followed by reaction with a dihalo substituted alkane in base to give 49. The 9-phenylfluorenyl group is then replaced with BOC and the resulting compound 50 is reacted with an immobilized free amine (e.g. compound 12, Scheme II) in a solid phase synthesis procedure.

SCHEME IX

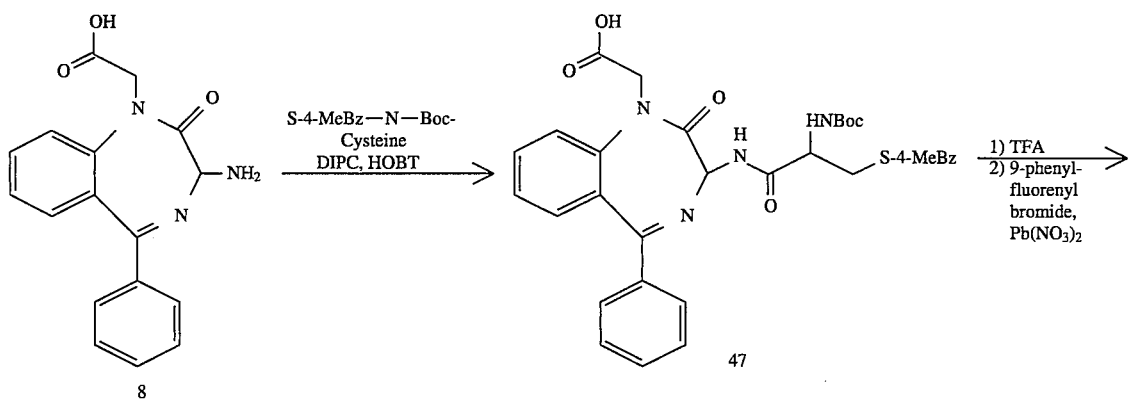

-continued
SCHEME IX
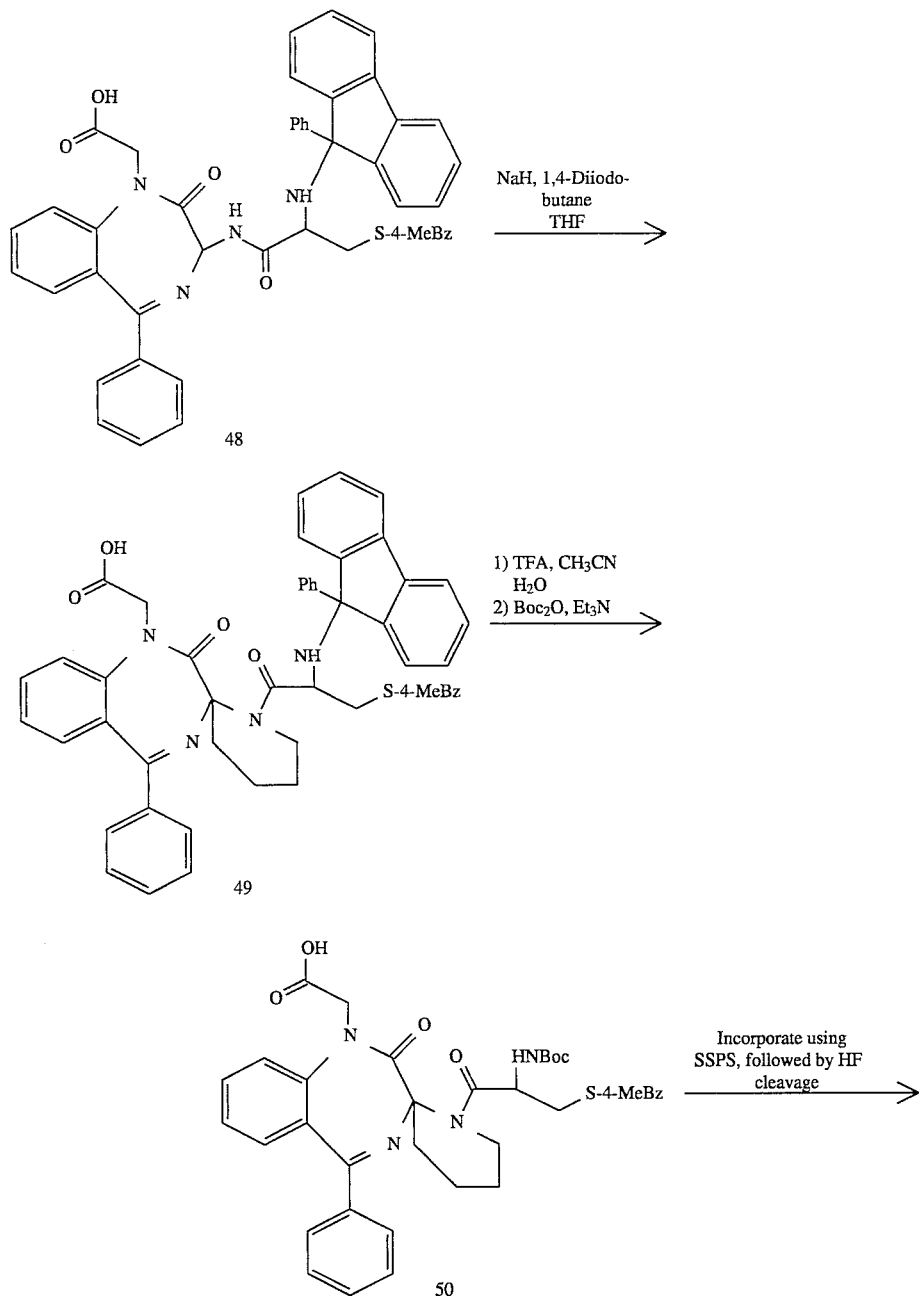
Benzodiazepines of the instant invention with a hydroxamic or carboxylic terminus at C-3 may be made according to Scheme X. Compound 14 from Scheme II may be treated with an acid anhydride in N-methyl-morpholine (NMM) to produce 52 contemplated to be a suitable ras FT inhibitor. 52 in turn may be coupled to a hydroxamic acid and cleaved to produce 54.

SCHEME X
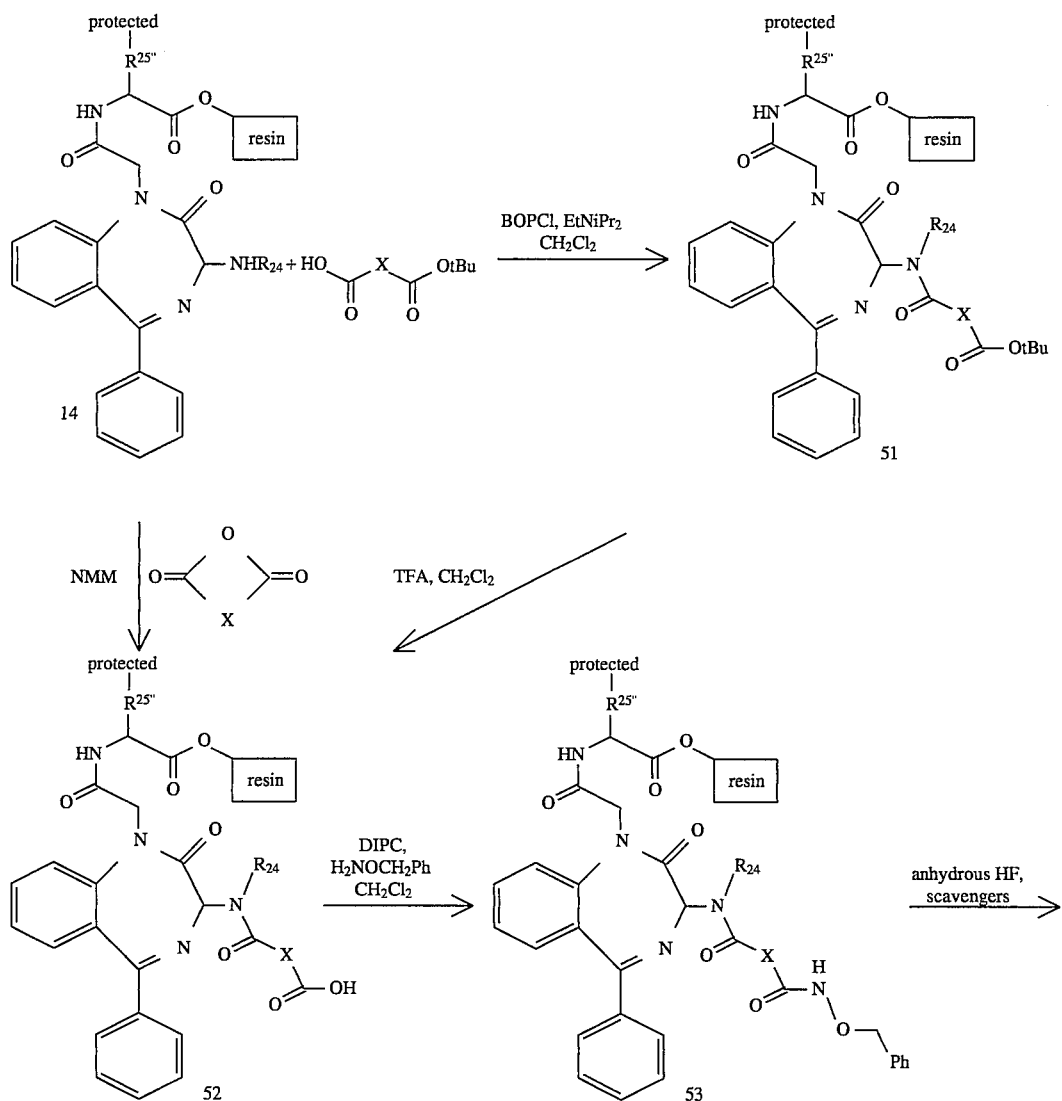

-continued
SCHEME X

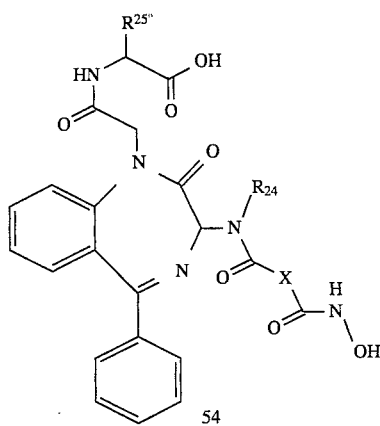

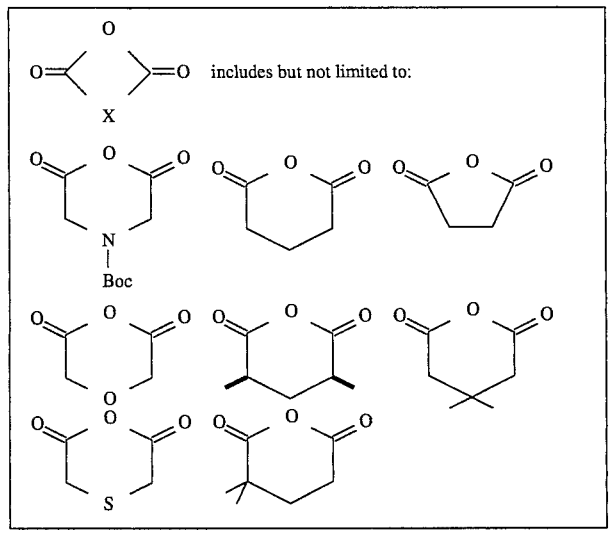

Benzodiazepine compounds 16 and 22 of Schemes II and III, where $R^{24}$ is hydrogen may be convereted to heterocycles of formulae IXa–IXd according to Scheme XI. Here, $R^{25'}$ and W are suitably blocked prior to reacting with the cyclizing agent, followed by deblocking and release from the resin as described in Schemes II and III.

SCHEME XI

-continued
SCHEME XI

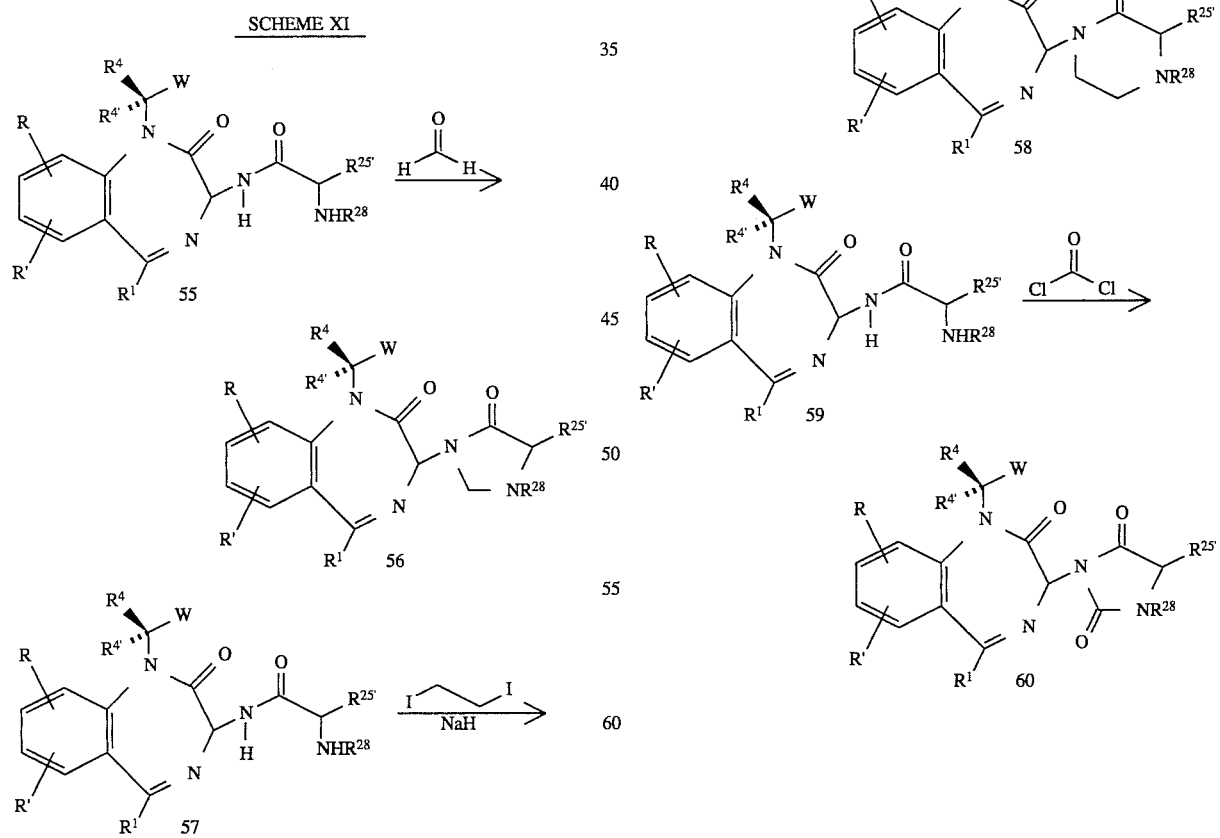

SCHEME XI -continued

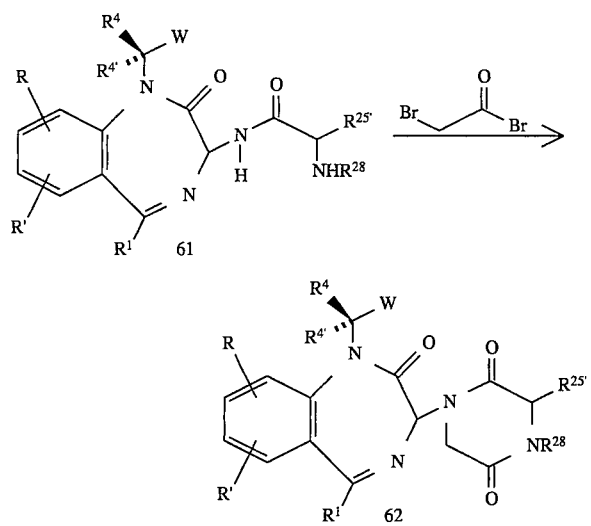

The imine nitrogen of the instant benzodiazepines may be cyclized with an amide nitrogen bonded to C-3 by first reacting 63 with bromoacetyl bromide followed by reduction of the imine and closure to give 64.

SCHEME XII

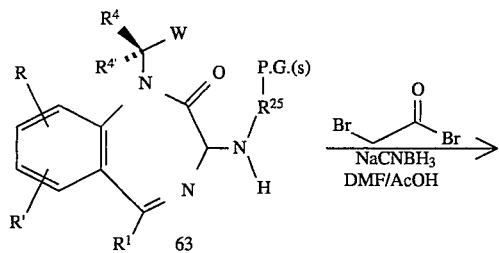

SCHEME XII -continued

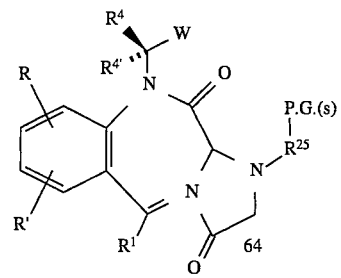

The synthesis of a class of compounds represented by formula (V) is shown in Scheme XIII. Reductive alkylation of the 2-amino-benzophenones 1 with an N-protected (preferably BOC) aldehyde using $NaCNBH_3$ gives 65. A wide variety of aldehydes derived from protected amino acids may be used in this reaction, including side chain protected natural amino acids (both D and L), substituted phenyl glycines, thiolysine, and the variety of synthetic, non-natural amino acids known to one skilled in the art. 65 is then acylated with an N-protected (preferably Fmoc) amino acid in the presence of DCC (see Scheme IV) to afford 66. 66 is then treated with base to form the benzodiazepine 67. This benzodiazepine is treated with Lawessons Reagent (Fluka) followed by MeI and then anhydrous HCl, followed by neutralization and heating to give the tricyclic compound 68. The optionally protected sidechain is deprotected to give 69.

SCHEME XIII

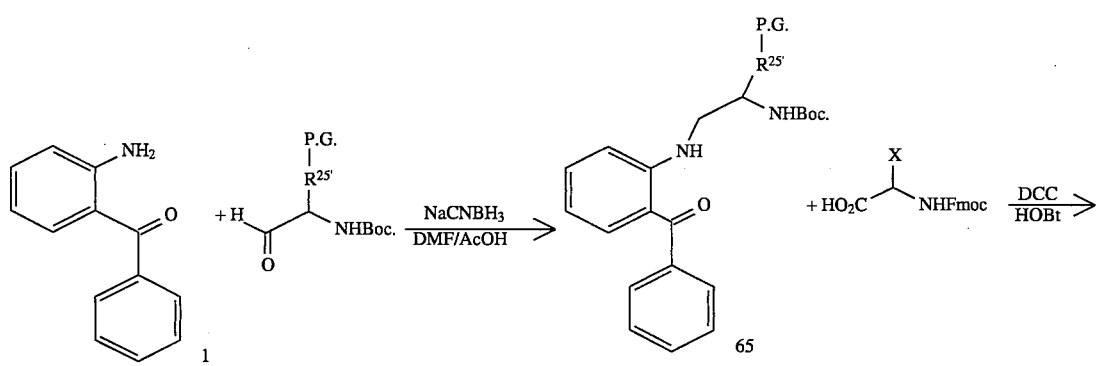

-continued
SCHEME XIII

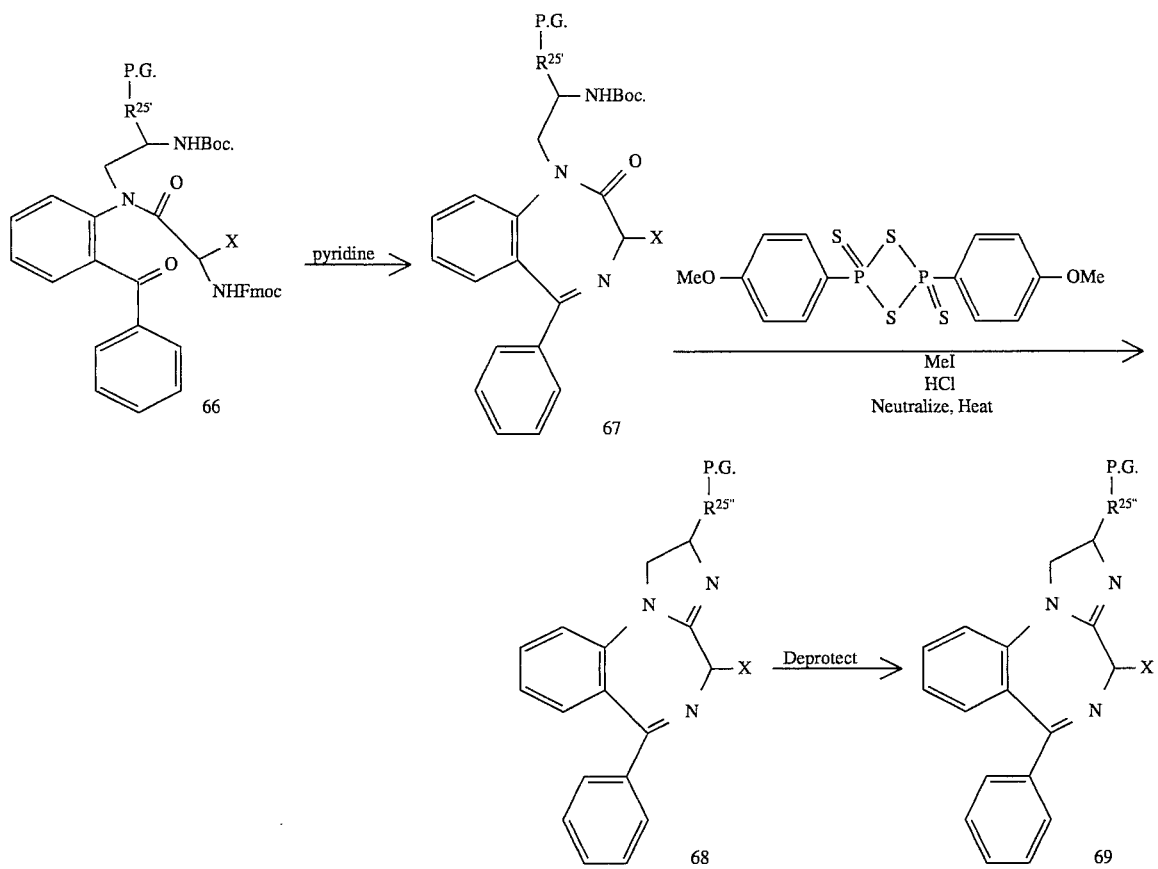

Compounds bearing a 3-ureido, 3-carbamoyl, or 3-thiocarbamoyl substituent on the benzodiazepine ring are synthesized as shown in Scheme XIV. Compound 9 from Scheme I may be esterified and reacted with TFA to yield 70. The 3-amino group is then converted to the isocyanate 71 with phosgene or 1,1'-carbonyldiimidazole. 71 may be converted into the corresponding ureido, carbamoyl, or thiocarbamoyl, by reacting it with suitably protected amines, alcohols, or thiols yielding 72, 73, and 74 respectively. A wide variety of protected amino acids having a free amino group are prefered in this reaction, including side chain protected natural amino acids (both D and L), substituted phenyl glycines, thiolysine, and a variety of synthetic, non-natural amino acids (e.g. thioproline, β-alanine, etc.) known to one skilled in the art (see e.g. U.S. Pat. No. 5,120,859, and WO 93/04081). Simple suitably protected alkylaminothiols and hydroxyalkylthiols may similarly be employed to produce 72, 73, or 74.

SCHEME XIV
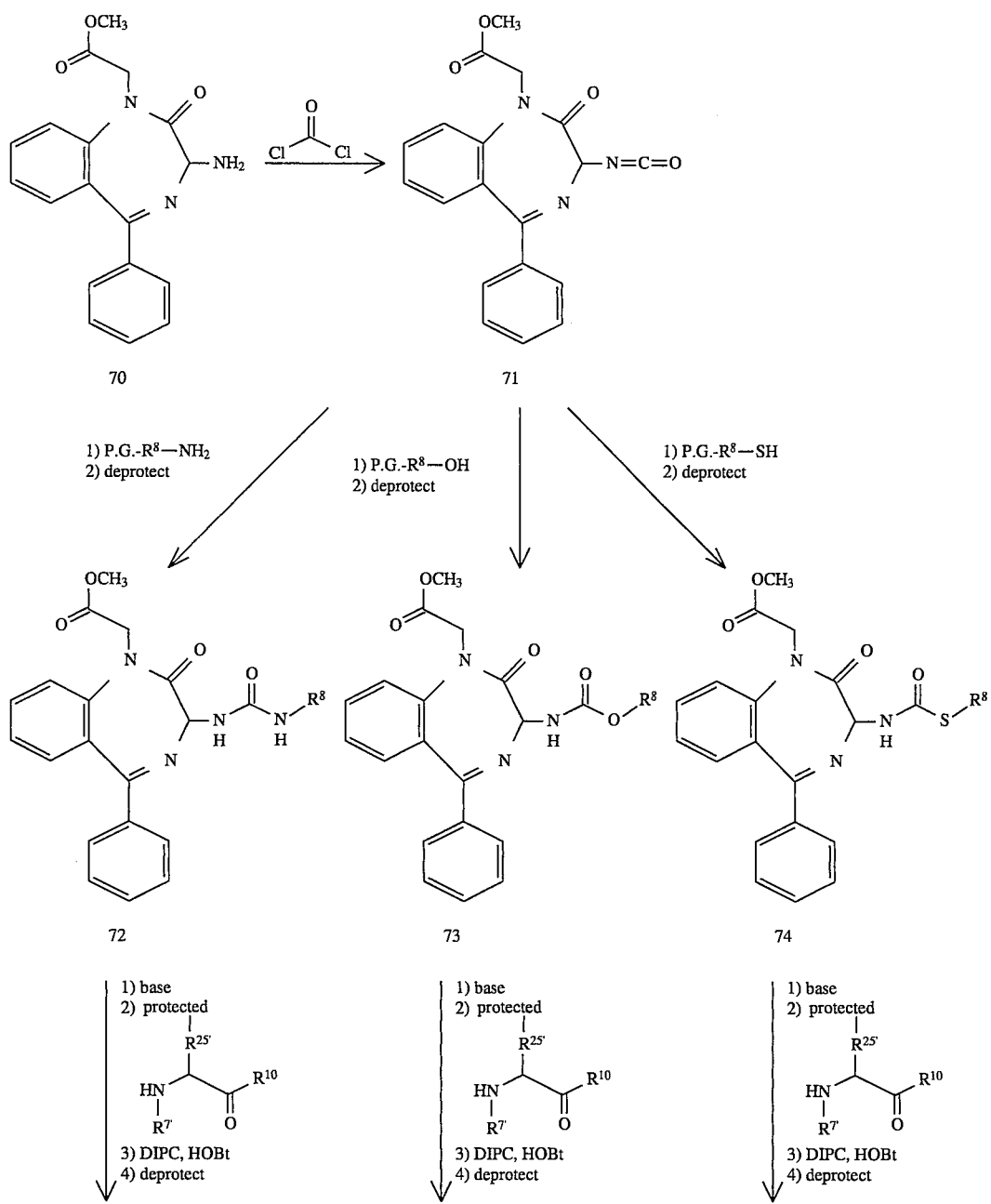

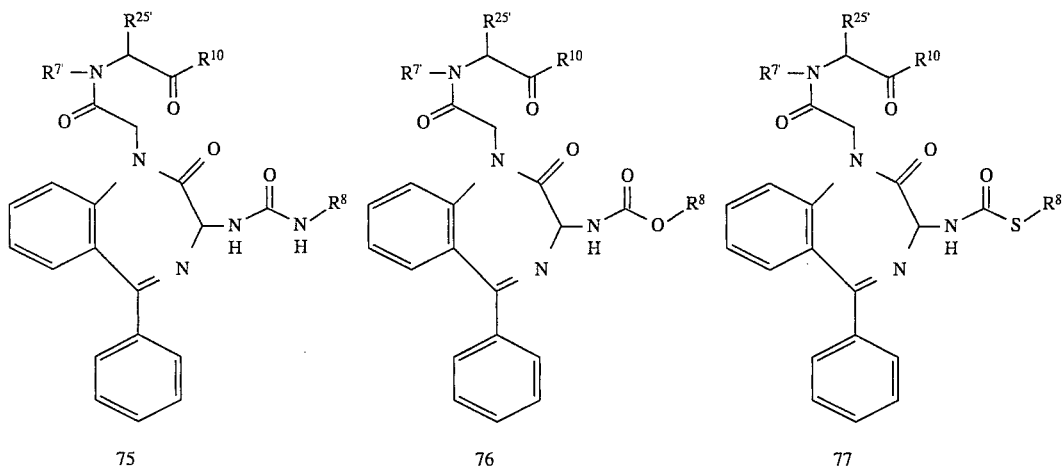
75  76  77
72, 73, or 74 may be used as inhibitors per se or further converted into compounds 75, 76, or 77 by coupling protected amino acids to the free acid forms of 72, 73, or 74 using the standard procedures shown above.
EXAMPLES
In Examples 1–8 the parenthetical compound numbers refer to the numbers in Scheme 1 below.
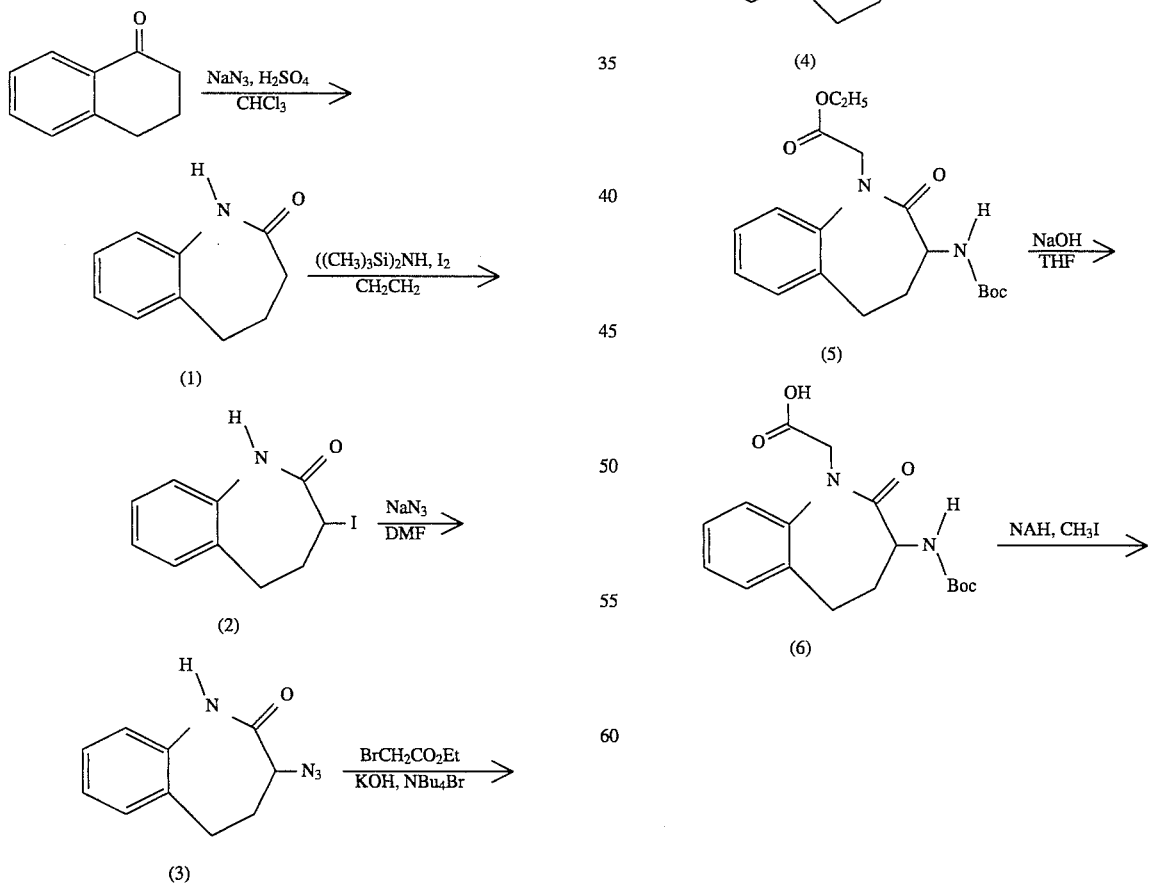

-continued
Scheme 1

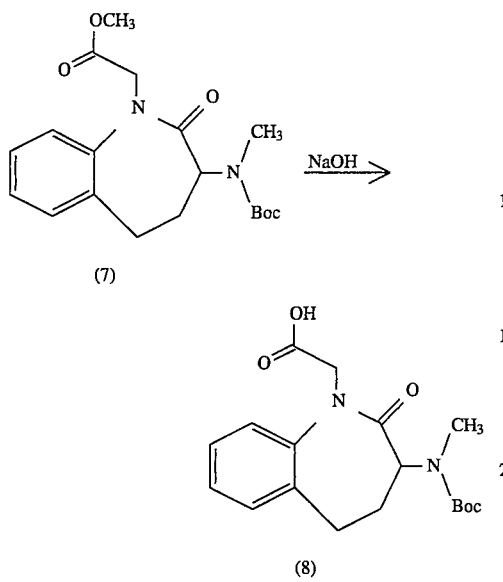

EXAMPLE 1

2,3,4,5-Tetrahydro-1H-[1]-benzazapin-2-one (1)

To a stirred suspension of 13.4 g (207 mmol) of sodium azide and 25.0 ml (188 mmol) of α-tetralone in 150 mL of chloroform, was added 50.0 mL of concentrated sulfuric acid, dropwise over 1 h. After 30 min., the chloroform phase was decanted and the acidic phase poured into 1 L of water. The precipitated solid was collected on a filter, washed with water, and recrystallized from 1 L of boiling water. The product was collected and dried under vacuum to yield 14.3 g (47%) of tan needles. $^1$H NMR (300 MHz, CDCl$_3$) d 8.63 (1H, bs), 7.24 (2H, m), 7.13 (1H, m), 7.03 (1H, d, J=8 Hz), 2.82 (2H, t, J=6 Hz), 2.38 (2H, t, J=6 Hz), 2.24 (2H, m).

EXAMPLE 2

3-Iodo-2,3,4,5-tetrahydro-1H-[1]-benzazapin-2-one (2)

A suspension of 34.2 g (212 mmol) of 2,3,4,5-tetrahydro-1H-[1]-benzazapin- 2-one and 224 mL (171.2 g, 1.06 mol) of hexamethyldisilazane in 400 mL of methylene chloride was heated at reflux for 15 min and cooled to 30° C. Iodine (161.5 g, 636 mmol) was added in one portion, the solution heated at reflux for 2.5 h, cooled, and poured into a 0° C. solution of 88.6 g of sodium sulfite in 800 mL of water, with vigorous stirring. The aqueous phase was separated, extracted with methylene choride and the combined organics were washed with water and concentrated in vacuo to approximately 200 mL. Toluene (800 mL) was added, the solution was concentrated to a slurry, and the product collected on a filter. Drying under vacuum gave 36.7 g (60%) of a tan powder. $^1$H NMR (300 MHz, CDCl$_3$) d 8.47 (1H, bs), 7.3-7.1 (3H, m), 7.06 (1H, d, J=8 Hz), 4.68 (1H, t, J=8.7 Hz), 2.97 (1H, m), 2.80-2.60 (3H, m).

EXAMPLE 3

3-Azido-2,3,4,5-tetrahydro-1H-[1]-benzazapin-2-one (3)

To a solution of 36.7 g (128 mmol) of 3-Iodo-2,3,4,5-tetrahydro-1H-[1]-benzazapin- 2-one in 200 mL of dimethylformamide was added 9.97 g (153 mmol) of sodium azide. After 3 h, the mixture was poured into 800 mL of ice water and the precipitate collected on a filter. After washing the solid successively with water, 3% aqueous sodium bisulfite, and water, the product was dried under vacuum to give 21.5 g (83%) of a tan powder. $^1$H NMR (300 MHz, CDCl$_3$) d 8.91 (1H, bs), 7.4-7.0 (4H, m), 3.89 (1H, t, J=9 Hz), 2.97 (1H, m), 2.73 (1H, m), 2.52 (1H, m), 2.32 (1H, m).

EXAMPLE 4

Ethyl 3-azido-2,3,4,5-tetrahydro-1H-[1]-benzazapin-2-one-1-acetate (4)

To a solution of 5.00 g (24.7 mmol) of 3-Azido-2,3,4,5-tetrahydro-1H-[1]-benzazapin- 2-one, 1.48 g (26.5 mmol) of powdered potassium hydroxide, and 780 mg (2.47 mmol) of tetrabutylammonium bromide in 25 mL of tetrahydrofuran was added 2.95 mL (4.42 g, 26.5 mmol) of ethyl bromoacetate. The mixture was rapidly stirred at ambient temperature for 4 h and partitioned between ethyl acetate and water. The organic phase was washed with water, dried (magnesium sulfate), and concentrated, to yield 6.43 g of an oil, used without further purification. $^1$H NMR (300 MHz, CDCl$_3$) d 7.38-7.13 (4H, m), 4.72 (1H, d, J=17 Hz), 4.42 (1H, d, J=17 Hz), 4.18 (2H, q, J=7 Hz), 3.75 (1H, m), 3.38 (1H, m), 2.70 (1H, m), 2.40 (2H, m), 1.26 (3H, t, J=7 Hz).

EXAMPLE 5

Ethyl 3-(tert-butoxycarbonylamino)-2,3,4,5-tetrahydro-1H-[1]-benzaza-pin-2-one- 1-acetate (5)

A suspension of 6.43 g of crude ethyl 3-azido-2,3,4,5-tetrahydro-1H-[1]-benzazapin- 2-one-1-acetate and 1 g of 10% palladium on carbon in 40 mL of ethanol was shaken under 50 psig H$_2$ for 12 h. The mixture was filtered through celite, concentrated to a foam, and redissolved in 100 ml of methylene chloride/1N aqueous sodium bicarbonate (1:1). Di-t-butyldicarbonate (10.8 g, 49.4 mmol) was added, the mixture was rapidly stirred at ambient temperature for 12 h, and partitioned between water and methylene chloride. The organic phase was separated and washed successively with 1N sodium bicarbonate, 1N sodium bisulfate, water, brine, and dried over magnesium sulfate. Concentration in vacuo gave a solid that was chromatographed (200 g silica gel 60, ethyl acetate/hexane 1:3 to 1:2). Recrystallization from ethyl acetate/hexane gave 5.93 g (69% from 3-azido- 2,3,4,5-tetrahydro-1H-[1]-benzazapin-2-one) of a colorless crystalline solid. $^1$H NMR (300 MHz, CDCl$_3$) d 7.3-7.1 (4H, m), 5.42 (1H, bd), 4.75 (1H, d, J=17 Hz), 4.33 (1H, d, J=17 Hz), 4.25 (1H, m), 4.17 (1H, bq, J=7 Hz), 3.32 (1H, m), 2.57 (2H, m), 1.98 (1H, m), 1.38 (9H, s), 1.24 (3H, t, J=7 Hz). Exact mass (FAB, M+H$^+$) calcd for C$_{19}$H$_{27}$N$_2$O$_5$: 363.1920; Found: 363.1929.

EXAMPLE 6

3-(tert-Butoxycarbonylamino)-2,3,4,5-tetrahydro-1H-[1]-benzazapin-2-one-1-acetic acid (6)

A solution of 5.00 g (14.3 mmol) of ethyl 3-(tert-butoxycarbonylamino)- 2,3,4,5-tetrahydro-1H-[1]-benzazapin-2-one-1-acetate in 30 mL of methanol was cooled to 0° C. and treated with 28.5 mL of 1N sodium hydroxide. Tetrahydrofuran was added until the mixture was homogeneous (about 10 mL) and the solution warmed to ambient temperature for 3 h. The volatiles were removed in vacuo and the residue was diluted with water and extracted with ether. The aqueous phase was acidified to pH 2 with 1N sodium bisulfate and extracted twice with ethyl acetate. The combined organics were washed with brine, dried over magnesium sulfate, and concentrated to 20 mL. Hexane was added and the resulting suspension was aged overnight at 0° C., filtered, and the solid dried in vacuo to give 4.62 g (100%) of colorless product. $^1$H NMR (300 MHz, CDCl$_3$) d 8.65 (1H, b), 7.3-7.1 (4H, m), 5.52 (1H, bd), 4.71 (1H, d, J=17 Hz), 4.40 (1H, d, J=17 Hz), 4.25 (1H, m), 3.25 (1H, m), 2.56 (2H, m), 1.98 (1H, m), 1.37 (9H, s). Exact mass (FAB, M+H$^+$) calcd for C$_{17}$H$_{23}$N$_2$O$_5$: 335.1607; Found: 335.1609.

EXAMPLE 7

Methyl 3-(tert-butoxycarbonylmethylamino)-2,3,4,5-tetrahydro-1H-[1] -benzazapin-2-one-1-acetate (7)

To a solution of 2.58 g (8.00 mmol) of 3-(tert-butoxycarbonylamino)- 2,3,4,5-tetrahydro-1H-[1]-benzazapin-2-one-1-acetic acid in 40 mL of tetrahydrofuran/dimethylformamide/glyme (6:1:1) was added 3.98 mL (64.0 mmol) of methyl iodide and 960 mg of sodium hydride (60% dispersion in mineral oil, 24.0 mmol). The suspension was heated at 50° C. (at which point it became homogeneous) for 3 h and cooled. 30 mL of 1N sodium bisulfate was added, the volatiles removed in vacuo, and the aqueous slurry extracted twice with ethyl acetate. The organic phase was washed with brine, dried over magnesium sulfate, filtered, and concentrated. Chromatography (150 g silica gel 60, ethyl acetate/hexane/acetic acid (40:60:1)) gave a solid that was recrystallized from methanol/water to yield 2.01 g (69%) of colorless product. $^1$H NMR (300 MHz, CDCl$_3$, spectrum broad due to carbamate rotomers) d 7.3- 7.1 (4H, m), 4.95-4.15 (3H, bm), 3.69 (3H, bs), 3.35 (1H, m), 3.02 (3H, s), 2.68 (1H, m), 2.50 (1H, m), 2.15 (1H, m), 1.39 (4.5H, bs), 1.29 (4.5H, bs). Mass spec. (FAB, M+H$^+$) calcd for C$_{19}$H$_{27}$N$_2$O$_5$: 363.19; Found: 363.1.

EXAMPLE 8

3-(tert-Butoxycarbonylmethylamino )-2,3,4,5-tetrahydro-1H-[1]-benz-azapin-2-one-1-acetic acid (8)

To a 0° C. methanolic solution of 1.59 g (4.39 mmol) of methyl 3-(tert-butoxycarbonylmethylamino)- 2,3,4,5-tetrahydro-1H-[1]-benzazapin-2-one-1-acetate was added 8.6 mL of 1N sodium hydroxide and 5 mL of tetrahydrofuran. The mixture was magnetically stirred for 3 h at ambient temperature and concentrated in vacuo to remove the volatiles. The slurry was diluted with water, extracted with ether (discarded), and acidified to pH 2 with 1N sodium hydrogen sulfate. The aqueous phase was extracted twice with ethyl acetate and the combined organics were washed with brine, dried over magnesium sulfate, filtered, and concentrated to a colorless foam. $^1$H NMR (300 MHz, CDCl$_3$) d 8.40 (1H, b), 7.35-7.05 (4H, m), 4.80 (1H, m), 4.50 (1H, m), 4.25 (1H, m), 3.25 (1H, m), 3.00 (3H, s), 2.65 (1H, m), 2.45 (1H, m), 2.13 (1H, m), 1.38 (4.5H, bs), 1.27 (4.5H, bs). Exact mass (FAB, M+H$^+$) calcd for C$_{18}$H$_{25}$N$_2$O$_5$: 349.1763; Found: 349.1761.

EXAMPLE 9

N-[[3-(2-Amino-3-mercapto-1-oxopropyl) methylamino]-2,3,4,5-tetrahydro-2-oxo-1H-1-benzazepin-1-yl] acetyl]-L-methionine (9)

Scheme 2

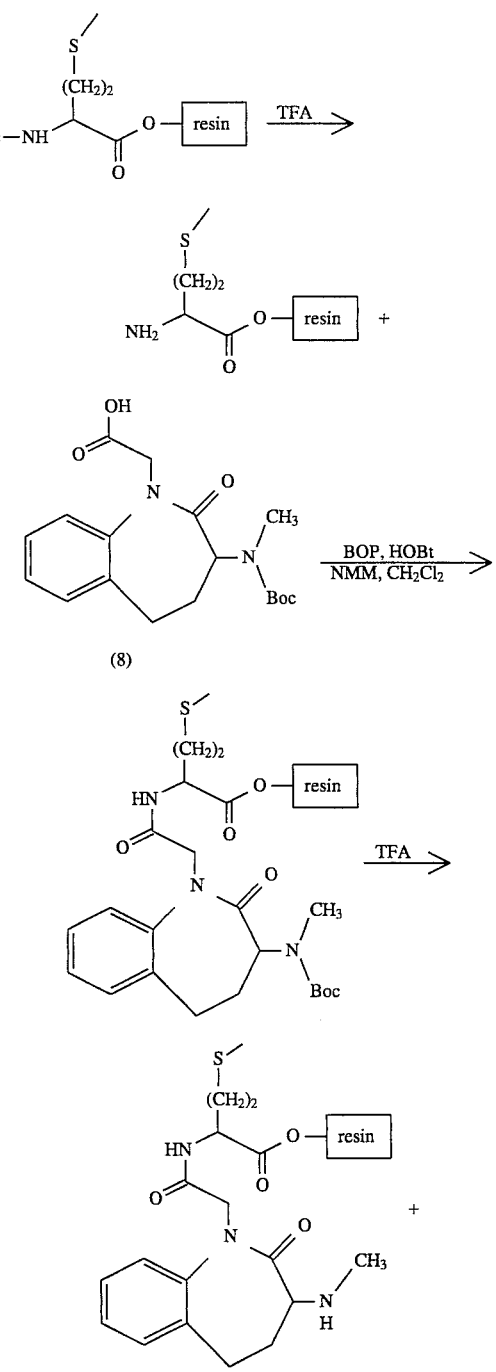

-continued
Scheme 2

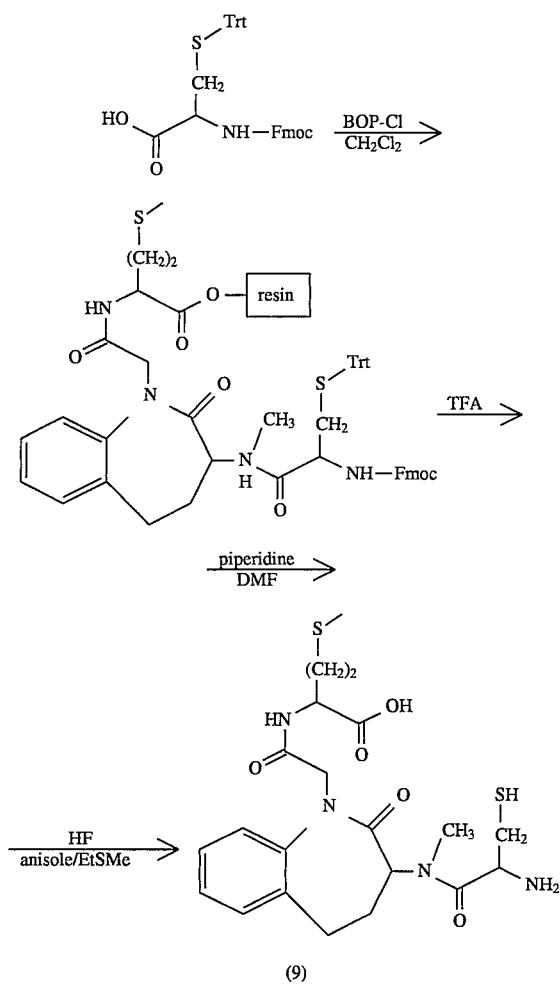

The compounds synthesized via the route shown in Scheme 2 followed standard solid-phase methodologies (Barany, G. and Merrifield, R. B. (1980) in "The Peptides", 2, 1–284. Gross, E. and Meienhofer, J. Eds. Academic Press, New York). 3-(tert-Butoxycarbonylmethylamino)-2,3,4,5-tetrahydro-1H-[1]-benz-azapin-2-one-1-acetic acid (1.6 mmol, 558 mg), benzotriazol-1-yloxy-tris-(dimethylamino)-phosphonium hexafluorophosphate (BOP, 1.6 mmol, 706 mg), N-methylmorpholine (NMM, 1.6 mmol, 217 ul), and N-hydroxbenztriazole (HOBt, 1.6 mmol, 175 mg) in dimethylacetamide (DMA, 30 ml) were added to deprotected L-methionine-linked Merrifield resin (Bachem, 1.5 gm, 0.71 meq/gm, 12hrs.). After wash (DMA, then dichloromethane (DCM)) and deprotection steps (45% TFA/5% anisole/5% EtSMe/DCM), the resin was neutralized (20% Et₃N/DCM) and washed (DCM). Next, Fmoc-(S-trityl)-L-cysteine (4.3 mmol, 2.5 gm), bis(2-oxo-3-oxazolidinyl)phosphinic chloride (BOP-Cl, 4.7 mmol, 1.2 gm), and diisopropylethylamine (9.4 mmol, 1.6 ml) were combined and added to the resin (DCM, 30 ml, 10 hrs). After removal of the Fmoc (20% piperidine/DMA) and trityl (45% TFA/5% EtSMe/5% anisole/DCM) protecting groups the resin was washed with MeOH, dried under vacuum, cleaved from the resin (32 ml, HF/10% anisole/5% EtMeS, 0° C., 1 hr.) and purified via HPLC. Purification of 119 mg of crude material (Vydac C18, ACN/water/0.1% TFA) afforded the product, N-[[3-(2-amino-3-mercapto-1-oxopropyl) methylamino]-2,3,4,5-tetrahydro- 2-oxo-1H-1-benzazepin-1-yl] acetyl]-L-methionine, as two separable diastereomers (opposite configuration at C-3 of the benzodiazepine) designated 9A (24 mg) and 9B (27 mg) corresponding to the early and late eluting peaks respectively.

Mass (electrospray, M+H⁺) calc: 483.1 found: 482.8 (9A), 482.8 (9B).

EXAMPLE 10

N-[[3-(2-Amino-3-mercapto-1-oxopropyl) amino]-2,3,4,5-tetrahydro-2-oxo-1H- 1-benzazepin-1-yl] acetyl]-L-methionine (10)

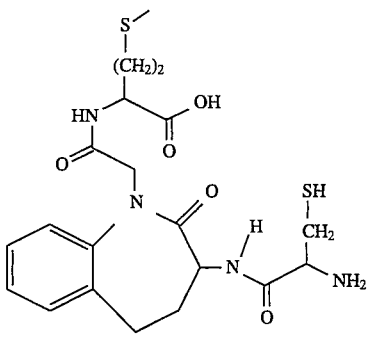

The title compound was prepared using the procedure of Example 9 in which 3-(tert-butoxycarbonylamino)-2,3,4,5-tetrahydro-1H-[1]-benzazapin-2-one- 1-acetic acid (428 mg, 1.3 mmol) was coupled to L-methionine resin (1.2 gms, 0.71 mmol/gm) with BOP (565 mg, 1.3 mmol), NMM (170 ul, 1.3 mmol), and HOBt (140 mg, 1.3 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 102 mg of the crude material yielded the two diastereomers 10A (18 mg) and 10B (12 mg).

Mass (electrospray, M+H⁺) calc: 469.1 found: 468.8 (10A), 468.8 (10B).

In Examples 11–17 the parenthetical compound numbers refer to the numbers in Scheme 3 below.

Scheme 3

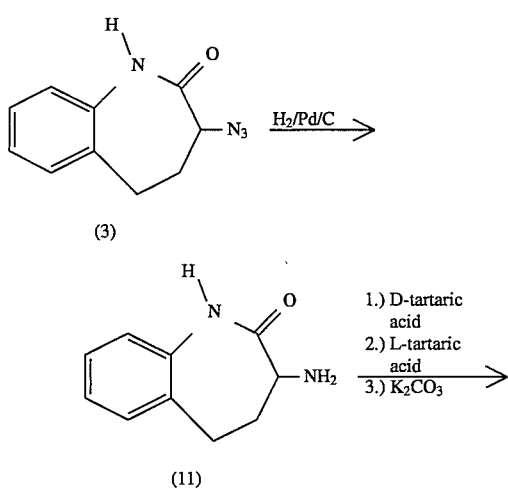

-continued
Scheme 3

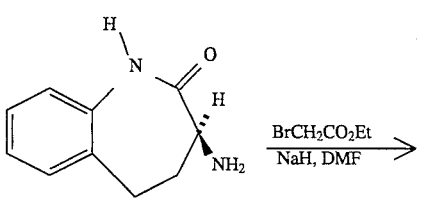

(13)

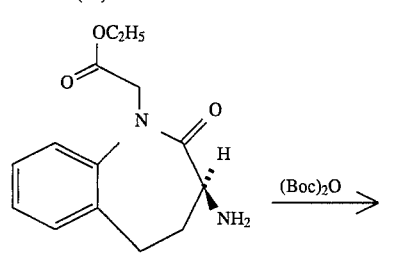

(14)

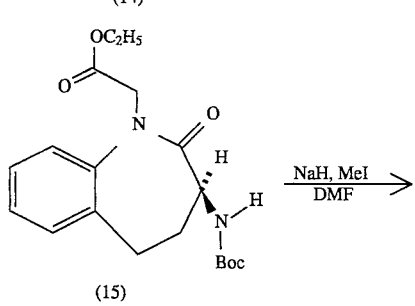

(15)

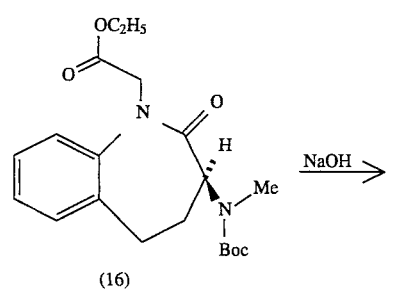

(16)

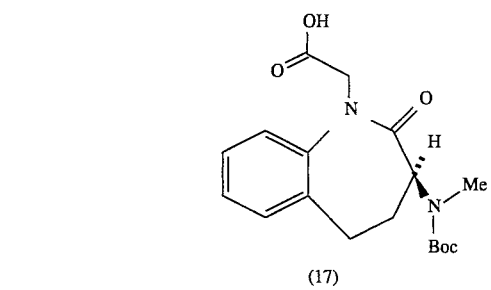

(17)

EXAMPLE 11

3-Amino-2,3,4,5-tetrahydro-1H-[1]-benzazapin-2-one (11)

To a suspension of 10.0 g (49.4 mmol) of 3-azido-2,3,4,5-tetrahydro-1H-[1]-benzazapin-2-one (Example 3 above) in 100 mL of methanol/ethanol (1:1) was added 1 g of 10% palladium on charcoal and the flask was purged with nitrogen and charged with 55 psig hydrogen. The mixture was shaken for 5 h, filtered through celite and concentrated. The residue was recrystallized from MeOH to give 6.77 g (78%) in two crops. $^1$H NMR (300 MHz, CDCl$_3$) d 8.38 (1H, bs), 7.3-7.1 (3H, m), 6.98 (1H, d, J=8 Hz), 3.42 (1H, dd, J=11, 7 Hz), 2.90 (1H, m), 2.70-2.40 (2H, m), 1.89 (1H, m), 1.78 (bs, 2H).

EXAMPLE 12

3(R)-Amino-2,3,4,5-tetrahydro-1H-[1]-benzazapin-2-one (12)

A suspension of 6.75 g (38.3 mmol) of 3-amino-2,3,4,5-tetrahydro-1H-[1]-benzazapin- 2-one and 5.18 g (34.5 mmol) of D-tartaric acid in 80 ml of ethanol/water (4:1) was warmed to effect solution and aged overnight at ambient temperature. The crystals were collected, recrystallized again from ethanol/water, and dried under vacuum to give 4.61g (37%) of purified D-tartrate salt. The salt was dissolved in water, solid potassium carbonate was added until the pH was 10–11, and the solution extracted four times with methylene chloride. The combined organics were dried over magnesium sulfate, filtered, and concentrated in vacuo to give 2.03 g (30% overall) of the 3(R)-amine. [α]D=+407° (c=1, MeOH); lit. Fisher, M. H.; et al EP 513974-A1, 2/28/92, [α]D=+455° (c=1, MeOH).

EXAMPLE 13

3(S)-Amino-2,3,4,5-tetrahydro-1H-[1]-benzazapin-2-one (13)

The mother liquors from Example 12, enriched in the 3(S)-isomer were free-based as above, treated with L-tartaric acid (1 eq), and recrystallized from ethanol/water. The crystals were collected, free-based with aqueous potassium carbonate and extracted as above. Drying and concentration gave 1.50 g (22% overall) of the 3(S)-amine.

EXAMPLE 14

Ethyl 3(S)-3-amino-2,3,4,5-tetrahydro-1H-[1]-benzazapin-2-one-1-acetate (14)

To a solution of 1.50 g (8.51 mmol) of 3(S)-amino-2,3,4,5-tetrahydro-1H-[1]-benzazapin-2-one in 20 mL of dimethylformamide at 0° C. was added 340 mg (8.51 mmol, 60% disp. in mineral oil) of sodium hydride. The suspension was warmed to ambient temperature for 1.5 h, recooled to 0° C., and treated with 1.42 g (0.948 mL, 8.51 mmol) of ethyl bromoacetate in 5 mL of dimethylformamide. The ice bath was removed, and after 1 h the mixture was concentrated in vacuo. The residue was partitioned between ethyl acetate and 1N sodium bicarbonate, the organic phase removed, washed with brine, dried over magnesium sulfate, and concentrated. Trituration with ether gave 767 mg (34%) of a colorless solid in the first crop. [α]D=–295° (c=0.95, EtOH); (lit. Watthey, J. W. H.; et al *J. Med. Chem.* 1985, 28, 1511., [α]D=–285.5° (c=0.99, EtOH)). $^1$H NMR (300 MHz, CDCl$_3$) d 7.30-7.10 (4H, m), 4.62 (1H, d, J=17.8 Hz), 4.45 (1H, d, J=17.8 Hz), 4.19 (2H, q, J=7 Hz), 3.43 (1H, m), 3.23 (1H, m), 2.58 (1H, m), 2.41 (1H, m), 1.78 (2H, bs), 1.26 (3H, t, J=7 Hz).

EXAMPLE 15

Ethyl 3(S)-3-(tert-butoxycarbonylamino)-2,3,4,5-tetrahydro-1H-[1]-benzazepin- 2-one-1-acetate (15)

Di-t-butyl-dicarbonate (1.23 g, 5.62 mmol) was added to a slurry of 737 mg (2.81 mmol) of Ethyl 3(S)-3-amino-2,3,4,5-tetrahydro-1H-[1]-benzazapin-2-one- 1-acetate in 20 mL methylene chloride/water (1:1) and the mixture was rapidly stirred at ambient temperature for 30 min. The organic phase was separated and washed with 1N sodium bicarbonate, brine, dried over magnesium sulfate, and filtered. Concentration in vacuo gave a foam that was chromatographed (70 g silica gel 60, ethyl acetate/hexane (1:2)) to give 987 mg (97%) of a colorless foam identical with material prepared above (Example 5).

EXAMPLE 16

Ethyl 3(S)-3-(tert-butoxycarbonylmethylamino)-2,3,4,5-tetrahydro-1H-[1] -benzazapin-2-one-1-acetate (16)

To a 0° C. solution of 488 mg (1.35 mmol) of Ethyl 3(S)-3-(tert-butoxycarbonylamino)- 2,3,4,5-tetrahydro-1H-[1]-benzazapin-2-one-1-acetate in 5 mL of dimethylformamide was added 0.170 mL (2.69 mmol) of methyl iodide and 59 mg of sodium hydride (60% dispersion in mineral oil, 1.48 mmol). The suspension was stirred at ambient temperature for 15 h and partitioned between ethyl acetate and 1N sodium bicarbonate. The organic phase was washed with 3% sodium bisulfite, water, brine, dried over magnesium sulfate, filtered, and concentrated. Chromatography (35 g silica gel 60, ethyl acetate/hexane (1:3)) gave 410 mg (81%) of a colorless foam. $^1$H NMR (300 MHz, CDCl$_3$, spectrum broad due to carbamate rotomers) d 7.3-7.1 (4H, m), 4.90-4.05 (5H, bm), 3.35 (1H, bm), 3.01 (3H, s), 2.65 (1H, m), 2.48 (1H, m), 2.15 (1H, m), 1.4-1.1 (12H, b).

EXAMPLE 17

(S)-3-(tert-Butoxycarbonylmethylamino)-2,3,4,5-tetrahydro-1H-[1]-benzazepin- 2-one-1-acetic acid (17)

To a 0° C. solution of 410 mg (1.09 mmol) of Ethyl 3(S)-3-(tert-butoxycarbonylmethylamino)- 2,3,4,5-tetrahydro-1H-[1]-benzazapin-2-one-1-acetate in 6 mL of tetrahydrofuran/water (2:1) was added 2.2 mL of 1N sodium hydroxide. The mixture was magnetically stirred for 3 h at ambient temperature and concentrated in vacuo to remove the volatiles. The slurry was diluted with water, extracted with ether (discarded), and acidified to pH 2 with 1N sodium hydrogen sulfate. The aqueous phase was extracted twice with ethyl acetate and the combined organics were washed with brine, dried over magnesium sulfate, filtered, and concentrated to a colorless foam. This material was identical with racemic material prepared above (Example 8). [α]D= –177° (c=0.90, EtOH).

EXAMPLE 18

N-[[3(S)-3-(2-Amino-3-mercapto-1-oxopropyl) methylamino]-2,3,4,5-tetrahydro-2-oxo-1H-1-benzazepin-1-yl]acetyl]-L-methionine (18)

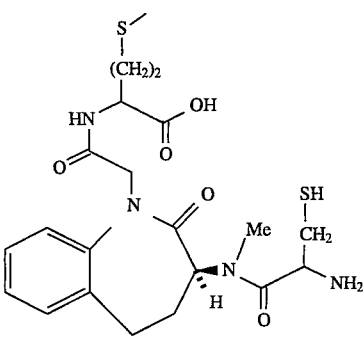

The title compound was prepared using the procedure of Example 9 in which 3(S)-3-(tert-butoxycarbonylmethylamino)-2,3,4,5-tetrahydro-1H-[1]-benzazepin- 2-one-1-acetic acid (338 mg, 0.8 mmol) was coupled to L-methionine resin (0.75 gm, 0.71 mmol/gm) using BOP (353 mg, 0.8 mmol), NMM (108 ul, 0.8 mmol), and HOBt (88 mg, 0.8 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). HPLC analysis of the product showed that it was identical to a single diastereomer of the compound shown in Example 9. Co-injection of the compound prepared in Example 18 with the diastereomeric mixture of compounds prepared in Example 9 showed that the material prepared in Example 18 co-eluted with the first peak (9A) of Example 9. Therefore, for these compounds and all other molecules of similar structure described here we can conclude the configuration at the 3-carbon of the seven-membered ring is such that the 3(S) isomer elutes first (A peak) and the 3(R) isomer follows (B peak). It should be noted that in the benzodiazepine series the assignment of stereochemistry reverses from that of the benzazepine compound discussed in this example due to a shift in priority of the atoms bound to C-3 of the seven-membered ring. Therefore, in the benzodiazepine examples discussed below, we can conclude that the 3(R) isomer elutes first, and the 3(S) isomer follows.

In Examples 19–26 the parenthetical compound numbers refer to the numbers in Scheme 4 below.

Scheme 4

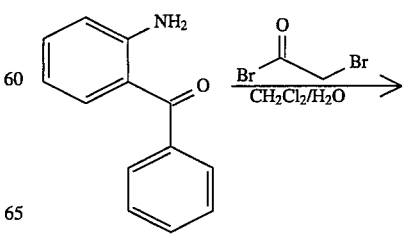

333
-continued
Scheme 4
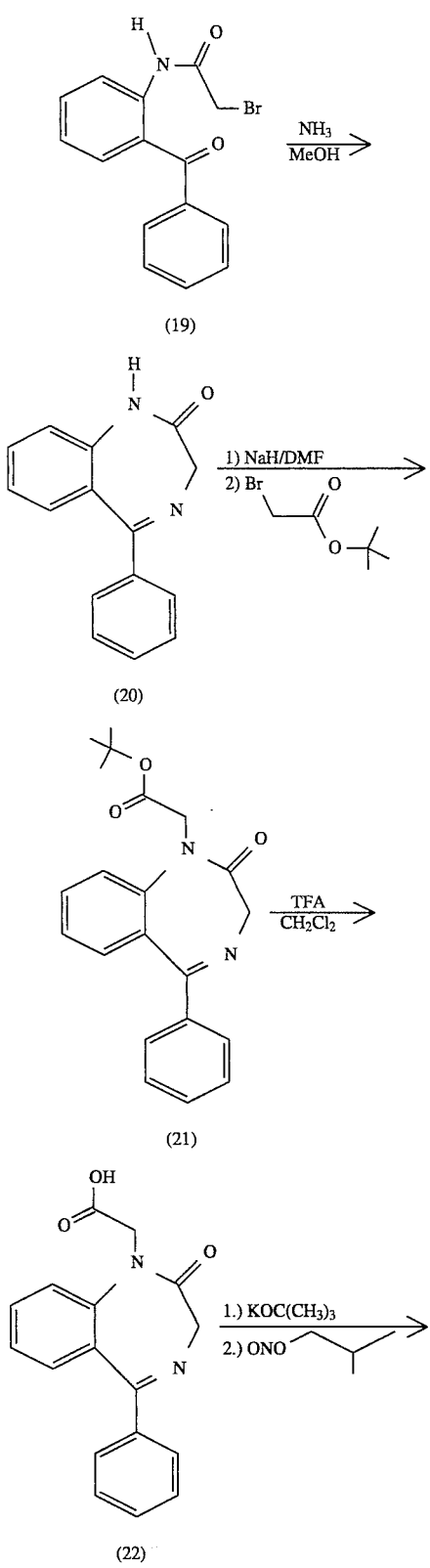
334
-continued
Scheme 4
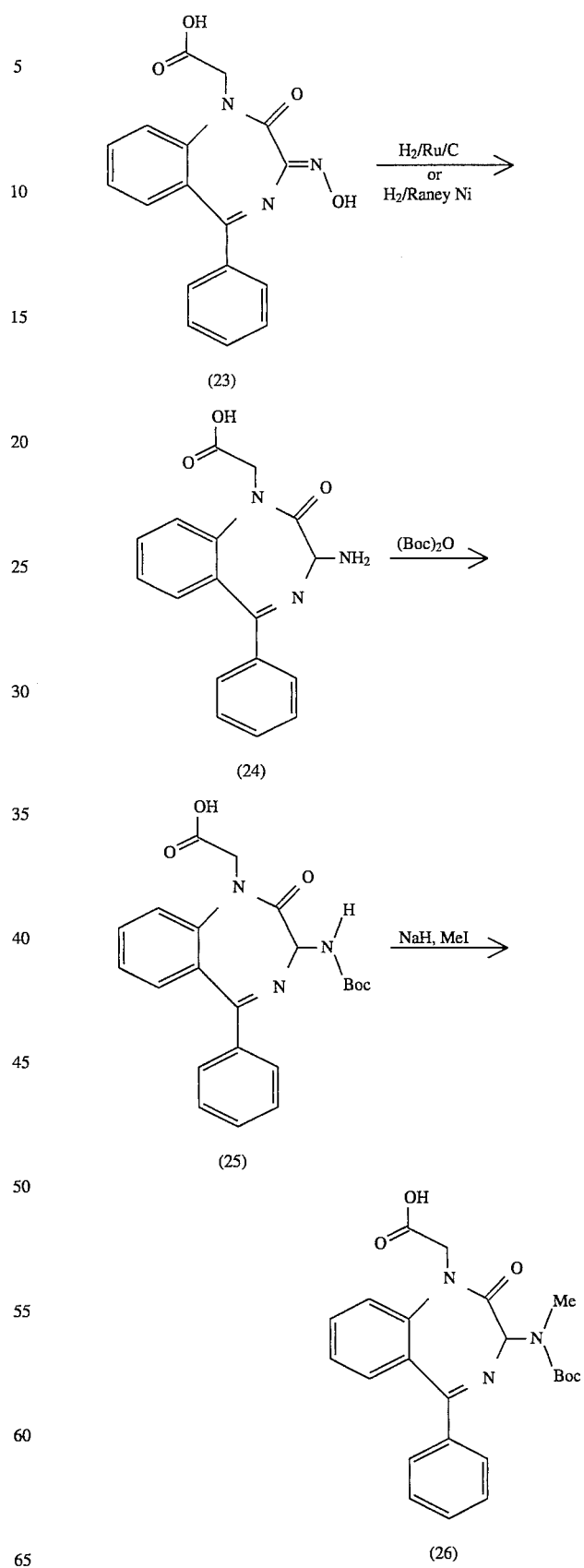

EXAMPLE 19

2-Bromoacetamido-benzophenone (19)

A solution of bromoacetyl bromide (100 mL, 1.15 mol, Aldrich) dissolved in dichloromethane (300 mL) was added over 30 min to a solution of 2-aminobenzophenone (197 g, 1.0 mol, Fluka) dissolved in dichloromethane (1.3 L) and water (100) mL) cooled to −10° C. under vigorous mechanical stirring. The resulting mixture was stirred for an additional 1 h at −5° C. and then was allowed to warm to ambient temperature. The layers were separated, and the organic extract was washed with dilute sodium bicarbonate, then was dried over sodium sulfate. Evaporation afforded 309.8 g (95%) of 2-bromoacetamidobenzophenone as off-white crystals.

EXAMPLE 20

2,3-Dihydro-5-phenyl-1H-1,4-benzodiazepin-2-one (20)

A suspension of 2-bromoacetamidobenzophenone (275 g, 0.86 mol) in methanol (1 L) was treated with a solution of saturated ammonia in methanol (3 L), and the resulting solution was stirred at ambient temperature for 6 h, then was heated at reflux for an additional 4 h. After cooling, water (500 mL) was added, and the solution was concentrated by evaporation to about 1 L in volume, yielding crystalline 2,3-dihydro-5-phenyl-1H-1,4-benzodiazepin- 2-one (20) (200.7 g, 98%).

EXAMPLE 21 tert-Butyl-2,3-dihydro-5-phenyl-1H-1,4-benzodiazepin-2-one-1-acetate (21)

A 1 L round-bottomed flask was equipped with a magnetic stirring bar and nitrogen inlet and was sequentially charged with 100 g (0.423 mol) of 2,3-dihydro- 5-phenyl-1H-1,4-benzodiazepin-2-one, 600 mL of 1-methyl-2-pyrrolidinone (Aldrich, anhydrous), 97 mL (117 g, 0.601 mol) of tert-butyl bromoacetate (Aldrich), and 194 g (0.595 mol) of cesium carbonate (Aldrich). After stirring overnight at room temperature, the reaction mixture was diluted with 2 L H$_2$O and extracted with EtOAc (3×600 mL). The combined organic extracts were washed with H$_2$O (4×300 mL) and brine (200 mL), dried with anhydrous Na$_2$SO$_4$, filtered, and concentrated under reduced pressure to provide 202 g of a solid. This material was recrystallized from hexanes/EtOAc to provide 123 g (83%) of tert-butyl-2,3-dihydro-5-phenyl-1H-1,4-benzodiazepin- 2-one-1-acetate (21) as a white crystalline solid.

EXAMPLE 22

2,3-dihydro-5-phenyl-1H-1,4-benzodiazepin-2-one-1-acetic acid (22)

A solution of tert-butyl-2,3-dihydro-5-phenyl-1H-1,4-benzodiazepin-2-one- 1-acetate (58 g, 0.172 mol) in neat trifluoroacetic acid (100 mL) was stirred overnight, followed by evaporation and retreatment with an additional amount of TFA (100 mL). The mixture was evaporated, and the residue was dissolved in dichloromethane, and was washed with water and brine. The organic layer was dried over sodium sulfate and evaporated to yield 2,3-dihydro- 5-phenyl-1H-1,4-benzodiazepin-2-one-1-acetic acid (22) (48.4 g, 100%) as a yellow foam.

EXAMPLE 23

3-oximino-2,3-dihydro-5-phenyl-1H-1,4-benzodiazepin-2-one-1-acetic acid (23)

A solution of 2,3-dihydro-5-phenyl-1H-1,4-benzodiazepin-2-one-1-acetic acid (22) (30 g, 0.106 mol) in glyme (1 L) was cooled to −5° C. and degassed under nitrogen. Solid potassium tert-butoxide (47.7 g, 0.43 mol) was added portionwise, and the resulting red solution was stirred for 30 min at 0°–5° C. A solution of isobutyl nitrite (13.8 mL, 0.117 mol, Aldrich) in glyme (20 mL) was then added, producing an orange-yellow solid. The mixture was neutralized with acetic acid (200 mL) with slight warming, and then was evaporated. The residue was partitioned between butanol and brine, and the organic layer was dried over sodium sulfate. Additional residual inorganics precipitated on standing, and were removed by filtration. Addition of hexane to the butanol solution afforded a crude precipitate (34.3 g), which was recrystallized from ethyl acetate-ethanol to yield 3-oximino-2,3-dihydro-5-phenyl-1H-1,4-benzodiazepin-2-one-1-acetic acid (23) (21.85 g, 66%).

EXAMPLE 24

3-Amino-2,3-dihydro-5-phenyl-1H-1,4-benzodiazepin-2-one-1-acetic acid (24)

A solution of 3-oximino-2,3-dihydro-5-phenyl-1H-1,4-benzodiazepin-2-one- 1-acetic acid (15.0 g, 48 mmol) in methanol (1 L) was hydrogenated over catalytic ruthenium on carbon (5.0 g, Aldrich) at 40 psi and 70° C. for 4 days. The catalyst was removed by filtration, and the solution was evaporated to yield a crude solid (13.5 g). Flash chromatography (50 ethyl acetate: 49 methanol: 1 water) yielded pure 3-amino-2,3-dihydro-5-phenyl-1H-1,4-benzodiazepin-2-one-1-acetic acid (9.69 g).

Alternatively, a solution of 3-oximino-2,3-dihydro-5-phenyl-1H-1,4-benzodiazepin- 2-one-1-acetic acid (33 g, 102 mmol) in methanol (200 ml) containing 2 ml acetic acid, was hydrogenated over Raney Nickel (1:1 by weight to oxime, washed twice with water than once with ethanol) at 65 psi and 70 C for 1½ days. The catalyst was removed by suction filtration through celite, and the solution evaporated to yield crude 3-amino-2,3-dihydro- 5-phenyl-1H-1,4-benzodiazepin-2-one-1-acetic acid which was used directly in the next step (see alternative synthesis in Example 25 below).

EXAMPLE 25

3-(tert-Butoxycarbonyl)amino-2,3-dihydro-5-phenyl-1H-1,4-benzodiazepin-2-one- 1-acetic acid (25)

A solution of 3-amino-2,3-dihydro-5-phenyl-1H-1,4-benzodiazepin-2-one- 1-acetic acid (1.0 g, 3.37 mmol) in DMF (10 mL) and water (5 mL) was treated with triethylamine (0.34 g, 3.37 mmol) and di-tert-butyl dicarbonate (0.73 g, 3.37 mmol) under nitrogen. After stirring at ambient temperature overnight, the mixture was evaporated and the residue was partitioned between ethyl acetate and water (pH=2 w/6N HCl). The organic extract was dried over sodium sulfate and evaporated. Flash chromatography (80 ethyl acetate: 19 methanol: 1 water) of the residue afforded 3-(tert-butoxycarbonyl)amino- 2,3-dihydro-5-phenyl-1H-1, 4-benzodiazepin-2-one-1-acetic acid (940 mg) as a yellow solid.

$^1$HNMR: consistent with structure

Mass (electrospray, M+H⁺) calc: 410.2 found: 410.0.

Alternatively, 3-amino-2,3-dihydro-5-phenyl-1H-1,4-benzodiazepin-2-one- 1-acetic acid prepared above (alternative synthesis, Example 24) in THF (100 ml) and water (100 ml) was cooled to 0 C and di-tert-butyl dicarbonate (28.8 g, 132 mmol) was added under nitrogen followed by 1N NaOH until the pH of the solution was ~10. The solution was allowed to come to ambient temperature, stirred overnight, and cooled again to 0° C. and acidified (pH ~3) with dropwise addition of concentrated H2SO4. The solution was partitioned (EtOAc) and the organic extract dried over sodium sulfate and evaporated. The residue was recrystallized from 120 ml MeOH yielding 18 g (44 mmol, 37%) of 3-(tert-butoxycarbonyl)amino-2,3-dihydro-5-phenyl-1H-1, 4-benzodiazepin- 2-one-1-acetic acid as yellow needles.

EXAMPLE 26

3-(tert-Butoxycarbonyl)methylamino-2,3-dihydro-5-phenyl-1H-1,4-benzodiazepin- 2-one-1-acetic acid (26)

An oven-dried, 100 mL round-bottomed flask was equipped with a magnetic stirring bar and nitrogen inlet and was sequentially charged with 4.628 g (11.3 mmol) of 3-(tert-butoxycarbonyl)amino-2,3-dihydro-5-phenyl-1H-1,4-benzodiazepin-2-one-1-acetic acid, 50 mL of anhydrous THF (Aldrich), and 2.80 mL (6.38 g, 45.0 mmol) of methyl iodide (Aldrich). The reaction flask was cooled to –5° C. in an ice/acetone bath and 1.18 g (29.5 mmol) of a 60% oil dispersion of sodium hydride was added in portions over a 5 min period (caution: vigorous gas evolution). After a 50-min period, the reaction mixture was quenched with a 5% (w/v) aqueous solution of citric acid, diluted with H₂O and extracted with EtOAc (3×40 mL). The combined organics were washed with H₂O (30 mL), brine (30 mL), dried with anhydrous Na₂SO₄, filtered, and concentrated under reduced pressure to provide 6.27 g of a viscous yellow oil. Flash chromatography of the crude material on 150 g of silica using 43:55:2 EtOAc/hexanes/AcOH as eluent yielded 4.54 g (10.7 mmol, 95%) of 3-(tert-butoxycarbonyl)methylamino-2,3-dihydro-5-phenyl- 1H-1,4-benzodiazepin-2-one-1-acetic acid as a clear glass.

1HNMR consistent with structure.

Mass calc for C23H26N3O5: 424.1872 found: 424.1909

EXAMPLE 27

N-[[3-[(2-amino-3-mercapto-1-oxopropyl)methylamino]-2,3-dihydro-2-oxo-5-phenyl-1H-1,4-benzodiazepin-1-yl]acetyl]-L-methionine (27)

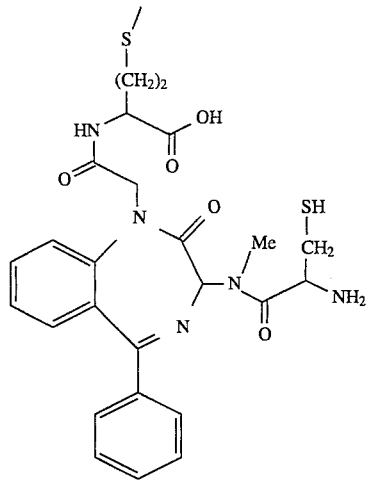

The title compound was prepared using the procedure of Example 9 in which 3-(tert-butoxycarbonyl)methylamino-2,3-dihydro-5-phenyl-1H-1,4-benzodiazepin- 2-one-1-acetic acid (675 mg, 1.6 mmol) was coupled to L-methionine resin (1.5 gms, 0.71 mmol/gm) with BOP (710 mg, 1.6 mmol), HOBt (220 mg, 1.6 mmol), and NMM (180 ul, 1.6 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 107 mg of the crude material yielded the two diastereomers 27A (27 mg) and 27B (15 mg).

Mass (FAB, M+H⁺) calc: 558.2 found:558.3 (27A), 558.3 (27B).

EXAMPLE 28

N-[[3-[(2-amino-3-mercapto-1-oxopropyl)amino]-2,3-dihydro-2-oxo-5-phenyl-1H-1,4-benzodiazepin-1-yl]acetyl]-L-methionine (28)

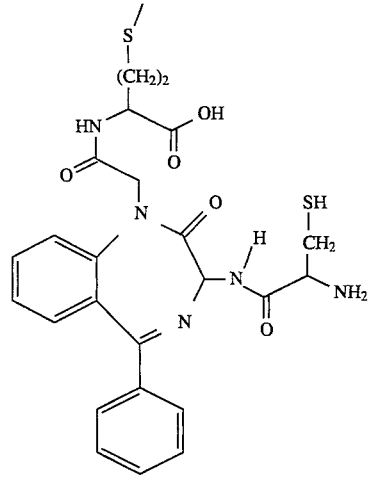

The title compound was prepared using the procedure of Example 9 in which 3-(tert-butoxycarbonyl)amino-2,3-dihydro-5-phenyl-1H-1,4-benzodiazepin- 2-one-1-acetic acid (1.3 gm, 3.2 mmol) was coupled to L-methionine resin (1.5 gms, 0.71 mmol/gm) with BOP (1.4 gm, 3.2 mmol), HOBt (430 mg, 1.6 mmol), and NMM (350 ul, 3.2 mmol). Again, after deprotection and washing steps, Fmoc-L-(S-trityl) cysteine (2.5 gm, 4.7 mmol) was coupled using BOP (1.9 gm, 4.3 mmol), HOBt (600 mg, 4.3 mmol), and NMM (500 μl, 4.3 mmol). Purification of 107 mg of the crude material yielded the two diastereomers 28A (38 mg) and 28B (14 mg).

Mass (electrospray, M+H$^+$) calc: 544.2 found:544.8 (28A), 544.8 (28B).

EXAMPLE 29

N-[[3-[(3-mercapto-1-oxopropyl)methylamino]-2,3-dihydro-2-oxo-5-phenyl-1H-1,4-benzodiazepin-1-yl]acetyl]-L-methionine (28)

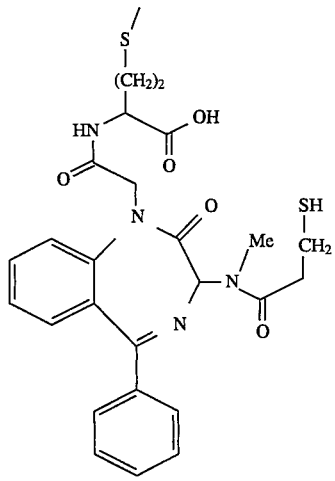

The title compound was prepared using the procedure of Example 9 in which 3-(tert-butoxycarbonyl)methylamino-2,3-dihydro-5-phenyl-1H-1,4-benzodiazepin- 2-one-1-acetic acid (0.45 gm, 1.1 mmol) was coupled to L-methionine resin (1.0 gms, 0.71 mmol/gm) with BOP (0.47 gm, 1.1 mmol), HOBt (150 mg, 1.1 mmol), and NMM (120 ul, 1.1 mmol). Again, after deprotection and washing steps, (S-methylbenzyl)propionic acid (0.6 gm, 2.8 mmol) was coupled using BOP-Cl (0.8 gm, 3.1 mmol) and DIPEA (1.09 ml, 6.2 mmol). Purification of 150 mg of the crude material yielded the two diastereomers as an unseparable mixture 29A+B (9.5 mg).

Mass (electrospray, M+H$^+$) calc: 543.2 found:543.3 (29A+B).

EXAMPLE 30

N-[[3-[(2-amino-3-mercapto-1-oxopropyl)amino]-2,3-dihydro-2-oxo-5-phenyl-1H-1,4-benzodiazepin-1-yl]acetyl]-L-serine (30)

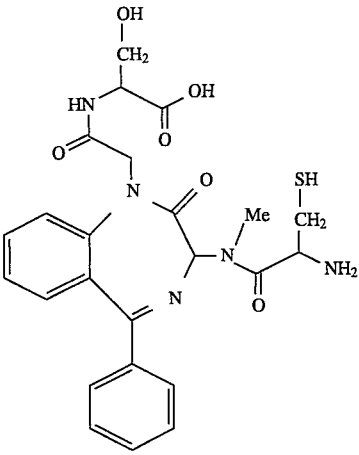

The title compound was prepared using the procedure of Example 9 in which 3-(tert-butoxycarbonyl)methylamino-2,3-dihydro-5-phenyl-1H-1,4-benzodiazepin- 2-one-1-acetic acid (0.47 gm, 1.1 mmol) was coupled to L-(O-benzyl)serine resin (0.8 gms, 0.92 mmol/gm) with BOP (0.49 gm, 1.1 mmol), HOBt (150 mg, 1.1 mmol), and NMM (120 μl, 1.1 mmol). Again, after deprotection and washing steps, Fmoc-L-(S-trityl) cysteine (1.65 gm, 2.8 mmol) was coupled using BOP-Cl (0.8 gm, 3.1 mmol) and DIPEA (1.09 ml, 6.2 mmol). Purification of 160 mg of the crude material yielded the two diastereomers 30A (14 mg) and 30B (12 mg).

Mass (electrospray, M+H$^+$) calc: 514.1 found:513.5 (30A), 513.5 (30B).

EXAMPLE 31

N-[[3-[(2-amino-3-mercapto-1-oxopropyl)methylamino]-2,3-dihydro-2-oxo-5-phenyl-1H-1,4-benzodiazepin-1-yl]acetyl]-L-leucine (31)

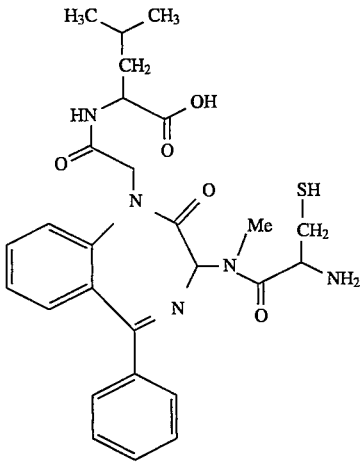

The title compound was prepared using the procedure of Example 9 in which 3-(tert-butoxycarbonyl)methylamino-2,3-dihydro-5-phenyl-1H-1,4-benzodiazepin- 2-one-1-acetic acid (0.45 gm, 1.1 mmol) was coupled to L-leucine resin (1.5 gms, 0.47 mmol/gm) with BOP (0.47 gm, 1.1 mmol), HOBt (140 mg, 1.1 mmol), and NMM (120 ul, 1.1 mmol). Again, after deprotection and washing steps, Fmoc-L-(S-trityl) cysteine (1.65 gm, 2.8 mmol) was coupled using BOP-Cl (0.8 gm, 3.1 mmol) and DIPEA (1.09 ml, 6.2 mmol). Purification of 86 mg of the crude material yielded the two diastereomers 31A (16 mg) and 31B (15 mg).
Mass (electrospray, M+H$^+$) calc: 540.2 found:540.3 (31A), 540.3 (31B).

EXAMPLE 32

N-[[3-[(2-acetylamino-3-mercapto-1-oxopropyl)methylamino]-2,3-dihydro-2-oxo-5-phenyl-1H-1,4-benzodiazepin-1-yl]acetyl]-L-methionine (32)

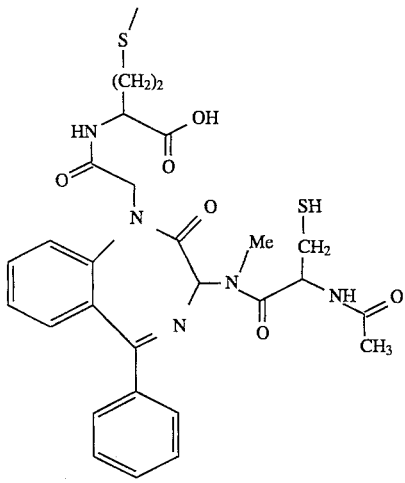

The title compound was prepared using the procedure of Example 9 in which the synthesis of Example 27 was conducted, and the amino-terminus acetylated via treatment with acetic anhydride (5%) in 5% NMM/DCM for 5 min. Purification of 204 mg of the crude material yielded the two diastereomers 32A (30 mg) and 32B (36 mg).

Mass (electrospray, M-H$^+$) calc: 598.2 found:598.1 (32A), 598.1 (32B).

EXAMPLE 33

N-[[3-[(2-amino-3-mercapto-1-oxopropyl)methylamino]-2,3-dihydro-2-oxo-5-phenyl-1H-1,4-benzodiazepin-1-yl]acetyl]-L-methionine amide (33)

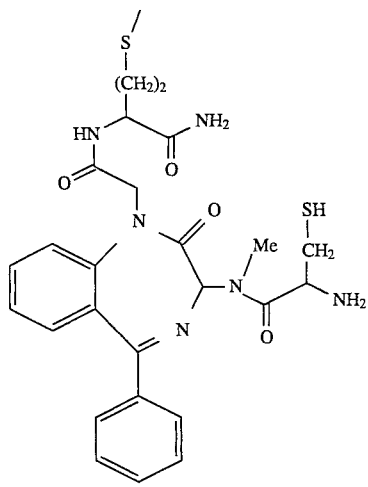

The title compound was prepared using the procedure of Example 9 in which Boc-L-methionine (0.6 gm, 2.4 mmol) was coupled to MBHA-resin (1.5 gm, 0.53 mmol/gm) using BOP (0.33 gm, 2.4 mmol), HOBt (0.26 gm, 2.4 mmol), and NMM (130 μl, 2.4 mmol). Following suitable deprotection and washing steps, 3-(tert-butoxycarbonyl)methylamino-2,3-dihydro-5-phenyl-1H- 1,4-benzodiazepin-2-one-1-acetic acid (0.5 mg, 1.2 mmol) was coupled with BOP (0.53 mg, 1.2 mmol), HOBt (160 mg, 1.2 mmol), and NMM (130 μl, 1.2 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 300 mg of the crude material yielded the two diastereomers 33A (43 mg) and 33B (42 mg).
Mass (electrospray, M-H$^+$) calc: 557.2 found:557.9 (33A), 556.9 (33B).

EXAMPLE 34

N-[[3-[(2-amino-3-mercapto-1-oxopropyl)methylamino]-2,3-dihydro-2-oxo-5-phenyl-1H-1,4-benzodiazepin-1-yl]acetyl]-L-phenylalanine (34)

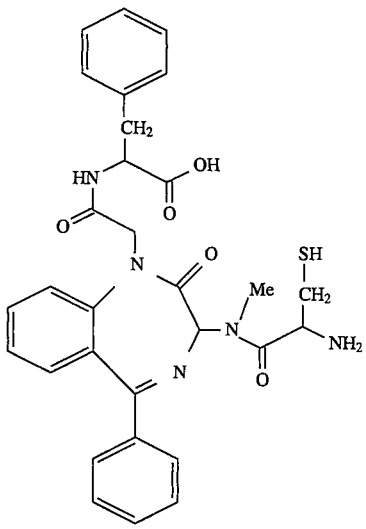

The title compound was prepared using the procedure of Example 9 in which 3-(tert-butoxycarbonyl)methylamino-2,3-dihydro-5-phenyl-1H-1,4-benzodiazepin- 2-one-1-acetic acid was coupled to L-phenylalanine resin. Again, after deprotection and washing steps, Fmoc-L-(S-trityl) cysteine was coupled as above. Purification of 106 mg of the crude material yielded the two diastereomers 34A (39 mg) and 34B (32 mg).

Mass (electrospray, M+H$^+$) calc: 574.2 found:574.3 (34A), 574.3 (34B).

EXAMPLE 35

N-[[3-[(2-amino-3-mercapto-1-oxopropyl)methylamino]-2,3-dihydro-2-oxo-5-phenyl-1H-1,4-benzodiazepin-1-yl]acetyl]-L-alanine (35)

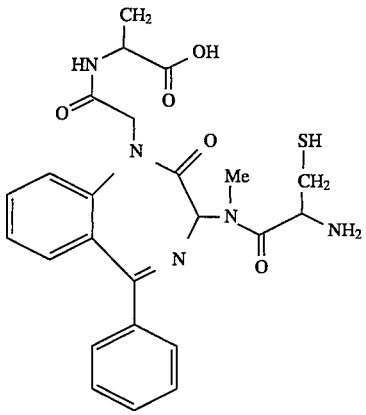

The title compound was prepared using the procedure of Example 9 in which 3-(tert-butoxycarbonyl)methylamino-2,3-dihydro-5-phenyl-1H-1,4-benzodiazepin- 2-one-1-acetic acid was coupled to L-alanine resin. Again, after deprotection and washing steps, Fmoc-L-(S-trityl) cysteine was coupled as above. Purification of 116 mg of the crude material yielded the two diastereomers 35A (26 mg) and 35B (28 mg).

Mass (electrospray, M+H$^+$) calc: 498.2 found: 498 (35A), 498 (35B).

EXAMPLE 36

N-[[3-[(2-amino-3-mercapto-1-oxopropyl)methylamino]-2,3-dihydro-2-oxo-5-phenyl-1H-1,4-benzodiazepin-1-yl]acetyl]-L-proline (36)

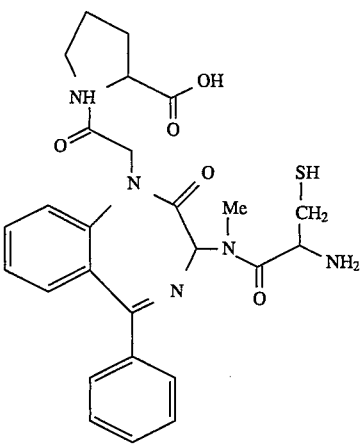

The title compound was prepared using the procedure of Example 9 in which 3-(tert-butoxycarbonyl)methylamino-2,3-dihydro-5-phenyl-1H-1,4-benzodiazepin- 2-one-1-acetic acid was coupled to L-alanine resin. Again, after deprotection and washing steps, Fmoc-L-(S-trityl) cysteine was coupled as above. Purification of 114 mg of the crude material yielded the two diastereomers 36A (28 mg) and 36B (27 mg).

Mass (electrospray, M+H$^+$) calc: 524.2 found: 524.3 (36A), 524.3 (36B).

EXAMPLE 37

N-[[3-(2-Amino-3-mercapto-1-oxopropyl)methylamino]-2,3-dihydro-2-oxo-5-phenyl-1H-1,4-benzodiazepin-1-yl] acetyl]-L-methionine methyl ester (37)

Scheme 5

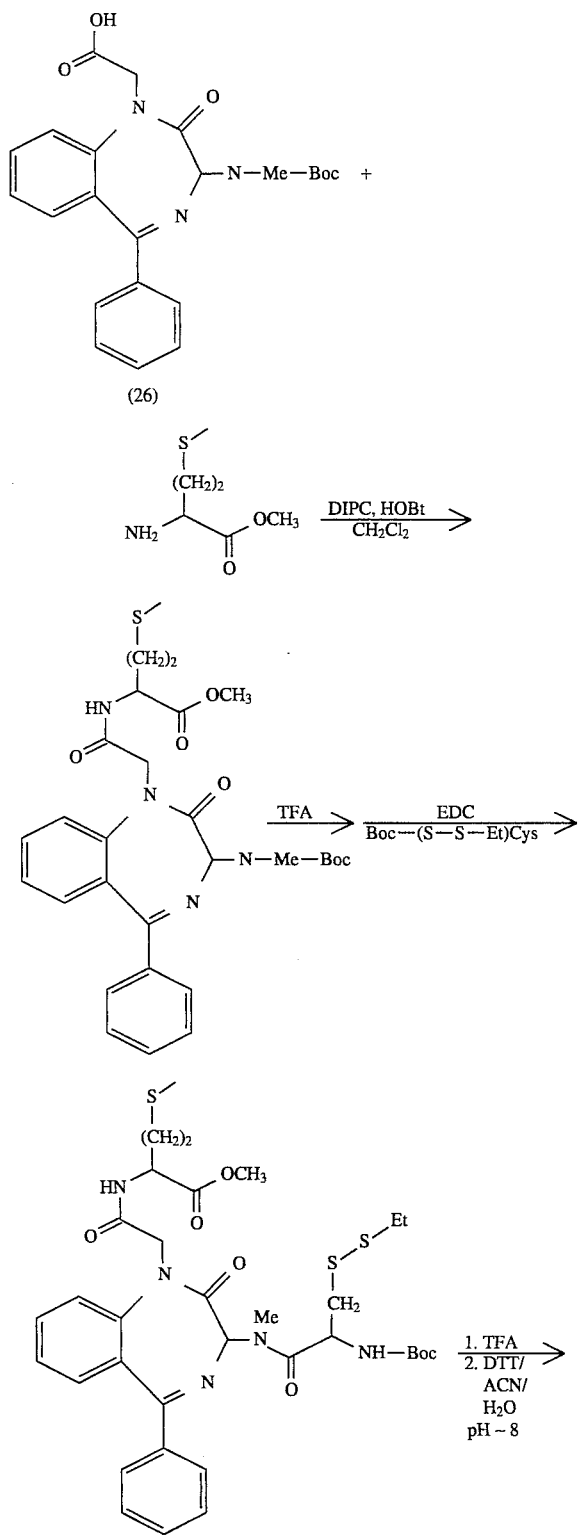

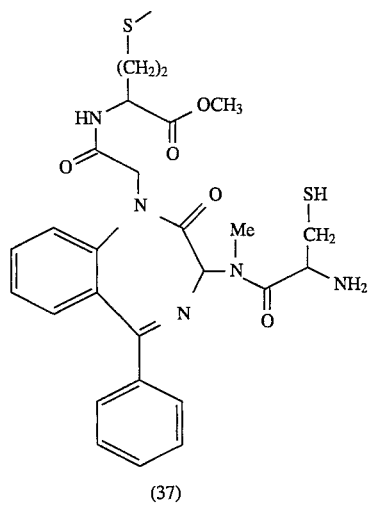

(37)

3-(tert-Butoxycarbonyl)methylamino-2,3-dihydro-5-phenyl-1H-1,4-benzodiazepin- 2-one-1-acetic acid (5.5 mmol, 2.3 gm), L-methionine methyl ester (16.5 mmol, 2.7 gm, Sigma), diisopropylcarbodiimide (DIPC, 6.6 mmol, 1.04 ml), and HOBt (6.6 mmol, 0.9 gm) were combined in DCM (20 ml). After 10 hrs, the reaction was diluted (DCM, 90 ml), extracted (0.1N $H_2SO_4$ then brine), dried ($MgSO_4$), and concentrated to yield 3.5 gm (113%) of crude N-[[3-(tert-butoxycarbonyl)methylamino- 2,3-dihydro-2-oxo-5-phenyl-1H-1, 4-benzodiazepin- 1-yl] acetyl]-L-methionine methyl ester.

0.75 gm of this material was deprotected (30% TFA, 30 ml, 3 hrs), concentrated, neutralized via extraction in 100 ml EtOAc (saturated $NaHCO_3$ then brine), and purified (silica, DCM/MeOH/$Et_3$N 99:1:0.2%) to yield N-[[3-amino- 2,3-dihydro-2-oxo-5-phenyl-1H-1, 4-benzodiazepin-1-yl] acetyl]-L-methionine methyl ester as a clear oil (0.55 gm, 89%).

Reaction of this material with Boc-(S-ethylthio)-cysteine (3.6 mmol, 0.99 gm), 1-(3-dimethylaminopropyl)-3-ethyl-carbodiimide hydrochloride (EDC, 3.6 mmol, 0.68 gm), and HOBt (1.2 mmol, 0.16 gm) in DMF (10 ml, 12 hrs) was followed by concentration, aqueous workup and chromatography (as above), to yield N-[[3-[(2-(tert-butoxycarbonyl)amino-3-mercapto-1-oxopropyl)methylamino]-2,3-dihydro-2-oxo-5-phenyl-1H-1,4-benzodiazepin-1-yl]acetyl]-L-methionine methyl ester (0.82 gm, 93%). After removal of the Boc-( 30% TFA as above) and ethylthio- (60 mg dithiothreitol, 20 ml 50% ACN/$H_2O$, pH 7.5) protecting groups, N-[[3-(2-amino-3-mercapto-1-oxopropyl) methylamino]-2, 3-dihydro-2-oxo-5-phenyl-1H-1, 4-benzodiazepin- 1-yl] acetyl]-L-methionine methyl ester was purified by HPLC (Vydac C18, ACN/$H_2O$/TFA) which resolved each of diastereomers possessing opposite configuration at C-3. These isomers were designated A and B as before (see Example 9). Purification of 120 mg of the crude material yielded the two diastereomers 37A (26 mg) and 37B (30 mg).

Mass (electrospray, M+H$^+$) calc: 572.2 found: 572.3 (37A), 572.3 (37B).

EXAMPLE 38

N-[[3-(2-Amino-3-ethylthiomercapto-1-oxopropyl)methylamino]-2,3-dihydro- 2-oxo-5-phenyl-1H-1,4-benzodiazepin-1-yl] acetyl]-L-methionine methyl ester (38)

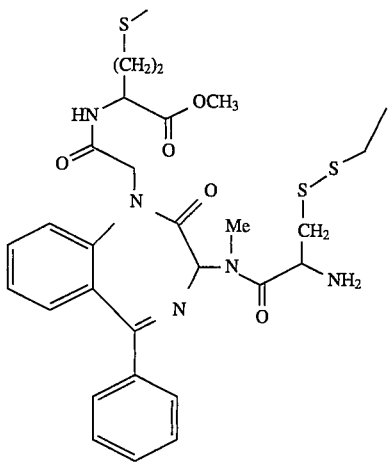

The title compound was prepared using the procedure of Example 37 in which an identical procedure was performed, omitting the step for removal of the ethylthio protecting group. Purification of 140 mg of the crude material yielded the two diastereomers 38A (30 mg) and 38B (30 mg).
Mass (electrospray, M+H⁺) calc: 632.3 found: 631.9 (38A), 631.9 (38B).

EXAMPLE 39

N-[[3-(2-Amino-3-mercapto-1-oxopropyl)methylamino]-2,3-dihydro-2-oxo-5-phenyl- 1H-1,4-benzodiazepin-1-yl] acetyl]-L-methionine ethyl ester (39)

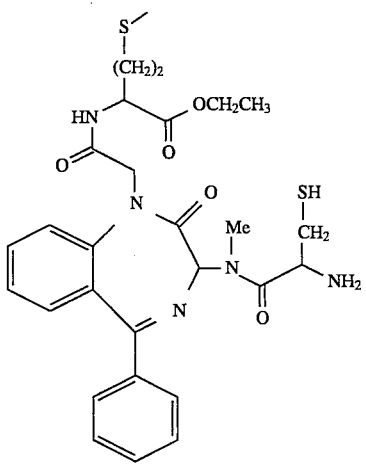

The title compound was prepared using the procedure of Example 37 in which 3-(tert-butoxycarbonyl)methylamino-2,3-dihydro-5-phenyl-1H-1,4-benzodiazepin- 2-one-1-acetic acid (0.85 mmol, 0.36 gm), L-methionine ethyl ester (2.55 mmol, 0.45 gm), DIPC (1.02 mmol, 0.16 ml), and HOBt (1.02 mmol, 0.14 gm) were combined in the first step. Subsequent reactions to yield the title compound were completed in a manner similar to that shown in Example 37. Purification of 150 mg of the crude material yielded the two diastereomers 39A (21 mg) and 39B (22 mg).
Mass (electrospray, M+H⁺) calc: 586.3 found: 585.9 (39A), 585.9 (39B).

EXAMPLE 40

N-[[3-(2-Amino-3-ethylthiomercapto-1-oxopropyl)methylamino]-2,3-dihydro-2-oxo-5-phenyl-1H-1,4-benzodiazepin-1-yl] acetyl]-L-methionine ethyl ester (40)

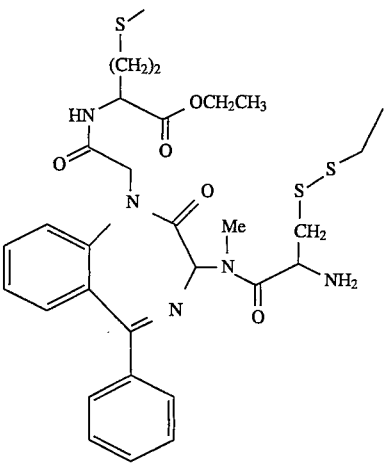

The title compound was prepared using the procedure of Example 37 in which an identical procedure was performed, omitting the step for removal of the ethylthio protecting group. Purification of 150 mg of the crude material yielded the two diastereomers 40A and 40B.
Mass (electrospray, M+H⁺) calc: 646.3 found: 645.7 (40A), 645.7 (40B).

EXAMPLE 41

N-[[3-(2-Amino-3-mercapto-1-oxopropyl)methylamino]-2,3-dihydro-2-oxo-5-phenyl-1H-1,4-benzodiazepin-1-yl] acetyl]-L-methionine cyclohexyl ester (41)

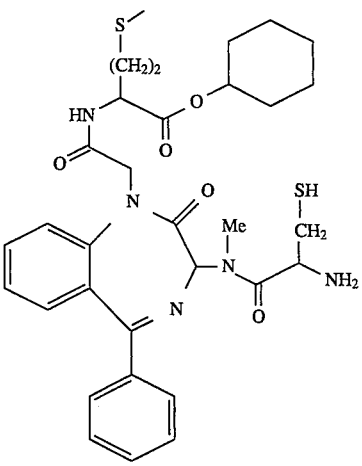

L-methionine cyclohexyl ester was prepared by combining Boc-L-methionine (2.5 g, 10 mmol), cyclohexanol (3.12 ml, 30 mmol), DIPC (1.9 ml, 12 mmol) and 4-dimethylaminopyridine (DMAP, 0.12 g, 1.0 mmol) in DCM, followed by aqueous workup, flash chromatography (silica, hexane/ EtOAc (4:1)), removal of the Boc protecting group (4N HCl/dioxane, 2 h), and basic workup (EtOAc/sat. $Na_2CO_3$).

The title compound was prepared using the procedure of Example 37 in which 3-(tert-butoxycarbonyl)methylamino-2,3-dihydro-5-phenyl-1H-1,4-benzodiazepin- 2-one-1-acetic acid (3.3 mmol, 1.4 gm), L-methionine cyclohexyl ester (6.6 mmol, 1.53 gm), DIPC (3.96 mmol, 0.62 ml), and HOBt (3.96 mmol, 0.54 gm) were combined in the first step. Subsequent reactions to yield the title compound were completed in a manner similar to that shown in Example 37. Purification of 150 mg of the crude material yielded the two diastereomers 41A (35 mg) and 41B (37 mg).
Mass (electrospray, M+H$^+$) calc: 640.3 found: 640.1 (41A), 640.1 (41B).
The following examples were prepared similarly to above syntheses.

EXAMPLE 42

N-[[3-[(2-ethylamino-3-mercapto-1-oxopropyl)methylamino]-2,3-dihydro-2-oxo-5-phenyl-1H-1,4-benzodiazepin-1-yl]acetyl]-L-methionine (42)

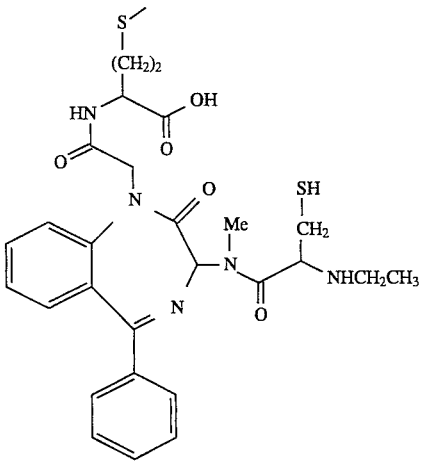

The title compound was prepared as above with the addition of a step following deprotection of the N-terminal Boc-residue on cysteine. This step allowed attachment of an ethyl moiety on nitrogen through reductive amination using acetaldehyde and sodium cyanoborohydride in DMF/1% AcOH. The molecule was then cleaved, purified and analyzed as above.

EXAMPLE 43

N-[[3-[(2-methylthiazolidine-4-carboxyl)methylamino]-2,3-dihydro-2-oxo-5-phenyl-1H-1,4-benzodiazepin-1-yl]acetyl]-L-methionine (43)

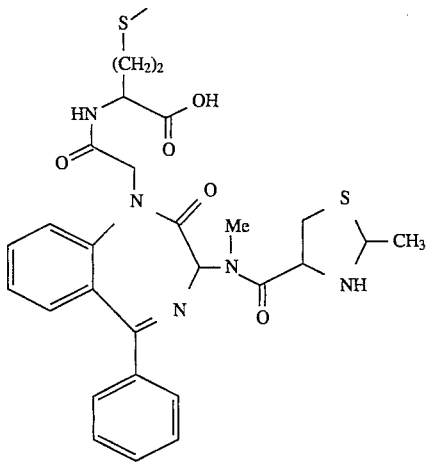

The title compound was prepared by coupling N-Boc-2-methyl thiazolidine-4-carboxylic acid instead of cysteine. Purified and analyzed as above.

EXAMPLE 44

N-[[3-[(2-Amino-3-mercapto-1-oxopropyl)methylamino]-2,3-dihydro-2-oxo-5-phenyl-1H-1,4-benzodiazepin-1-yl]acetyl]-L-cysteine (44)

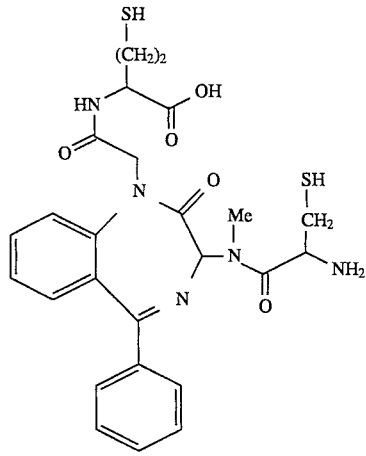

The title compound was prepared following the protocol shown in Example 9, except S-(4-methylbenzyl)-N-Boc-L-cysteine-linked Merrifield resin was used.

EXAMPLE 45

N-[[3-[(2-amino-3-hydroxy-1-oxopropyl)methylamino]-2,3-dihydro-2-oxo-5-phenyl-1H-1,4-benzodiazepin-1-yl]acetyl]-L-methionine (45)

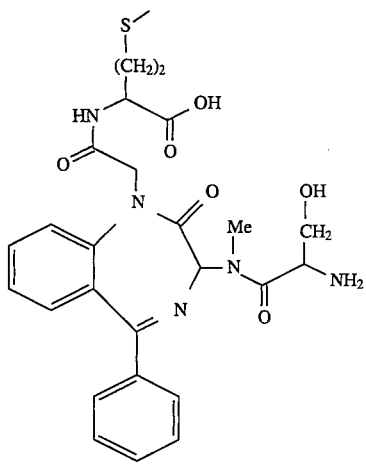

The title compound was prepared following the protocol shown in Example 9, except O-(tert-butyl)-N-Boc-L-serine was used in place of cysteine.

EXAMPLE 46

N-[[3-[(2-amino-3-mercapto-1-oxopropyl)methylamino]-2,3-dihydro-2-oxo-5-phenyl-1H-1,4-benzodiazepin-1-yl]acetyl]-L-leucine tetrazole (46)

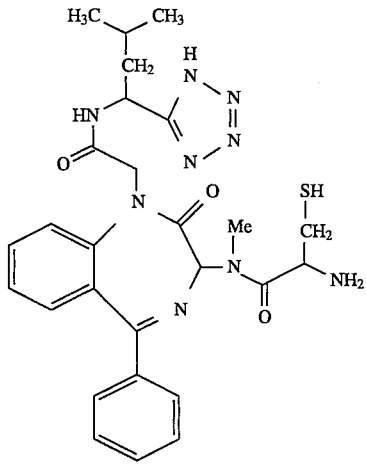

The title compound was prepared using a similar procedure to that shown for Example 37, except that tetrazole derivative of leucine, denoted as L-leucine tetrazole, was used instead of a carboxy-terminal ester. The synthesis of this material is shown below in Scheme 6.

Scheme 6

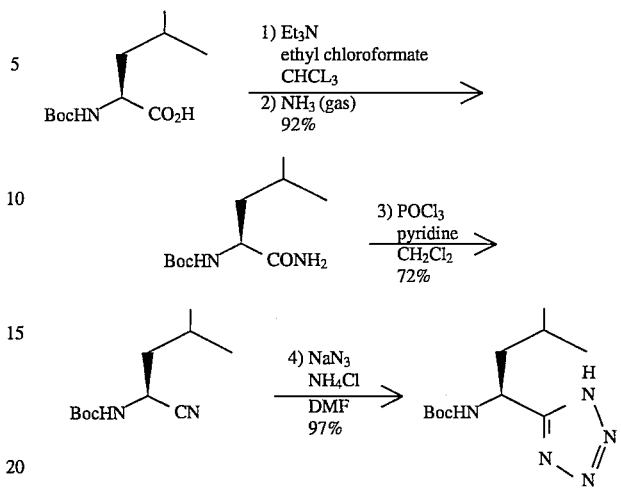

steps 1 and 2)

The N-Boc-L-leucine monohydrate (10 g, 40.2 mmol) and triethylamine (5.6 mL, 40.2 mmol) were dissolved in 50 mL dry chloroform and cooled to 0° C. Ethyl chloroformate (3.84 mL, 40.2 mmol) was add dropwise and stirred for 10 minutes. 40 mL dry chloroform saturated with ammonia was added, stirred for 15 minutes, then warmed to ambient temperature and stirred for 1 hr. Evaporation of the solvent gave the crude product which was washed with aqueous NaHCO$_3$ then with water. The product was collected by filtration, washed with water, and dried by vacuum to yield 8.53g (37.1 mmol, 92% yield) of the desired amide as a white solid. R$_f$=0.36 (75%EtOAc/hexanes). $^1$H NMR (300MHz, CD$_3$OD): 4.05 (1H, br t), 1.70 (1H, m), 1.50 (2H, m), 1.45 (9H, s), 0.95 (6H, dd).

step 3)

The N-Boc-L-leucine amide (6.45g, 28 mmol) was dissolved in 40 mL dry pyridine and cooled to –5° C. Phosphorous oxychloride (3.66 mL, 39.3 mmol), in 6 mL dry methylene chloride was added dropwise and the solution was stirred at –5° C. for 1 hr. Ice water was added to the reaction and the nitrile was extracted with EtOAc (3×200 mL). The combined organics were washed successively with 100 mL water, 1N HCl (2×100 mL), aq. NaHCO$_3$ (2×100 mL) and 100 mL water. The organics were dried over MgSO$_4$ and concentrated to yield 4.27g (20.1 mmol, 72% yield) as a light yellow solid. R$_f$=0.79 (75%EtOAc/hexanes). $^1$H NMR (300MHz, CD$_3$OD): 4.45 (1H, br t), 1.75 (1H, m), 1.65 (2H, dd), 1.45 (9H, s), 0.95 (6H, dd). IR: 2240 cm$^{-1}$.

step 4)

The N-Boc-L-leucine nitrile (1.65g, 7.78 mmol), sodium azide (0.53g, 8.15 mmol) and ammonium chloride (0.46g, 8.6 mmol) were dissolved in 7 mL dry DMF and the flask was placed in a 105° C. oil bath. After 7 hr., sodium azide (0.26g, 4.0 mmol) and ammonium chloride (0.27g, 5.0 mmol) were added and the solution was stirred overnight at 105° C. Cooled and concentrated. Flash chromatography (7% MeOH in methylene chloride ramping to 25% MeOH in methylene chloride) provided 1.93g (7.56 mmol, 97% yield) as a white solid. R$_f$=0.33 (10%MeOH/methylene chloride). $^1$H NMR (300MHz, CD$_3$OD): 5.90 (1H, s), 5.15 (1H, br t), 1.60-1.90 (3H, m), 1.40 (9H, s), 0.95 (6H, dd).

preparation of the title compound:

The N-Boc-L-leucine tetrazole (0.45g, 1.75 mmol) was suspended in 5 mL 4N HCl/dioxane. Dissolves is 10 min. Concentrated after 2 hr. to a tan foam. Dissolved in 5 mL water and taken to pH=9 with 1N NaOH. The resulting free-amine was concentrated to a white solid and used directly in the coupling reaction (below). $R_f$=0.20 (25%MeOH/methylene chloride). $^1$H NMR (300MHz, CD$_3$OD): 4.40 (1H, br m), 3.65 (1H, m), 1.90 (1H, m), 1.75 (1H, m), 1.25 (1H, m) 0.95(6H, dd).

Coupling reactions were identical to those describe in Example 37. The leucine tetrazole was suspended in 3 mL CH$_2$Cl$_2$ - does not dissolve. 3-(tert-Butoxycarbonylmethylamino- 2,3-dihydro-5-phenyl-1H-1,4-benzodiazepin-2-one- 1-acetic acid (0.343g, 0.81 mmol), HOBT (0.17g, 1.26 mmol) and DIPC (1.1 mL, 1.1 mmol) were added and the solution was stirred overnight. Workup and coupling of the cysteine was identical to the procedure for Example 37. Purification of 50 mg of the crude material yielded the two diastereomers 46A (7 mg) and 46B (8 mg).

Mass (electrospray, M+H$^+$) calc: 564.2 found: 564.3 (46A), 564.3 (46B).

EXAMPLE 47

N-[[3-[(2-amino-3-mercapto-1-oxopropyl)methylamino]-2,3-dihydro-2-oxo-5-phenyl-1H-1,4-benzodiazepin-1-yl]acetyl]-L-methionine tetrazole (47)

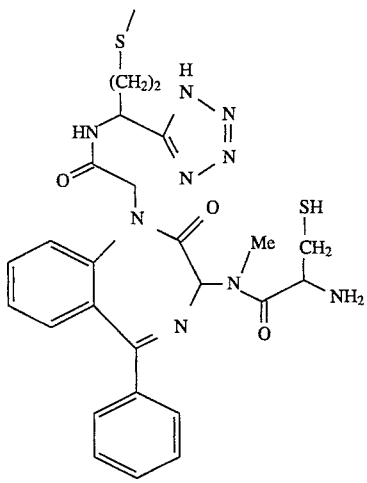

Synthesis of the title material was identical to that describe in Example 46, substituting methionine for leucine. Purification of 50 mg of the crude material yielded the two diastereomers 47A (5 mg) and 47B (5 mg).

Mass (electrospray, M+H$^+$) calc: 582.2 found: 582.4 (47A), 582.4 (47B).

EXAMPLE 48

N-[[3-[(2-amino-3-mercapto-1-oxopropyl)methylamino]-2,3-dihydro-2-oxo-5-phenyl-1H-1,4-benzodiazepin-1-yl]propionyl]-L-methionine (48)

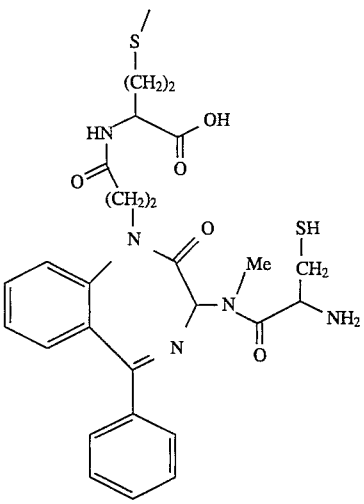

The title compound was prepared using a procedure similar to that described for Example 9, substituting the acetyl modification at the N-1 of the benzodiazepine with a propionyl moiety. This was accomplished using a modification of the protocol used for the preparation of compound 26. Purification of 105 mg of the crude material yielded the two diastereomers 48A (20 mg) and 48B (18 mg).

Mass (electrospray, M+H$^+$) calc: 572.2 found: 573.1 (48A), 573.1 (48B).

EXAMPLE 49

In vitro inhibition of CAAX farnesyltransferase

All compounds were tested for in vitro inhibition of CAAX protein farnesyltransferase. The enzyme was isolated and purified to homogeneity from rat brain homogenates by sequential ammonium sulfate fractionation, Mono Q ion-exchange chromatography, and peptide affinity chromatography as described in Reiss, Y., Seabra, M. C., Goldstein, J. L., and Brown, M. S. *Methods: A Companion to Methods in Enzymology* 1, 241–245 (1990). Alternatively, recombinant CAAX protein farnesyltransferase was also used in this assay. Recombinant enzyme was produced in a baculovirus expression system as in O'Reilly, D. R., Miller, L. K., and Luckow, V. A. Baculovirus Expression Vectors: A Laboratory Manual (W. H. Freeman and Co., New York, 1992) and in Reiss, Y., Brown, M. S., Goldstein, J. L., *in preparation*. 72 hrs after infection, the cells were harvested and disrupted and the enzyme isolated by chromatography on Q-Sepharose. The recombinant farnesyltransferase was judged to be ~90% pure by Comassie blue staining after SDS gel electrophoresis.

In each experiment, varying concentrations of the inhibitor were mixed with the enzyme, and the amount of [3H] farnesyl transferred from all-trans-[3H]farnesyl pyrophosphate to recombinant p21H-ras was measured in a filter binding assay as described in Reiss, Y., Goldstein, J. L., Seabra, M. C., Casey, P. J., and Brown, M. S. *Cell* 62, 81–88 (1990). Briefly, the assay mixture contained, in a final volume of 50 µl, 50 mM Tris-chloride (pH 7.5), 50 µM $ZnCl_2$, 3 mM $MgCl_2$, 20 mM KCl, 5 mM dithiothreitol (DTT), 0.4% (v/v) octyl-β-glucoside, 1% (v/v) dimethyl sulfoxide (DMSO), 0.6 µM all-trans-[3H]farnesyl pyrophosphate (9730 dpm/pmol; Dupont-New England Nuclear), 40 µM recombinant p21H-ras (see Reiss, Y., Goldstein, J. L., Seabra, M. C., Casey, P. J., and Brown, M. S. *Cell* 62, 81–88 (1990)), 10 ng purified CAAX farnesyltransferase and concentrations of the indicated inhibitor (varying from 0.1 nM to 10 µM). After incubation for 30 min at 37 C, the amount of [3H]farnesyl group transferred to p21H-ras was measured by precipitation with SDS/trichloroacetic acid, filtration onto nitrocellulose, and scintillation counting. Immediately before use, each inhibitor to be tested was diluted into a solution containing 2.5% DMSO, 10 mM DTT, and 0.5% octyl-β-glucoside, and added to the 50 µl reaction mixture in a volume of 20 µl. $EC_{50}$ values were obtained as the estimated concentration of inhibitor yielding 50% of the [3H]-recovered in control samples (no inhibitor).

Structures of the compounds tested are reproduced below. Compound numbers also refer to example numbers above. Table D below shows the results of the CAAX farnesyltransferase assay for each diastereomer (A and B) (except where noted, compound 29).

TABLE A

| cpd. | $R^8$ | $R^{24}$ | $R^{25}$ |
|---|---|---|---|
| 27 | $CH((CH_2)_2SCH_3)COOH$ | $CH_3$ | $CH(CH_2SH)NH_2$ |
| 28 | $CH((CH_2)_2SCH_3)COOH$ | H | $CH(CH_2SH)NH_2$ |
| 29 | $CH((CH_2)_2SCH_3)COOH$ | $CH_3$ | $(CH_2)_2SH$ |
| 30 | $CH(CH_2OH)COOH$ | $CH_3$ | $CH(CH_2SH)NH_2$ |
| 31 | $CH(CH_2CH(CH_3)_2)COOH$ | $CH_3$ | $CH(CH_2SH)NH_2$ |
| 32 | $CH((CH_2)_2SCH_3)COOH$ | $CH_3$ | $CH(CH_2SH)NHCOCH_3$ |
| 33 | $CH((CH_2)_2SCH_3)CONH_2$ | $CH_3$ | $CH(CH_2SH)NH_2$ |
| 34 | $CH(CH_2C_6H_5)COOH$ | $CH_3$ | $CH(CH_2SH)NH_2$ |
| 35 | $CH(CH_3)COOH$ | $CH_3$ | $CH(CH_2SH)NH_2$ |
| 42 | $CH((CH_2)_2SCH_3)COOH$ | $CH_3$ | $CH(CH_2SH)NHC_2H_5$ |
| 43 | $CH((CH_2)_2SCH_3)COOH$ | $CH_3$ | $CH(-CH_2SCH(CH_3)-)NH$ |
| 44 | $CH(CH_2SH)COOH$ | $CH_3$ | $CH(CH_2SH)NH_2$ |
| 45 | $CH((CH_2)_2SCH_3)COOH$ | $CH_3$ | $CH(CH_2OH)NH_2$ |

TABLE B

| cpd. | $R^8$ | $R^{24}$ | $R^{25}$ |
|---|---|---|---|
| 37 | $CH((CH_2)_2SCH_3)CO_2CH_3$ | $CH_3$ | $CH(CH_2SH)NH_2$ |
| 39 | $CH((CH_2)_2SCH_3)CO_2CH_2CH_3$ | $CH_3$ | $CH(CH_2SH)NH_2$ |
| 41 | $CH((CH_2)_2SCH_3)CO_2C_6H_{11}$ | $CH_3$ | $CH(CH_2SH)NH_2$ |
| 46 | $CH(CH_2CH(CH_3)_2)CN_4H$ | $CH_3$ | $CH(CH_2SH)NH_2$ |
| 47 | $CH((CH_2)_2SCH_3)CN_4H$ | $CH_3$ | $CH(CH_2SH)NH_2$ |

TABLE C

| cpd. | $R^8$ | $R^{24}$ | $R^{25}$ | $R^1$ | $T_1-T_2$ | Z |
|---|---|---|---|---|---|---|
| 9 | $CH((CH_2)_2SCH_3)COOH$ | $CH_3$ | $CH(CH_2SH)NH_2$ | H | $CH-CH_2$ | $CH_2$ |
| 10 | $CH((CH_2)_2SCH_3)COOH$ | H | $CH(CH_2SH)NH_2$ | H | $CH-CH_2$ | $CH_2$ |
| 48 | $CH((CH_2)_2SCH_3)COOH$ | $CH_3$ | $CH(CH_2SH)NH_2$ | $C_6H_5$ | $C=N$ | $CH_2CH_2$ |

TABLE D

In vitro Inhibition of CAAX Farnesyltransferase

| compound | $EC_{50}$ (μM) "A" | $EC_{50}$ (μM) "B" |
|---|---|---|
| 9 | 1.2 | 0.024 |
| 10 | 1.6 | 1.4 |
| 27 | 0.8 | 0.0003 |
| 28 | 0.38 | 0.431 |
| 29 (unseparable) | 1.8 | 1.8 |
| 30 | 10.0 | 0.0084 |
| 31 | 0.084 | 0.0021 |
| 32 | 1.2 | 8.0 |
| 33 | 2.2 | 0.019 |
| 34 | 0.54 | 0.0005 |
| 35 | >10 | 0.022 |
| 36 | >10 | 0.048 |
| 37 | 0.19 | 0.05 |
| 39 | 8.0 | 0.11 |
| 41 | 4.2 | 0.074 |
| 42 | 0.58 | 0.018 |
| 43 | 0.32 | 0.006 |
| 44 | 3.0 | 0.0045 |
| 45 | >10 | >10 |
| 46 | 0.26 | 0.0016 |
| 47 | 0.44 | 0.0046 |
| 48 | 2.5 | 0.004 |

EXAMPLE 50

Figure 1B:
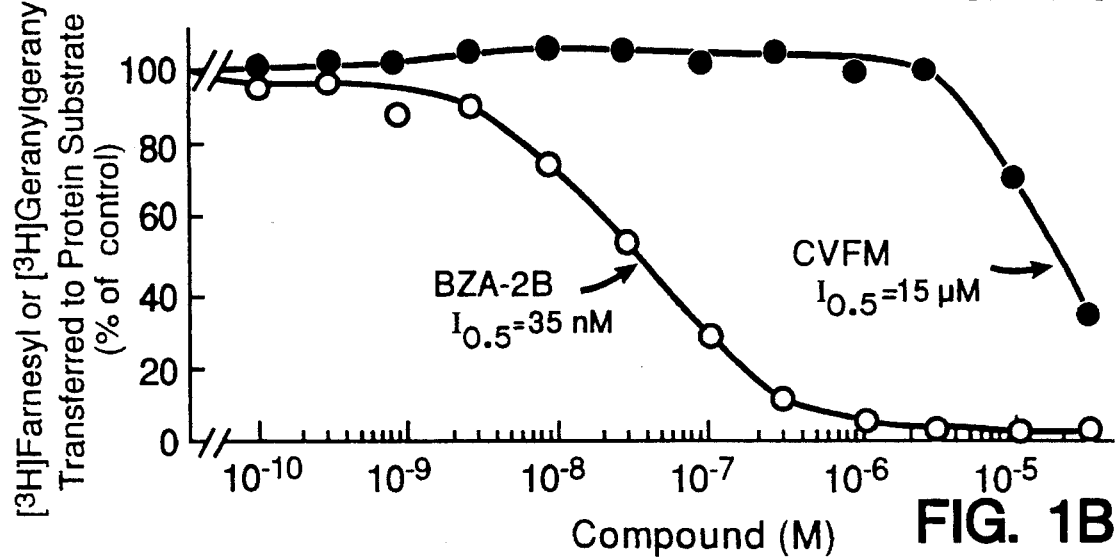
Figure 1C:
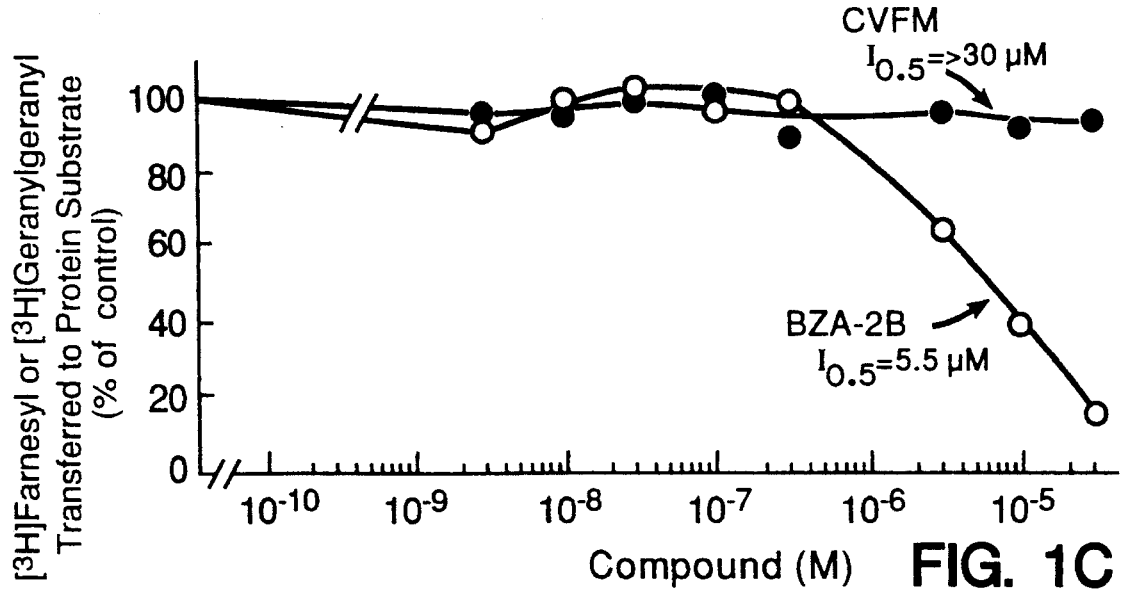

Differential inhibition of CAAX farnesyltransferase, CAAX GG transferase, and Rab GG transferase FIG. 1 compares the inhibitory activity of compound 27B (denoted as BZA- 2B in the figure) on the three known protein prenyltransferases. The compound inhibited recombinant ras CAAX farnesyltransferase by 50% at 0.26 nM, which was nearly 200-fold lower than the inhibitory concentration for the tetrapeptide CVFM. Two other prenyltransferases, both of which transfer 20-carbon geranylgeranyl (GG) groups, have been identified in rat brain. One of these, CAAX GG transferase, attaches GG groups to proteins that terminate in CAAX sequences in which X is leucine. The other enzyme, Rab GG transferase, recognizes a different class of substrates that do not terminate in CAAX sequences. Compound 27B (denoted as BZA-2B in FIG. 1) inhibited the CAAX GG transferase at a concentration more than 100-fold higher than that required to inhibit CAAX farnesyltransferase ($IC_{0.5}$=35 nM; FIG. 1B) and even less active on the third enzyme ($IC_{0.5}$=5.5 μM, FIG. 1C).

The conditions used to assay the inhibition of CAAX farnesyltransferase are identical to those described above for the in vitro assay described in Example 50. In FIG. 1B the assay mixture contained, in a final volume of 50 μl, 50 mM sodium Hepes (pH 7.2), 5 mM $MgCl_2$, 5 mM DTT, 0.3 mM Nonidet P-40, 0.2% octyl β-glucoside, 1% DMSO, 0.5 μM all trans [3H]geranylgeranyl pyrophosphate (33,000 dpm/pmol; ARC, Inc.), 5 μM recombinant $p21^H$-rasCVLL, 6.3 μg partially purified CAAX GG transferase (see Seabra, M. C., Reiss, Y., Casey, P. J., Brown, M. S., and Goldstein, J. L. *Cell* 268, 4055 (1993)) and varying concentrations of the indicated inhibitor. In FIG. 1C, the assay mixture contained in a final volume of 50 μl, 50 mM sodium Hepes (pH 7.2), 5 mM $MgCl_2$, 5 mM DTT, 0.3 mM Nonidet P-40, 0.2% octyl β-D-glucoside, 1% DMSO, 0.5 μM all trans [3H]geranylgeranyl pyrophosphate (33,000 dpm/pmol; ARC, Inc.), 2 μM recombinant Rab1A, 2 ng each of purified Components A and B of Rab GG transferase (see Seabra, M. C., Goldstein, J. L., Sudhof, T. C., and Brown, M. S. *J. Biol. Chem.* 267, 14497 (1992)) and varying concentrations of the indicated inhibitor.

EXAMPLE 51

Figure 2A:
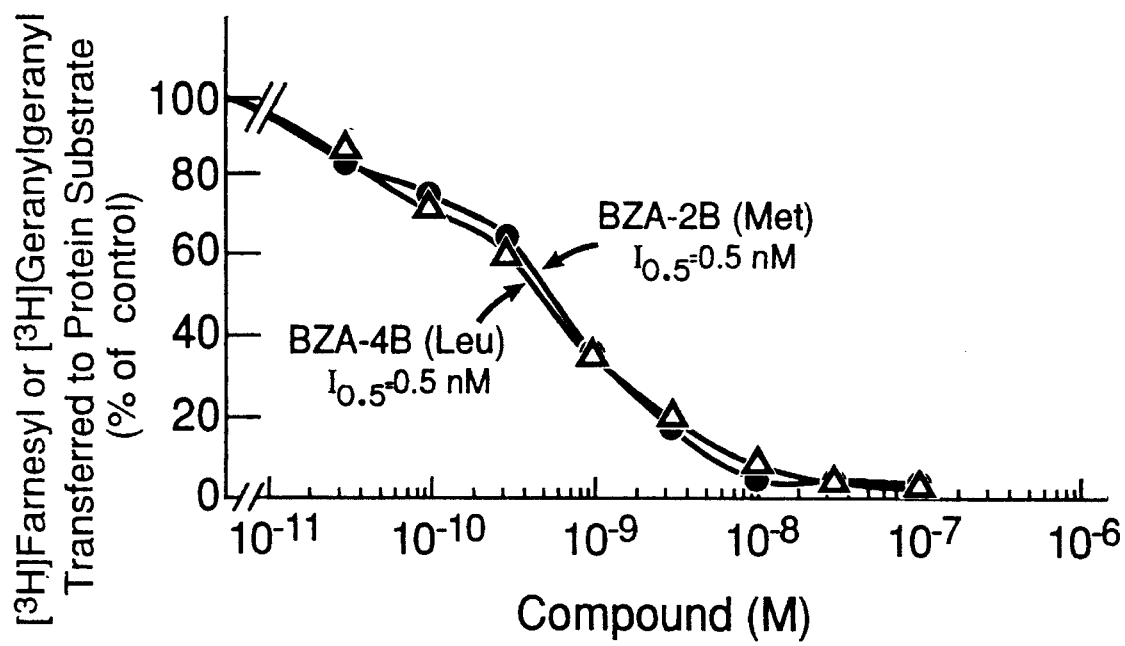
FIGS. 2A and 2B Differential inhibition of CAAX farnesyltransferase (A) and CAAX GG transferase (B) by compound 27B (denoted as BZA-2B in the figure, closed circles) and compound 31B (denoted as BZA-4B in the figure, open triangles).
Figure 2B:
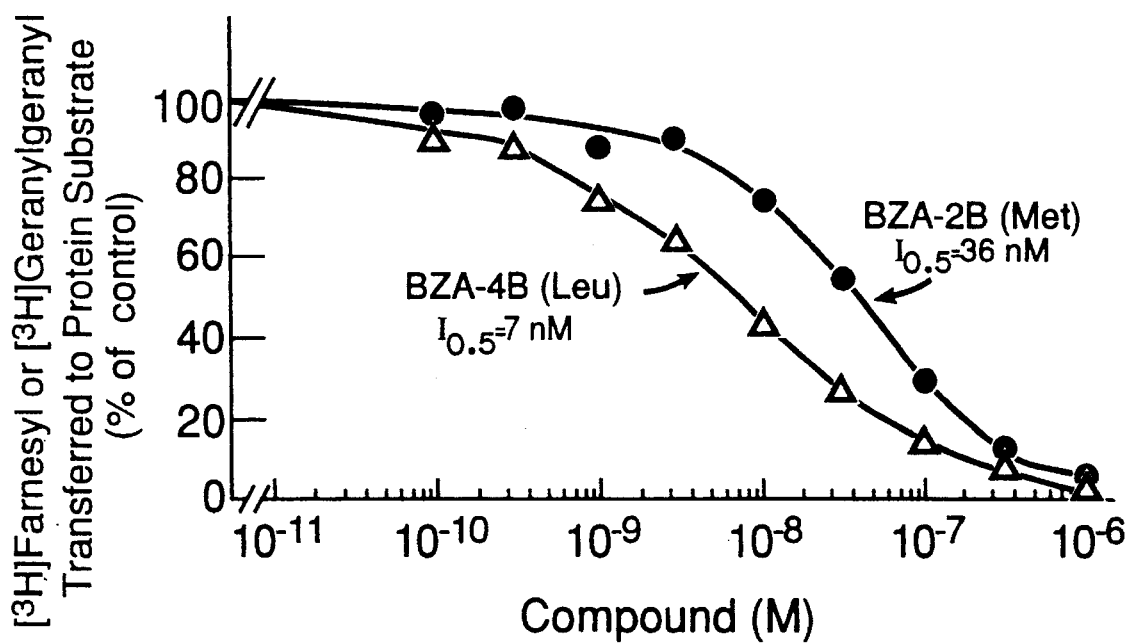

Differential inhibition of CAAX farnesyltransferase and geranylgeranyltransferase FIG. 2 shows that compound 27B (denoted as BZA-2B in the figure) which contains a C-terminal methionine, and compound 31B (denoted as BZA-4B in the figure) which contains leucine, were equally potent in inhibiting CAAX farnesyltransferase ($IC_{0.5}$=0.5 nM) (FIG. 2A). This result is surprising because leucine-terminated peptides are much less effective than methionine-terminated peptides in inhibiting farnesylation of p21H-ras. Apparently, important binding determinants are defined by the cysteine and benzodiazepine substituents. The CAAX geranylgeranyltransferase was 5-fold more sensitive to the leucine-terminated inhibitor (FIG. 2B).

Each assay was carried out as described in Examples 49 and 50.

EXAMPLE 52

Quantitation of Farnesyl Group Transfer

As shown for some peptides, several inhibitors tightly bind the enzyme and inhibit its activity, yet are not a substrate for the enzyme. The ability of each compound to act as a substrate for the CAAX farnesyltransferase was examined directly using thin layer chromatography (see Table E) as described in Goldstein, J. L., Brown, M. S., Stradley, S. J., Reiss, Y., and Gierasch, L. M. *J. Biol. Chem.* 266, 15575–15578 (1991) and Brown, M. S., Goldstein, J. L., Paris, K. J., Burnier, J. P., and Marsters, Jr., J. C. *Proc. Natl. Acad. Sci. USA* 89, 8313 (1992). Briefly, each 25 ul reaction mixture contained 50 mM Tris-chloride (pH 7.5), 50 μM $ZnCl_2$, 3 mM $MgCl_2$, 20 mM KCl, 1 mM dithiothreitol (DTT), 0.2% (v/v) octyl-β-glucoside, either 0.6 or 2.4 μM all-trans-[3H]farnesyl pyrophosphate (44,000 dpm/pmol; Dupont-New England Nuclear), ~5 ng purified CAAX farnesyltransferase and 90 pmol of the inhibitor to be tested (3.6 μM). After incubation at 37° C. for 30 min, the reaction was stopped by addition of 2 μl of 250 mM EDTA, and the entire reaction mixture was spotted onto a plastic-backed Silica Gel G thin layer sheet (20×20 cm, Brinkmann Inst.) and placed in a tank containing n-propyl alcohol/ammonium hydroxide/water (6:3:1 v/v/v). The chromatogram was run for 3 hr, after which it was either subjected to autoradiography or quantified by scintillation counting (see Brown, M. S., Goldstein, J. L., Paris, K. J., Burnier, J. P., and Marsters, Jr., J. C. *Proc. Natl. Acad. Sci. USA* 89, 8313 (1992)).

TABLE E

In vitro Farnesylation by CAAX Farnesyltransferase

| compound | % farnesylation [a]"A" | % farnesylation [a]"B" |
|---|---|---|
| 9 | <1 | <1 |
| 10 | 20 | <1 |
| 27 | 5 | <1 |
| 28 | 9 | <1 |
| 29 | <1 | <1 |
| 30 | <1 | <1 |
| 31 | <1 | <1 |
| 32 | 110 | <1 |
| 34 | | <1 |
| 37 | <1 | 2 |
| 43 | <1 | <1 |
| 46 | | <1 |

[a] % farnesylation measured as a percentage of [3H]farnesyl transferred to the compound relative to a separate experiment using a good substrate, the tetrapeptide CVIM.

EXAMPLE 53

Assay of Inhibition of CAAX Farnesyltransferase in Cultured Cells.

To study farnesylation in intact cells we used Met18b-2 cells, a line of Chinese hamster ovary (CHO) cells that takes up [3H]mevalonate efficiently (see Faust, J., and Krieger, M. *J. Biol. Chem.* 262, 1966 (1987)) owing to the production of a mevalonate transport protein (see Kim, C. M., Goldstein, J. L., Brown, M. S. *J. Biol. Chem.* 267, 23113 (1992)). The [3H]mevalonate is converted by the cells into [3H]farnesyl pyrophosphate and [3H]geranylgeranyl pyrophosphate, which are then attached to proteins (Kim, C. M., Goldstein, J. L., Brown, M. S. *J. Biol. Chem.* 267, 23113 (1992)). In the assay, stock cultures of Met18b-2 cells were seeded at a density of 3×105 cells per 60 mm dish in 3 ml of medium A (Dulbecco's modified Eagle medium/Ham's F12 medium (1:1, v/v) containing 100 U/ml penicillin and 100 μg/ml streptomycin) supplemented with 5% (v/v) fetal calf serum (FCS). On day 3, each monolayer was refed with 1 ml medium A supplemented with 1% FCS (dialyzed against 0.15M NaCl). At this point the cells were treated with 100 μM compactin (see Brown, M. S., Faust, J. R., Goldstein, J. L., Kaneko, I., and Endo, A. *J. Biol. Chem.* 253, 1121 (1978)) which blocks the synthesis of unlabeled mevalonate within the cells. Each compound was dissolved at 25 mM in DMSO/10 mM DTT immediately before use and 10 μl of this solution added directly. After 2 hr. incubation at 37° C., each monolayer received 100 μCi [3H]mevalonate (60 Ci/mmol, American Radiolabeled Chemicals, Inc.) added in 100 μl of the medium A, and the incubation continued for 4 hr. The cells were harvested by rinsing three times with 3 ml of 50 mM Tris-HCl/0.15M NaCl (pH 7.5). 300 μl of lysis buffer (0.5× Dulbecco's phosphate-buffered saline containing 1% Triton X-100, 5 μg/ml leupeptin, 5 μg/ml pepstatin, 0.5 mM phenylmethylsulfonyl fluoride, and 0.05 U/ml aprotinin) was added to each monolayer. After incubation on ice for 5 min., the lysates were centrifuged 30 seconds in a microfuge at 12,000 g. The resulting supernatant was tranferred to a new tube, and each pellet was resuspended in 60 μl of lysis buffer. Protein concentrations were determined using the BCA protein assay reagent (Pierce) according to the manufacturer's instructions. Detergent-soluble (supernatant) and -insoluble (pellet) samples were mixed with 2× SDS sample buffer (see Laemmli, U. K. *Nature* 227, 680 (1970)) and heated at 95° C. for 5 min before electrophoresis. Each lane contained 90 μg protein, and was run on a 12.5% SDS-polyacrylamide gel. The gel was dried, treated with ENTENSIFY (NEN-DuPont), and exposed to Kodak XOMAT-AR film for 9 h at −80° C. to allow visualization of all prenylated proteins. Migration of [14C]methylated molecular weight standards (Amersham) were used as markers.

Figure 3:
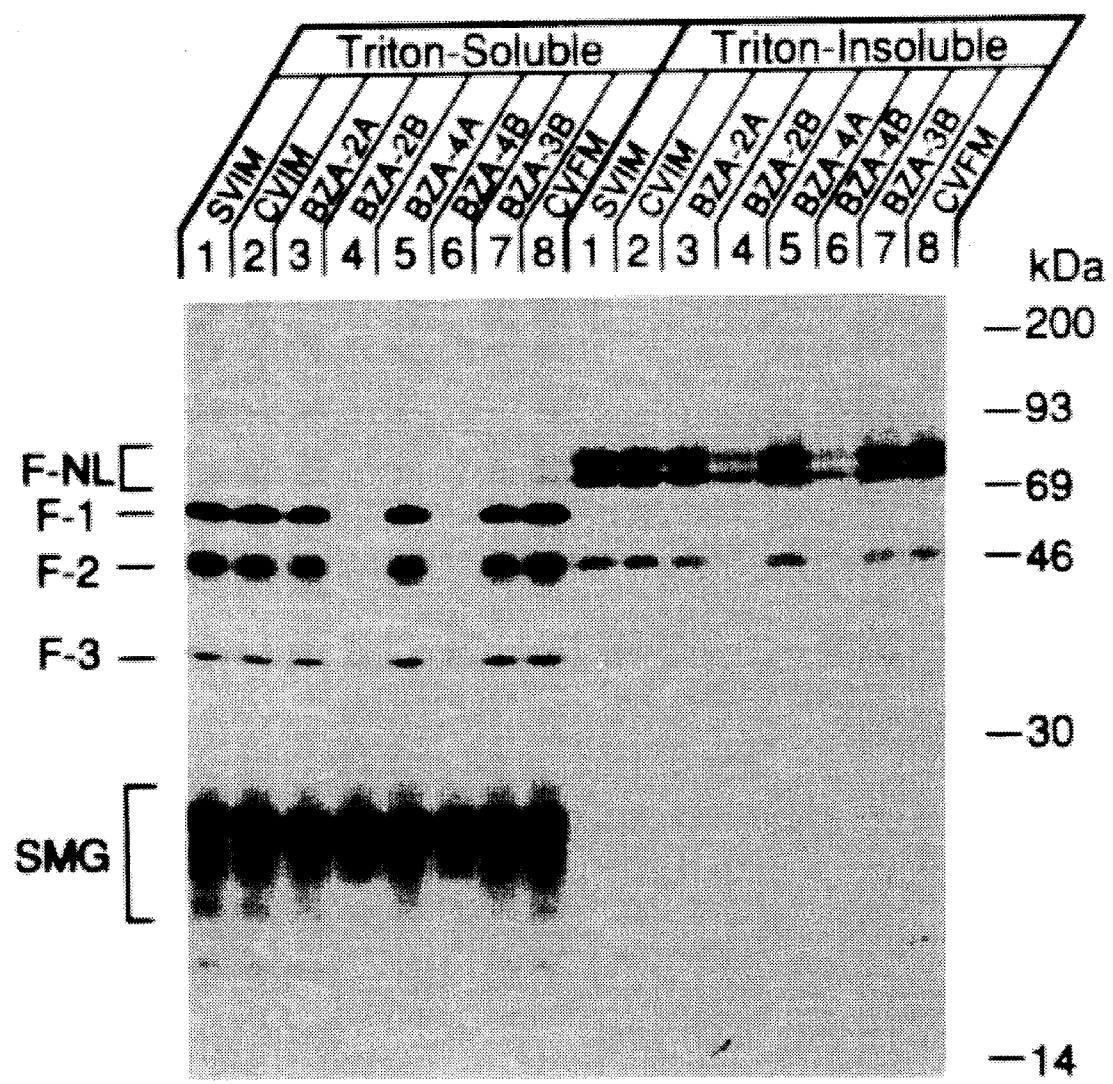
FIG. 3 Inhibition of [3H]mevalonate incorporation into prenylated proteins in monolayers of hamster Met18b-2 cells by compound 31B (denoted as BZA-4B in the figure). Effects of control peptides SVIM, CVIM and CVFM as well as compound 27A (BZA-2A in the figure) and 31A (BZA-4A in the figure) are also shown.

The results of this assay are shown in FIG. 3, using a final concentration of 250 μM for each inhibitor. Pilot experiments showed that the tetrapeptide SVIM which does not inhibit prenyltransferases did not alter the pattern of farnesylated proteins in the cells, and this was used as a control for all experiments. The Triton-soluble proteins marked F1 and F2 (unknown functions) have been shown previously to be farnesylated (see Reese, J. H., and Maltese, W. A. *Mol. Cell. Biochem.* 104, 109 (1991) and James, G., Brown, M. S., and Goldstein, J. L., unpublished observations). Protein F3 has been recently purified in the Brown and Goldstein laboratory, and was also demonstrated to be farnesylated. The labeled bands in the 20 to 27-kDa range consist largely of low molecular weight GTP binding proteins, the vast majority of which are geranylgeranylated. The major proteins in the Triton-insoluble pellet are the nuclear lamins A and B, which are farnesylated (see Farnsworth, C. C., Wolda, S. L., Gelb, M. H., and Glomset, J. A. *J. Biol. Chem.* 264, 20422 (1989)). As shown in the figure, none of the control peptides or control benzodiazepine-peptideomimetics altered the prenylation of proteins in intact cells. The high affinity inhibitors 27B and 31B (denoted as BZA-2B and BZA-4B in the figure respectively) markedly decreased the labeling of all three Triton-soluble farnesylated proteins (F1 to F3) and reduced moderately the labeling of the farnesylated lainins (F-NL). The inhibitors had little effect on the low molecular weight GTP binding proteins (SMG).

EXAMPLE 54

Dose Dependence of Inhibition of CAAX Farnesyltransferase in Cultured Cells

Figure 4:
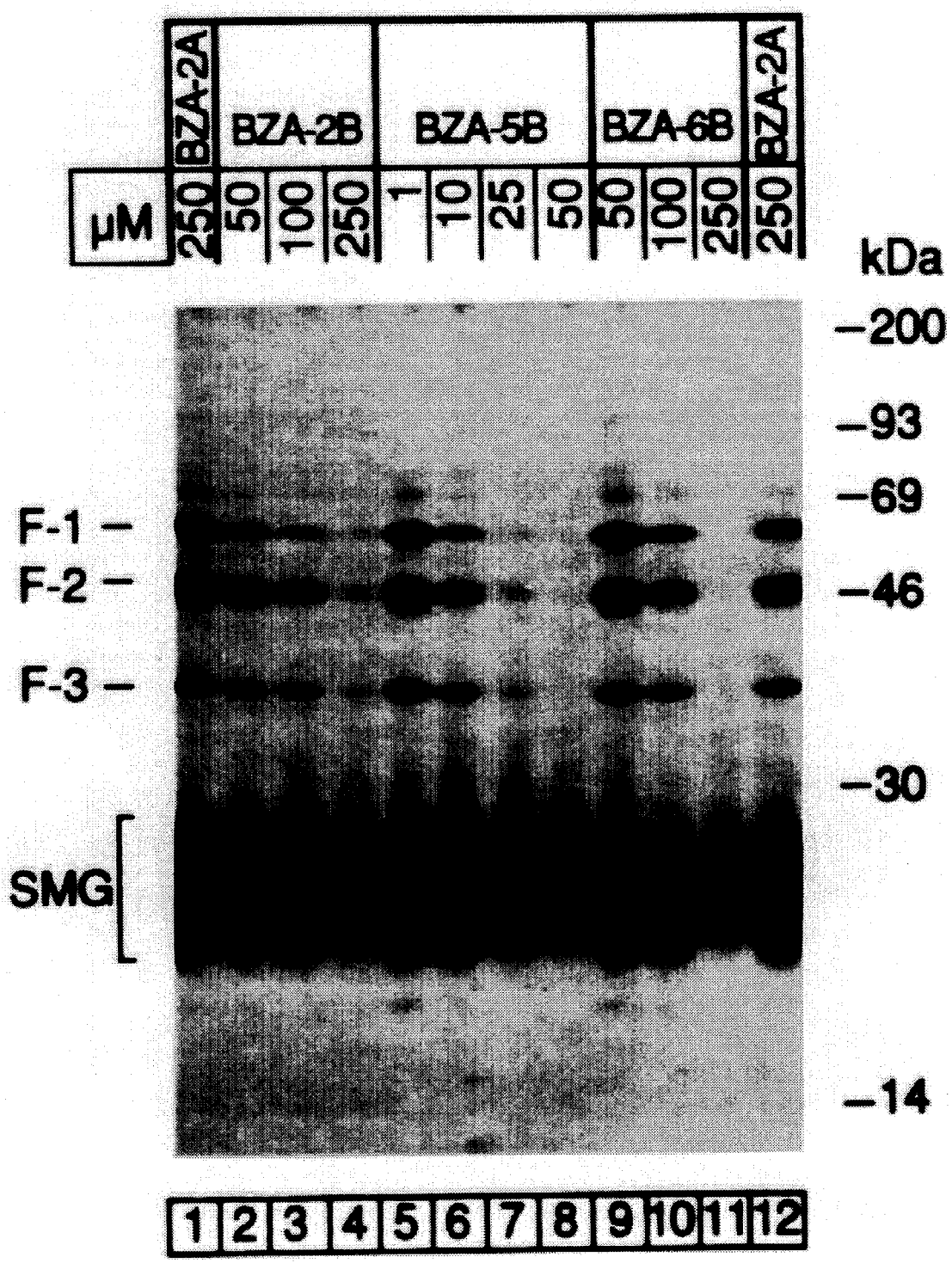
FIG. 4 Dose dependence of inhibition of [3H]mevalonate incorporation into prenylated proteins in monolayers of hamster met18b-2 cells by compound 27B (denoted as BZA-2B in the figure) and compound 37B (denoted as BZA-5B in the figure) and compound 33B (denoted as BZA-6B in the figure).

Using the same cells and procedures followed above for Example 53, we measured the dose dependence upon the inhibition of farnesylation in intact cells. Concentration curves for three of the more potent inhibitors are shown in FIG. 4 for the Triton-soluble proteins. The pro-drug, compound 37B (denoted as BZA-5B in the figure), was much more potent than the parent, compound 27B (denoted as BZA-2B in the figure). Compound 37B inhibited the farnesylation of F1–3 detectably at 10 μM, and almost completely at 25 μM. Compound 33B, the C-terminal amide, was of intermediate potency.

EXAMPLE 55

Immunoprecipitation of [3H]-labeled ras Proteins

Figure 5:
FIG. 5 Inhibition of [3H]mevalonate incorporation into p21H-ras proteins in Met18b-2 cells by compound 37B (denoted as BZA-5B in the figure). Triton soluble fractions (lanes 1–5) and the same fractions following immunoprecipitation with an anti-ras monoclonal antibody (lanes 6–10) are also shown.
Figure 6A:
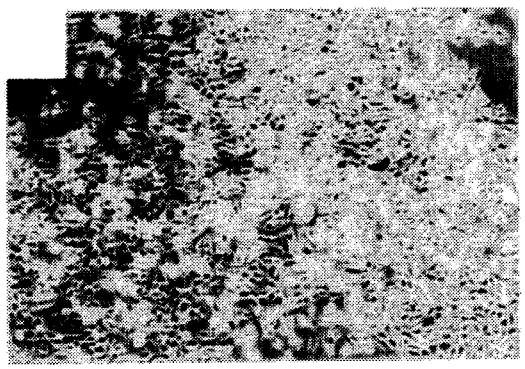
FIGS. 6A–6F Morphology of H-ras(Val12)-transformed rat-1 fibroblasts (A,B), src-transformed rat-1 firbroblasts (C,D), and untrasformed rat-1 fibroblasts (E,F) incubated in the presence of either compound 27A, N-[[3-(2(S)-amino-3-mercapto- 1-oxopropyl)methylamine]-2,3-dihydro-2-oxo-5-phenyl-1H-1,4-benzodiazepin- 1-yl]acetyl]-L-methionine (isomer A) denoted BZA-2A in the figure (A,C,E) or compound 27B, N-[[3-(2(S)-amino-3-mercapto-1-oxopropyl)methylamine]-2,3-dihydro-2-oxo-5-phenyl-1H-1,4-benzodiazepin-1-yl]acetyl]-L-methionine (isomer B) (B,D,F).
Figure 6B:
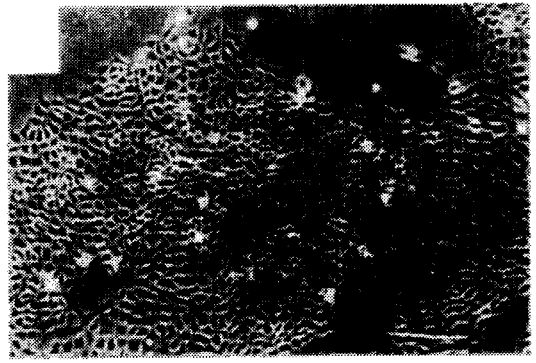
Figure 6C:
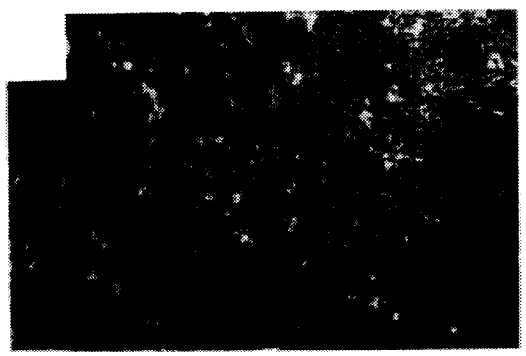
Figure 6D:
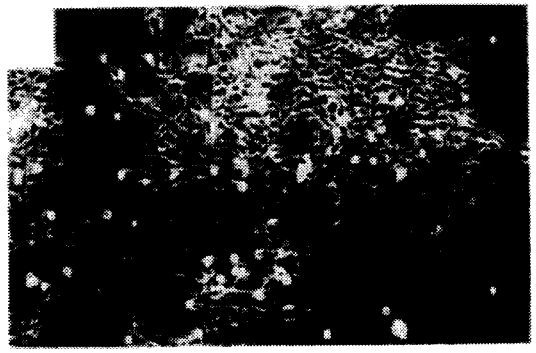
Figure 6E:
Figure 6F:
Figure 7A:
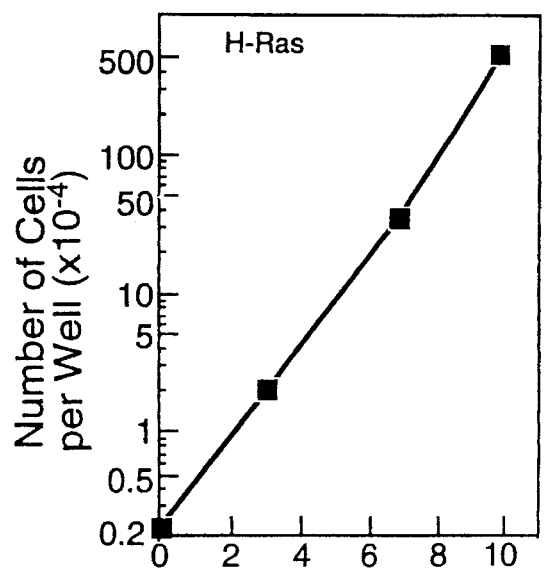
FIGS. 7A–7F Effects of farnesyltransferase inhibition on ras-transformed rat-1 fibroblasts (A, B), src-transformed rat-1 fibroblasts (C, D), and untransformed parental rat-1 fibroblasts (E, F). Growth rate of cell lines in the absence (A, C, E) and presence (B, D, F) of the inhibitor BZA-5B is shown.
Figure 7B:
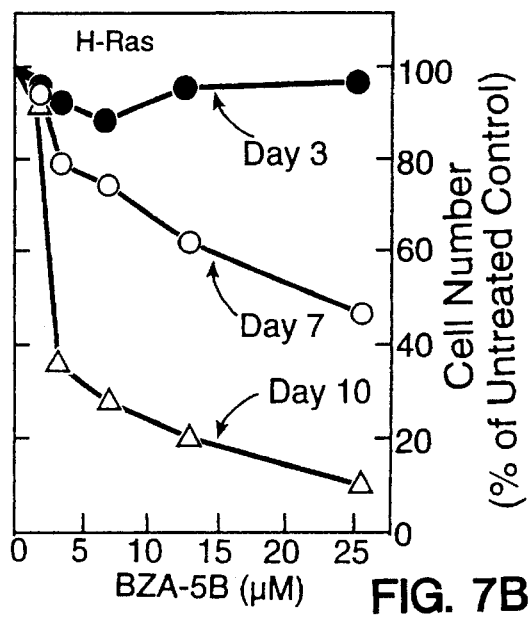
Figure 7C:
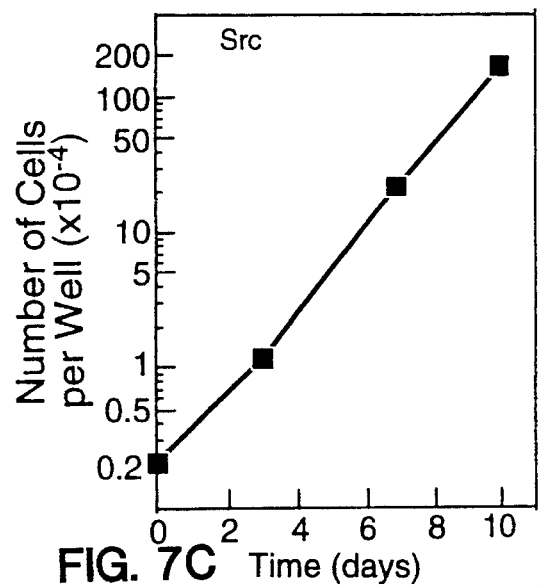
Figure 7D:
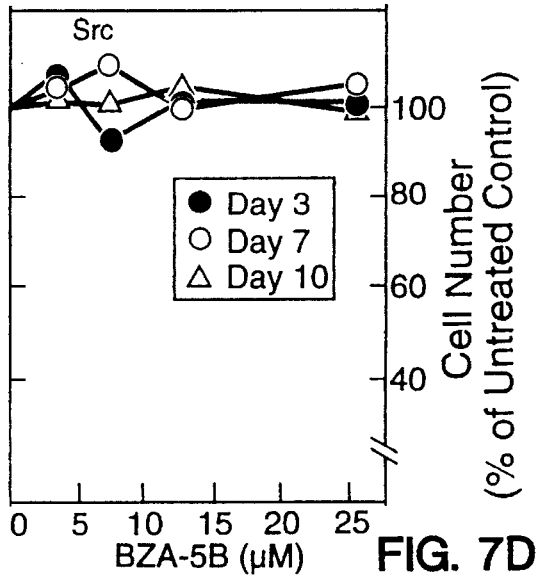
Figure 7E:
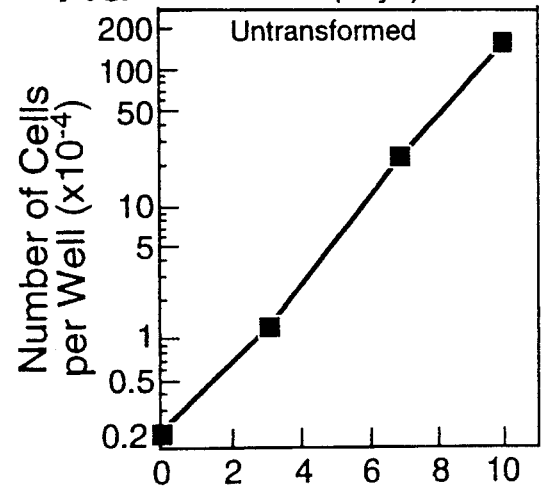
Figure 7F:
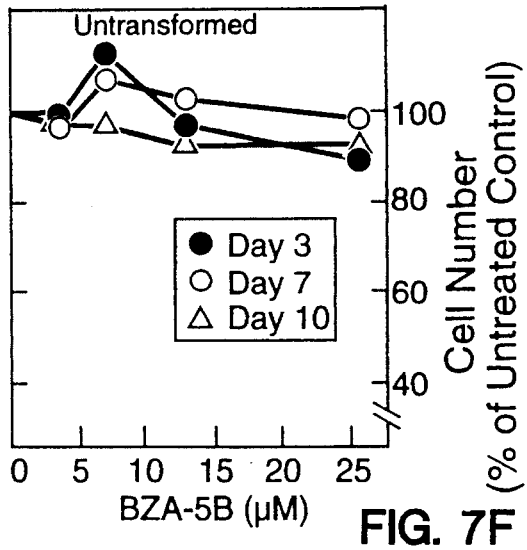

To demonstrate the inhibition of farnesylation of ras proteins directly (see FIG. 5), Met18b-2 cells were incubated with [3H]mevalonate and then immunoprecipitated the cell lysates with a monoclonal antibody that reacts with all four ras proteins. In each experiment, aliquots of the Triton X-100 fraction (300 μg protein, prepared as described above) were incubated with 1 μg anti-ras monoclonal antibody (Oncogene Sciences, Inc.) overnight at 4° C. on a rotating platform. Immune complexes were precipitated by addition of 25 μl Protein A-agarose suspension that had been pre-coated with goat anti-rat IgG (Oncogene Sciences, Inc.) according to the manufacturer's instructions. After a 30 min incubation at 4° C., the agarose beads were pelleted by centrifugation and washed 5 times with 1 ml each of wash solution (50 mM Tris-HCl, 50 mM NaCl, 0.5% (w/v) deoxycholate, 0.5% (v/v) Nonidet P-40, and 0.1% (w/v) SDS at pH 7.5). 75 μl of 1× SDS sample buffer was added and each sample heated for 5 min at 95° before electrophoresis as above. As seen in FIG. 5, shows increasing the concentration of compound 37B (denoted as BZA-5B in the figure) did not detectably inhibit the incorporation of radioactivity into the abundant SMG proteins, most of which are geranylgeranylated (lanes 2–4). However, at 50 μM the compound abolished incorporation of [3H] mevalonate into immunoprecipitated ras proteins (lanes 7–9). Inhibition was readily detectable at 10 μM. The control molecules, the tetrapeptide SVIM and compound 27A (denoted as BZA-2A in the figure), had no effect.

EXAMPLE 56

Assay of Changes in Morphology of ras-transformed Cells.

As shown in FIG. 6, rat-1 fibroblasts transformed with an activated mutant of p21H-ras (Val 12) grow in multilayered clumps, indicative of malignant transformation. Compound 27A (denoted as BZA-2A in the figure) and compound 27B (denoted as BZA-2B in the figure) were added at 250 μM to test whether these compounds would induce reversion to a more normal phenotype as had been previously shown with microinjection of anti-ras antibodies (see Feramisco, J. R. et al Nature 314, 639 (1985)). The H-ras transformed cells, denoted as rat 2.2 cells, were generated by transfection of rat-1 fibroblasts as described (see Seeburg, P. H., Colby, W. W., Capon, D. J., Goeddel, D. V., and Levinson, A. D. Nature 312, 71 (1984)). Cells that overgrew the monolayer were extracted and plated onto agar to obtain a cell line displaying a fully transformed phenotype. Untransformed rat-1 fibroblasts and src-transformed rat-1 fibroblasts were also treated. The src-transformed cells were generated by cotransfection of rat-1 fibroblasts with pSV3.Neo.src, a vector containing the gene for src as well as the gene that confers G418 resistance, both under control of SV40 early promoters. G418-resistant cell clones that diplayed a transformed phenotype were used to generate the cell line. On day 0, cells were plated in monolayer culture at 3×103 cells per well (24-well plates) in 1 ml DMEM supplemented with 10% FCS, 100 U/ml penicillin, 10 μg/ml streptomycin, 2% DMSO, and 0.5 mM DTT with and without 200 μM inhibitor. On day 3, the cells were refed with the same medium. On day 5, the cells were photographed under contrast at a magnification of 100×. Incubation of ras transformed rat 2.2 cells with compound 27B (denoted as BZA-2B in the figure) for 5 days reversed the transformed phenotype (FIG. 6B) while compound 27A (denoted as BZA- 2A in the figure) had no effect (FIG. 6A). Clearly, after 5 days, the rat 2.2 cells display a more normal, flattened cell morphology and grew to lower cell density. This change in morphology is remarkably similar to that seen following injection of anti-ras antibodies into ras-transformed cells (see Feramisco, J. R. et al Nature 314, 639 (1985)). Rat-1 fibroblasts transformed with the src oncogene also grew in a multilayered pattern (FIG. 6C), but this was not affected by compound 27A or compound 27B (FIG. 6D). The compounds also had no apparent effect on the morphology of untransformed rat-1 fibroblasts (FIG. 6E and F).

EXAMPLE 57

Effect of Farnesyltransferase inhibition on cell growth in transformed and untransformed cells To examine the effects of farnesyltransferase inhibition on cell growth, three cell lines (ras-transformed rat-1, src-transformed rat-1, and parental rat-1 cells) were seeded (see FIG. 7) at low density and allowed to grow for 10 days in the absence or presence of increasing concentrations of BZA-5B (compound 37). See Example 56 for description of cells. On day 0, cells were plated in monolayer culture at 2×103 cells per well (24-well plates) in 1 ml DMEM supplemented with 10% fetal calf serum, 100 U/ml penicillin, 100 μg/ml streptomycin, 0.5 mM DTT, 0.025% DMSO, and the indicated concentration of BZA-5B (compound 37). On days 3 and 7, cells were washed and refed with the same medium. At the time indicated in FIG. 7, cells were harvested by trypsinization and counted in a Coulter counter. Panels A, C, E show the growth rate of each cell line in the absence of inhibitor. Panels B, D, F show the inhibition of growth as a function of concentration of BZA-5B at each time point. The "100% values" correspond to the appropriate cell numbers in Panels A, C, E at the indicated time. Each value represents a single incubation. As shown in the panels A, C, and E, all three cell lines grew logarithmically with no added inhibitor. In the presence of BZA-5B, the growth of ras-transformed fibroblasts was inhibited in a time- and dosage-dependent manner, reaching ~90% inhibition after 10 days in the presence of 25 μM BZA-5B (Panel B). The growth of src-transformed (Panel D) and untransformed cells (Panel F) were not affected at concentrations of BZA-5B up to 25 μM. These results show that this inhibitor specifically slows the growth of intact ras-transformed cells with no effect on "normal" non-transformed cells, suggesting that these inhibitors are potential treatments for tumors in which oncogenic ras may play a role.

All references cited herein are expressly incorporated by reference.

What is claimed is:

1. A compound represented by structural formula (II):

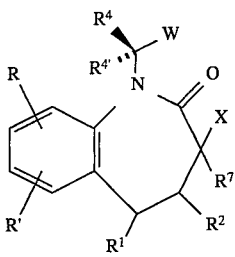

(II)

where
R and R' are independently selected from the group
  hydrogen,
  halo(F, Cl, Br, I),
  $C_1$–$C_6$ alkyl,
  halo(F, Cl, Br, I)$C_1$–$C_6$ alkyl,
  $C_1$–$C_6$ alkoxy,
  hydroxy,
  hydroxy-$C_1$–$C_6$ alkyl,
  $C_1$–$C_6$ alkylcarbonyl, and
  $C_1$–$C_6$ alkyloxycarbonyl;
$R^1$ and $R^2$ are independently selected from the group
  hydrogen,
  $C_1$–$C_6$ alkyl,
  halo(F, Cl, Br, I)-$C_1$–$C_6$ alkyl, and

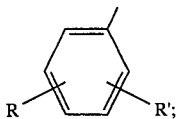

$R^1$ and $R^2$ taken together may form a covalent bond or fused benzene substituted with R and R';
$R^4$ and $R^{4'}$ are independently selected from the group
  hydrogen,
  halo(F, Cl, Br, I),
  $C_1$–$C_6$ alkyl,
  halo(F, Cl, Br, I)$C_1$–$C_6$ alkyl,
  phenyl, and
  benzyl;
$R^7$ selected from the group
  hydrogen,
  halo(F, Cl, Br, I),
  $C_1$–$C_6$ alkyl, and
  halo(F, Cl, Br, I)$C_1$–$C_6$ alkyl;
W is selected from the group
  $C(=O)$—$NR^{7'}R^8$,
  $CH_2$—$C(=O)$—$NR^{7'}R^8$,
  $CR^{8'}(OH)$—$CHR^7R^8$,
  $CHR^{8'}$—$CHR^7R^8$,
  $CHR^{8'}$—$CHR^7R^8$,
  $CR^{8'}CR^7R^8$ (E or Z),
  $C(=O)$—$CHR^7R^8$,
  $CHR^{8'}$—$NR^7R^8$,
  $CHR^{8'}$—O—$R^8$,
  $CHR^{8'}$—$S(O)_u$—$R^8$ where u is 0, 1, or 2,
  $CR^{8'}=N$—$R^8$,
  $CHR^{8'}$—$R^8$,
  W',
  $C_1$–$C_3$alkyl-W',
  $C_6$–$C_{12}$aryl-W',
  $C_6$–$C_{12}$aryl-$C_1$–$C_3$alkyl-W',
  heterocycle-W',
  heterocycle-$C_1$–$C_3$alkyl-W',
  $C_1$–$C_2$alkyl-$C_6$–$C_{10}$aryl-W', and
  $C_1$–$C_2$alkyl-heterocycle-W',
  where any heterocycle is a 5- or 6-member saturated or unsaturated ring containing 1 to 3 heteroatoms selected from O, N, and S;
W' is selected from one to three substituents selected from the group
  hydrogen,
  $SR^9$,
  $SSR^9$,
  $SC(=O)$—$R^9$,
  $OR^9$,
  $C(=NH)$—$NH_2$,
  $N=CH$—$NH_2$,
  $NH$—$CH=NH$,
  $R^8$, and
  V;
$R^{7'}$ is selected from the group
  hydrogen,
  benzyl,
  $C_1$–$C_4$alkyl, and
  halo(F, Cl, Br, I)$C_1$–$C_4$alkyl;
$R^{8'}$ is selected from the group
  hydrogen,
  $C_1$–$C_4$alkyl, and
  halo(F, Cl, Br, I)$C_1$–$C_4$alkyl;
$R^{7'}$ and $R^8$ together with the nitrogen to which they are bonded may form a pyrrolidinyl or piperidyl ring optionally substituted with one or two groups selected from
  $SR^9$,
  $SSR^9$,
  $SC(=O)$—$R^9$,
  $OR^9$,
  $C(=O)NHOH$,
  $NHR^9$,
  $C(=O)NR^{27}R^{28}$, and
  V;
$R^8$ is selected from the group unsubstituted and substituted
  $C_1$–$C_8$alkyl,
  $C_1$–$C_4$alkyl-Z-$C_1$–$C_4$alkyl, where Z is S or O,
  $C_2$–$C_4$alkyl-NR-$C_2$–$C_4$alkyl,
  $C_2$–$C_8$alkenyl,
  $C_6$–$C_{12}$aryl$C_1$–$C_3$alkyl,
  indol-3-yl-$C_1$–$C_3$alkyl, and
  imidazol-4-yl-$C_1$–$C_3$alkyl,
  where any aryl moiety is optionally substituted with —$OR^9$ and V, and
  where any alkyl or alkenyl group is optionally substituted with one to three groups selected from
  $SR^9$,
  $SSR^9$,
  $SC(=O)$—$R^9$,
  $OR^9$,
  $C(=NH)$—$NH_2$,
  $N=CH$—$NH_2$, NH—CH=NH,
NH—C(=NH)—NH$_2$,
C(=O)NHOH,
NHR$^9$,
C(=O)NR$^{27}$R$^{28}$, and
V;

V is selected from the group
COR$^{10}$,
SO$_3$R$^{13}$,
NHSO$_2$CF$_3$,
PO(OR$^{13}$)$_2$,
SO$_2$NHR$^{10}$,
CONHOR$^{13}$,
C(OH)R$^{10}$PO(OR$^{13}$)$_2$,
CN,
SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
OH,
SH,
C$_1$–C$_4$alkyl,
C$_1$–C$_4$alkoxy,
CF$_3$,
halo(F, Cl, Br, I),
NO$_2$,
COOH,
COO—(C$_1$–C$_4$alkyl),
NH$_2$,
NH(C$_1$–C$_4$alkyl), and
N(C$_1$–C$_4$alkyl)$_2$,
CONHSO$_2$R$^{15}$,
SO$_2$NHCOR$^{15}$,
CONHSO$_2$R$^{13}$,
CH$_2$CONHSO$_2$R$^{15}$,
NHCONHSO$_2$R$^{15}$,
NHSO$_2$NHCOR$^{15}$,
CONHNHSO$_2$CF$_3$,
CON(OH)R$^{13}$,
CONHCOCF$_3$,
CONHSO$_2$R$^{10}$,
CONHSO$_2$R$^{11}$,
CONHSO$_2$R$^{13}$,

[tetrazole structure with R$^{19}$],

—CH$_2$—[tetrazole with R$^{19}$],

—CONH—[tetrazole with R$^{19}$],

[pyrazole structure with CF$_3$ and NH], and

[pyrazoline structure with R$^{16}$ and NH];

R$^9$ is selected from the group
hydrogen,
methyl,
ethyl,
isopropyl,
phenyl, and
benzyl;

R$^{10}$ is selected from the group
hydroxy,
C$_1$–C$_8$-alkoxy,
C$_3$–C$_{12}$-alkenoxy,
C$_6$–C$_{12}$-aryloxy,
C$_1$–C$_6$-alkyl-C$_6$–C$_{12}$-aryloxy,
di-C$_1$–C$_8$-alkylamino-C$_1$–C$_8$-alkoxy,
alkanoylamino-C$_1$–C$_8$-alkoxy selected from the group
acetylaminoethoxy,
nicotinoylaminoethoxy, and
succinamidoethoxy, and
C$_1$–C$_8$-alkanoyloxy-C$_1$–C$_8$-alkoxy,
C$_6$–C$_{12}$-aryl-C$_1$–C$_8$-alkoxy where the aryl group is unsubstituted or substituted with one to three of the groups
nitro,
halo(F, Cl, Br, I),
C$_1$–C$_4$-alkoxy, and
amino,
hydroxy-C$_2$–C$_8$-alkoxy,
dihydroxy-C$_3$–C$_8$-alkoxy, and
NR$^{11}$R$^{12}$;

R$^{11}$ and R$^{12}$ are independently selected from the group
hydrogen,
C$_1$–C$_6$ alkyl,
C$_2$–C$_6$ alkanoyl,
C$_1$–C$_6$ alkanoyl substituted with from one to three groups selected from
nitro,
halo(F, Cl, Br, I),
C$_1$–C$_4$-alkoxy, and
amino, and
C$_6$–C$_{12}$-aryl-C$_1$–C$_8$-alkyl where the aryl group is unsubstituted or substituted with one to three of the groups selected from
nitro,
halo(F, Cl, Br, I), and
C$_1$–C$_4$-alkoxy;

R$^{13}$ is selected from the group
hydrogen,
C$_1$–C$_6$ alkyl, halo(F, Cl, Br, I)-$C_1$-$C_6$ alkyl,
phenyl,
benzyl, and
$CH_2$—O—$COCH_3$;
$R^{15}$ is selected from the group
- $C_6$-$C_{14}$aryl, heteroaryl, where the heteroaryl is a 5- or 6-member aromatic ring containing 1 to 3 heteroatoms selected from O, N, and S and where the heteroaryl is unsubstituted or substituted with one or two substituents selected from the group
  - OH,
  - SH,
  - $C_1$-$C_4$alkyl,
  - $C_1$-$C_4$alkoxy,
  - $CF_3$,
  - halo(F, Cl, Br, I),
  - $NO_2$,
  - COOH,
  - COO—($C_1$-$C_4$alkyl),
  - $NH_2$,
  - NH($C_1$-$C_4$alkyl), and
  - N($C_1$-$C_4$alkyl)$_2$,
- $C_3$-$C_7$-cycloalkyl,
- $C_1$-$C_4$-alkyl, unsubstituted or substituted with a substituent selected from the group
  - $C_6$-$C_{14}$aryl,
  - heteroaryl as defined above,
  - OH,
  - SH,
  - $C_1$-$C_4$-alkyl,
  - $C_1$-$C_4$-alkoxy,
  - $C_1$-$C_4$-alkylthio,
  - $CF_3$,
  - halo(F, Cl, Br, I),
  - $NO_2$,
  - $CO_2H$,
  - $CO_2$—($C_1$-$C_4$)-alkyl,
  - $NH_2$,
  - N[($C_1$-$C_4$)-alkyl]$_2$,
  - NH[($C_1$-$C_4$)-alkyl],
  - $PO_3H$, and
  - PO(OH)($C_1$-$C_4$)-alkoxy, and
- ($C_1$-$C_4$)-perfluoroalkyl;

$R^{16}$ is selected from the group
- CN,
- $NO_2$,
- $COOR^{13}$,
- $C_1$-$C_6$-perfluoroalkyl, and
- $CF_3$;

$R^{19}$ is selected from the group
- hydrogen,
- $C_1$-$C_6$alkyl,
- $C_2$-$C_6$alkenyl,
- $C_1$-$C_6$alkoxy,
- $C_2$-$C_6$alkoxyalkyl,
- $CH_2$—O—$COCH_3$, and
- benzyl, where the phenyl moiety is unsubstituted or substituted with a group selected from
  - $NO_2$,
  - $NH_2$,
  - OH, and
  - $OCH_3$;

X is selected from the group
- $NR^{24}$—C(=O)—$R^{25}$,
- $NR^{24}$—CH(OH)—$R^{25}$, and
- $NR^{24}$—S(O)$_u$—$R^{25}$ where u is 0, 1, or 2, $R^{24}$ is selected from the group
- $C_1$-$C_6$alkyl, and
- halo(F, Cl, Br, I)$C_1$-$C_6$alkyl;

$R^{25}$ is selected from $R^{25'}$,

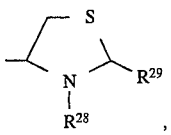

and

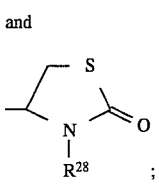

$R^{25'}$ is selected from the group
- $C_1$-$C_6$alkyl,
- $C_2$-$C_6$alkenyl,
- $C_1$-$C_6$alkylamine,
- $C_2$-$C_6$alkenylamine, and
- halo(F, Cl, Br, I)$C_1$-$C_6$alkyl where any alkyl or alkenyl moiety is substituted with $NR^{27}R^{28}$ and one or more groups selected from
- SH and
- $SSR^{26}$;

$R^{26}$ is selected from
- hydrogen,
- $C_1$-$C_6$alkyl,
- halo(F, Cl, Br, I)$C_1$-$C_6$alkyl, and
- $C_1$-$C_6$alkanoyl;

$R^{27}$ and $R^{28}$ are independently selected from the group
- hydrogen,
- $C_1$-$C_6$alkyl,
- phenyl,
- napthyl,
- benzyl,
- $CH_2$napthyl (a or b),
- $C_1$-$C_6$alkanoyl,
- $C_1$-$C_6$cycloalkanoyl,
- $C_6$-$C_{10}$aroyl,
- $C_6$-$C_{10}$aryl$C_1$-$C_6$alkanoyl,
- $C_1$-$C_6$alkylsulfonyl,
- $C_6$-$C_{10}$arylsulfonyl,
- $C_6$-$C_{10}$aryl$C_1$-$C_6$alkylcarbamoyl,
- cinnamoyl,
- heterocyclecarbonyl,
- $C_1$-$C_6$alkoxycarbonyl,
- $C_6$-$C_{10}$aryloxycarbonyl,
- $C_6$-$C_{10}$aryl$C_1$-$C_6$alkoxycarbonyl, and
- pyroglutamyl;

$R^{27}$ and $R^{28}$ together with the nitrogen atom to which they are bonded may form a cyclic amine represented by

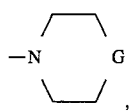

or a cyclic imide represented by

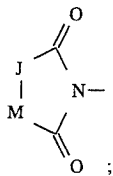

G is selected from —$CH_2$—, O, $S(O)_u$ where u is 0, 1, or 2, and $NR^{28}$;
J-M is selected from $C_2$–$C_4$alkylene and $C_2$–$C_4$alkenylene;
$R^{29}$ is selected from hydrogen and $C_1$–$C_3$alkyl; and pharmaceutically acceptable salts thereof.

2. The compound of claim 1 where $R^{24}$ is methyl.

3. The compound of claim 2 that is substantially free of its diastereomer.

4. The compound of claim 3 that has the R configuration about the 3-carbon of the seven-member ring.

5. The compound of claim 3 that has the S configuration about the 3-carbon of the seven-member ring.

6. The compound of claim 3 wherein
$R^1$ is phenyl and $R^2$ is hydrogen.

7. The compound of claim 6 wherein
X is $NR^{24}$—$C(=O)R^{25}$.

8. The compound of claim 7 wherein
$R^{25}$ is $C_1$–$C_6$alkyl substituted with —$SSR^{26}$ and $NR^{27}R^{28}$.

9. The compound of claim 8 wherein
$R^{26}$ is $C_1$–$C_6$alkyl and
$R^{27}$ and $R^{28}$ are both hydrogen.

10. The compound of claim 9 wherein
—$C(=O)R^{25}$ is the cysteine residue.

* * * * *